US012693298B1

(12) United States Patent
Juarez et al.

(10) Patent No.: US 12,693,298 B1
(45) Date of Patent: Jul. 28, 2026

(54) ANTI-VEDOLIZUMAB ANTIBODIES AND USES THEREOF

(71) Applicant: Takeda Pharmaceutical Company Limited, Osaka (JP)

(72) Inventors: Julius Juarez, Lexington, MA (US); Brandi Lynn Bailey, Lexington, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 602 days.

(21) Appl. No.: 18/148,109

(22) Filed: Dec. 29, 2022

Related U.S. Application Data

(60) Provisional application No. 63/266,276, filed on Dec. 30, 2021.

(51) Int. Cl.
| | |
|---|---|
| *G01N 33/68* | (2006.01) |
| *C07K 16/28* | (2006.01) |
| *C07K 16/42* | (2006.01) |
| *G01N 33/532* | (2006.01) |
| *A61K 39/00* | (2006.01) |

(52) U.S. Cl.
CPC ....... *G01N 33/686* (2013.01); *C07K 16/2839* (2013.01); *C07K 16/4241* (2013.01); *G01N 33/532* (2013.01); *A61K 2039/505* (2013.01); *A61K 2039/545* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 9,663,579 | B2 | 5/2017 | Fox |
| 9,764,033 | B2 | 9/2017 | Diluzio |
| 10,004,808 | B2 | 6/2018 | Fox |
| 10,040,855 | B2 | 8/2018 | Diluzio |
| 10,143,752 | B2 | 12/2018 | Fox |
| 11,560,434 | B2 | 1/2023 | Diluzio |
| 12,053,526 | B2 | 8/2024 | Scholz |
| 12,171,832 | B2 | 12/2024 | Fox |
| 12,286,479 | B2 | 4/2025 | Fox |
| 2019/0231878 | A1 | 8/2019 | Brown et al. |
| 2022/0370617 | A1 | 11/2022 | Diluzio et al. |
| 2023/0312727 | A1 | 10/2023 | Diluzio et al. |
| 2025/0000981 | A1 | 1/2025 | Diluzio et al. |
| 2025/0034263 | A1 | 1/2025 | Diluzio et al. |
| 2025/0041424 | A1 | 2/2025 | Diluzio et al. |
| 2025/0288679 | A1 | 9/2025 | Diluzio et al. |
| 2025/0295786 | A1 | 9/2025 | Diluzio et al. |

OTHER PUBLICATIONS

Abreu et al. Transcriptional Behavior of Regulatory T Cells Predicts IBD Patient Responses to Vedolizumab Therapy. Inflamm Bowel Dis. Dec. 1, 2022;28(12): 1800-1812. doi: 10.1093/ibd/izac151.

(Continued)

*Primary Examiner* — Aurora M Fontainhas

(74) *Attorney, Agent, or Firm* — Womble Bond Dickinson (US) LLP

(57) ABSTRACT

The invention provides methods and compositions related to anti-idiotypic antibodies that specifically bind to vedolizumab, and uses thereof.

21 Claims, 37 Drawing Sheets

Specification includes a Sequence Listing.

(56)     References Cited

OTHER PUBLICATIONS

Boden et al. Identification of Candidate Biomarkers Associated with Response to Vedolizumab in Inflammatory Bowel Disease. Dig Dis Sci. Sep. 2018;63(9):2419-2429. doi: 10.1007/s10620-018-4924-8. Epub Jan. 25, 2018.

Fiorucci et al. Immunephenotype Predicts Response to Vedolizumab: Integrating Clinical and Biochemical Biomarkers in the Treatment of Inflammatory Bowel Diseases. Dig Dis Sci. Sep. 2018;63(9):2168-2171. doi: 10.1007/s10620-018-5039-y.

Coletta et al. Immunological Variables Associated With Clinical and Endoscopic Response to Vedolizumab in Patients With Inflammatory Bowel Diseases. J Crohns Colitis. Sep. 16, 2020;14(9):1190-1201. doi: 10.1093/ecco-jcc/jjaa035.Erratum in: J Crohns Colitis. Jul. 14, 2022;16(6): 1010. doi: 10.1093/ecco-jcc/jab107.

Gonzalez-Vivo M, et al. Memory T Cell Subpopulations as Early Predictors of Remission to Vedolizumab in Ulcerative Colitis. Front Med (Lausanne). Jun. 15, 2022;9:837294. doi: 10.3389/fmed.2022.837294.

De Galan C, et al. Role of integrin expression in the prediction of response to vedolizumab: A prospective real-life multicentre cohort study. Clin Transl Med. Apr. 2022;12(4):e769. doi: 10. 1002/ctm2.769.

Tertiary Screen 1 by FACS against Vedolizumab/Natalizumab-loaded HuT78 Cells

FIG. 3C

| Hyb Supe ID | Ved FACS MFI (EXPT1) | Ved FACS MFI (EXPT2) | Nat FACS MFI (EXPT1) |
|---|---|---|---|
| 5-N17 | 221318 | 292030 | 14235 |
| 3-I10 | 175478 | 204367 | 13855 |
| 4-J24 | 134417 | 139633 | 15491 |
| 4-D5 | 132112 | 82839 | 12479 |
| 6-C13 | 98122 | 79202 | 14874 |
| 6-C8 | 90312 | 182292 | 15387 |
| 2-B4 | 88459 | 101573 | 11356 |
| 4-I18 | 83413 | 93811 | 13260 |
| 6-K19 | 74430 | 125864 | 16025 |
| 6-D8 | 194019 | 204367 | 35623 |
| 2-J3 | 132112 | 175478 | 25118 |
| 5-O20 | 94135 | 144551 | 29907 |
| 3-F3 | 166596 | 87245 | 21034 |
| 6-I19 | 71904 | 138670 | 16466 |
| 2-18 | 123706 | 102632 | 27928 |

FIG. 3C-1

| Hyb Supe ID | Nat FACS MFI (EXPT2) | Ved ELISA RLU | huIgG1 ELISA RLU | Ved/a4b7 Complex ELISA RLU | huIgG1/a4b7 complex ELISA RLU |
|---|---|---|---|---|---|
| 5-N17 | 14477 | 133576 | 10397 | 123191 | 14739 |
| 3-I10 | 10654 | 130268 | 15433 | 160749 | 15238 |
| 4-J24 | 11984 | 72554 | 3566 | 90920 | 4092 |
| 4-D5 | 10690 | 184429 | 5441 | 206907 | 8357 |
| 6-C13 | 9319 | 63341 | 1737 | 58424 | 1687 |
| 6-C8 | 13082 | 96515 | 2676 | 111156 | 3093 |
| 2-B4 | 8747 | 52156 | 1119 | 87894 | 1017 |
| 4-I18 | 9831 | 181299 | 10856 | 144692 | 12450 |
| 6-K19 | 12777 | 378805 | 5677 | 401443 | 6558 |
| 6-D8 | 31377 | 185328 | 3451 | 245558 | 3278 |
| 2-J3 | 30320 | 66852 | 7006 | 96362 | 7064 |
| 5-O20 | 43032 | 125241 | 6949 | 102186 | 8279 |
| 3-F3 | 42009 | 408386 | 38671 | 445068 | 53163 |
| 6-I19 | 14774 | 456017 | 75169 | 433875 | 85868 |
| 2-I8 | 38286 | 483070 | 101170 | 508484 | 106198 |

Vedolizumab

| | Ab concentration | |
|---|---|---|
| | 0 | Count |
| | 0.0017 µg/mL | 1679 |
| | 0.005 µg/mL | 1417 |
| | 0.015 µg/mL | 1719 |
| | 0.05 µg/mL | 1400 |
| | 0.14 µg/mL | 1422 |
| | 0.41 µg/mL | 1459 |
| | 1.22 µg/mL | 1403 |
| | 3.7 µg/mL | 1380 |
| | 11 µg/mL | 1531 |
| | 33 µg/mL | 1646 |
| | 100 µg/mL | 1391 |
| | 300 µg/mL | 1194 |

| | Ab concentration | |
|---|---|---|
| | 0 | Count |
| | 0.0017 µg/mL | 1880 |
| | 0.005 µg/mL | 1549 |
| | 0.015 µg/mL | 1496 |
| | 0.05 µg/mL | 1284 |
| | 0.14 µg/mL | 1265 |
| | 0.41 µg/mL | 1370 |
| | 1.22 µg/mL | 1320 |
| | 3.7 µg/mL | 1367 |
| | 11 µg/mL | 1557 |
| | 33 µg/mL | 1650 |
| | 100 µg/mL | 1565 |
| | 300 µg/mL | 1585 |

Natalizumab

RL1-H :: RL1-H

RL1-H :: RL1-H

*Ab concentration*

| | 0 | Count |
|---|---|---|
| ▨ | 0.0017 µg/mL | 1673 |
| ▨ | 0.005 µg/mL | 1250 |
| ▨ | 0.015 µg/mL | 1324 |
| ▫ | 0.05 µg/mL | 1108 |
| ⊠ | 0.14 µg/mL | 1487 |
| ▨ | 0.41 µg/mL | 1383 |
| ⊡ | 1.22 µg/mL | 1339 |
| ▨ | 3.7 µg/mL | 1349 |
| ⊡ | 11 µg/mL | 1445 |
| ▨ | 33 µg/mL | 1468 |
| ▨ | 100 µg/mL | 1469 |
| ▫ | 300 µg/mL | 1475 |

Duplicate of huIgG1 isotype
▨ negative control
▫ *negative control*

Secondary antibody:
*Jackson ImmunoResearch,
code: 709-605-149*
Alexa Fluor® 647 AffiniPure
Donkey Anti-Human IgG (H+L)

B cell Vedo/anti-Vedo

FIG. 5C

Monocyte Vedo+/anti-Vedo+

FIG. 5D

Other Cells Vedo+/anti-Vedo+

FIG. 7B

ANTI-VEDOLIZUMAB ANTIBODIES AND USES THEREOF

RELATED APPLICATIONS

This application claims priority to U.S. Provisional Appln. No. 63/266,276, filed on Dec. 30, 2021. The contents of the foregoing application are hereby incorporated by reference.

SEQUENCE LISTING

The instant application contains a Sequence Listing which has been submitted in XML format via PatentCenter and is hereby incorporated by reference in its entirety. Said XML copy, created on Dec. 22, 2022, is named T103022 1300US_SL.xml and is 81,258 bytes in size.

FIELD OF THE INVENTION

The present invention relates to methods and compositions related anti-idiotypic antibodies that specifically bind vedolizumab and uses thereof.

BACKGROUND OF THE INVENTION

Inflammatory bowel disease (IBD), such as ulcerative colitis and Crohn's disease can be a debilitating and progressive disease involving inflammation of the gastrointestinal tract. IBD treatments have included anti-inflammatory drugs (e.g., corticosteroids and sulfasalazine), immunosuppressive drugs (e.g., 6-mercaptopurine, cyclosporine and azathioprine) and surgery (e.g., colectomy). Podolsky, *New Engl. J. Med.*, 325:928-937 (1991) and Podolsky, *New Engl. J. Med.*, 325:1008-1016 (1991). As the disease progresses, treatment progresses into regimens that expose patients to progressive risk of side effects and loss of quality of life.

Integrin receptors are important for regulating both lymphocyte recirculation and recruitment to sites of inflammation (Carlos, T. M. and Harlan, J. M., *Blood,* 84:2068-2101 (1994)). The human α4β7 integrin has several ligands, one of which is the mucosal vascular addressin MAdCAM-1 (Berlin, C., et al., *Cell* 74: 185-195 (1993); Erle, D. J., et al., *J. Immunol.* 153:517-528 (1994)), which is expressed on high endothelial venules in mesenteric lymph nodes and Peyer's patches (Streeter, P. R., et al., *Nature* 331:41-46 (1998)). As such, the α4β7 integrin acts as a homing receptor that mediates lymphocyte migration to intestinal mucosal lymphoid tissue (Schweighoffer, T., et al., *J. Immunol.* 151: 717-729 (1993)). In primate studies, administration of an exclusive antagonist of α4β7 integrin resulted in a decrease in the frequency of β7+ lymphocytes in gastrointestinal tissue and an increase in α4β7+ memory helper T lymphocytes in peripheral blood (Fedyk, E. R., et al., *Inflamm. Bowel Dis.* 18: 2107-2119 (2012)).

Antibodies against human α4β7 integrin, such as murine monoclonal antibody Act-1 (mAb Act-1), interfere with α4β7 integrin binding to mucosal addressin cell adhesion molecule-1 (MAdCAM-1) present on high endothelial venules in mucosal lymph nodes. Act-1 was originally isolated by Lazarovits, A. I., et al., *J. Immunol.* 133:1857-1862 (1984), from mice immunized with human tetanus toxoid-specific T lymphocytes and was reported to be a mouse IgG1/κ antibody. Subsequent analysis of the antibody by Schweighoffer, T., et al., *J. Immunol.* 151:717-729 (1993) demonstrated that it can bind to a subset of human memory CD4+T lymphocytes which selectively express the α4β7 integrin. Entyvio™ (vedolizumab), an anti-α4β7 integrin monoclonal antibody (mAb) with structural features derived from Act-1, is indicated for treating ulcerative colitis (UC) and Crohn's disease (CD). Studies reporting the activity of vedolizumab in treating these disorders (Feagen et al. *NEJM* 369:699-710 (2013) and Sandborn et al. *NEJM* 369:711-721 (2013)) showed varying levels of success depending on the disorder and nature of prior therapies. As these were lengthy studies and there are a growing number of treatment options available to patients, there is a need to identify patients who can benefit from vedolizumab therapy in their treatment. One way to identify these patients is through detecting anti-α4β7 antibody in biologic samples. This information can help guide expedient and accurate treatment decisions to promote effective management of disease.

SUMMARY OF THE INVENTION

The invention relates to anti-idiotypic antibodies raised against an anti-α4β7 antibody, compositions and kits for the antibodies, methods for identifying patients who are responding to therapy comprising an anti-α4β7 antibody, such as vedolizumab, or antigen binding fragment thereof, and methods and kits for treatment of inflammatory bowel disease (IBD) in patients, e.g., human patients, who are characterized by marker analysis for favorable outcome to treatment. Early in the course of treatment with an anti-α4β7 antibody, e.g., with vedolizumab, factors measured from the patient, e.g., from biological samples of the patient, indicate whether the patient is responding to treatment and/or whether adjustments to treatment are needed.

In one aspect, pharmacodynamics factors can indicate whether a patient is responding to treatment with an anti-α4β7 antibody, such as vedolizumab or an antigen binding fragment thereof. An anti-α4β7 antibody, such as vedolizumab, binds α4β7 integrin on blood cells, such as derived from the lymphoid and/or myeloid lineages of hematopoietic cells. The profiles of blood cells in tissues and blood can change as a result of administration of an α4β7 integrin antagonist. When such antagonist is an anti-α4β7 antibody or antigen binding fragment thereof, such changes can be detected and/or measured by the anti-idiotypic antibodies or antigen binding fragments thereof provided herein. Detecting blood cells from IBD patients bound by an anti-α4β7 antibody or antigen binding fragment thereof provides the result of treatment with the anti-α4β7 antibody or antigen binding fragment thereof and characterizes patients for additional treatment, such as continued treatment with the anti-α4β7 antibody or antigen binding fragment thereof, adjustment of the dosage regimen with the anti-α4β7 antibody or antigen binding fragment thereof and/or combining treatment with another agent that complements the treatment with the anti-α4β7 antibody or antigen binding fragment.

In an embodiment, a pharmacodynamic factor is the amount of anti-α4β7 antibody or antigen binding fragment thereof bound to α4β7 integrin. In another embodiment, a pharmacodynamic factor is the amount of unbound α4β7 integrin.

In an embodiment, a pharmacodynamic factor is the number of lymphocytes or myeloid-derived cells bound to an anti-α4β7 antibody or antigen-binding fragment thereof. In another embodiment, a pharmacodynamic factor is the type of lymphocyte or myeloid-derived cell bound to an anti-α4β7 antibody or antigen-binding fragment thereof. In some embodiments, other information derived from the cells or a biological sample comprising the cells can include the location of the cells, markers associated with the cells or extent of inflammation. One or a combination of pharmacodynamic factors and additional information, such as results of detecting markers, e.g., phenotypic markers, associated with the cells and/or clinical data, can provide a profile of the effect of the treatment with the anti-α4β7 antibody or antigen binding fragment thereof.

In another aspect, provided herein is a method of determining a vedolizumab profile of a human patient, the method comprising: contacting a biological sample comprising a population of cells from a human patient with an anti-idiotypic antibody, or an antigen-binding fragment thereof, with binding specificity to vedolizumab, under conditions in which the anti-idiotypic antibody, or antigen-binding fragment thereof, binds to vedolizumab, wherein the human patient was administered vedolizumab prior to obtaining the biological sample; and detecting a level of vedolizumab bound to cells in the biological sample with the anti-idiotypic antibody, or antigen-binding fragment thereof, thereby determining the vedolizumab profile of the human patient.

In a further aspect, provided herein is a method of determining a vedolizumab profile of a human patient, the method comprising: contacting a biological sample from a human patient with an anti-idiotypic antibody, or an antigen-binding fragment thereof, with binding specificity to vedolizumab, under conditions in which the anti-idiotypic antibody, or antigen-binding fragment thereof, binds to vedolizumab, wherein the human patient was administered vedolizumab prior to obtaining the biological sample; separating the biological sample into two or more subsets of cells; detecting vedolizumab with the anti-idiotypic antibody, or antigen-binding fragment thereof, in each subset of cells; and identifying a subset of cells bound by vedolizumab based on the detection of vedolizumab with the anti-idiotypic antibody, thereby determining the vedolizumab profile of the human patient.

In some embodiments, the subsets of cells are separated by flow cytometry.

In some embodiments, the cells are immune cells. In some embodiments, the immune cell is a T cell (e.g., a memory T cell, a naïve T cell, a regulatory T cell), a B cell, a NK cell, a monocyte, a dendritic cell, a plasma cell, and/or an eosinophil. In some embodiments, the immune cell is a dendritic cell. In some embodiments, the immune cell is a T lymphocyte. In some embodiments, T lymphocyte is an effector memory T cell, a naïve T cell, and/or a regulatory T cell. In some embodiments, the cell expresses one or more phenotypic markers selected from CD3, CD4, CD6, CD11c, CD14, CD16, CD19, CD25, CD28, CD38, CD45RA, CD64, CD127, CCR7, CCR9, FoxP3, GPR15, Th17, or miR-301a.

In some embodiments, the biological sample is a blood sample. In some embodiments, the biological sample is a tissue sample (e.g., colon biopsy).

In some embodiments, the biological sample is obtained from the human patient 1 week, 2 weeks, 4 weeks, 6 weeks, 8 weeks, 10 weeks, 12 weeks, and/or 14 weeks following administration of vedolizumab to the human patient.

In some embodiments, the method further comprises collecting a biological sample from the human patient prior to administration of vedolizumab, thereby collecting a baseline sample.

In some embodiments, the method further comprises comparing the level of vedolizumab bound to cells in the human patient or presence of vedolizumab on the subset of cells to a reference level to determine if the human patient is responsive or non-responsive to treatment with vedolizumab.

In some embodiments, the reference level is a baseline sample obtained from the human patient prior to treatment with vedolizumab. In some embodiments, the method further comprises adjusting a dosing regimen of vedolizumab.

In some embodiments, the human patient has an inflammatory bowel disease. In some embodiments, the inflammatory bowel disease is Crohn's disease, pouchitis, or ulcerative colitis.

In some embodiments, the human patient has graft versus host disease (GvHD) or HIV.

In some embodiments, the anti-idiotypic antibody comprises a detectable label. In some embodiments, the detectable label is selected from the group consisting of an oligonucleotide, horseradish peroxidase (HRP), alkaline phosphatase, galactosidase, glucoamylase, lysozyme, a saccharide oxidase, a heterocyclic oxidase coupled with an enzyme that employs hydrogen peroxide to oxidize a dye, biotin/avidin, a spin label, a bacteriophage label, a metal, a heavy metal isotope (e.g., a lanthanide metal), and a stable free radical.

In some embodiments, the anti-idiotypic antibody is detected by flow cytometry, immunohistochemistry, Cellular Indexing of Transcriptomes and Epitopes by Sequencing (CITE-Seq), mass cytometry (CyTOF), lateral flow assay, or oligonucleotide sequencing.

In some embodiments, the method further comprises measuring the level of α4β1, αLβ2, αEβ7, α6β1, and/or α6β4 in the biological sample.

In some embodiments, the method further comprises measuring the fecal calprotectin, C-reactive protein (CRP), and/or albumin concentration in the biological sample.

In some embodiments, the anti-idiotypic antibody recognizes an epitope on vedolizumab corresponding to the epitope of antibody N17. In some embodiments, the anti-idiotypic antibody competes with antibody N17.

In some embodiments, the anti-idiotypic antibody does not compete with vedolizumab binding to α4β7 integrin.

In some embodiments, the anti-idiotypic antibody, or antigen-binding fragment thereof, comprises (i) a heavy chain variable region comprising a CDR1 domain comprising the amino acid sequence as set forth in SEQ ID NO:1, a CDR2 domain comprising the amino acid sequence as set forth in SEQ ID NO: 2, and a CDR3 domain comprising the amino acid sequence as set forth in SEQ ID NO: 3; and a light chain variable region comprising a CDR1 domain comprising the amino acid sequence as set forth in SEQ ID NO: 4, a CDR2 domain comprising the amino acid sequence as set forth in SEQ ID NO: 5; and a CDR3 domain comprising the amino acid sequence as set forth in SEQ ID NO: 6;

(ii) a heavy chain variable region comprising a CDR1 domain comprising the amino acid sequence as set forth in SEQ ID NO:11, a CDR2 domain comprising the amino acid sequence as set forth in SEQ ID NO: 12, and a CDR3 domain comprising the amino acid sequence as set forth in SEQ ID NO: 13; and a light chain variable region comprising a CDR1 domain comprising the amino acid sequence as set forth in SEQ ID NO: 14, a CDR2 domain comprising the amino acid sequence as set forth in SEQ ID NO: 15; and a CDR3 domain comprising the amino acid sequence as set forth in SEQ ID NO: 16;

(iii) a heavy chain variable region comprising a CDR1 domain comprising the amino acid sequence as set forth in SEQ ID NO:21, a CDR2 domain comprising the amino acid sequence as set forth in SEQ ID NO: 22, and a CDR3 domain comprising the amino acid sequence as set forth in SEQ ID NO: 23; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26;

(iv) a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 32; and a light chain variable region comprising a CDR1 domain comprising the amino acid sequence as set forth in SEQ ID NO: 33, a CDR2 domain comprising the amino acid sequence as set forth in SEQ ID NO: 25; and a CDR3 domain comprising the amino acid sequence as set forth in SEQ ID NO: 26;

(v) a heavy chain variable region comprising a CDR1 domain comprising the amino acid sequence as set forth in SEQ ID NO:38, a CDR2 domain comprising the amino acid sequence as set forth in SEQ ID NO: 39, and a CDR3 domain comprising the amino acid sequence as set forth in SEQ ID NO: 40; and a light chain variable region comprising a CDR1 domain comprising the amino acid sequence as set forth in SEQ ID NO: 41, a CDR2 domain comprising the amino acid sequence as set forth in SEQ ID NO: 42; and a CDR3 domain comprising the amino acid sequence as set forth in SEQ ID NO: 43;

(vi) a heavy chain variable region comprising a CDR1 domain comprising the amino acid sequence as set forth in SEQ ID NO:48, a CDR2 domain comprising the amino acid sequence as set forth in SEQ ID NO: 49, and a CDR3 domain comprising the amino acid sequence as set forth in SEQ ID NO: 50; and a light chain variable region comprising a CDR1 domain comprising the amino acid sequence as set forth in SEQ ID NO: 51, a CDR2 domain comprising the amino acid sequence as set forth in SEQ ID NO: 52; and a CDR3 domain comprising the amino acid sequence as set forth in SEQ ID NO: 53;

(vii) a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26;

(viii) a heavy chain variable region comprising a CDR1 domain comprising the amino acid sequence as set forth in SEQ ID NO:63 a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26; or (ix) a heavy chain variable region comprising a CDR1 domain comprising the amino acid sequence as set forth in SEQ ID NO:68 a CDR2 domain comprising the amino acid sequence as set forth in SEQ ID NO: 69, and a CDR3 domain comprising the amino acid sequence as set forth in SEQ ID NO: 70; and a light chain variable region comprising a CDR1 domain comprising the amino acid sequence as set forth in SEQ ID NO: 71, a CDR2 domain comprising the amino acid sequence as set forth in SEQ ID NO: 72; and a CDR3 domain comprising the amino acid sequence as set forth in SEQ ID NO: 73.

In one embodiment, the anti-idiotypic antibody, or antigen-binding fragment thereof, comprises a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26.

In some embodiments, the anti-idiotypic antibody, or antigen-binding fragment thereof, comprises:

(i) a heavy chain variable region comprising the amino acid sequence as set forth in SEQ ID NO: 7, and a light chain variable region comprising the amino acid sequence as set forth in SEQ ID NO: 8;

(ii) a heavy chain variable region comprising the amino acid sequence as set forth in SEQ ID NO: 17, and a light chain variable region comprising the amino acid sequence as set forth in SEQ ID NO: 18;

(iii) a heavy chain variable region comprising the amino acid sequence as set forth in SEQ ID NO: 27, and a light chain variable region comprising the amino acid sequence as set forth in SEQ ID NO: 28;

(iv) a heavy chain variable region comprising the amino acid sequence as set forth in SEQ ID NO: 34, and a light chain variable region comprising the amino acid sequence as set forth in SEQ ID NO: 35;

(v) a heavy chain variable region comprising the amino acid sequence as set forth in SEQ ID NO: 44, and a light chain variable region comprising the amino acid sequence as set forth in SEQ ID NO: 45;

(vi) a heavy chain variable region comprising the amino acid sequence as set forth in SEQ ID NO: 54, and a light chain variable region comprising the amino acid sequence as set forth in SEQ ID NO: 55;

(vii) a heavy chain variable region comprising the amino acid sequence as set forth in SEQ ID NO: 59, and a light chain variable region comprising the amino acid sequence as set forth in SEQ ID NO: 60;

(viii) a heavy chain variable region comprising the amino acid sequence as set forth in SEQ ID NO: 64, and a light chain variable region comprising the amino acid sequence as set forth in SEQ ID NO: 65; or (ix) a heavy chain variable region comprising the amino acid sequence as set forth in SEQ ID NO: 74, and a light chain variable region comprising the amino acid sequence as set forth in SEQ ID NO: 75.

In one embodiment, the anti-idiotypic antibody, or antigen-binding fragment thereof, comprises a heavy chain variable region comprising the amino acid sequence as set forth in SEQ ID NO: 59, and a light chain variable region comprising the amino acid sequence as set forth in SEQ ID NO: 60.

In some embodiments, the anti-idiotypic antibody, or antigen-binding fragment thereof, is an scFv, a single domain antibody, or a diabody.

In another aspect, provided herein is a method of treating a human patient having an inflammatory bowel disease (IBD), the method comprising administering a dose of vedolizumab to the human patient having IBD, wherein the human patient is characterized as having a responsive vedolizumab profile of vedolizumab-bound immune cells 1 to 2 weeks after administration of vedolizumab to the human patient, thereby treating the human patient having IBD. In some embodiments, a responsive vedolizumab profile comprises immune cells which express low amounts of α4β1, αLβ2, αΕβ7, α6β1, and/or 0604.

In a further aspect, provided herein is a method of treating a human patient having an inflammatory bowel disease (IBD), the method comprising administering to the human patient having IBD a dose of vedolizumab, wherein the human patient is characterized as having an increased level of vedolizumab bound to immune cells relative to a reference level, wherein the level of vedolizumab is determined 1 to 2 weeks after a prior administration of vedolizumab, such that the human patient having IBD is treated.

In another aspect, provided herein is a method of treating a human patient having inflammatory bowel disease (IBD), the method comprising administering to the human patient a dose of vedolizumab and a dose of an additional therapeutic agent, wherein the human patient is characterized as having an increased level of vedolizumab bound to immune cells relative to a reference level, wherein the level of vedolizumab is determined 1 to 2 weeks after a prior administration of vedolizumab to the human patient, such that the human patient having IBD is treated.

In some embodiments, the additional therapeutic agent is an IL-23 inhibitor, a JAK inhibitor, a checkpoint inhibitor, or a TNF alpha inhibitor.

In another aspect, provided herein is a method of treating a human patient having an inflammatory bowel disease (IBD), the method comprising administering a dose of vedolizumab to the patient at an initial time point, measuring the amount of vedolizumab-bound immune cells in a biological sample obtained from the human patient about two weeks after the initial time point; and administering one or more doses of vedolizumab to the human patient if the level of vedolizumab-bound immune cells in the biological sample is increased relative to a reference level.

In some embodiments, the immune cell is a T cell, a B cell, a NK cell, a monocyte, a dendritic cell, a plasma cell, and/or an eosinophil. In some embodiments, the immune cell is a dendritic cell.

In some embodiments, the immune cell is a T cell.

In some embodiments, the T cell is an effector memory T cell, a naïve T cell, and/or a regulatory T cell. In some embodiments, the immune cell expresses one or more phenotypic markers selected from CD3, CD4, CD6, CD11c, CD14, CD16, CD19, CD25, CD28, CD38, CD45RA, CD64, CD127, CCR7, CCR9, FoxP3, GPR15, Th17, and miR-301a.

In some embodiments, the responsive vedolizumab profile has a low amount of α4β1-, αLβ2-, αΕβ7-, α6β1-, or 0604-expressing cells. In some embodiments, the responsive vedolizumab profile comprises immune cells which express low amounts of α4β1, αLβ2, αΕβ7, α6β1, and/or α6β4.

In some embodiments, vedolizumab is measured on immune cells in a biological sample obtained from the patient. In some embodiments, the biological sample is a blood sample.

In some embodiments, the level of vedolizumab bound to the immune cells is measured by a FACS analysis.

In some embodiments, the inflammatory bowel disease is Crohn's disease, pouchitis, or ulcerative colitis.

In some embodiments, the method further comprises measuring the level of vedolizumab-bound immune cells in a biological sample collected from the patient by contacting the cells with an anti-idiotypic antibody or antigen-binding fragment thereof, comprising:

(i) a heavy chain variable region comprising a CDR1 domain comprising the amino acid sequence as set forth in SEQ ID NO:1, a CDR2 domain comprising the amino acid sequence as set forth in SEQ ID NO: 2, and a CDR3 domain comprising the amino acid sequence as set forth in SEQ ID NO: 3; and a light chain variable region comprising a CDR1 domain comprising the amino acid sequence as set forth in SEQ ID NO: 4, a CDR2 domain comprising the amino acid sequence as set forth in SEQ ID NO: 5; and a CDR3 domain comprising the amino acid sequence as set forth in SEQ ID NO: 6;

(ii) a heavy chain variable region comprising a CDR1 domain comprising the amino acid sequence as set forth in SEQ ID NO:11, a CDR2 domain comprising the amino acid sequence as set forth in SEQ ID NO: 12, and a CDR3 domain comprising the amino acid sequence as set forth in SEQ ID NO: 13; and a light chain variable region comprising a CDR1 domain comprising the amino acid sequence as set forth in SEQ ID NO: 14, a CDR2 domain comprising the amino acid sequence as set forth in SEQ ID NO: 15; and a CDR3 domain comprising the amino acid sequence as set forth in SEQ ID NO: 16;

(iii) a heavy chain variable region comprising a CDR1 domain comprising the amino acid sequence as set forth in SEQ ID NO:21, a CDR2 domain comprising the amino acid sequence as set forth in SEQ ID NO: 22, and a CDR3 domain comprising the amino acid sequence as set forth in SEQ ID NO: 23; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26;

(iv) a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 32; and a light chain variable region comprising a CDR1 domain comprising the amino acid sequence as set forth in SEQ ID NO: 33, a CDR2 domain comprising the amino acid sequence as set forth in SEQ ID NO: 25; and a CDR3 domain comprising the amino acid sequence as set forth in SEQ ID NO: 26;

(v) a heavy chain variable region comprising a CDR1 domain comprising the amino acid sequence as set forth in SEQ ID NO:38, a CDR2 domain comprising the amino acid sequence as set forth in SEQ ID NO: 39, and a CDR3 domain comprising the amino acid sequence as set forth in SEQ ID NO: 40; and a light chain variable region comprising a CDR1 domain comprising the amino acid sequence as set forth in SEQ ID NO: 41, a CDR2 domain comprising the amino acid sequence as set forth in SEQ ID NO: 42; and a CDR3 domain comprising the amino acid sequence as set forth in SEQ ID NO: 43;

(vi) a heavy chain variable region comprising a CDR1 domain comprising the amino acid sequence as set forth in SEQ ID NO:48, a CDR2 domain comprising the amino acid sequence as set forth in SEQ ID NO: 49, and a CDR3 domain comprising the amino acid sequence as set forth in SEQ ID NO: 50; and a light chain variable region comprising a CDR1 domain comprising the amino acid sequence as set forth in SEQ ID NO: 51, a CDR2 domain comprising the amino acid sequence as set forth in SEQ ID NO: 52; and a CDR3 domain comprising the amino acid sequence as set forth in SEQ ID NO: 53;

(vii) a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26;

(viii) a heavy chain variable region comprising a CDR1 domain comprising the amino acid sequence as set forth in SEQ ID NO:63 a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26; or (ix) a heavy chain variable region comprising a CDR1 domain comprising the amino acid sequence as set forth in SEQ ID NO:68 a CDR2 domain comprising the amino acid sequence as set forth in SEQ ID NO: 69, and a CDR3 domain comprising the amino acid sequence as set forth in SEQ ID NO: 70; and a light chain variable region comprising a CDR1 domain comprising the amino acid sequence as set forth in SEQ ID NO: 71, a CDR2 domain comprising the amino acid sequence as set forth in SEQ ID NO: 72; and a CDR3 domain comprising the amino acid sequence as set forth in SEQ ID NO: 73.

In some embodiments, the method comprises measuring the level of vedolizumab-bound immune cells in a biological sample collected from the patient, by contacting the immune cells with an anti-idiotypic antibody or antigen-binding fragment thereof, wherein the anti-idiotypic antibody, or antigen-binding fragment thereof, comprises:

(i) a heavy chain variable region comprising the amino acid sequence as set forth in SEQ ID NO: 7, and a light chain variable region comprising the amino acid sequence as set forth in SEQ ID NO: 8;

(ii) a heavy chain variable region comprising the amino acid sequence as set forth in SEQ ID NO: 17, and a light chain variable region comprising the amino acid sequence as set forth in SEQ ID NO: 18;

(iii) a heavy chain variable region comprising the amino acid sequence as set forth in SEQ ID NO: 27, and a light chain variable region comprising the amino acid sequence as set forth in SEQ ID NO: 28;

(iv) a heavy chain variable region comprising the amino acid sequence as set forth in SEQ ID NO: 34, and a light chain variable region comprising the amino acid sequence as set forth in SEQ ID NO: 35;

(v) a heavy chain variable region comprising the amino acid sequence as set forth in SEQ ID NO: 44, and a light chain variable region comprising the amino acid sequence as set forth in SEQ ID NO: 45;

(vi) a heavy chain variable region comprising the amino acid sequence as set forth in SEQ ID NO: 54, and a light chain variable region comprising the amino acid sequence as set forth in SEQ ID NO: 55;

(vii) a heavy chain variable region comprising the amino acid sequence as set forth in SEQ ID NO: 59, and a light chain variable region comprising the amino acid sequence as set forth in SEQ ID NO: 60;

(viii) a heavy chain variable region comprising the amino acid sequence as set forth in SEQ ID NO: 64, and a light chain variable region comprising the amino acid sequence as set forth in SEQ ID NO: 65; or (ix) a heavy chain variable region comprising the amino acid sequence as set forth in SEQ ID NO: 74, and a light chain variable region comprising the amino acid sequence as set forth in SEQ ID NO: 75.

In some embodiments, the levels of vedolizumab-bound immune cells in the biological sample are detected by flow cytometry. In other embodiments, the levels of vedolizumab-bound immune cells in the biological sample are detected by mass cytometry.

In another aspect, provided herein is vedolizumab for use in a method of treating a human patient having an inflammatory bowel disease (IBD), wherein the human patient is characterized as having an increased level of vedolizumab-bound immune cells relative to a reference level 1 to 2 weeks after a dose of 300 mg vedolizumab by intravenous administration.

In another aspect, provided herein is vedolizumab for use in a method of treating a human patient having an inflammatory bowel disease (IBD), wherein the human patient is characterized as having an increased level of vedolizumab-bound immune cells relative to a reference level 1 to 2 weeks after a dose of 108 mg vedolizumab by subcutaneous administration.

In another aspect, provided herein is vedolizumab for use in a method of treating a human patient having an inflammatory bowel disease (IBD) wherein the human patient is characterized as having a responsive vedolizumab profile 1 to 2 weeks after a dose of 300 mg vedolizumab by intravenous administration.

In another aspect, provided herein is vedolizumab for use in a method of treating a human patient having an inflammatory bowel disease (IBD) wherein the human patient is characterized as having a responsive vedolizumab profile 1 to 2 weeks after a dose of 108 mg vedolizumab by subcutaneous administration.

In another aspect, provided herein is a method of detecting vedolizumab in a biological sample comprising α4β7 integrin comprising contacting the biological sample with an anti-idiotypic antibody or antigen-binding fragment thereof, comprising:

(i) a heavy chain variable region comprising a CDR1 domain comprising the amino acid sequence as set forth in SEQ ID NO:1, a CDR2 domain comprising the amino acid sequence as set forth in SEQ ID NO: 2, and a CDR3 domain comprising the amino acid sequence as set forth in SEQ ID NO: 3; and a light chain variable region comprising a CDR1 domain comprising the amino acid sequence as set forth in SEQ ID NO: 4, a CDR2 domain comprising the amino acid sequence as set forth in SEQ ID NO: 5; and a CDR3 domain comprising the amino acid sequence as set forth in SEQ ID NO: 6;

(ii) a heavy chain variable region comprising a CDR1 domain comprising the amino acid sequence as set forth in SEQ ID NO:11, a CDR2 domain comprising the amino acid sequence as set forth in SEQ ID NO: 12, and a CDR3 domain comprising the amino acid sequence as set forth in SEQ ID NO: 13; and a light chain variable region comprising a CDR1 domain comprising the amino acid sequence as set forth in SEQ ID NO: 14, a CDR2 domain comprising the amino acid sequence as set forth in SEQ ID NO: 15; and a CDR3 domain comprising the amino acid sequence as set forth in SEQ ID NO: 16;

(iii) a heavy chain variable region comprising a CDR1 domain comprising the amino acid sequence as set forth in SEQ ID NO:21, a CDR2 domain comprising the amino acid sequence as set forth in SEQ ID NO: 22, and a CDR3 domain comprising the amino acid sequence as set forth in SEQ ID NO: 23; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26;

(iv) a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 32; and a light chain variable region comprising a CDR1 domain comprising the amino acid sequence as set forth in SEQ ID NO: 33, a CDR2 domain comprising the amino acid sequence as set forth in SEQ ID NO: 25; and a CDR3 domain comprising the amino acid sequence as set forth in SEQ ID NO: 26;

(v) a heavy chain variable region comprising a CDR1 domain comprising the amino acid sequence as set forth in SEQ ID NO:38, a CDR2 domain comprising the amino acid sequence as set forth in SEQ ID NO: 39, and a CDR3 domain comprising the amino acid sequence as set forth in SEQ ID NO: 40; and a light chain variable region comprising a CDR1 domain comprising the amino acid sequence as set forth in SEQ ID NO: 41, a CDR2 domain comprising the amino acid sequence as set forth in SEQ ID NO: 42; and a CDR3 domain comprising the amino acid sequence as set forth in SEQ ID NO: 43;

(vi) a heavy chain variable region comprising a CDR1 domain comprising the amino acid sequence as set forth in SEQ ID NO:48, a CDR2 domain comprising the amino acid sequence as set forth in SEQ ID NO: 49, and a CDR3 domain comprising the amino acid sequence as set forth in SEQ ID NO: 50; and a light chain variable region comprising a CDR1 domain comprising the amino acid sequence as set forth in SEQ ID NO: 51, a CDR2 domain comprising the amino acid sequence as set forth in SEQ ID NO: 52; and a CDR3 domain comprising the amino acid sequence as set forth in SEQ ID NO: 53;

(vii) a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26;

(viii) a heavy chain variable region comprising a CDR1 domain comprising the amino acid sequence as set forth in SEQ ID NO:63 a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26; or (ix) a heavy chain variable region comprising a CDR1 domain comprising the amino acid sequence as set forth in SEQ ID NO:68 a CDR2 domain comprising the amino acid sequence as set forth in SEQ ID NO: 69, and a CDR3 domain comprising the amino acid sequence as set forth in SEQ ID NO: 70; and a light chain variable region comprising a CDR1 domain comprising the amino acid sequence as set forth in SEQ ID NO: 71, a CDR2 domain comprising the amino acid sequence as set forth in SEQ ID NO: 72; and a CDR3 domain comprising the amino acid sequence as set forth in SEQ ID NO: 73.

In some embodiments, the method comprises detecting vedolizumab in a biological sample comprising α4β7 integrin comprising contacting the biological sample with an anti-idiotypic antibody or antigen-binding fragment thereof, wherein the anti-idiotypic antibody, or antigen-binding fragment thereof, comprises:

(i) a heavy chain variable region comprising the amino acid sequence as set forth in SEQ ID NO: 7, and a light chain variable region comprising the amino acid sequence as set forth in SEQ ID NO: 8;

(ii) a heavy chain variable region comprising the amino acid sequence as set forth in SEQ ID NO: 17, and a light chain variable region comprising the amino acid sequence as set forth in SEQ ID NO: 18;

(iii) a heavy chain variable region comprising the amino acid sequence as set forth in SEQ ID NO: 27, and a light chain variable region comprising the amino acid sequence as set forth in SEQ ID NO: 28;

(iv) a heavy chain variable region comprising the amino acid sequence as set forth in SEQ ID NO: 34, and a light chain variable region comprising the amino acid sequence as set forth in SEQ ID NO: 35;

(v) a heavy chain variable region comprising the amino acid sequence as set forth in SEQ ID NO: 44, and a light chain variable region comprising the amino acid sequence as set forth in SEQ ID NO: 45;

(vi) a heavy chain variable region comprising the amino acid sequence as set forth in SEQ ID NO: 54, and a light chain variable region comprising the amino acid sequence as set forth in SEQ ID NO: 55;

(vii) a heavy chain variable region comprising the amino acid sequence as set forth in SEQ ID NO: 59, and a light chain variable region comprising the amino acid sequence as set forth in SEQ ID NO: 60;

(viii) a heavy chain variable region comprising the amino acid sequence as set forth in SEQ ID NO: 64, and a light chain variable region comprising the amino acid sequence as set forth in SEQ ID NO: 65; or (ix) a heavy chain variable region comprising the amino acid sequence as set forth in SEQ ID NO: 74, and a light chain variable region comprising the amino acid sequence as set forth in SEQ ID NO: 75.

In another aspect, provided herein is an anti-vedolizumab antibody, or an antigen-binding fragment thereof, comprising (i) a heavy chain variable region comprising a CDR1 domain comprising the amino acid sequence as set forth in SEQ ID NO:1, a CDR2 domain comprising the amino acid sequence as set forth in SEQ ID NO: 2, and a CDR3 domain comprising the amino acid sequence as set forth in SEQ ID NO: 3; and a light chain variable region comprising a CDR1 domain comprising the amino acid sequence as set forth in SEQ ID NO: 4, a CDR2 domain comprising the amino acid sequence as set forth in SEQ ID NO: 5; and a CDR3 domain comprising the amino acid sequence as set forth in SEQ ID NO: 6;

(ii) a heavy chain variable region comprising a CDR1 domain comprising the amino acid sequence as set forth in SEQ ID NO:11, a CDR2 domain comprising the amino acid sequence as set forth in SEQ ID NO: 12, and a CDR3 domain comprising the amino acid sequence as set forth in SEQ ID NO: 13; and a light chain variable region comprising a CDR1 domain comprising the amino acid sequence as set forth in SEQ ID NO: 14, a CDR2 domain comprising the amino acid sequence as set forth in SEQ ID NO: 15; and a CDR3 domain comprising the amino acid sequence as set forth in SEQ ID NO: 16;

(iii) a heavy chain variable region comprising a CDR1 domain comprising the amino acid sequence as set forth in SEQ ID NO:21, a CDR2 domain comprising the amino acid sequence as set forth in SEQ ID NO: 22, and a CDR3 domain comprising the amino acid sequence as set forth in SEQ ID NO: 23; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26;

(iv) a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 32; and a light chain variable region comprising a CDR1 domain comprising the amino acid sequence as set forth in SEQ ID NO: 33, a CDR2 domain comprising the amino acid sequence as set forth in SEQ ID NO: 25; and a CDR3 domain comprising the amino acid sequence as set forth in SEQ ID NO: 26;

(v) a heavy chain variable region comprising a CDR1 domain comprising the amino acid sequence as set forth in SEQ ID NO:38, a CDR2 domain comprising the amino acid sequence as set forth in SEQ ID NO: 39, and a CDR3 domain comprising the amino acid sequence as set forth in SEQ ID NO: 40; and a light chain variable region comprising a CDR1 domain comprising the amino acid sequence as set forth in SEQ ID NO: 41, a CDR2 domain comprising the amino acid sequence as set forth in SEQ ID NO: 42; and a CDR3 domain comprising the amino acid sequence as set forth in SEQ ID NO: 43;

(vi) a heavy chain variable region comprising a CDR1 domain comprising the amino acid sequence as set forth in SEQ ID NO: 48, a CDR2 domain comprising the amino acid sequence as set forth in SEQ ID NO: 49, and a CDR3 domain comprising the amino acid sequence as set forth in SEQ ID NO: 50; and a light chain variable region comprising a CDR1 domain comprising the amino acid sequence as set forth in SEQ ID NO: 51, a CDR2 domain comprising the amino acid sequence as set forth in SEQ ID NO: 52; and a CDR3 domain comprising the amino acid sequence as set forth in SEQ ID NO: 53;

(vii) a heavy chain variable region comprising a CDR1 domain comprising the amino acid sequence as set forth in SEQ ID NO: 31, a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26;

(viii) a heavy chain variable region comprising a CDR1 domain comprising the amino acid sequence as set forth in SEQ ID NO: 63 a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26; or (ix) a heavy chain variable region comprising a CDR1 domain comprising the amino acid sequence as set forth in SEQ ID NO: 68 a CDR2 domain comprising the amino acid sequence as set forth in SEQ ID NO: 69, and a CDR3 domain comprising the amino acid sequence as set forth in SEQ ID NO: 70; and a light chain variable region comprising a CDR1 domain comprising the amino acid sequence as set forth in SEQ ID NO: 71, a CDR2 domain comprising the amino acid sequence as set forth in SEQ ID NO: 72; and a CDR3 domain comprising the amino acid sequence as set forth in SEQ ID NO: 73.

In some embodiments, the method further comprises measuring the amount of vedolizumab in the sample.

In another aspect, provided herein is an anti-vedolizumab antibody, or an antigen-binding fragment thereof, comprising (i) a heavy chain variable region comprising the amino acid sequence as set forth in SEQ ID NO: 7, and a light chain variable region comprising the amino acid sequence as set forth in SEQ ID NO: 8;

(ii) a heavy chain variable region comprising the amino acid sequence as set forth in SEQ ID NO: 17, and a light chain variable region comprising the amino acid sequence as set forth in SEQ ID NO: 18;

(iii) a heavy chain variable region comprising the amino acid sequence as set forth in SEQ ID NO: 27, and a light chain variable region comprising the amino acid sequence as set forth in SEQ ID NO: 28;

(iv) a heavy chain variable region comprising the amino acid sequence as set forth in SEQ ID NO: 34, and a light chain variable region comprising the amino acid sequence as set forth in SEQ ID NO: 35;

(v) a heavy chain variable region comprising the amino acid sequence as set forth in SEQ ID NO: 44, and a light chain variable region comprising the amino acid sequence as set forth in SEQ ID NO: 45;

(vi) a heavy chain variable region comprising the amino acid sequence as set forth in SEQ ID NO: 54, and a light chain variable region comprising the amino acid sequence as set forth in SEQ ID NO: 55;

(vii) a heavy chain variable region comprising the amino acid sequence as set forth in SEQ ID NO: 59, and a light chain variable region comprising the amino acid sequence as set forth in SEQ ID NO: 60;

(viii) a heavy chain variable region comprising the amino acid sequence as set forth in SEQ ID NO: 64, and a light chain variable region comprising the amino acid sequence as set forth in SEQ ID NO: 65; or (ix) a heavy chain variable region comprising the amino acid sequence as set forth in SEQ ID NO: 74, and a light chain variable region comprising the amino acid sequence as set forth in SEQ ID NO: 75.

In another aspect, provided herein is an anti-vedolizumab antibody that binds to an epitope of an antibody provided herein (e.g., an antibody in Table 1).

In some embodiments, the anti-vedolizumab antibody, or antigen-binding fragment thereof is an IgG isotype. In some embodiments, the IgG isotype is an IgG1, IgG2A, IgG2B, IgG2C or IgG3.

In some embodiments, the anti-vedolizumab antibody, or antigen-binding fragment thereof is an scFv, a single domain antibody, or a diabody.

In some embodiments, the anti-vedolizumab antibody, or antigen-binding fragment thereof, is conjugated to an agent selected from the group consisting of an imaging agent, a therapeutic agent, a cytotoxic agent, an oligonucleotide, and an immunoadhesion molecule. In some embodiments, the agent is an imaging agent selected from the group consisting of a radiolabel, an enzyme, a fluorescent label, a luminescent label, a bioluminescent label, a magnetic label, a metal label (e.g., a heavy metal isotope), and biotin.

In some embodiments, the imaging agent is a radiolabel selected from the group consisting of: 3H, 14C, 35S, 90Y, 99Tc, 111In, 125I, 131I, 177Lu, 166Ho, and 153Sm.

In another aspect, provided herein is an isolated nucleic acid encoding the amino acid sequence of an anti-idiotypic antibody provided herein (e.g., an antibody in Table 1).

In another aspect, provided herein is a vector comprising an isolated nucleic acid provided herein.

In a further aspect, provided herein is a host cell comprising a vector provided herein.

In another aspect, provided herein is a method of detecting anti-drug antibodies (ADAs) to vedolizumab in a biological sample from a patient, the method comprising: incubating a biological sample from a human patient who was administered vedolizumab, with an anti-α4β7 antibody and a labeled anti-idiotypic antibody, or an antigen-binding fragment thereof, that binds to vedolizumab; and detecting the presence of ADAs in the biological sample by measuring the ability of the ADAs to compete with the labeled anti-idiotypic antibody, or an antigen-binding fragment thereof, for binding to the anti-α4β7 antibody, wherein the anti-α4β7 antibody comprises a heavy chain (HC) variable region comprising a HC CDR1, HC CDR2, and a HC CDR3 amino acid sequences as set forth in SEQ ID NOS: 79, 80, and 81, respectively; and comprises a light chain (LC) variable region comprising a LC CDR1, LC CDR2, and a LC CDR3 amino acid sequences as set forth in SEQ ID NOS: 83, 84, and 85, respectively.

In some embodiments, prior to incubation, cells are isolated from the biological sample and the isolated cells are incubated with the anti-α4β7 antibody and the labeled anti-idiotypic antibody, or an antigen-binding fragment thereof.

In some embodiments, detection of the anti-idiotypic antibody without competition is assessed as a positive control.

Ins some embodiments, the labeled anti-idiotypic antibody comprises a fluorescent label.

In some embodiments, flow cytometry is used to detect binding of the labeled anti-idiotypic antibody.

In some embodiments, a decrease in fluorescence intensity from the labeled anti-idiotypic antibody indicates competition with the ADAs.

In some embodiments, the anti-α4β7 antibody comprises a HC variable region as set forth in the amino acid sequence of SEQ ID NO: 78, and comprises a LC variable region as set forth in the amino acid sequence of SEQ ID NO: 82.

In some embodiments, the patient has Crohn's disease or ulcerative colitis.

In some embodiments, the biological sample is a serum sample.

In one aspect, the anti-idiotypic antibodies or antigen binding fragments thereof described herein bind the target anti-α4β7 antibody (e.g., vedolizumab) without interfering with the target antibody's ability to bind to its target, e.g., α4β7 integrin. In some embodiments, the anti-idiotypic antibodies detect the anti-α4β7 antibody or fragment thereof bound to a cell, i.e., a blood cell (e.g., a cell of lymphoid or myeloid lineage). The cell can be selected from the group consisting of a T-lymphocyte (i.e., T cell, e.g., a memory T cell or regulatory T cell), a B-lymphocyte (i.e., B cell), a natural killer (NK) cell, a monocyte, a dendritic cell, a plasma cell, and an eosinophil. In some embodiments, the immune cell is a dendritic cell. In some embodiments, the cell is a T lymphocyte. The T lymphocyte can be an effector memory cell, a regulatory cell, or a naïve T cell.

In some embodiments, the cell can be identified by detection of a marker, e.g., a phenotypic marker, such as CD3, CD4, CD6, CD11c, CD14, CD16, CD19, CD25, CD28, CD38, CD45RA, CD64, CD127, CCR7, CCR9, FoxP3, GPR15, Th17, CD161, CCR6, HLA-DR, CD1, or miR-301a, or a combination thereof.

In one aspect, the anti-idiotypic antibodies or antigen binding fragments thereof described herein detect anti-α4β7 antibodies or antigen binding fragments thereof for measuring the clearance of an anti-α4β7 antibody in a biological sample (e.g., blood sample) or other pharmacokinetic parameter. In an embodiment, the biological sample is obtained from a patient suffering from inflammatory bowel disease (IBD) and who was administered at least two doses of the anti-α4β7 antibody within the previous four months.

In another aspect, measurements of pharmacokinetic or pharmacodynamic factors using the anti-idiotypic antibodies described herein may be combined with clinical measures during early treatment to identify a patient who will respond or is responding to treatment with an anti-α4β7 antibody, such as vedolizumab. In one embodiment, the clinical measure is mucosal healing. In another embodiment, the clinical measure is deep remission. In an embodiment of mucosal healing, amount of ulceration of the digestive tract or deep remission, the method may comprise measuring an endoscopic subscore, e.g., from the Mayo score or a simple endoscopic score for Crohn's Disease (SES-CD), Magnetic Resonance Index of Activity (MaRIA) score, Patient Reported Outcomes, C-reactive protein (CRP) concentration, serum albumin concentration, and/or fecal calprotectin concentration.

In another aspect, measurements of pharmacodynamic factors using the anti-idiotypic antibodies described herein may be combined with measures of inflammation to identify a patient who will respond or is responding to treatment with an anti-α4β7 antibody, such as vedolizumab. Measures of inflammation include amounts of fecal calprotectin, amounts of C-reactive protein (CRP) and amount of albumin. In some embodiments, the method comprises measuring the fecal calprotectin concentration. In some embodiments, methods described herein comprise measuring albumin concentration. An albumin concentration greater than 3.2 g/dL further identifies the patient for continued treatment with an anti-α4β7 antibody, e.g., vedolizumab. The albumin concentration can be greater than 3.5 g/dL, greater than 4.0 g/dL, or greater than 4.7 g/dL, in the range of 3.3 to 5.0 g/dL, in the range of 3.5 to 5.0 g/dL, in the range of 3.8 to 5.0 g/dL or in the range of 4.0 to 5.0 g/dL.

In another aspect, measurements of serum concentration of an α4β7 antibody, such as vedolizumab, using the anti-idiotypic antibodies or antigen binding fragments thereof described herein may be combined with a pharmacodynamic assay for α4β7 integrin, e.g., on circulating blood cells, e.g., lymphocytes. In an embodiment, low or minimum levels of free α4β7 integrin, such as less than 10% or less than 5% of the baseline levels, may predict the effectiveness of the anti-α4β7 antibody. In an embodiment, the free α4β7 integrin may be measured by the amount of MAdCAM binding to the α4β7 integrin. In another embodiment, the free α4β7 integrin may be measured by the amount of anti-α4β7 antibody binding to the α4β7 integrin.

In another aspect, measurements of serum concentration of α4β7 antibody, such as vedolizumab, using the anti-idiotypic antibodies described herein may be combined with measuring the immune response to the anti-α4β7 antibody. In an embodiment, a low or absent immune response to anti-α4β7 antibody may predict the ability to respond or maintain a response or remission of the IBD afflicting the patient. In an embodiment, the immune response to the anti-α4β7 antibody may be measured using an anti-idiotypic antibody directed to the anti-α4β7 antibody.

In one aspect, the invention relates to therapeutic methods which further include the step of continuing or modifying therapy in a human patient, accordingly, where factors measured as described herein indicate whether there is continued benefit of the therapy.

The invention also relates to the heavy chains, light chains and antigen-binding portions of the heavy chains and light chains of the anti-idiotypic antibodies or antigen binding fragments thereof described herein. The invention also relates to fusion proteins comprising an anti-idiotypic antibody or portion thereof (e.g., heavy chain, light chain, variable region) of the invention and a non-immunoglobulin moiety. The invention also relates to immunoconjugates comprising an anti-idiotypic antibody or antigen-binding fragment of the invention and a second moiety, such as a detectable label, e.g., a radionuclide (e.g., a radioactive ion)), a metal (e.g., a heavy metal isotope), an enzyme, e.g., horseradish peroxidase or alkaline phosphatase, or an indirect labeling agent, e.g., biotin or an oligonucleotide.

The invention also relates to isolated and/or recombinant nucleic acids encoding the anti-idiotypic antibodies, antigen-binding fragments, heavy chains, light chains and portions of the heavy chains and light chains of the antibodies described herein, or fusion proteins and to expression constructs or vectors comprising same. The invention also relates to an expression construct comprising a recombinant nucleic acid molecule that encodes a heavy chain or an antigen-binding portion thereof, and to an expression construct comprising a recombinant nucleic acid molecule that encodes a light chain or an antigen-binding portion thereof. The invention also relates to a host cell that comprises a nucleic acid of the invention. The invention also relates to an isolated cell which produces a heavy chain or an antigen-binding portion thereof, and/or a light chain or an antigen-binding portion thereof.

The invention also relates to a composition comprising an anti-idiotypic antibody or antigen-binding fragment thereof, e.g., a monoclonal antibody (e.g. a heavy chain or antigen-binding portion thereof, a light chain or antigen-binding portion thereof, a chimeric antibody or antigen-binding fragment thereof), or an immuno-conjugate of an antibody described herein and a physiologically acceptable carrier.

The invention further relates to assays for use in measuring the factors described herein for identifying a patient who will respond or is responding to treatment with an anti-α4β7 antibody, such as vedolizumab. In some embodiments, the assay is a pharmacodynamic assay for antigen-bound anti-α4β7 antibody or an antigen binding fragment thereof. In an embodiment, the assay measures the number of anti-α4β7 antibody-bound cells in a biological sample (e.g., blood sample or tissue sample) of a patient. In one embodiment, an increase in the number of anti-α4β7 antibody-bound cells relative to a reference level characterizes the patient as responding to the anti-α4β7 antibody.

In some embodiments, the reference level is a level of the anti-α4β7 antibody-bound cells in an untreated subject. The untreated subject may be a healthy subject or a subject having IBD. Alternatively, the reference level may be the level of the anti-α4β7 antibody-bound cells detected in a patient prior to treatment (e.g., a baseline level). In some embodiments, the reference level is a pre-determined threshold level (e.g., as determined based on clinical studies of patient populations that are responsive and non-responsive to the anti-α4β7 antibody).

The invention also relates to kits for use in the methods and assays described herein. In one embodiment, a kit comprises an anti-idiotypic antibody or antigen binding fragment thereof with binding specificity for an anti-α4β7 antibody, such as vedolizumab, or antigen binding fragment thereof. In some embodiments, the kits or methods are useful in detecting or measuring characteristics, e.g., amounts of cell-bound anti-α4β7 antibody, presence or changes, of the hematological or immunological markers and cell dynamics in a biological sample, e.g., a sample obtained from an IBD patient, e.g., a human patient.

In another aspect, the compositions and methods of the invention provide disease, e.g., IBD, management strategies. In the foregoing aspects, the profile of the treatment result, combination of characteristics, e.g., numbers and identities of cell-bound anti-α4β7 antibody, composition or amount of markers, e.g., hematological or immunological, in a biological sample comprising lymphoid- and/or myeloid-derived cells, e.g., lymphocytes, monocytes, dendritic cells or eosinophils, or contents or products thereof, are measured. In one embodiment, the IBD is moderately to severely active ulcerative colitis. In another embodiment, the IBD is moderately to severely active Crohn's disease. In some embodiments, the patient may have had an inadequate response or lack of tolerance to a prior therapy, such as an immunomodulator or a corticosteroid or a tumor necrosis factor alpha (TNF) inhibitor. In one embodiment, the patient has had an inadequate response with, lost response to, or was intolerant to either conventional therapy or a tumor necrosis factor-alpha (TNFα) antagonist. Disease management strategy is undertaken when assay results reveal information about anti-α4β7 antibody treatment, e.g., whether the pharmacodynamic, pharmacokinetic, hematological cell profile or immunological factors indicates favorable outcome to therapy comprising the anti-α4β7 antibody, e.g., vedolizumab therapy. By measuring the factors and characterizing the treatment result, it is therefore possible to eliminate ineffective or inappropriate therapeutic agents or regimens. Thus, one can undertake a therapeutic regimen which is likely to benefit a particular patient or type of patient, e.g., whether a particular regimen should be started or avoided, continued, discontinued or altered. Such analyses can be made on a patient-by-patient basis, e.g., identifying and/or selecting for treatment an IBD patient who is demonstrating a favorable outcome upon administration of a therapeutic regimen, e.g., a therapeutic regimen comprising an anti-α4β7 antibody, such as vedolizumab or an antigen binding fragment thereof.

Additional methods include methods to identify new therapeutic combinations. Such methods include methods to identify an agent as useful in combination with an anti-α4β7 antibody, such as vedolizumab or an antigen binding fragment thereof, for treating an IBD, e.g., ulcerative colitis, pouchitis, or Crohn's disease (e.g., moderately to severely active disease, or disease wherein TNFα-inhibitor therapy failed), based on treatment result, e.g., the characteristics of the patient undergoing treatment with an anti-α4β7 antibody or antigen binding fragment thereof. The treatment result, e.g., the characteristics of the patient, e.g., a profile compiled from at least one of a pharmacodynamic factor, a pharmacokinetic factor, hematological composition and/or an immunological characteristic in a biological sample, e.g., peripheral blood sample, obtained from the patient can lead to confirmation or modification of treatment options. Treatment of IBD with vedolizumab includes an initial dose of 300 mg administered intravenously, followed by two 300 mg doses of the antibody 2 weeks and 6 weeks after the initial dose. Following the dose at 6 weeks, 300 mg of vedolizumab is intravenously administered every 8 weeks to the patient. Alternatively, a patient receives an intravenous dose of 300 mg of vedolizumab each at least at weeks 0 and 2 of treatment, and then subcutaneously at a dose of 108 mg every two weeks. If the patient is not responding to the therapeutic regimen, then treatment can be modified to increase dose of the anti-α4β7 antibody or antigen binding fragment thereof, such as to 450 mg or 600 mg, or to increase dosing frequency, such as administration every 8 weeks to every 4 weeks intravenously or once per week subcutaneously.

Further, results of studies on the hematological composition can characterize redundant trafficking of the cells expressing additional trafficking mediators, such as another target on the cells measured in the biological sample, e.g., another integrin, such as α4β1 integrin, αLβ2, αEβ7, α6β1, or α6β4, or cell signaling molecule or inflammatory mediator. Accordingly, an agent which in combination with an anti-α4β7 antibody, such as vedolizumab or an antigen binding fragment thereof, binds to or inhibits the activity of the other mediator, such as an IL-23 inhibitor, a JAK inhibitor, a checkpoint inhibitor, or a TNFα inhibitor would be a candidate agent for the combination to address disease severity or redundant trafficking.

The present invention is also directed to methods of treating an IBD patient, e.g., a human patient, with a therapeutic regimen, e.g., with an anti-α4β7 antibody, such as a vedolizumab or an antigen binding fragment thereof therapy regimen (e.g., alone, or in combination with an additional agent such as a biologic agent, e.g., a TNFα inhibitor, an IL-23 inhibitor, a checkpoint inhibitor, or a CD28 antagonist; or a small molecule, e.g., a JAK inhibitor, an antibiotic or an antimetabolite), which includes the step of selecting the patient for treatment with an anti-α4β7 antibody or antigen binding fragment thereof. The treatment result, e.g., the characteristics of the patient, e.g., a profile compiled from at least one of a pharmacodynamic factor, a pharmacokinetic factor, hematological composition and/or an immunological characteristic in a biological sample, e.g., peripheral blood sample, obtained from the patient, indicates that the patient is expected to have a favorable outcome, e.g., is responding to the therapeutic regimen. The method comprises continuing to treat the patient with the therapy, e.g., an anti-α4β7 antibody therapy, such as an anti-α4β7 antibody or an antigen binding fragment thereof therapy when the result indicates a favorable outcome. In some embodiments, a favorable outcome in the methods includes the use of vedolizumab or a pharmaceutically acceptable salt thereof for treating an IBD patient characterized as having blood cells, e.g., lymphoid- or myeloid-derived cells bound to the anti-α4β7 antibody, and wherein the blood cell is selected from the group consisting of T effector memory lymphocyte, B lymphocyte, a dendritic cell and an eosinophil. In some embodiments, a favorable outcome in the methods further includes the use of an IL-23 inhibitor or a JAK inhibitor.

Other features and advantages of the invention will be apparent from the following detailed description, drawings and from the claims.

BRIEF DESCRIPTION OF DRAWINGS

As shown in FIG. 1, in the second round of subcloning performed to identify stable subclones for 3 hybridomas, 'Clones A' and 'B' were identified for 2 J3; a 'B' clone was identified for 2 I8 and stable subclones were not be identified for 3 F3. The 'A' clones were expanded to generate saturated supernatants (100 mL) and were confirmed and isotyped by ELISA prior to purification.

As shown in FIG. 2, one mAb (6-D8-A) showed non-specific binding to hIgG1 but all other unlabeled mAbs had clean anti-idiotype profile in this screen.

FIGS. 3A-3C show data from FACS screening. Tertiary FACS screens were performed using non clonal saturated supernatants of 95 hits for binding to vedolizumab/HuT78 cells. FIG. 3A shows at least 10 hybridomas that bind specifically to vedolizumab/HUT78 cells and were identified by FACS. FIG. 3A also shows the counter screen by FACS against natalizumab/HuT78 cells. FIG. 3B shows the tertiary FACS screen overlay of the top 15 hits from the experiment with the results shown in FIG. 3A. FIG. 3C shows the focused view of the top 15 hits.

FIG. 4A shows the concentration values of vedolizumab, natalizumab and the F(ab')2 anti-idiotypic antibody, respectively, in the HuT78 cell line. FIG. 4B shows the EC50 values of vedolizumab, natalizumab and the F(ab')2 anti-idiotypic antibody, respectively, in the HuT78 cell line.

FIGS. 5A-5D graphically depict the results of a study analyzing detection of vedolizumab on T cells (i.e., CD3+ cells; FIG. 5A), B cells (i.e., CD19+ cells; FIG. 5B), Monocytes (i.e., CD64+ cells; FIG. 5C), and other cells (i.e., CD3–/19–/64– cells; FIG. 5D) by anti-vedolizumab idiotypic antibodies identified in Examples 1 and 2. Detection of vedolizumab by vedolizumab-AF647 primary staining of cells was assessed as a positive control ("Vedo-1" or "Vedo-2"; dashed line). The results are presented as the detected percentage of cells bound to vedolizumab (y-axis) for each of the indicated clones (x-axis). Clones J3, D8, 110, and N17 were screened the same day. Clones C13, D5, and J24 were screened on a later day with the J3 clone repeated on the later day ("J3-2").

FIGS. 7A-7E graphically depict the results of a study analyzing detection of vedolizumab on longitudinal PBMC samples from healthy donors by the anti-vedolizumab idiotypic antibody N17 identified in Examples 1 and 2. The anti-vedolizumab idiotypic antibody was used to assess the percentage of cells bound by vedolizumab for T cells (FIG. 7A), CD4+ T cells (FIG. 7B), CD8+ T cells (FIG. 7C), B cells (FIG. 7D), and monocytes/dendritic cells (FIG. 7E) at the indicated time-points. Detection of vedolizumab by vedolizumab-AF647 primary staining of cells was assessed as a positive control (Vedo-AF647). The results are presented as the detected percentage of cells bound to vedolizumab (y-axis) for each of the indicated cell types and time-points post-treatment (x-axis). "Sec" refers to a secondary control where the secondary antibody was added but not N17 (i.e., a negative control). "Pre" refers to a patient sample that was obtained before vedolizumab injection into the patient but in which both the N17 and secondary-AF647 antibody were added (i.e., an additional negative control).

DETAILED DESCRIPTION OF THE INVENTION

Figure 1:
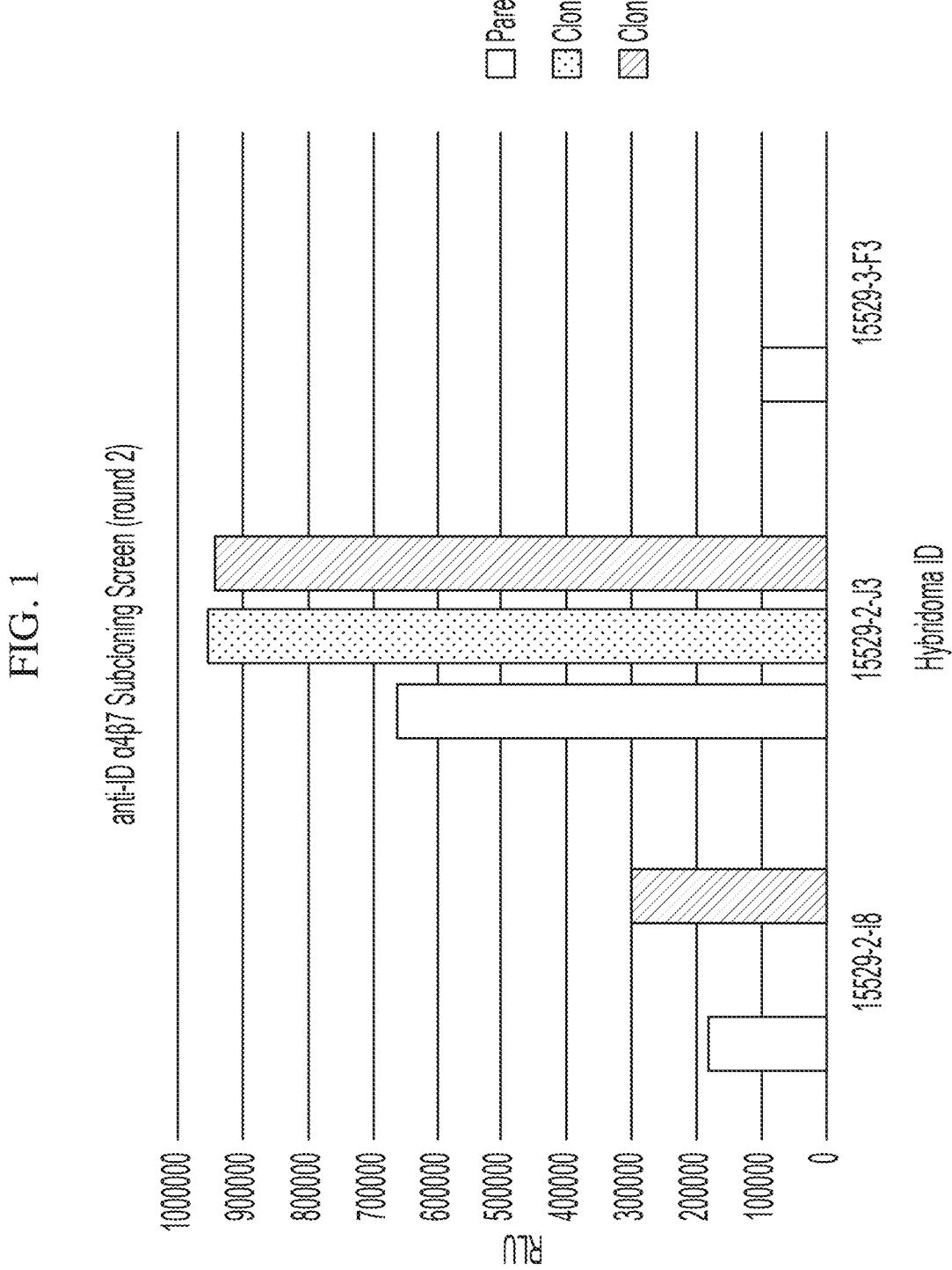
FIG. 1 shows ELISA screening data of the hybridomas selected for subcloning to identify monoclonal antibodies against vedolizumab. In the first round of clone screen, 2 independent clones ('Clone A' and 'Clone B') were identified for 7 of 10 hybridomas and a single clone ('Clone A') was identified for 1 hybridoma.

The invention relates to anti-idiotypic antibodies raised against anti-α4β7 antibodies, compositions and kits for the antibodies, methods for identifying patients who can respond to therapy comprising an anti-α4β7 antibody, methods for identifying a patient for continued treatment with the antibody, and methods and kits for treatment of inflammatory bowel disease (IBD) in patients, e.g., human patients, who are characterized by marker analysis for favorable (responsive) outcome to treatment. An α4β7 antibody may bind either chain of the heterodimeric-α4β7 integrin or a complex requiring both chains of the α4β7 integrin.

After the anti-α4β7 antibody or antigen binding fragment thereof binds its α4β7 integrin target on blood cells, it blocks trafficking of the blood cells to the secondary and tertiary lymphoid sites. A consequent rise of these cells in the peripheral blood indicates the effect of the binding in the diseased tissue. Measuring the anti-α4β7 antibody or antigen binding fragment thereof bound to cells in the periphery can indicate how many cells are blocked from trafficking to the diseased tissue, such as the colon or intestine. The cell types in the periphery can be quantified, e.g., by measuring the number of cells binding to the anti-α4β7 antibody or antigen binding fragment, and optionally, further characterized, such as by detecting and measuring additional markers, such as hematological markers, to generate (or compile) a profile of the cells bound to the antibody.

An α4β7 antibody which binds a complex comprising both chains of the α4β7 integrin, such as an anti-α4β7-integrin antibody (e.g., MLN0002), is described in PCT publications nos. WO98/06248 and WO07/61679, and vedolizumab Chemical Abstract Service (CAS, American Chemical Society) Registry number 943609-66-3. Vedolizumab, a humanized monoclonal antibody that binds specifically to the α4β7 integrin, is indicated for the treatment of patients with moderately to severely active ulcerative colitis (UC) and Crohn's disease (CD). Vedolizumab has a unique gut-selective mechanism of action that differs from that of other currently marketed biologic agents for the treatment for inflammatory bowel disease (IBD), including natalizumab and tumor necrosis factor-α (TNFα) antagonists. By binding to cell surface-expressed $\alpha_4\beta_7$ integrin, vedolizumab blocks the interaction of a subset of memory gut-homing T lymphocytes with mucosal addressin cell adhesion molecule-1 (MAdCAM-1) expressed on endothelial cells. Treatment methods using anti-$\alpha4\beta7$ integrin antibodies are described in publication nos. U.S. 2005/0095238, U.S. 2007/0122404, WO2012/151248 and WO 2012/151247. The pharmacokinetics of treatment using anti-$\alpha4\beta7$ antibodies also are described in publication nos. U.S. 2020/0155673 and U.S. 2019/0255172.

Previous methods (see e.g., Wyant et al., *Cytometry Part B Clin Cytom* 90: 168-76 (2016)) to try and assess the pharmacodynamic properties of an anti-$\alpha4\beta7$ antibody, such as vedolizumab, relied on receptor occupancy assays. These techniques provide limited information on the specific cell subsets impacted by vedolizumab as they have a negative readout i.e., the absence of signal due to blockade of $\alpha4\beta7$ integrin with vedolizumab. The anti-idiotypic e.g., anti-vedolizumab antibodies, provided herein, in contrast will allow quantitation of the levels of anti-$\alpha4\beta7$ antibody, e.g., vedolizumab, bound on specific cell subsets and will provide greater information on the cellular and molecular factors contributing to anti-$\alpha4\beta7$ antibody, e.g., vedolizumab, responses. Therefore, a better understanding of the result of treatment, e.g., the profile of factors detected and measured during anti-$\alpha4\beta7$ antibody treatment, may result in optimization of drug regimens. Anti-idiotypic antibodies directed against anti-$\alpha4\beta7$ antibodies described herein are provided to detect the anti-$\alpha4\beta7$ antibodies and be used in assays to measure pharmacodynamics and pharmacokinetics of the antibodies in IBD patients being treated with the antibodies. Having superior reagents to perform such assays early in the treatment program gives confidence in the results and the ability to identify patients who are responding to the treatment.

IBD patients who have severe disease or have failed treatment by other agents, such as TNF$\alpha$ inhibitors, may not completely respond to treatment with an anti-$\alpha4\beta7$ antibody, such as vedolizumab. The presence of neutralizing antibodies to the anti-$\alpha4\beta7$ antibody, such as vedolizumab, as well as low drug levels may underlie non-response but this may also be due to differences in the capacity of the anti-$\alpha4\beta7$ antibody, e.g., vedolizumab, to bind cells from these patients. This phenomenon may stem from differences in immune cell composition in these patients, levels of expression of $\alpha4\beta7$ integrin on immune cells and their internalization and recycling rate, or expression of additional trafficking mediators, such as integrins, that may function to bypass the inhibition of gut selective trafficking by the anti-$\alpha4\beta7$ antibody, such as vedolizumab. A profile of the anti-$\alpha4\beta7$ antibody treatment result, e.g., as generated by use of the anti-idiotypic antibodies or antigen binding fragments thereof described herein, further can be combined with detecting and measuring additional indicators, such as hematological markers to further characterize the immune cells. Together with the profile of bound anti-$\alpha4\beta7$ antibody, results indicating redundant trafficking, optionally further combined with results of measuring immunological markers of disease severity, can permit quick adjustment of treatment for nonresponders of the anti-$\alpha4\beta7$ antibody treatment.

I. Definitions

In order that the present invention may be more readily understood, certain terms are first defined. Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise.

The cell surface molecule, "$\alpha4\beta7$ integrin," or "$\alpha4\beta7$" (used interchangeably throughout) is a heterodimer of an $\alpha4$ chain (CD49D, ITGA4) and a $\beta7$ chain (ITGB7). Human $\alpha4$-integrin and $\beta7$-integrin genes GenBank (National Center for Biotechnology Information, Bethesda, Md.) RefSeq Accession numbers NM_000885 and NM_000889, respectively) are expressed by B and T lymphocytes, particularly memory CD4+ lymphocytes. Typical of many integrins, $\alpha4\beta7$ can exist in either a resting or activated state. Ligands for $\alpha4\beta7$ include vascular cell adhesion molecule (VCAM), fibronectin and mucosal addressin (MAdCAM (e.g., MAd-CAM-1)). An antibody that binds specifically to $\alpha4\beta7$ integrin is referred to herein as an "anti-$\alpha4\beta7$ antibody".

As used herein, an antibody, or antigen-binding fragment thereof, that has "binding specificity for the $\alpha4\beta7$ complex" binds to $\alpha4\beta7$, but not to $\alpha4\beta1$ or $\alpha_E\beta7$. Vedolizumab is an example of an antibody that has binding specificity for the $\alpha4\beta7$ complex.

The term "about" denotes that the thereafter following value is no exact value but is the center point of a range that is +1-5% of the value of the value. If the value is a relative value given in percentages the term "about" also denotes that the thereafter following value is no exact value but is the center point of a range that is +1-5% of the value, whereby the upper limit of the range cannot exceed a value of 100%.

The term "antibody" as used herein, is intended to refer to an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments, the antibody has a fragment crystallizable (Fc) region. In certain embodiments, the antibody is an IgG1 isotype and has a kappa light chain.

A "CDR" or "complementarity determining region" is a region of hypervariability interspersed within regions that are more conserved, termed "framework regions" (FR).

As used herein, the term "antigen binding fragment" or "antigen binding portion" of an antibody refers to Fab, Fab', F(ab')2, and Fv fragments, single chain antibodies, functional heavy chain antibodies (nanobodies), as well as any portion of an antibody having specificity toward at least one desired epitope, that competes with the intact antibody for specific binding (e.g., an isolated portion of a complementarity determining or variable region having sufficient framework sequences so as to bind specifically to an epitope). Antigen binding fragments can be produced by recombinant techniques, or by enzymatic or chemical cleavage of an antibody. For instance, papain or pepsin cleavage can be used to generate Fab or F(ab')2 fragments, respectively. Antibodies can also be produced in a variety of truncated forms using antibody genes in which one or more stop codons have been introduced upstream of the natural stop site. For example, a recombinant construct encoding the heavy chain of an F(ab')2 fragment can be designed to include DNA sequences encoding the CHI domain and hinge region of the heavy chain.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (i.e., epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen binding sequences derived from a non-human primate (e.g., Old World Monkey, Ape, etc.) and human constant region sequences.

"Antigen binding fragments" of a humanized anti-α4β7 antibody comprise at least the variable regions of the heavy and/or light chains of an anti-α4β7 antibody (e.g., SEQ ID NOs: 78 and 82). Examples of such antigen binding fragments include Fab fragments, Fab' fragments, scFv and F(ab')2 fragments of a humanized immunoglobulin known in the art. In one aspect, antigen binding fragments of an anti-α4β7 antibody inhibit binding of α4β7 integrin to one or more of its ligands (e.g., the mucosal addressin MAdCAM (e.g., MAdCAM-1), fibronectin).

Papain digestion of antibodies produces two identical antigen binding fragments, called "Fab" fragments, each with a single antigen binding site, and a residual "Fc" fragment, whose name reflects its ability to crystallize readily. Pepsin treatment yields an F(ab')2 fragment that has two antigen binding sites and is still capable of cross-linking antigen.

"Fv" is an antibody fragment which consists of a dimer of one heavy chain variable domain and one light chain variable domain in non-covalent association.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. In one aspect, the Fv polypeptide further comprises a polypeptide linker between the VH and VL domains which enables the scFv to form the desired structure for antigen binding. For a review of scFv see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen binding sites. Diabodies are described more fully in, for example, EP 404,097; WO 93/11161; and Hollinger et al., *Proc. Natl. Acad. Sci. USA*, 90:6444-6448 (1993).

An "amino acid sequence variant" antibody herein is an antibody with an amino acid sequence which differs from a main species antibody. Ordinarily, amino acid sequence variants will possess at least about 70%, at least about 80%, at least about 85%, at least about 90%, or at least about 95% homology with the main species antibody. The amino acid sequence variants possess substitutions, deletions, and/or additions of naturally occurring amino acids at certain positions within or adjacent to the amino acid sequence of the main species antibody, but retain antigen binding activity. Variations in sequence of the constant regions of the antibody will have less effect on the antigen binding activity than variations in the variable regions. In the variable regions, amino acid sequence variants will be at least about 90% homologous, at least about 95% homologous, at least about 97% homologous, at least about 98% homologous, or at least about 99% homologous with the main species antibody.

"Homology" is defined as the percentage of residues in the amino acid sequence variant that are identical after aligning the sequences and introducing gaps, if necessary, to achieve the maximum percent homology. Methods and computer programs for the alignment are well known in the art.

Depending on the amino acid sequence of the constant domain of their heavy chains, antibodies can be assigned to different "classes". There are five major classes of antibodies: IgA, IgD, IgE, IgG, and IgM, and several of these may be further divided into "subclasses" (isotypes), e.g., IgG1, IgG2, IgG3, IgG4, IgA, and IgA2 for humans and IgG1, IgG2A, IgG2B, IgG2C and IgG3 for mice. The heavy-chain constant domains that correspond to the different classes of antibodies are called α, δ, ε, γ, and μ, respectively. The subunit structures and three-dimensional configurations of different classes of immunoglobulins are well known.

The "light chains" of antibodies from any vertebrate species can be assigned to one of two clearly distinct types, called kappa (κ) and lambda (λ), based on the amino acid sequences of their constant domains.

The term "hypervariable region" when used herein refers to the amino acid residues of an antibody which are responsible for antigen binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest,* 5th Ed. Public Health Service, National Institutes of Health, Bethesda, Md. (1991)) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined. The hypervariable region or the CDRs thereof can be transferred from one antibody chain to another or to another protein to confer antigen binding specificity to the resulting (composite) antibody or binding protein.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues, e.g., CDR residues, from a hypervariable region of the recipient are replaced by residues, e.g., CDR residues, from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues, e.g., to further refine antibody performance. The humanized antibody optionally also will comprise at least a portion of an immunoglobulin constant region (Fc), typically that of a human immunoglobulin. For further details, see Jones et al., *Nature* 321: 522-525 (1986); Riechmann et al., *Nature* 332:323-329 (1988); and Presta, *Curr. Op. Struct. Biol.* 2:593-596 (1992).

An "affinity matured" antibody is one with one or more alterations in one or more hypervariable regions thereof which result in an improved affinity of the antibody for antigen, compared to a parent antibody which does not possess those alteration(s). In one aspect, affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.*

155:1994-2004 (1995); Jackson et al., *J. Immunol.* 154(7): 3310-9 (1995); and Hawkins et al., *J. Mol. Biol.* 226:889-896 (1992).

A "biological sample" may be any sample from a biological system, tissues or body fluids, such as an inflammatory exudate, blood, serum, plasma, bone marrow aspirate, saliva, mucosal secretions, urine, bowel fluid or feces. A biological sample may contain cells, e.g., lymphocytes, or be cell-free, optionally by manipulating the sample to remove cells.

An "immune cell" refers to cells that are of hematopoietic origin and that play a role in immune response. Immune cells include lymphocytes, such as B cells and T cells; natural killer cells; dendritic cells, and myeloid cells, such as monocytes, macrophages, eosinophils, mast cells, basophils, and granulocytes.

"Treatment" refers to both therapeutic treatment and prophylactic or preventative measures. Those in need of treatment include those already with the disease as well as those in which the disease or its recurrence is to be prevented. Hence, the patient to be treated herein may have been diagnosed as having the disease or may be predisposed or susceptible to the disease.

The terms "patient" and "subject" are used interchangeably herein. Preferably a patient is a human.

"Baseline" as used herein describes a value of a parameter which is measured prior to the initial dose of a therapeutic agent or initiation of a treatment. It can refer to a measurement on a sample obtained the same day, the day before, during the week before initial treatment, i.e., at a time period before the first dose when little change is expected until after the first dose and values of the measurement obtained after the first dose can be compared to this baseline value to represent the change caused by the dose.

As used herein, the term "vedolizumab profile" refers to a profile of a human subject that describes the cell types and/or levels of vedolizumab bound to cells following administration of vedolizumab to the subject. A subject's vedolizumab profile is determined, for example, by analyzing a biological sample from the subject for the presence of vedolizumab bound to cells in the sample, e.g., using an anti-idiotypic antibody, an antigen binding fragment thereof and/or an assay described herein.

An "anti-idiotypic" antibody is an antibody which recognizes unique determinants, e.g., CDRs or at least a portion of a hypervariable region, generally associated with the antigen-binding site, of an antibody. An anti-vedolizumab antibody is an anti-idiotypic antibody that specifically binds to vedolizumab. An anti-idiotypic antibody can be neutralizing or not neutralizing. In one embodiment, an anti-idiotypic anti-α4β7 antibody for use in the assays described herein can be specific for, and thus bind to, a variable region of the heavy and/or light chain of anti-α4β7 antibody, e.g., heavy chain variable region (SEQ ID NO: 78) and/or light chain variable region (SEQ ID NO: 82) of vedolizumab.

As used herein, the term "anti-drug antibody" or "ADA" is used in reference to an antibody that results from a patient's immune response to a biotherapeutic agent, such as an antibody, e.g., vedolizumab, following administration of the biotherapeutic agent to the patient. As used herein, the term refers to anti-vedolizumab antibodies generated by a human subject who was administered vedolizumab. In some embodiments the anti-drug antibody is a neutralizing antibody, i.e., it binds, e.g., sterically, to the antigen-binding site and prevents the binding of the biotherapeutic agent, e.g., vedolizumab, to its target, e.g., α4β7 integrin.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into a viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids.

An "isolated" antibody is one which has been identified and separated and/or recovered from a component of its natural environment. In some embodiments, the antibody is isolated from conditioned culture medium from a cell that expresses the antibody. In certain embodiments, the antibody will be purified (1) to greater than 95% by weight of protein as determined by the Lowry method, and alternatively, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

II. Anti-Idiotypic Antibodies that Bind to Anti-α4β7 Antibody Vedolizumab

In one aspect, this invention pertains to anti-idiotypic antibodies, or antigen binding fragments thereof, that bind to anti-α4β7 antibodies (e.g., anti-vedolizumab antibodies), or antigen-binding portions thereof that bind α4β7 integrin. In a further aspect, the anti-idiotypic antibodies or antigen binding fragments thereof described herein bind the target anti-α4β7 antibody (e.g., vedolizumab) without interfering with the target antibody's ability to bind to its target, e.g., α4β7 integrin. Amino acid sequences for the anti-idiotypic antibodies of the invention are provided in Table 1 along with corresponding nucleotide coding sequences. Various aspects of the invention relate to anti-idiotypic (Id) antibody, constructs, conjugates thereof, as well as nucleic acids, recombinant expression vectors, and host cells for making such anti-idiotypic antibodies. Methods of using anti-idiotypic antibodies to detect anti-α4β7 antibodies, or antigen-binding portions thereof, either in vitro or in vivo, are also encompassed by the invention, as outlined in Section III.

TABLE 1

| ANTIBODY NAME | DESCRIPTION | SEQUENCE | SEQ ID NO: |
|---|---|---|---|
| B4 | HC CDR1 (amino acid) | GFSLSSYE | 1 |
| B4 | HC CDR2 (amino acid) | IWTGGST | 2 |
| B4 | HC CDR3 (amino acid) | VGAPYDYGGFAY | 3 |
| B4 | LC CDR1 (amino acid) | KSLLHNDGITY | 4 |
| B4 | LC CDR2 (amino acid) | RMS | 5 |
| B4 | LC CDR3 (amino acid) | AQMLEFPYT | 6 |
| B4 | Heavy chain variable region (HCVR) (amino acid) | QVQLKESGPGLAAPSQNLFIT CTVSGFSLSSYEIHWFRQPPG KGLEWLGVIWTGGSTDYNSA LISRLNISKDNSKSLAFLNVNS LQTDDTAIYYCVGAPYDYGG FAYWGQGTLVTVSA | 7 |
| B4 | Light chain (LC) variable region (amino acid) | DIVMTQAAFSNPVTLGTSASI SCRSSKSLLHNDGITYLYWYL QRPGQSPQLLLFRMSNLASG VPDRFSGSGSGTDFTLRISRV EAEDVGVYYCAQMLEFPYTF GSGTKLEIK | 8 |
| B4 | Heavy chain variable region (nucleic acid) | CAGGTGCAGCTGAAGGAGT CAGGACCTGGCCTGGCGGC GCCCTCACAGAACCTGTTCA TCACATGTACCGTCTCAGGA TTCTCATTAAGCAGCTATGA AATACACTGGTTTCGCCAGC CTCCAGGAAAGGGTCTGGA GTGGCTGGGAGTGATATGG ACTGGTGGAAGTACAGATT ATAATTCAGCTCTCATATCC AGACTGAACATAAGTAAAG ACAACTCCAAGAGCCTAGCT | 9 |

TABLE 1-continued

| ANTIBODY NAME | DESCRIPTION | SEQUENCE | SEQ ID NO: |
|---|---|---|---|
| | | TTCTTAAATGTGAATAGTCT GCAAACTGATGACACAGCC ATATATTACTGTGTAGGAGC CCCCTATGATTACGGGGGGT TTGCTTATTGGGGCCAAGGG ACTCTGGTCACTGTCTCTGC A | |
| B4 | Light chain variable region (nucleic acid) | GATATTGTGATGACGCAGGC TGCATTCTCCAATCCAGTCA CTCTTGGAACGTCAGCTTCC ATCTCCTGCAGGTCTAGTAA GAGTCTCCTACATAATGATG GCATCACTTATTTGTATTGG TATCTGCAGAGGCCAGGCC AGTCTCCTCAGCTCCTGCTT TTTCGGATGTCCAACCTTGC CTCAGGAGTCCCAGACAGG TTCAGTGGCAGTGGGTCAGG AACTGATTTCACACTGAGAA TCAGCAGAGTAGAGGCTGA GGATGTGGGTGTTTATTACT GTGCTCAAATGCTAGAATTC CCGTATACGTTCGGATCGGG GACCAAGCTGGAAATAAAA | 10 |
| I8 | HC CDR1 (amino acid) | GYTFTSYN | 11 |
| I8 | HC CDR2 (amino acid) | IYPGNGDT | 12 |
| I8 | HC CDR3 (amino acid) | ARGWFHWYFDV | 13 |
| I8 | LC CDR1 (amino acid) | SSISSNY | 14 |
| I8 | LC CDR2 (amino acid) | RTS | 15 |
| I8 | LC CDR3 (amino acid) | QQGSTIPLT | 16 |
| I8 | Heavy chain (HC) variable region (amino acid) | QAYLQQSGAELVRPGASVKM SCKASGYTFTSYNMHWVKQ TPRQGLEWIGAIYPGNGDTSY NQKFKGKATLTVDKSSSTAY MQLSSLTSEDSAVYFCARGW FHWYFDVWGTGTTVTVSS | 17 |
| I8 | Light chain (LC) variable region (amino acid) | EIVLTQSPTAMAASPGEKITIT CSASSSISSNYLHWYLQKPGF SPKLLIYRTSNLASGVPARFS GSGSGTSYSLTIGTMEAEDVA TYYCQQGSTIPLTFGAGTRLE LK | 18 |
| I8 | Heavy chain variable region (nucleic acid) | CAGGCTTATCTACAGCAGTC TGGGGCTGAGCTGGTGAGG CCTGGGGCCTCAGTGAAGAT GTCCTGCAAGGCTTCTGGCT ACACATTTACCAGTTACAAT ATGCACTGGGTAAAGCAGA CACCTAGACAGGGCCTGGA ATGGATTGGAGCTATTTATC CAGGAAATGGTGATACTTCC TACAATCAGAAGTTCAAGG GCAAGGCCACACTGACTGT AGACAAATCCTCCAGCACA GCCTACATGCAGCTCAGCAG CCTGACATCTGAAGACTCTG CGGTCTATTTCTGTGCAAGA GGATGGTTTCACTGGTACTT CGATGTCTGGGGCACAGGG ACCACGGTCACCGTCTCCTC A | 19 |
| I8 | Light chain variable region (nucleic acid) | GAAATTGTGCTCACCCAGTC TCCAACCGCCATGGCTGCAT CTCCCGGGGAGAAGATCAC TATCACCTGCAGTGCCAGCT | 20 |

TABLE 1-continued

| ANTIBODY NAME | DESCRIPTION | SEQUENCE | SEQ ID NO: |
|---|---|---|---|
| | | CAAGTATAAGTTCCAATTAC TTGCATTGGTATCTGCAGAA GCCAGGATTCTCCCCTAAAC TCTTGATTTATAGGACATCC AATCTGGCTTCTGGAGTCCC AGCTCGCTTCAGTGGCAGTG GGTCTGGGACCTCTTACTCT CTCACAATTGGCACCATGGA GGCTGAAGATGTTGCCACTT ACTACTGCCAGCAGGGTAGT ACTATACCGCTCACGTTCGG TGCTGGGACCAGGCTGGAG CTGAAA | |
| J3 | HC CDR1 (amino acid) | GFSLTNYG | 21 |
| J3 | HC CDR2 (amino acid) | IWSGGST | 22 |
| J3 | HC CDR3 (amino acid) | ARIGGYGTTYEDGMDY | 23 |
| J3 | LC CDR1 (amino acid) | ESVDNFGISF | 24 |
| J3 | LC CDR2 (amino acid) | RAS | 25 |
| J3 | LC CDR3 (amino acid) | QQSNKDPLT | 26 |
| J3 | Heavy chain (HC) variable region (amino acid) | QVQLKQSGPGLVQPSQSLSIT CTVSGFSLTNYGVHWVRQSP GKGLEWLGVIWSGGSTDYNA AVISRLTISKDNSKSQVFFKM NSLQADDTAIYYCARIGGYG TTYEDGMDYWGQGTSVTVS S | 27 |
| J3 | Light chain (LC) variable region (amino acid) | DIVLTQSPASLAVSLGQRATIS CRASESVDNFGISFMHWYQQ KSGQPPKLLIYRASNLESGIPA RFSGSGSRTDFTLTINPVETDD VATYYCQQSNKDPLTFGAGT KLELK | 28 |
| J3 | Heavy chain variable region (nucleic acid) | CAGGTGCAGCTGAAGCAGT CAGGACCTGGCCTAGTGCA GCCCTCACAGAGCCTGTCCA TCACCTGCACAGTCTCTGGT TTCTCATTAACTAACTATGG TGTACACTGGGTTCGCCAGT CTCCAGGAAAGGGTCTGGA GTGGCTGGGAGTGATATGG AGTGGTGGAAGCACAGACT ATAATGCAGCTGTCATATCC AGACTGACCATCAGCAAGG ACAATTCCAAGAGCCAAGTT TTCTTTAAAATGAACAGTCT GCAAGCTGATGACACAGCC ATTTATTACTGTGCCAGAAT AGGGGGCTACGGTACTACCT ACGAGGATGGTATGGACTA CTGGGGTCAAGGAACCTCA GTCACCGTCTCCTCA | 29 |
| J3 | Light chain variable region (nucleic acid) | GACATTGTGCTGACCCAATC TCCAGCTTCTTTGGCTGTGT CTCTAGGGCAGAGGGCCAC CATCTCCTGCAGAGCCAGCG AAAGTGTTGATAATTTTGGC ATTAGTTTTATGCACTGGTA CCAGCAGAAATCAGGACAG CCACCCAAACTCCTCATCTA TCGTGCATCCAACCTAGAAT CTGGGATCCCTGCCAGGTTC AGTGGCAGTGGGTCTAGGA CAGACTTCACCCTCACCATT AATCCTGTGGAGACTGATGA TGTTGCAACCTATTACTGTC AGCAAAGTAATAAGGATCC | 30 |

TABLE 1-continued

| ANTIBODY NAME | DESCRIPTION | SEQUENCE | SEQ ID NO: |
|---|---|---|---|
| | | GCTCACGTTCGGTGCTGGGA CCAAGCTGGAGCTGAAA | |
| I10 | HC CDR1 (amino acid) | GFSLTSYG | 31 |
| I10 | HC CDR2 (amino acid) | IWSGGST | 22 |
| I10 | HC CDR3 (amino acid) | ARIGGYGTSYEDGMDY | 32 |
| I10 | LC CDR1 (amino acid) | ESVDNFGVSF | 33 |
| I10 | LC CDR2 (amino acid) | RAS | 25 |
| I10 | LC CDR3 (amino acid) | QQSNKDPLT | 26 |
| I10 | Heavy chain (HC) variable region (amino acid) | QVQLKQSGPGLVQPSQSLSIT CTVSGFSLTSYGVHWVRQSP GKGLEWLGVIWSGGSTDYNA AFRSRLTISKDNSKSQVFFKM NSLQADDTAIYYCARIGGYG TSYEDGMDYWGQGTSVTVSS | 34 |
| I10 | Light chain (LC) variable region (amino acid) | DIVLTQSPASLAVSLGQRATIS CRASESVDNFGVSFMHWYQ QKPGQPPKLLIYRASNLESGIP ARFSGSGSRTDFTLTINPVETD DVATYYCQQSNKDPLTFGAG TKLELK | 35 |
| I10 | Heavy chain variable region (nucleic acid) | CAGGTGCAGCTGAAGCAGT CAGGACCTGGCCTAGTGCA GCCCTCACAGAGCCTGTCCA TCACCTGCACAGTCTCTGGT TTCTCATTAACTAGCTATGG TGTACACTGGGTTCGCCAGT CTCCAGGAAAGGGTCTGGA GTGGCTGGGAGTGATATGG AGTGGTGGAAGCACAGACT ATAATGCAGCTTTCAGATCC AGACTGACCATCAGCAAGG ACAATTCCAAGAGCCAAGTT TTCTTTAAAATGAACAGTCT GCAAGCTGATGACACAGCC ATATATTACTGTGCCAGAAT AGGGGGCTACGGTACTAGC TACGAGGATGGTATGGACT ACTGGGGTCAAGGAACCTC AGTCACCGTCTCCTCA | 36 |
| I10 | Light chain variable region (nucleic acid) | GACATTGTGCTGACCCAATC TCCAGCTTCTTTGGCTGTGT CTCTAGGGCAGAGGGCCAC CATCTCCTGCAGAGCCAGCG AAAGTGTTGATAATTTTGGC GTTAGTTTTATGCACTGGTA TCAACAGAAACCAGGACAG CCACCCAAACTCCTCATCTA TCGTGCATCCAACCTAGAAT CTGGGATCCCTGCCAGGTTC AGTGGCAGTGGGTCTAGGA CAGACTTCACCCTCACCATT AATCCTGTGGAGACTGATGA TGTTGCAACCTATTACTGTC AGCAAAGTAATAAGGATCC GCTCACGTTCGGTGCTGGGA CCAAGCTGGAACTGAAA | 37 |
| D5 | HC CDR1 (amino acid) | GFTFSSYG | 38 |
| D5 | HC CDR2 (amino acid) | ISSGGSYT | 39 |
| D5 | HC CDR3 (amino acid) | ARHGTGVGFDY | 40 |
| D5 | LC CDR1 (amino acid) | QSLLDSDGKTY | 41 |
| D5 | LC CDR2 (amino acid) | LVS | 42 |

TABLE 1-continued

| ANTIBODY NAME | DESCRIPTION | SEQUENCE | SEQ ID NO: |
|---|---|---|---|
| D5 | LC CDR3 (amino acid) | WQGTHFPQT | 43 |
| D5 | Heavy chain (HC) variable region (amino acid) | EVQLVESGGDLVKPGGSLKL SCAASGFTFSSYGMSWVRQT PDKRLEWVASISSGGSYTHYP DSVKGRFTISRDNAKNTLYLQ MSSLKSEDTAMYYCARHGTG VGFDYWGQGTTLTVSS | 44 |
| D5 | Light chain (LC) variable region (amino acid) | DVVMTQTPLTLSVTIGQPASI SCKSSQSLLDSDGKTYLNWL LQRPGQSPKRLIYLVSKLDSG VPDRFTGSGSGTDFTLKISRV EAEDLGVYYCWQGTHFPQTF GGGTKLEIK | 45 |
| D5 | Heavy chain variable region (nucleic acid) | GAGGTGCAGCTGGTGGAGT CTGGGGGAGACTTAGTGAA GCCTGGAGGGTCCCTGAAA CTCTCCTGTGCTGCCTCTGG ATTCACTTTCAGTAGCTATG GCATGTCTTGGGTTCGCCAG ACTCCAGACAAGAGGCTGG AGTGGGTCGCATCCATTAGT AGTGGTGGTAGTTACACCCA CTATCCAGACAGTGTGAAG GGGCGATTCACCATCTCCAG AGACAATGCCAAGAACACC CTGTACCTGCAAATGAGCAG TCTGAAGTCTGAGGACACA GCCATGTATTACTGTGCAAG ACATGGGACTGGGGTCGGTT TTGACTACTGGGGCCAAGGC ACCACTCTCACAGTCTCCTC A | 46 |
| D5 | Light chain variable region (nucleic acid) | GATGTTGTGATGACCCAGAC TCCACTCACTTTGTCGGTTA CCATTGGACAACCAGCCTCC ATCTCTTGCAAGTCAAGTCA GAGCCTCTTAGATAGTGATG GAAAGACATATTTGAATTGG TTGTTACAGAGGCCAGGCCA GTCTCCAAAGCGCCTAATCT ATCTGGTGTCTAAACTGGAC TCTGGAGTCCCTGACAGGTT CACTGGCAGTGGATCAGGG ACAGATTTCACACTGAAAAT CAGCAGAGTGGAGGCTGAG GATTTGGGAGTTTATTATTG CTGGCAAGGTACACATTTTC CTCAGACGTTCGGTGGAGGC ACCAAGCTGGAAATCAAA | 47 |
| J24 | HC CDR1 (amino acid) | GFTFSDYG | 48 |
| J24 | HC CDR2 (amino acid) | ISNLAYSI | 49 |
| J24 | HC CDR3 (amino acid) | AREDGTTGESAMDY | 50 |
| J24 | LC CDR1 (amino acid) | KSISKY | 51 |
| J24 | LC CDR2 (amino acid) | SGS | 52 |
| J24 | LC CDR3 (amino acid) | QQHYEYPYT | 53 |
| J24 | Heavy chain (HC) variable region (amino acid) | EVKLVESGGGLVQPGGSLKL SCAASGFTFSDYGMAWVRQ APRKGPEWVGFISNLAYSIYY ADTVTGRFTISRENAKNTLYL EMSSLRSEDTAMYYCAREDG TTGESAMDYWGQGTSVTVSS | 54 |

TABLE 1-continued

| ANTIBODY NAME | DESCRIPTION | SEQUENCE | SEQ ID NO: |
|---|---|---|---|
| J24 | Light chain (LC) variable region (amino acid) | DVQITQSPSYLAASPGETITIN CRASKSISKYLAWYQEKPGK TNKLLIYSGSTLQSGIPSRFSG SGSGTDFTLTISSLEPEDFAMY YCQQHYEYPYTFGSGTKLEM K | 55 |
| J24 | Heavy chain variable region (nucleic acid) | GAGGTGAAGCTGGTGGAGT CTGGGGGAGGCTTAGTGCA GCCTGGAGGGTCCCTGAAA CTCTCCTGTGCAGCCTCTGG ATTCACTTTCAGTGACTACG GAATGGCGTGGGTTCGACA GGCTCCAAGGAAGGGGCCT GAGTGGGTAGGATTCATTAG TAATTTGGCGTATAGTATCT ACTATGCAGACACTGTGACG GGCCGATTCACCATCTCTAG AGAGAATGCCAAGAACACC CTGTACCTGGAAATGAGCA GTCTGAGGTCTGAGGACAC GGCCATGTATTACTGTGCAA GAGAGGATGGCACTACGGG AGAAAGTGCTATGGACTACT GGGGTCAAGGAACCTCAGT CACCGTCTCCTCA | 56 |
| J24 | Light chain variable region (nucleic acid) | GATGTCCAGATAACCCAGTC TCCATCTTATCTTGCTGCAT CTCCTGGAGAAACCATTACT ATTAATTGCAGGGCAAGTA AGAGCATTAGCAAATATTTA GCCTGGTATCAAGAGAAAC CTGGGAAAACTAATAAGCTT CTTATCTACTCTGGATCCAC TTTGCAATCTGGAATTCCAT CAAGGTTCAGTGGCAGTGG ATCTGGTACAGATTTCACTC TCACCATCAGTAGCCTGGAG CCTGAAGATTTTGCAATGTA TTACTGTCAACAGCACTATG AATACCCGTACACGTTCGGC TCGGGGACAAAGTTGGAAA TGAAG | 57 |
| N17 | HC CDR1 (amino acid) | GFSLTSYG | 31 |
| N17 | HC CDR2 (amino acid) | IWSGGST | 22 |
| N17 | HC CDR3 (amino acid) | ARIGGYGTTYEDAMDY | 58 |
| N17 | LC CDR1 (amino acid) | ESVDNFGISF | 24 |
| N17 | LC CDR2 (amino acid) | RAS | 25 |
| N17 | LC CDR3 (amino acid) | QQSNKDPLT | 26 |
| N17 | Heavy chain (HC) variable region (amino acid) | QVQLKQSGPGLVQPSQSLSIT CTVSGFSLTSYGVHWVRQSP GKGLEWLGVIWSGGSTDYNA AFISRLTISKDNSKTQVFFKM NSLQADDTAIYYCARIGGYG TTYEDAMDYWGQGTSVTVS S | 59 |
| N17 | Light chain (LC) variable region (amino acid) | DIALTQSPASLAVSLGQRATIS CRASESVDNFGISFMHWYQQ KPGQPPKVLIYRASKLESGIPA RFSGSGSRTDFTLTINPVETED VATYYCQQSNKDPLTFGAGT KLELK | 60 |
| N17 | Heavy chain variable region (nucleic acid) | CAGGTGCAGCTGAAGCAGT CAGGACCTGGCCTAGTGCA GCCCTCACAGAGCCTGTCCA TCACCTGCACAGTCTCTGGT | 61 |

TABLE 1-continued

| ANTIBODY NAME | DESCRIPTION | SEQUENCE | SEQ ID NO: |
|---|---|---|---|
| | | TTCTCATTAACTAGCTATGG TGTACACTGGGTTCGCCAGT CTCCAGGAAAGGGTCTGGA GTGGCTGGGAGTGATATGG AGTGGTGGAAGCACAGACT ATAATGCAGCTTTCATATCC AGACTGACCATCAGCAAGG ACAATTCCAAGACCCAAGTT TTCTTTAAAATGAACAGTCT GCAAGCTGATGACACAGCC ATATATTACTGTGCCAGAAT AGGGGGCTACGGTACTACCT ACGAGGATGCTATGGACTA CTGGGGTCAAGGAACCTCA GTCACCGTCTCCTCA | |
| N17 | Light chain variable region (nucleic acid) | GACATTGCGCTGACCCAATC TCCAGCTTCTTTGGCTGTGT CTCTAGGGCAGAGGGCCAC CATCTCCTGCAGAGCCAGCG AAAGTGTTGATAATTTTGGC ATTAGTTTTATGCACTGGTA CCAGCAGAAACCAGGACAG CCACCCAAAGTCCTCATCTA TCGTGCATCCAAGCTAGAAT CTGGGATCCCTGCCAGGTTC AGTGGCAGTGGGTCTAGGA CAGACTTCACCCTCACCATT AATCCTGTGGAGACTGAAG ATGTTGCAACCTATTACTGT CAGCAAAGTAATAAGGATC CTCTCACGTTCGGTGCTGGG ACCAAGCTGGAGCTGAAA | 62 |
| C13 | HC CDR1 (amino acid) | GFSLTSYG | 63 |
| C13 | HC CDR2 (amino acid) | IWSGGST | 22 |
| C13 | HC CDR3 (amino acid) | ARIGGYGTTYEDAMDY | 58 |
| C13 | LC CDR1 (amino acid) | ESVDNFGISF | 24 |
| C13 | LC CDR1 (amino acid) | RAS | 25 |
| C13 | LC CDR1 (amino acid) | QQSNKDPLT | 26 |
| C13 | Heavy chain (HC) variable region (amino acid) | QVQLKQSGPGLVQPSQSLSVT CTVSGFSLTSYGVHWVRQSP GKGLEWLGVIWSGGSTDYNA AFISRLTISKDNSKSQVFFKM NSLQADDTAIYYCARIGGYG TTYEDAMDYWGQGTSVTVS S | 64 |
| C13 | Light chain (LC) variable region (amino acid) | DIVLTQSPASLSVSLGQRATIS CRASESVDNFGISFMFWYQQ KPGQPPRLLIYRASNLESGIPA RFSGSGSRTDFTLTINPVETDD VATYYCQQSNKDPLTFGAGT KLELK | 65 |
| C13 | Heavy chain variable region (nucleic acid) | CAGGTGCAGCTGAAGCAAT CAGGACCTGGCCTAGTGCA GCCCTCACAGAGCCTGTCCG TCACCTGCACAGTCTCTGGT TTCTCATTAACTAGCTATGG TGTACACTGGGTTCGCCAGT CTCCAGGAAAGGGTCTGGA GTGGCTGGGAGTGATATGG AGTGGTGGAAGCACAGACT ATAATGCAGCTTTCATATCC AGACTGACCATCAGCAAGG ACAATTCCAAGAGCCAAGTT TTCTTTAAAATGAACAGTCT GCAAGCTGATGACACAGCC ATATATTACTGTGCCAGAAT | 66 |

TABLE 1-continued

| ANTIBODY NAME | DESCRIPTION | SEQUENCE | SEQ ID NO: |
|---|---|---|---|
| | | AGGGGGCTACGGTACTACCT ACGAGGATGCTATGGACTA CTGGGGTCAAGGAACCTCA GTCACCGTCTCCTCA | |
| C13 | Light chain variable region (nucleic acid) | GACATTGTGCTGACCCAATC TCCAGCTTCTTTGTCTGTGTC TCTAGGGCAGAGGGCCACC ATCTCCTGCAGAGCCAGCGA AAGTGTTGATAATTTTGGCA TTAGTTTTATGTTTTGGTACC AGCAGAAACCAGGACAGCC ACCCAGACTCCTCATCTATC GTGCATCCAACCTAGAATCT GGGATCCCTGCCAGGTTCAG TGGCAGTGGGTCTAGGACA GACTTCACCCTCACCATTAA TCCTGTGGAGACTGATGATG TTGCAACCTATTACTGTCAG CAAAGTAATAAGGATCCGC TCACGTTCGGTGCTGGGACC AAGCTGGAGCTGAAA | 67 |
| D8 | HC CDR1 (amino acid) | GYTFTDYN | 68 |
| D8 | HC CDR2 (amino acid) | INPNNGGT | 69 |
| D8 | HC CDR3 (amino acid) | ARDLVYYFDY | 70 |
| D8 | LC CDR1 (amino acid) | QSIGRS | 71 |
| D8 | LC CDR2 (amino acid) | YAS | 72 |
| D8 | LC CDR3 (amino acid) | QQSNSWPFT | 73 |
| D8 | Heavy chain (HC) variable region (amino acid) | EVQLQQSGPELVKPGASVKIP CKASGYTFTDYNMDWVKQS HGKSLEWIGDINPNNGGTIYN QKFKGKATLTVDKSSSTAYM ELRSLTSEDTAVYYCARDLV YYFDYWGQGTTLTVSS | 74 |
| D8 | Light chain (LC) variable region (amino acid) | DILLTQSPAILSVSPGERVSFS CRASQSIGRSIHWYQQRINGS PRLLIKYASESISGIPSRFSGSG SGTDFTLSINSVESEDIADYYC QQSNSWPFTFGSGTKLEIK | 75 |
| D8 | Heavy chain variable region (nucleic acid) | GAGGTCCAGCTGCAACAGT CTGGACCTGAGCTGGTGAA GCCTGGGGCTTCAGTGAAG ATACCCTGCAAGGCTTCTGG ATACACATTCACTGACTACA ACATGGACTGGGTGAAGCA GAGCCATGGAAAGAGCCTT GAGTGGATTGGAGATATTA ATCCTAACAATGGTGGTACT ATCTACAACCAGAAGTTCAA GGGCAAGGCCACATTGACT GTAGACAAGTCCTCCAGCAC AGCCTACATGGAGCTCCGCA GCCTGACATCTGAGGACACT GCAGTCTATTACTGTGCAAG AGACCTCGTTTACTACTTTG ACTACTGGGGCCAAGGCAC CACTCTCACAGTCTCCTCA | 76 |
| D8 | Light chain variable region (nucleic acid) | GACATCTTGCTGACTCAGTC TCCAGCCATCCTGTCTGTGA GTCCAGGAGAAAGAGTCAG TTTCTCCTGCAGGGCCAGTC AGAGCATTGGCAGAAGCAT ACACTGGTATCAGCAAAGA ACAAATGGTTCTCCAAGGCT TCTCATAAAGTATGCTTCTG AGTCTATCTCTGGGATCCCT | 77 |

TABLE 1-continued

| ANTIBODY NAME | DESCRIPTION | SEQUENCE | SEQ ID NO: |
|---|---|---|---|
| | | TCCAGGTTTAGTGGCAGTGG ATCAGGGACAGATTTTACTC TTAGCATCAACAGTGTGGAG TCTGAAGATATTGCAGATTA TTACTGTCAACAAAGTAATA GCTGGCCATTCACGTTCGGC TCGGGGACAAAGTTGGAAA TAAAA | |

In one embodiment, an anti-idiotypic antibody that binds to vedolizumab comprises CDR-H1, CDR-H2, and CDR-H3 in the heavy chain variable region (VH), and CDR-L1, CDR-L2, and CDR-L3 in a light chain variable region (VL).

In one embodiment, an anti-idiotypic antibody (B4) that binds to vedolizumab comprises a heavy chain variable region comprising a CDR1 domain comprising the amino acid sequence as set forth in SEQ ID NO:1, a CDR2 domain comprising the amino acid sequence as set forth in SEQ ID NO: 2, and a CDR3 domain comprising the amino acid sequence as set forth in SEQ ID NO: 3; and a light chain variable region comprising a CDR1 domain comprising the amino acid sequence as set forth in SEQ ID NO: 4, a CDR2 domain comprising the amino acid sequence as set forth in SEQ ID NO: 5; and a CDR3 domain comprising the amino acid sequence as set forth in SEQ ID NO: 6.

In one embodiment, an anti-idiotypic antibody (I8) that binds to vedolizumab comprises a heavy chain variable region comprising a CDR1 domain comprising the amino acid sequence as set forth in SEQ ID NO:11, a CDR2 domain comprising the amino acid sequence as set forth in SEQ ID NO: 12, and a CDR3 domain comprising the amino acid sequence as set forth in SEQ ID NO: 13; and a light chain variable region comprising a CDR1 domain comprising the amino acid sequence as set forth in SEQ ID NO: 14, a CDR2 domain comprising the amino acid sequence as set forth in SEQ ID NO: 15; and a CDR3 domain comprising the amino acid sequence as set forth in SEQ ID NO: 16.

In one embodiment, an anti-idiotypic antibody (J3) that binds to vedolizumab comprises a heavy chain variable region comprising a CDR1 domain comprising the amino acid sequence as set forth in SEQ ID NO:21, a CDR2 domain comprising the amino acid sequence as set forth in SEQ ID NO: 22, and a CDR3 domain comprising the amino acid sequence as set forth in SEQ ID NO: 23; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26. In one embodiment, J3 competes with N17 for binding vedolizumab, i.e., it binds the same or similar epitope as N17.

In one embodiment, an anti-idiotypic antibody (I10) that binds to vedolizumab comprises a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 32; and a light chain variable region comprising a CDR1 domain comprising the amino acid sequence as set forth in SEQ ID NO: 33, a CDR2 domain comprising the amino acid sequence as set forth in SEQ ID NO: 25; and a CDR3 domain comprising the amino acid sequence as set forth in SEQ ID NO: 26. In one embodiment, 110 competes with N17 for binding vedolizumab, i.e., it binds the same or similar epitope as N17.

In one embodiment, an anti-idiotypic antibody (D5) that binds to vedolizumab comprises a heavy chain variable region comprising a CDR1 domain comprising the amino acid sequence as set forth in SEQ ID NO:38, a CDR2 domain comprising the amino acid sequence as set forth in SEQ ID NO: 39, and a CDR3 domain comprising the amino acid sequence as set forth in SEQ ID NO: 40; and a light chain variable region comprising a CDR1 domain comprising the amino acid sequence as set forth in SEQ ID NO: 41, a CDR2 domain comprising the amino acid sequence as set forth in SEQ ID NO: 42; and a CDR3 domain comprising the amino acid sequence as set forth in SEQ ID NO: 43.

In one embodiment, an anti-idiotypic antibody (J24) that binds to vedolizumab comprises a heavy chain variable region comprising a CDR1 domain comprising the amino acid sequence as set forth in SEQ ID NO:48, a CDR2 domain comprising the amino acid sequence as set forth in SEQ ID NO: 49, and a CDR3 domain comprising the amino acid sequence as set forth in SEQ ID NO: 50; and a light chain variable region comprising a CDR1 domain comprising the amino acid sequence as set forth in SEQ ID NO: 51, a CDR2 domain comprising the amino acid sequence as set forth in SEQ ID NO: 52; and a CDR3 domain comprising the amino acid sequence as set forth in SEQ ID NO: 53.

In one embodiment, an anti-idiotypic antibody (N17) that binds to vedolizumab comprises a heavy chain variable region comprising a CDR1 domain comprising the amino acid sequence as set forth in SEQ ID NO:31, a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26. In one embodiment, N17 competes with J3, 110 and C13 for binding vedolizumab, i.e., they bind the same or similar epitope of vedolizumab.

In one embodiment, an anti-idiotypic antibody (C13) that binds to vedolizumab comprises a heavy chain variable region comprising a CDR1 domain comprising the amino acid sequence as set forth in SEQ ID NO:63 a CDR2 domain comprising the amino acid sequence as set forth in SEQ ID NO: 22, and a CDR3 domain comprising the amino acid sequence as set forth in SEQ ID NO: 58; and a light chain variable region comprising a CDR1 domain comprising the amino acid sequence as set forth in SEQ ID NO: 24, a CDR2 domain comprising the amino acid sequence as set forth in SEQ ID NO: 25; and a CDR3 domain comprising the amino acid sequence as set forth in SEQ ID NO: 26. In one embodiment, C13 competes with N17 for binding vedolizumab, i.e., it binds the same or similar epitope as N17.

In one embodiment, an anti-idiotypic antibody (D8) that binds to vedolizumab comprises a heavy chain variable region comprising a CDR1 domain comprising the amino acid sequence as set forth in SEQ ID NO:68 a CDR2 domain comprising the amino acid sequence as set forth in SEQ ID NO: 69, and a CDR3 domain comprising the amino acid sequence as set forth in SEQ ID NO: 70; and a light chain variable region comprising a CDR1 domain comprising the amino acid sequence as set forth in SEQ ID NO: 71, a CDR2 domain comprising the amino acid sequence as set forth in SEQ ID NO: 72; and a CDR3 domain comprising the amino acid sequence as set forth in SEQ ID NO: 73.

In one embodiment, an anti-idiotypic antibody (B4) that binds to vedolizumab comprises a heavy chain variable region comprising the amino acid sequence as set forth in SEQ ID NO: 7, and a light chain variable region comprising the amino acid sequence as set forth in SEQ ID NO: 8.

In one embodiment, an anti-idiotypic antibody (I8) that binds to vedolizumab comprises heavy chain variable region comprising the amino acid sequence as set forth in SEQ ID NO: 17, and a light chain variable region comprising the amino acid sequence as set forth in SEQ ID NO: 18.

In one embodiment, an anti-idiotypic antibody (J3) that binds to vedolizumab comprises a heavy chain variable region comprising the amino acid sequence as set forth in SEQ ID NO: 27, and a light chain variable region comprising the amino acid sequence as set forth in SEQ ID NO: 28.

In one embodiment, an anti-idiotypic antibody (I10) that binds to vedolizumab comprises a heavy chain variable region comprising the amino acid sequence as set forth in SEQ ID NO: 34, and a light chain variable region comprising the amino acid sequence as set forth in SEQ ID NO: 35.

In one embodiment, an anti-idiotypic antibody (D5) that binds to vedolizumab comprises a heavy chain variable region comprising the amino acid sequence as set forth in SEQ ID NO: 44, and a light chain variable region comprising the amino acid sequence as set forth in SEQ ID NO: 45.

In one embodiment, an anti-idiotypic antibody (J24) that binds to vedolizumab comprises a heavy chain variable region comprising the amino acid sequence as set forth in SEQ ID NO: 54, and a light chain variable region comprising the amino acid sequence as set forth in SEQ ID NO: 55.

In one embodiment, an anti-idiotypic antibody (N17) that binds to vedolizumab comprises a heavy chain variable region comprising the amino acid sequence as set forth in SEQ ID NO: 59, and a light chain variable region comprising the amino acid sequence as set forth in SEQ ID NO: 60.

In one embodiment, an anti-idiotypic antibody (C13) that binds to vedolizumab comprises a heavy chain variable region comprising the amino acid sequence as set forth in SEQ ID NO: 64, and a light chain variable region comprising the amino acid sequence as set forth in SEQ ID NO: 65.

In one embodiment, an anti-idiotypic antibody (D8) that binds to vedolizumab comprises a heavy chain variable region comprising the amino acid sequence as set forth in SEQ ID NO: 74, and a light chain variable region comprising the amino acid sequence as set forth in SEQ ID NO: 75.

Antibodies that bind to the same epitope on vedolizumab as those antibodies described herein in Table 1 are also considered part of the disclosure.

It will be appreciated that antibodies that are generated need not initially possess a particular desired isotype but, rather, the antibody as generated may possess any isotype and still possess desired binding to the anti-α4β7 antibody.

For example, in the Examples, the anti-idiotypic antibodies were generated in mouse hybridomas and have mouse isotypes. The isotype of these antibodies may be switched thereafter, e.g., to another mouse isotype, or to isotypes of other species, such as rat, goat, sheep, horse, chicken, rabbit or human, using conventional techniques that are known in the art. Such techniques include the use of direct recombinant techniques (see e.g., U.S. Pat. No. 4,816,397), cell-cell fusion techniques (see e.g., U.S. Pat. No. 5,916,771), among others. In some embodiments, the anti-idiotypic antibody comprises sequences encoding the mouse IgG2a constant region. In some embodiments, the mouse IgG2a comprises mutations that render the encoded antibody unable to bind to the mouse Fc receptor. In other embodiments, the anti-idiotypic antibody comprises sequences encoding the human IgG1 constant region or the human IgG1 constant region with mutations that render the encoded antibody unable to bind to the human Fc receptor.

Accordingly, as antibody candidates are generated that meet desired "structural" attributes as discussed above, they can be provided with at least certain additional "functional" attributes that are desired through isotype switching. In an embodiment the variable region or antigen binding fragment thereof of an anti-idiotypic antibody described herein can be coupled to a constant region (or fragment thereof) other than the constant region it was generated with, e.g., a constant region (or fragment thereof) from another antibody or to a synthetic constant region (or fragment thereof). In certain embodiments the constant region is an IgG1 or IgG2 constant region (or fragment thereof). Sequence changes can be made in the variable or constant regions to modify effector activity, conjugate chemistry or secondary reagent binding of the antibody molecule.

In some embodiments, the anti-idiotypic antibodies provided herein are chimeric antibodies. A chimeric antibody is a molecule in which different portions of the antibody are derived from different animal species, such as antibodies having a variable region derived from a murine monoclonal antibody and a human immunoglobulin constant region. See e.g., Morrison, *Science,* 229: 1202-1207 (1985); Oi et al., *BioTechniques,* 4: 214 (1986); Gillies et al., *J. Immunol. Methods,* 125: 191-202 (1989); U.S. Pat. Nos. 5,807,715; 4,816,567; and 4,816,397. In addition, techniques developed for the production of "chimeric antibodies" by splicing genes from a mouse antibody molecule of appropriate antigen specificity together with genes from a human antibody molecule of appropriate biological activity can be used. See, for example, Morrison et al., *Proc. Natl. Acad. Sci. USA,* 81: 6851-6855 (1984); Neuberger et al., *Nature,* 312: 604-608 (1984); Takeda et al., *Nature,* 314: 452-454 (1985), which are incorporated herein by reference in their entireties.

In some embodiments, the anti-idiotypic antibodies provided herein are CDR Grafted antibodies. The CDR sequences of the binding proteins described in Table 1 may be used to make CDR-grafted antibodies to modulate the properties of the original antibody/binding protein. Such properties include but are not limited to binding kinetics, affinity, biological activities, species cross-reactivity, molecule cross-reactivity, epitope, physicochemical properties, pharmacokinetic properties, pharmacodynamic properties, or pharmacological properties. CDR-grafted antibodies comprise heavy and light chain variable region sequences from a human antibody, a non-human primate antibody or other species antibody (acceptor) wherein one or more of the CDR regions of VH and/or VL are replaced with CDR sequences of the (donor) original anti-idiotypic antibody capable of binding anti-α4β7 antibody using, e.g., recombinant, techniques available in the art. A framework sequence from any human, non-human primate, or other species antibody may serve as the template for CDR grafting. However, straight chain replacement onto such a framework often leads to some loss of binding affinity to the antigen. The more homologous a human, or other species, antibody is to the original antibody, the less likely the possibility that combining the anti-idiotypic CDRs with the new human, non-human primate, or other species, framework will introduce distortions in the CDRs that could reduce affinity or other properties. Therefore, in some embodiments, the variable framework that is chosen to replace the original variable region framework apart from the CDRs has at least a 30%, at least a 40%, at least a 50%, at least a 60%, at least a 70%, at least an 80% or at least an 85% sequence identity with the original antibody variable region framework. Even using a highly homologous human, non-human primate or other species framework to graft CDRs of the original anti-idiotypic antibody capable of binding anti-α4β7 antibody, the resulting grafted antibody may still lose binding affinity to antigen to some degree. In this case, to regain the affinity it can help to include at least one or more key framework residue(s) substitution of the original antibody to the corresponding position of the newly grafted antibody. Such a key residue may be selected from the group consisting of a residue adjacent to a CDR, a glycosylation site residue, a rare residue, a residue capable of interacting with an anti-α4β7 antibody, a canonical residue; a contact residue between a heavy chain variable region and a light chain variable region, a residue within a Vernier zone, and a residue in a region that overlaps between a Chothia-defined variable heavy chain CDR1 and a Kabat-defined first heavy chain framework.

In embodiments of CDR-grafted anti-idiotypic antibodies described herein, framework residues in the acceptor framework regions may be substituted with the corresponding residue from the CDR donor antibody to alter, e.g., improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., U.S. Pat. No. 5,585,089 (Queen et al.); Riechmann et al., *Nature*, 332: 323-327 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

The anti-idiotypic antibodies that are produced and characterized herein with respect to binding anti-α4β7 antibody provide for the design of other therapeutic or diagnostic modalities including other antibodies, other antagonists, or chemical moieties other than antibodies. Such modalities include, without limitation, antibodies having similar binding activity or functionality, advanced antibody therapeutic and diagnostic agents, such as bispecific antibodies, immunoconjugates, and radiolabeled agents, generation of peptide agents, particularly intrabodies, and small molecules. In certain embodiments, an anti-idiotypic antibody is labeled, e.g., with an engineered tag, for detection or isolation for analytical, diagnostic, or prognostic purposes. Examples of labels or engineered tags include, but are not limited to, a fusion moiety (which can add can add amino acid residues, e.g., two, three, four, five, preferably six histidine residues which can bind nickel or cobalt on an affinity column); an epitope tag, e.g., a portion of c-myc oncogene (myc-tag), a FLAG tag (U.S. Pat. No. 4,703,004), a hemagglutinin (HA) tag, a T7 gene 10 tag, a V5 tag, an HSV tag, or a VSV-G tag which can bind a tag-specific antibody; or a cofactor, e.g., biotin, which can bind streptavidin (see also US20110110936, which is incorporated by reference with respect to labels and tags disclosed therein). Furthermore, as discussed above, the effector function of the antibodies of the invention may be changed by isotype switching to an IgG1, IgG2, IgG3, IgG4, IgD, IgA1, IgA2, IgE, or IgM for various in vivo uses such as for therapy or imaging.

In connection with bispecific antibodies, bispecific antibodies may be generated that comprise (i) two antibodies, one with a specificity to an anti-α4β7 antibody and another to a second molecule that are conjugated together, (ii) a single antibody that has one chain specific to an anti-α4β7 antibody and a second chain specific to a second molecule, or (iii) a single chain antibody that has specificity to an anti-α4β7 antibody and the other molecule. Such bispecific antibodies may be generated using techniques that are known. For example, bispecific antibodies may be produced by crosslinking two or more antibodies (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Protein Biology division of ThermoFisher Scientific, Waltham, MA. See also, e.g., Fanger et al. *Immunomethods* 4:72-81 (1994), Winter and Harris *Immunol Today* 14:43-46 (1993) and Wright et al. *Crit. Reviews in Immunol.* 12125-168 (1992) and in connection with (iii) see e.g., Traunecker et al. *Int. J. Cancer* (Suppl.) 7:51-52 (1992). Songsivilai & Lachmann *Clin. Exp. Immunol.* 79: 315-321 (1990), Kostelny et al. *J. Immunol.* 148:1547-1553 (1992).

In addition, "Kappabodies" (Ill. et al. "Design and construction of a hybrid immunoglobulin domain with properties of both heavy and light chain variable regions" *Protein Eng* 10:949-57 (1997)), "Minibodies" (Martin et al. *EMBO J.* 13:5303-9 (1994), U.S. Pat. No. 5,837,821), "Diabodies" (Holliger et al. *Proc Natl Acad Sci USA* 90:6444-6448 (1993)), or "Janusins" (Traunecker et al. *EMBO J.* 10:3655-3659 (1991) and Traunecker et al. *Int J Cancer Suppl* 7:51-52 (1992)) can also be prepared.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

In another aspect, the invention provides an isolated nucleic acid encoding one or more amino acid sequences of the anti-idiotypic antibody described herein.

In one embodiment, the invention provides an isolated nucleic acid encoding a polypeptide selected from the group consisting of: a polypeptide comprising a heavy chain variable domain, wherein the heavy chain variable domain comprises one or more of a CDR-H1, a CDR-H2, and a CDR-H3 as described above; a polypeptide comprising a light chain variable domain, wherein the light chain variable domain comprises one or more of a CDR-L1, a CDR-L2, and a CDR-L3 as described above; and a combination of both polypeptides.

One aspect of the invention pertains to an isolated nucleic acid encoding an anti-idiotypic antibody, a construct, a conjugate, or a binding portion thereof, described herein. In one embodiment is an isolated nucleic acid that encodes a polypeptide selected from the group consisting of: a polypeptide comprising a heavy chain variable domain, wherein the heavy chain variable domain comprises a CDR-H1, a CDR-H2, or a CDR-H3 described above; a polypeptide comprising a light chain variable domain, wherein the light chain variable domain comprises a CDR-L1, a CDR-L2, or a CDR-L3 as described above; and a combination of both polypeptides. In some embodiments, the nucleic acid comprises one or more nucleotide sequences listed in Table 1, comprises a sequence at least 90%, at least 95%, at least 97%, at least 98% or at least 99% identical to a nucleotide sequence listed in Table 1, or comprises a nucleotide sequence encoding one or more polypeptide sequences listed in Table 1.

A further embodiment provides a vector comprising an isolated nucleic acid described herein. In one embodiment, the vector is selected from the group consisting of: pcDNA, pTT (Durocher et al., *Nucl. Acids Res.*, 30(2e9): 1-9 (2002)), pTT3 (pTT with additional multiple cloning sites), pEFBOS (Mizushima et al., *Nucl. Acids. Res.*, 18 (17): 5322 (1990)), pSecTag2, pCEP4, pPICZ (Invitrogen division of ThermoFisher Scientific, Waltham, MA), pBV, pJV, and pBJ.

In another aspect of the invention there is provided a host cell, e.g., a host cell in culture, comprising the nucleic acid described herein. The host cell can be transformed with the vector described above by any known method for introducing polynucleotides into a host cell, including, for example packaging the polynucleotide in a virus (or into a viral vector) and transducing a host cell with the virus (or vector) or by transfection procedures known in the art, for introducing heterologous polynucleotides into mammalian cells, e.g., dextran-mediated transfection, calcium phosphate precipitation, polybrene mediated transfection, protoplast fusion, electroporation, encapsulation of the polynucleotide(s) into liposomes and direct microinjection of the DNA molecule. The transformation procedure used depends upon the host to be transformed.

A variety of host-expression vector systems can be utilized to express the binding proteins described herein. Such host-expression systems represent vehicles by which the coding sequences of interest may be produced and subsequently purified, but also represent cells which may, when transformed or transfected with the appropriate nucleotide coding sequences, express a binding protein that binds to anti-α4β7 antibody in situ. The host cell can be a prokaryotic or eukaryotic cell. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*)

transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., HUT78, COS, CHO, BHK, 293, 3T3, NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)). In an embodiment, the vector comprises an EF-1a promoter to drive expression of each antibody chain. Vectors comprising this promoter for antibody production are described in U.S. Patent Application Publication No. 2004/0033561 A1, the entire teachings of which are incorporated by reference.

In one embodiment, a prokaryotic host cell is *Escherichia coli*. In bacteria, embodiments of vectors include, but are not limited to, the *E. coli* expression vector pUR278 (Ruther et al., *EMBO J.* 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)); and the like. In other embodiments, the eukaryotic cell is selected from the group consisting of a protist cell, an animal cell, a plant cell, and a fungal cell. In some embodiments, the host cell is a mammalian cell including, but not limited to, 293, CHO and COS cells. An embodiment of a fungal cell is *Saccharomyces cerevisiae*. An embodiment of an insect cell is an Sf9 cell. In an insect system, *Autographa californica* nuclear polyhedrosis virus (AcNPV) can be used as a vector to express foreign genes.

The anti-idiotypic anti-α4β7 antibodies described herein may be produced by expression of nucleic acid sequences encoding each chain in living cells, e.g., cells in culture, for example the hybridoma of origin or a recombinant cell. In some embodiments, the anti-idiotypic antibody can be produced by expressing nucleic acids encoding the CDRs, and/or variable regions described in Table 1. In some embodiments, the anti-idiotypic antibody may be produced by expressing nucleic acid described in Table 1 or portions thereof encoding the CDRs or variable regions of the antibody.

It will be appreciated that antibodies that are generated need not initially possess a particular desired isotype but, rather, the antibody as generated may possess any isotype and still possess desired binding to the anti-α4β7 antibody. For example, the effector function of the antibodies of the invention may be changed by isotype switching to an IgG1, IgG2, IgG3, IgG4, IgD, IgA1, IgA2, IgE, or IgM for various in vivo uses such or for in vitro assays, therapy or imaging. In some embodiments, the nucleic acid further comprises sequences encoding the mouse IgG2a constant region. In some embodiments, the nucleic acid portion encoding the mouse IgG2a comprises mutations that render the encoded antibody unable to bind to the mouse Fc receptor. In other embodiments, the nucleic acid further comprises sequences encoding the human IgG1 constant region or the human IgG1 constant region with mutations to that render the encoded antibody unable to bind to the human Fc receptor.

The invention also relates to a method of preparing an anti-idiotypic antibody comprising maintaining a hybridoma cell or a host cell (e.g., a host cell that contains one or more recombinant nucleic acids that encode an anti-idiotypic antibody (e.g., a light chain and a heavy chain) described herein) under conditions appropriate for expression of an anti-idiotypic antibody. For example, methods of expression of antibody molecules include the use of host cells wherein a first recombinant nucleic acid molecule encoding an antibody molecule, e.g., a rabbit antibody light chain or a humanized version thereof, and a second recombinant nucleic acid molecule encoding an antibody molecule, e.g., a rabbit antibody heavy chain or a humanized version thereof, are comprised in a single expression vector. In other embodiments, they are in separate vectors. For expression of an anti-idiotypic antibody, a host cell can be maintained under any suitable conditions. For example, a host cell can be cultured on a substrate or in suspension. In one embodiment, the host cells are maintained under appropriate conditions, immunoglobulin chains are expressed and an anti-idiotypic antibody is produced. In some embodiments, the method further comprises the step of isolating the anti-idiotypic antibody. Antibodies of the invention may also be produced transgenically through the generation of a mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See, e.g., U.S. Pat. Nos. 5,827,690, 5,756,687, 5,750,172, and 5,741,957

Anti-idiotypic antibodies used in methods described herein, e.g., in in vitro or in vivo detection, e.g., diagnostic, staging, or imaging methods, may be directly or indirectly labeled with a detectable agent to facilitate detection of the bound or unbound binding agent. Indirect labeling includes contacting with a secondary antibody, such as an anti-mouse antibody, which binds the anti-idiotypic antibody, e.g., the Fc portion of the antibody. The secondary antibody may be conjugated to a detectable agent or to a moiety which binds to a label or enzymatically converts a substance into a detectable substance. Suitable detectable agents include various biologically active enzymes, ligands, prosthetic groups, fluorescent materials, luminescent materials, chemiluminescent materials, bioluminescent materials, chromophoric materials, electron dense materials, paramagnetic (e.g., nuclear magnetic resonance active) materials, and radioactive materials described herein. Various methods of labeling polypeptides and glycoproteins are known in the art and may be used. Examples of labels for polypeptides, such as an anti-idiotypic antibody, include, but are not limited to, the following: radioisotopes or radionuclides (e.g., indium ($^{111}$In), iodine ($^{131}$I or $^{125}$I), yttrium ($^{90}$Y), lutetium ($^{177}$Lu), actinium ($^{225}$Ac), bismuth (212Bi or $^{213}$Bi), sulfur ($^{35}$S), carbon ($^{14}$C), tritium ($^3$H), rhodium ($^{188}$Rh), technetium ($^{99}$mTc), praseodymium, or phosphorous ($^{32}$P) or a positron-emitting radionuclide, e.g. carbon-11 ($^{11}$C), potassium-40 ($^{40}$K), nitrogen-13 ($^{13}$N), oxygen-15 ($^{15}$O)$_9$ fluorine-18 ($^{18}$F), and iodine-121 ($^{121}$I)), fluorescent labels (e.g., FITC, rhodamine, lanthanide phosphors), enzymatic labels (e.g. horseradish peroxidase, beta-galactosidase, luciferase, alkaline phosphatase), chemiluminescent, biotinyl groups (which can be detected by a marked avidin, e.g. a molecule containing a streptavidin moiety and a fluorescent marker or an enzymatic activity that can be detected by optical or calorimetric methods), and predetermined polypeptide epitopes recognized by a secondary reporter (e.g. leucine zipper pair sequences, binding sites for secondary antibodies, metal binding domains, epitope tags). In some embodiments, labels are attached by spacer arms of various lengths to reduce potential steric hindrance.

In an embodiment, the invention provides a conjugate comprising an anti-idiotypic, e.g., an anti-vedolizumab antibody described herein conjugated to an agent. In certain embodiments, the agent is selected from the group consisting of: a detectable agent, an imaging agent, a therapeutic agent, a cytotoxic agent, and an immunoadhesin molecule. One embodiment provides a labeled conjugate wherein the anti-idiotypic antibody portion of the invention is derivatized or linked to another functional molecule (e.g., another peptide or protein). For example, a labeled anti-idiotypic antibody of the invention can be derived by functionally linking an antibody or antibody portion (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

Useful detectable agents with which the anti-idiotypic antibody portion of the invention may be derivatized include fluorescent compounds. Exemplary fluorescent detectable agents include fluorescein, fluorescein isothiocyanate, rhodamine, 5-dimethylamine-1-naphthalenesulfonyl chloride, phycoerythrin and the like. An antibody may also be derivatized with detectable enzymes, such as alkaline phosphatase, horseradish peroxidase, glucose oxidase and the like. When an antibody, either the anti-idiotypic antibody or a secondary detection antibody, is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding, e.g., detection through streptavidin coupled with a detectable agent.

In one embodiment, an imaging agent is selected from the group consisting of: a radiolabel, an enzyme, a fluorescent label (e.g., fluoresceine), a luminescent label, a bioluminescent label, a magnetic label, a metal label (e.g., a heavy metal isotope), and biotin. In some embodiments, the imaging agent is a radiolabel selected from the group consisting of $^3$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm. In some embodiments, the therapeutic or cytotoxic agent is selected from the group consisting of: an anti-metabolite, an alkylating agent, an antibiotic, a growth factor, a cytokine, an anti-angiogenic agent, an anti-mitotic agent, an anthracycline, toxin, and an apoptotic agent.

Examples of other labels include fluorophores such as rare earth chelates, such as comprising europium, samarium or terbium, or fluorescein and its derivatives, rhodamine and its derivatives, dansyl, umbelliferone, luciferases, e.g., firefly luciferase and bacterial luciferase (U.S. Pat. No. 4,737,456), luciferin, cyanine (Cy) fluorescent dyes such as Cy3, or Cy5), AF647, Alexa Fluor 488, Alexa Fluor 592, Oregon green and 2,3-dihydrophthalazinediones. Metal labels, such as from the lanthanide series, e.g., Pr, Nd, Pm, Sm, Eu, Gd, Dy, Ho, Er, Tm, Yb and Lu aid detection by mass cytometry, e.g., CyTOF. Other exemplary labels for direct or indirect detection of an anti-idiotypic antibody include moieties which enzymatically convert a substance into a detectable substance, such as horseradish peroxidase (HRP), alkaline phosphatase, galactosidase, glucoamylase, lysozyme, saccharide oxidases, e.g., glucose oxidase, galactose oxidase, and glucose 6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, moieties which bind to a detectable substance, such as biotin which can bind to an avidin-conjugated label, spin labels, bacteriophage labels, stable free radicals, and the like.

Labeled antibody molecules can be used, for example, diagnostically and/or experimentally in a number of contexts, including (i) to isolate a predetermined antigen by standard techniques, such as affinity chromatography or immunoprecipitation; (ii) to detect a predetermined antigen (e.g., in a cellular lysate, in a biological sample, in a tissue specimen or cell supernatant) in order to evaluate the abundance and pattern of expression of the protein; (iii) to monitor protein levels in a biological sample as part of a clinical testing procedure, e.g., to determine the efficacy of a given treatment regimen.

Anti-idiotypic antibodies for use in monitoring the effectiveness of treatment of IBD with an anti-α4β7 antibody bind to the hypervariable region of the anti-α4β7 antibody. For generating anti-idiotypic antibodies, a fragment of the anti-α4β7 antibody, such as a pepsin-treated fragment, without one or more constant regions may provide a focused antibody pool easier to screen for specific anti-idiotypic antibodies.

III. Methods of Using Anti-Idiotypic Antibodies

The antibodies and immunoconjugates described herein can be used to detect the presence or absence of anti-α4β7 antibody, e.g., to detect the presence or absence of anti-α4β7 antibody in an ex vivo biological sample obtained from a subject (i.e., in vitro detection), or to detect the presence or distribution or absence of anti-α4β7 antibody in a patient (i.e., in vivo detection). Such detection methods are useful to detect or diagnose a variety of disorders, or to guide therapeutic or economic decisions or actions. The term "detecting" as used herein encompasses quantitative or qualitative detection. The present invention provides anti-idiotypic antibodies for use in a method for treating or maintaining remission in a patient having inflammatory bowel disease (IBD), graft versus host disease, or HIV with an anti-α4β7 antibody, e.g., vedolizumab.

Biological samples can be assayed without significant manipulation. In some embodiments, tissue, e.g., a biopsy sample from inflamed tissue, is frozen so sections have minimal fixation which can destroy epitopes. In other embodiments, whole blood, e.g., a peripheral blood sample, is used to detect immune cells, e.g., eosinophils, after red blood cell lysis. Some sample manipulation is helpful for assays of other immune cells. Blood samples can be clotted to collect serum without cells. For analyzing immune cells, blood collection containers can comprise an anti-coagulant, e.g., heparin, ethylene-diaminetetraacetic acid (EDTA), sodium citrate or citrate solutions and optionally may comprise additives to preserve blood integrity, such as dextrose or albumin or buffers, e.g., phosphate or Ringer's. A protein stabilizer, e.g., an agent that inhibits proteases, such as serine proteases, cysteine proteases, etc. can be added to the sample. Several protease inhibitors, such as cocktails of inhibitors for more than one protease are readily available. An RNA stabilizer, e.g., an agent that inhibits RNAse, can be added to the sample. RNA can be isolated using standard procedures (see e.g., Chomczynski and Sacchi (1987) *Anal. Biochem.* 162:156-159), solutions (e.g., trizol, TRI REAGENT® (Molecular Research Center, Inc., Cincinnati, OH; see U.S. Pat. No. 5,346,994) or kits (e.g., a QIAGEN® Group RNEASY® isolation kit (Valencia, CA) or LEUKO-LOCK™ Total RNA Isolation System, Ambion division of Applied Biosystems, Austin, TX).

Examples of blood collection containers comprising a stabilizer are PAXGENE® tubes (PREANALYTIX, Valencia, CA), useful for RNA stabilization upon blood collection, and CELLSAVE Preservation tubes (Janssen Diagnostics, LLC), useful for the stabilization of circulating immune cells upon blood collection. Peripheral blood samples can be modified, e.g., fractionated, sorted or concentrated (e.g., to result in samples enriched with a particular immune cell type (e.g., for a reference sample)). Examples of modified samples include separation of white blood cells from red blood cells (e.g., differential centrifugation through a dense sugar or polymer solution (e.g., FICOLL® solution (Amersham Biosciences division of GE healthcare, Piscataway, NJ) or HISTOPAQUE®-1077 solution, Sigma-Aldrich Biotechnology LP and Sigma-Aldrich Co., St. Louis, MO)) and/or positive selection by binding cells to a selection agent e.g., a reagent which binds to a marker (e.g., a B-cell marker, such as CD19, CD20 or CD138, or T cell subtype marker) for direct isolation (e.g., the application of a magnetic field to solutions of cells comprising magnetic beads (e.g., from Miltenyi Biotec, Auburn, CA) which bind to the cell markers) or fluorescent-activated cell sorting).

The biological sample, e.g., blood, modified blood or tissue biopsy, can be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker or anti-α4β7 antibody in the sample.

In a pharmacodynamic example, the method comprises measuring antigen-bound anti-α4β7 antibody (e.g., vedolizumab) or an antigen binding fragment thereof in a biological sample from a patient. In one embodiment, the assay measures the amount (e.g., percentage) of anti-α4β7 antibody bound cells and/or the types of anti-α4β7 antibody-bound cells in a biological sample of a patient (e.g., blood sample or tissue sample), as determined in an assay using an anti-idiotypic antibody specific for an anti-α4β7 antibody (e.g., vedolizumab) described herein.

Accordingly, in one aspect, provided herein is a method of determining a vedolizumab profile of a human patient (e.g., a human patient previously administered vedolizumab). The method can include contacting a biological sample having a population of cells from a human patient (e.g., a human patient administered vedolizumab prior to obtaining the biological sample) with an anti-idiotypic antibody, or an antigen-binding fragment thereof, with binding specificity to vedolizumab, under conditions in which the anti-idiotypic antibody, or antigen-binding fragment thereof, binds to vedolizumab; and detecting a level of vedolizumab bound to cells in the biological sample and/or detecting a subset of cells bound by vedolizumab with the anti-idiotypic antibody, or antigen-binding fragment thereof, in the population of cells; thereby determining the vedolizumab profile of the human subject.

In another aspect, provided herein is a method of compiling or determining a cell profile of vedolizumab in a human patient (e.g., in a biological sample from a human patient previously administered vedolizumab). The method may include contacting a biological sample from a human patient (e.g., a human patient administered vedolizumab prior to obtaining the biological sample) with an anti-idiotypic antibody, or an antigen-binding fragment thereof, with binding specificity to vedolizumab, under conditions in which the anti-idiotypic antibody, or antigen-binding fragment thereof, binds to vedolizumab; separating the biological sample into two or more subsets of cells (e.g., using flow cytometry); detecting vedolizumab with the anti-idiotypic antibody, or antigen-binding fragment thereof, in each subset of cells; and identifying a subset of cells bound by vedolizumab based on the detection of vedolizumab with the anti-idiotypic antibody, thereby determining the vedolizumab profile in the human patient. The method further can include quantifying the number of cells of each subset bound to vedolizumab in the biological sample.

In a further aspect, provided herein is a method of treating a patient having an inflammatory bowel disease (IBD) by administering a dose of vedolizumab to a patient characterized as having a favorable vedolizumab profile of vedolizumab-bound cells (e.g., a vedolizumab profile indicative of responsiveness to vedolizumab). In some embodiments, the patient is characterized as having a favorable vedolizumab profile of vedolizumab-bound immune cells at least 1 day, 2 days, 3 days, 4 days, 5 days, 6 days, 1 week, at least 2 weeks, at least 3 weeks, 4 weeks, 5 weeks, 6 weeks, 7 weeks, 12 weeks, 13 weeks, or 14 weeks after administering vedolizumab to the patient.

In another aspect, provided is a method of treating a patient having an inflammatory bowel disease (IBD) by administering to the patient a dose of vedolizumab, wherein the human patient is characterized as having an increased level of vedolizumab bound to cells (e.g., immune cells) relative to a reference level, wherein the level of vedolizumab is determined at least 1 day, 2 days, 3 days, 4 days, 5 days, 6 days, 1 week, at least 2 weeks, at least 3 weeks, 4 weeks, 5 weeks, 6 weeks, 7 weeks, 12 weeks, 13 weeks, or 14 weeks after a prior administration of vedolizumab to the patient (e.g., thereby treating the IBD, e.g., maintaining or inducing remission of the IBD).

Further provided herein is a method of treating a patient having an inflammatory bowel disease (IBD) by administering to the patient a dose of vedolizumab and a dose of an additional therapeutic agent, wherein the patient is characterized as having an increased level of vedolizumab bound to cells (e.g., immune cells) relative to a reference level, wherein the level of vedolizumab is determined at least 1 day, 2 days, 3 days, 4 days, 5 days, 6 days, 1 week, at least 2 weeks, at least 3 weeks, 4 weeks, 5 weeks, 6 weeks, 7 weeks, 12 weeks, 13 weeks, or 14 weeks after a prior administration of vedolizumab to the patient (e.g., thereby treating the IBD, e.g., maintaining or inducing remission of the IBD). In some embodiments, the additional therapeutic agent is an IL-23 inhibitor, e.g., brazikumab, guselkumab, risankizumab, briakinumab, tildrakizumab, mirikizumab, or ustekinumab, a JAK inhibitor, e.g., tofacitinib, upadacitinib or filgotinib, a checkpoint inhibitor, e.g., pembrolizumab, nivolumab, or atezolizumab, a CD28 inhibitor, e.g., lulizumab, an IL-22 inhibitor, e.g., efmarodocokin alfa, a sphingosine-1 phosphate receptor inhibitor, e.g., ozanimod, or a TNFα inhibitor, e.g., adalimumab, infliximab, certolizumab pegol or golimumab. In some embodiments, ICAM-1 and VCAM-1 expression on endothelial cells can be downmodulated by treatment with anti-inflammatory agents such as anti-TNFα and JAK inhibitor treatment. Identification of patients with high risk of non-response to vedolizumab due to redundant trafficking may benefit from early combination treatment approaches, which may increase the efficacy of vedolizumab through inhibition of these other trafficking pathways.

In yet a further aspect, provided herein is a method of treating a human patient having an inflammatory bowel disease (IBD) by administering a dose of vedolizumab to the patient at an initial time point; subsequently measuring the amount of vedolizumab-bound cells (e.g., immune cells) in a biological sample obtained from the patient at least 1 day, 2 days, 3 days, 4 days, 5 days, 6 days, 1 week, at least 2 weeks, at least 3 weeks, 4 weeks, 5 weeks, 6 weeks, 7 weeks, 12 weeks, 13 weeks, or 14 weeks after the initial time point, and, and administering one or more doses (e.g., additional doses) of vedolizumab to the patient if the amount of vedolizumab-bound immune cells in the biological sample is increased relative to a reference level.

Further provided is an anti-α4β7 antibody, e.g., vedolizumab, for use in a method of treating a patient having an inflammatory bowel disease (IBD) characterized by an increased level of vedolizumab-bound of cells (e.g., immune cells) relative to a reference level at least 1 day, 2 days, 3 days, 4 days, 5 days, 6 days, 1 week, at least 2 weeks, at least 3 weeks, 4 weeks, 5 weeks, 6 weeks, 7 weeks, 12 weeks, 13 weeks, or 14 weeks after a dose of 300 mg vedolizumab by intravenous administration.

Additionally, provided is an anti-α4β7 antibody, e.g., vedolizumab for use in a method of treating a patient having an inflammatory bowel disease (IBD) characterized by an increased level of vedolizumab-bound of cells (e.g., immune cells) relative to a reference level at least 1 day, 2 days, 3 days, 4 days, 5 days, 6 days, 1 week, at least 2 weeks, at least 3 weeks, 4 weeks, 5 weeks, 6 weeks, 7 weeks, 12 weeks, 13 weeks, or 14 weeks after a dose of 108 mg vedolizumab by subcutaneous administration.

In some embodiments, an increase in the levels of anti-α4β7 antibody (e.g., vedolizumab) bound cells relative to a reference level or the presence of vedolizumab on cells (e.g., a subset of cells in a biological sample) characterizes the patient as responding to the anti-α4β7 antibody. In some embodiments, the reference level is a level of the anti-α4β7 antibody bound cells in an untreated subject or biological sample therefrom. For example, the untreated subject may be a healthy subject. Alternatively, the reference level may be the level of the anti-α4β7 antibody-bound cells detected in a patient prior to treatment (e.g., a baseline level). In some embodiments, the reference level is a pre-determined threshold level (e.g., as determined based on clinical studies of patient populations that are responsive and non-responsive to the anti-α4β7 antibody). For example, the reference level or capacity for vedolizumab binding may be determined by binding vedolizumab in vitro to an isolated cell sample from an untreated subject and quantifying the cells bound to the vedolizumab or characterizing the types and/or quantities thereof of cells which bind to vedolizumab in these samples. By comparing the levels or presence of anti-α4β7 antibody (e.g., vedolizumab) bound cells in a biological sample obtained from a vedolizumab-treated subject to a reference value as described herein, it can be determined as to whether the candidate subject is responsive or non-responsive to treatment with the anti-α4β7 antibody.

In some embodiments, an increased level of vedolizumab-bound cells (e.g., immune cells) relative to a reference or baseline level is a percentage increase that is, for example, at least 1%, at least 5%, at least 10%, at least 20%, at least 30%, at least 40%, at least 50%, at least 60%, at least 70%, at least 80%, at least 90%, at least 100%, at least 150%, at least 200%, at least 300%, at least 400%, or at least 500% or more above a reference value. In some embodiments, an increased level of vedolizumab-bound cells (e.g., immune cells) relative to a reference or baseline level is a percentage increase that is, for example, 1%, 5%, 10%, 20%, 30%, 40%, 50%, 60%, 70%, 80%, 90%, 100%, 150%, 200%, 300%, 400%, 500% or more above a reference value.

For example, the biological sample comprising vedolizumab-bound cells can be a peripheral blood sample from a vedolizumab-treated subject. An increase in the number of vedolizumab-bound cells in the peripheral blood sample can indicate response to vedolizumab. No or minimal increase, e.g., less than 50%, less than 40%, less than 30%, less than 20%, less than 10%, less than 5% above a reference or baseline value, in the number of vedolizumab-bound cells in the peripheral blood sample or an increase that is not maintained for 5 days, 10 days, 2 weeks, 3 weeks, 4 weeks, 5 weeks, 6 weeks, 7 weeks, or 8 weeks, can indicate nonresponse to vedolizumab or redundant trafficking of the cells.

In another example, the biological sample comprising vedolizumab-bound cells can be a sample from a secondary lymphoid organ, e.g., spleen, lymph node or Peyer's patch, or tertiary lymphoid tissue, e.g., cryptopatches or lymphoid follicles, from a vedolizumab-treated subject. A decrease in the number of vedolizumab-bound cells in the biological sample from the secondary lymphoid organ or tertiary lymphoid tissue can indicate response to vedolizumab. No or minimal decrease, e.g., less than 50%, less than 40%, less than 30%, less than 20%, less than 10%, less than 5% below a reference value, in the number of vedolizumab-bound cells in the secondary lymphoid organ or tertiary lymphoid tissue sample or an increase that is not maintained for 5 days, 10 days, 2 weeks, 3 weeks, 4 weeks, 5 weeks, 6 weeks, 7 weeks, or 8 weeks, can indicate nonresponse to vedolizumab or redundant trafficking of the cells.

The pharmacodynamic methods provided herein may be used to measure vedolizumab binding to a variety of cell types following vedolizumab administration (e.g., to evaluate treatment response). For example, in some embodiments, the vedolizumab-bound cell is an immune cell. In some embodiments, the immune cell is a T cell (e.g., an effector memory T cell, a naïve T cell, and/or a regulatory T cell), a B cell, a natural killer (NK) cell, a monocyte, a dendritic cell, a plasma cell, and/or an eosinophil. The cells can be sorted and/or identified based on phenotypic markers characteristic of each cell type using known detection methods, such as flow cytometry (e.g., FACS; multi-color flow cytometry), mass cytometry (CyTOF) and/or immunohistochemistry. For example, in some embodiments, the immune cell expresses one or more phenotypic markers selected from the group consisting of CD3, CD4, CD6, CD11c, CD14, CD16, CD19, CD25, CD28, CD38, CD45RA, CD64, CD127, CCR7, CCR9, FoxP3, GPR15, Th17, CD161, CCR6, HLA-DR, CD1, and miR-301a. Phenotypic markers for various cell types are known in the art (see, e.g., Maecker, Holden T., J. Philip McCoy, and Robert Nussenblatt. "Standardizing immunophenotyping for the human immunology project." *Nature Reviews Immunology* 12.3 (2012): 191-200.). Exemplary markers for certain cell types are provided in the table below.

| Cell Type | Exemplary Markers |
| --- | --- |
| CD4+ T cell | CD3+, CD4+ |
| CD8+ T cell | CD3+, CD8+ |
| Naïve CD4+ T cell | CD3+, CD4+, CCR7+, CD45RA+ |
| Central memory CD4+ T cell | CD3+, CD4+, CCR7+, CD45RA– |
| Effector CD4+ T cell | CD3+, CD4+, CCR7–, CD45RA+ |
| Effector memory CD4+ T cell | CD3+, CD4+, CCR7–, CD45RA– |
| Naïve CD8+ T cell | CD3+, CD8+, CCR7+, CD45RA+ |
| Central memory CD8+ T cell | CD3+, CD8+, CCR7+, CD45RA– |
| Effector CD8+ T cell | CD3+, CD8+, CCR7–, CD45RA+ |
| Effector memory CD8+ T cell | CD3+, CD8+, CCR7–, CD45RA– |
| Activated CD4+ T cell | CD3+, CD4+, CD38+, HLA-DR+ |
| Activated CD8+ T cell | CD3+, CD8+, CD38+, HLA-DR+ |
| Regulatory T cell (Treg cell) | CD3+, CD4+, CCR4+, CD25+, CD127low, FoxP3+ |
| Memory Treg cell | CD3+, CD4+, CCR4+, CD25+, CD127low, CD45RO+ |
| Naïve Treg cell | CD3+, CD4+, CCR4+, CD25+, CD127low, CD45RO– |
| Activated Treg cell | CD3+, CD4+, CCR4+, CD25+, CD127low, HLA-DR+ |
| Th1 cell | CD3+, CD4+, CXCR3+, CCR6– |
| Th17 cell | CD3+, CD4+, CXCR3–, CCR6+ |
| Th2 cell | CD3+, CD4+, CXCR3–, CCR6– |
| B cell | CD19+, CD45+, CD38–, CD27+/– |
| Plasma cell | CD45+, CD38+, CD27+, CD138+, CD78+, CD319+, BCMA+, IL-6+, CD3–, CD19–, CD20– |
| Natural killer cell (NK cell) | CD56+, CD16+, CD94+, NKp46+, CD3– |
| Classical monocyte | CD14+/++, CD16–, CD64+ |
| Non-classical monocyte | CD14+/–, CD16+/++, CD64+ |
| Intermediate monocyte | CD14+/++, CD16+, CD64+ |
| Dendritic cell | HLA-DR+, CD11c+, CD24+, CD45+, CD123+, CD3–, CD19,– CD14–, Siglec F–, CD20– |
| Eosinophil | CD193+, CD45+, CD125+, F4/80+, Siglec 8+, CD16– |

Further, assessment of vedolizumab levels on immune cells in the blood (e.g., memory T cells, plasma cells, dendritic cells, monocytes, Tregs as well as naïve B and T cells) relative to expression of other integrins such as $\alpha 4\beta 1$, $\alpha L\beta 2$, $\alpha E\beta 7$, and/or $\alpha 6\beta 1$ can provide information on the presence of redundant trafficking pathways and their contribution to non-response to vedolizumab. Biological samples (e.g., peripheral blood samples) can be collected at baseline and at various time points e.g., weeks 1, 2, 3, 4, 5, 6, 7, 8, 9, 10, 11, 12, 13, or 14 weeks following drug administration to assess the levels of vedolizumab bound to various cell types. The levels of accumulating immune cells and the ratio of cells bound with vedolizumab vs other integrins may be utilized as biomarkers to assess potential response to vedolizumab. Additionally, when used in combination with phenotypic markers as well as antibodies to various integrins e.g., $\alpha 4$, $\alpha E$, $\alpha L$, $\alpha 6$, $\beta 1$, $\beta 2$ and $\beta 7$, the methods herein can be used to characterize the presence of redundant trafficking molecules on different immune cells and the potential for these molecules to impact treatment response to vedolizumab.

Accordingly, in some embodiments, the method further comprises measuring the level of an integrin other than $\alpha 4\beta 7$ (e.g., $\alpha 4\beta 1$, $\alpha L\beta 2$, $\alpha E\beta 7$, $\alpha 6\beta 1$, or 0604) in the biological sample. In further embodiments, the method additionally comprises detecting phenotypic markers and/or various integrins on cells, such as $\alpha 4$, $\alpha E$, $\alpha L$, $\beta 1$, $\beta 2$, $\beta 7$ and $\alpha 6$ (CD49f).

In some embodiments, the method includes detecting vedolizumab bound to T cells (e.g., using an anti-idiotypic antibody provided herein). The terms "T lymphocyte" and "T cell" are used interchangeably, and refer to a cell that expresses a T cell antigen receptor (TCR) capable of recognizing an antigen when displayed on the surface of antigen presenting cells or matrix together with one or more MHC molecules or, one or more non-classical MHC molecules. T cells include thymocytes, immature T lymphocytes, mature T lymphocytes, resting T lymphocytes, or activated T lymphocytes, and differentiate from lymphoid progenitor cells in the bone marrow. The T cells can be CD4+ T cells, CD8+ T cells, CD4+CD8+ T cells, or CD4'CD8' cells. The T cells can also be T helper cells, such as T helper 1 (TH1), or T helper 2 (TH2) cells, or TH17 cells, as well as cytotoxic T cells, regulatory T cells, natural killer T cells, naïve T cells, memory T cells, or gamma delta T cells. T-cells can be identified based on the presence of CD3 (i.e., CD3+). T cells that differ from each other by at least one marker, such as CD4, are referred to herein as "subsets" of T cells.

In one embodiment, the T cell is a CD4+ T cell (i.e., CD3+CD4+). CD4+ T cells are a subset of T cells that express CD4 on their surface and are associated with cell-mediated immune response. They are characterized by the secretion profiles following stimulation, which may include secretion of cytokines such as IFN-gamma, TNF-alpha, IL-2, IL-4 and IL-10. On T-lymphocytes, CD4 antigens define the helper/inducer subset of T cells (Th cells).

In one embodiment, the T cell is a CD8+ T cell (i.e., CD3+CD8+). CD8+ T cells include a subset of T cells which express CD8 on their surface, are MHC class 1-restricted, and function as cytotoxic T cells (Tc cells). CD8 molecules are differentiation antigens found on thymocytes and on cytotoxic and suppressor T-lymphocytes.

In one embodiment, the T cell is a memory T cell. Memory T cells are a subset of antigen-specific T cells that persist long-term after an infection has resolved. They quickly expand to large numbers of effector T cells upon reexposure to their cognate antigen, thus providing the immune system with "memory" against past infections. Memory T cells comprise two subtypes: central memory T cells (TCM cells) and effector memory T cells (TEM cells). Memory cells may be either CD4+ or CD8+. In one embodiment, the T cell is a CD4+ effector memory T cell. For example, the CD4+ effector memory T cell can be characterized based on the presence of CD3 and CD4 and the absence of CD45RA and/or CCR7.

In one embodiment, the T cell is a regulatory T cell. Regulatory T cells (i.e., Treg cells), formerly known as suppressor T cells, are crucial for the maintenance of immunological tolerance. They resemble the conventional alpha beta TCR expressing CD4 positive cells. They can be further characterized by the co expression of CD25 and Foxp3 proteins. Their primary role is to shut down T cell-mediated immunity toward the end of an immune reaction and to suppress auto-reactive T cells that escaped the process of negative selection in the thymus. Two major classes of CD4+ regulatory T cells have been described, including the naturally occurring Treg cells and the adaptive Treg cells. Naturally occurring Treg cells (i.e., CD4+CD25+FoxP3+ Treg cells) arise in the thymus, whereas the adaptive Treg cells (e.g., Tr1 cells, Th3 cells) may originate during a normal immune response.

In some embodiments, the method includes detecting vedolizumab bound to B cells (e.g., using an anti-idiotypic antibody provided herein). B cells are lymphocytes that are derived from lymphoid progenitor cells in the bone marrow and then move to secondary lymphoid tissue, where they may become antibody-producing cells. B cells can be identified by the presence of CD19 (CD19+). B cells can further be assessed based on other markers, such as the presence of CD45 and the absence of CD38.

In some embodiments, the method includes detecting vedolizumab bound to plasma cells (e.g., using an anti-idiotypic antibody provided herein). Plasma cells are white blood cells that originate in the lymphoid organs from B lymphocytes and secrete antibodies in response to presentation of antigens. Plasma cells may be characterized, for example, by the presence of CD45, CD38, CD27, CD138, CD78, CD319, BCMA, and/or IL-6 and by the absence of, e.g., CD3, CD19, and/or CD20.

In some embodiments, the method includes detecting vedolizumab bound to natural killer cells (e.g., using an anti-idiotypic antibody provided herein). Natural killer cells (NK cells) are cytotoxic lymphocytes involved in the innate immune response and differentiate from common lymphoid progenitor cells. In some embodiments, NK cells can be identified by the presence of CD56, CD16, CD94, and/or Natural cytotoxicity receptors (e.g., NKp46) and the absence of CD3 (i.e., CD56+, CD3– cells).

In some embodiments, the method includes detecting vedolizumab bound to monocytes (e.g., using an anti-idiotypic antibody provided herein). Monocytes are a type of leukocyte that arise from myeloid progenitor cells in the bone marrow and can differentiate into macrophages and conventional dendritic cells. Classical monocytes are characterized by high level expression of the CD14 cell surface receptor (CD14++CD16– or CD14+CD16–). Non-classical monocytes are characterized by low level expression of CD14 and additional co-expression of the CD16 receptor (CD14+CD16++ or CD14−CD16+). Intermediate monocytes are characterized by high level expression of CD14 and low level expression of CD16 (CD14++CD16+ or CD14+CD16+). Monocytes may also be characterized by the presence of CD64.

In some embodiments, the method includes detecting vedolizumab bound to dendritic cells (e.g., using an anti-idiotypic antibody provided herein). Dendritic cells are antigen-presenting cells derived from myeloid progenitor cells (e.g., macrophage-dendritic cell progenitor (MDP)) in the bone marrow, and include conventional dendritic cells and plasmacytoid dendritic cells. Dendritic cells may be characterized, for example, by the presence of HLA-DR, CD11c, CD24, CD45, and/or CD123 and by the absence of, e.g., CD3, CD19, CD14, Siglec F, and/or CD20.

In some embodiments, the method includes detecting vedolizumab bound to eosinophils (e.g., using an anti-idiotypic antibody provided herein). Eosinophils are a type of white blood cell that differentiate from common myeloid progenitors and, in turn, from myeloblasts. Eosinophils may be characterized, for example, by the presence of CD193, CD45, CD125, F4/80, and/or Siglec 8 and by the absence of CD16.

In some embodiments, the method using vedolizumab comprises the steps of administering two doses of vedolizumab to a patient suffering from IBD, wherein the second dose is administered about two weeks after the first dose is administered to the patient; waiting a period of time of about four weeks; measuring the patient's vedolizumab profile; and administering one or more further doses of vedolizumab to the patient if the patient's vedolizumab profile is favorable (e.g., if the patient has an increased level of vedolizumab-bound of cells (e.g., immune cells) relative to a reference level), as determined in an assay using an anti-idiotypic antibody specific for the anti-α4β7 antibody as described herein.

Alternatively, at least one dose of the anti-α4β7 antibody, e.g., vedolizumab may be administered to a patient suffering from IBD, waiting at least about two weeks, or optionally, a period of two to five weeks, and then measuring the patient's vedolizumab profile and administering one or more further doses of vedolizumab to the patient if the patient's vedolizumab profile is favorable (e.g., if the patient has an increased level of vedolizumab-bound of cells (e.g., immune cells) relative to a reference level) as determined by using the anti-idiotypic antibodies specific for anti-α4β7 antibody as described herein.

In another aspect, the present invention provides anti-idiotypic antibodies for use in a method of identifying a patient (e.g., a patient having mucosal healing) for continued treatment with vedolizumab. The method may comprise the steps of measuring the concentration of vedolizumab in a biological sample obtained from a patient suffering from IBD and who received at least two doses of vedolizumab within the previous four months (e.g., within the previous three months, within the previous two months), and identifying the patient for continued treatment with vedolizumab if the patient's vedolizumab profile is favorable (e.g., if the patient has an increased level of vedolizumab-bound cells (e.g., immune cells) relative to a reference level), as determined in an assay using an anti-idiotypic antibody specific for the anti-α4β7 antibody as described herein. In some embodiments, the patient received the last prior dose, e.g., the second dose, of vedolizumab about four weeks prior to the sampling of the biological sample for vedolizumab measurement. In other embodiments, the patient received the last prior dose 3 to 8 weeks prior to obtaining the biological sample for vedolizumab measurement.

Alternatively, the method of identifying a patient for continued treatment with an anti-α4β7 antibody, e.g., vedolizumab may comprise the steps of using an anti-idiotypic antibody described herein for measuring the concentration of vedolizumab in a biological sample obtained from a patient suffering from IBD and who received at least one dose of vedolizumab within the previous one or two months, and identifying the patient for continued treatment with vedolizumab if the patient's vedolizumab profile is favorable (e.g., if the patient has an increased level of vedolizumab-bound of cells (e.g., immune cells) relative to a reference level), as determined in an assay using an anti-idiotypic antibody specific for the anti-α4β7 antibody as described herein. In some embodiments, the patient received the prior dose of vedolizumab about two weeks, about three weeks, about four weeks, about five weeks or about six weeks prior to obtaining the biological sample for vedolizumab measurement.

Vedolizumab may be administered by any suitable method, such as by one or more of intravenous injection, subcutaneous injection, or infusion. In some embodiments, vedolizumab is administered at a dose of 50 mg, 100 mg, 180 mg, 300 mg, or 600 mg. In some embodiments, the vedolizumab is administered, for example subcutaneously, at a dose of 0.5 mg/kg, 1.0 mg/kg, 1.5 mg/kg, 2.0 mg/kg, 2.5 mg/kg, 3.0 mg/kg. 4.0 mg/kg, or 5.0 mg/kg, at a dose of 108 mg, 216 mg, 160 mg or 165 mg. The vedolizumab may be administered once per day, per week, per month, or per year. In some embodiments, the vedolizumab is administered at zero, two and six weeks, and then every four weeks or every eight weeks thereafter. In some embodiments, vedolizumab is administered one or more times, and then at least one month, at least six months, or at least one year later, vedolizumab is again administered one or more times. In some embodiments, 300 mg vedolizumab may be administered by intravenous infusion at zero, two, and six weeks, and then at four weeks intervals or eight week intervals thereafter. In some embodiments, 300 mg vedolizumab may be administered by intravenous infusion at zero, two, and six weeks, and then at two-, three- or four-week intervals, 108 mg of vedolizumab may be administered subcutaneously. Treatment methods using anti-α4β7 integrin antibodies are described in publication nos. US 2005/0095238, U.S. Pat. Nos. 10,040,855 and 10,004,808.

In some embodiments, the method of identifying a patient for continued treatment with an anti-α4β7 antibody, e.g., vedolizumab may comprise a clinical measure. A clinical measure may be mucosal healing. An endoscopic score decreased from baseline, e.g. 25% less, 35% less, 40% less, 45% less, 50% less, 55% less, 60% less, 65% less, or 75% less than baseline, may indicate mucosal healing. In ulcerative colitis, an endoscopic score of less than 4, less than 3, ≤1, or between 0 and 2 may help identify a patient for continued treatment. In Crohn's disease, a patient with mucosal healing, and thus a candidate for continued treatment with an anti-α4β7 antibody, e.g., vedolizumab, may have an assessment selected from the group consisting of endoscopic response, endoscopic remission, improvement in the MaRIA score, decrease in ulceration, and improvement in a mucosal healing parameter, e.g., an MREn parameter. In one embodiment, a MaRIA score is the sum of each segment calculation, wherein a sum that one would calculate for each segment=(1.56×wall thickness (mm))+(0.02×Relative Contrast Enhancement (RCE), e.g., after administration of intravenous contrast with gadolinium)+(5×edema)+(10×ulceration)). In some embodiments endoscopic response is achieved by about a 25% decrease, about a 40% decrease, about a 50% decrease, about a 60% decrease or about a 75% decrease in SES-CD score from baseline. In some embodiments, endoscopic remission is achieved by an SES-CD score of ≤6, ≤5, ≤4 or ≤3. In some embodiments, mucosal healing is achieved by a MaRIA score of <14, <13, <12, <11, <10, <9, <8, <7, <6, <5 or <4. In some embodiments a decrease in ulceration is selected from the group consisting of a decrease in the size of ulcers, a decrease in the percent of ulcerated surface, a decrease in the percent of affected surface and decrease in the narrowings of the canal. In some embodiments, the size of ulcers is less than 2 cm in diameter, 0.5 to 2 cm in diameter, 0.1 to 0.5 cm in diameter or <0.2 cm diameter. In some embodiments, the ulcerated surface is less than 30%, 10-30%, less than 10%, or 0. In some embodiments the affected surface is less than 75%, 50%-75%, less than 50%, less than 25% or unaffected. In some embodiments, the wall thickness is decreased by about 10%, about 15%, about 20%, about 25%, about 30%, about 20%-40% or more than 45% from baseline. In some embodiments, the bowel wall contrast (RCE) is decreased about 15%, about 20%, about 25%, about 30%, about 35%, about 40%, about 20%-40% or more than 40% from baseline. In some embodiments, the mural edema is decreased by about 25%, about 40%, about 50%, about 60%, about 70%, more than 75%, or about 70%-90% from baseline. In some embodiments, the perienteric vascularity is decreased by about 25%, about 30%, about 40%, about 50%, about 60%, about 50%-70%, about 75% or more than 75% from baseline.

In an embodiment, a Crohn's disease patient who is responsive to vedolizumab has an SES-CD of ≤4 at week 6, 10, 12, 14, 22 or 26 after initiating treatment. In an embodiment, a Crohn's disease patient who is responsive to vedolizumab has an endoscopic response or ≥50% reduction of SES-CD at week 6, 10, 12, 14, 22 or 26 after initiating treatment. In an embodiment, a Crohn's disease patient who is responsive to vedolizumab has a clinical remission or ≥70 or ≥100 point reduction of CDAI score at week 6, 10, 12, or 14 after initiating treatment. In an embodiment, a Crohn's disease patient who is responsive to vedolizumab has a MaRIA score of <15, <12, <10 or <7 at week 6, 10, 12, 14, respectively, globally or on a per segment basis, after initiating treatment. In an embodiment, a Crohn's disease patient who is responsive to vedolizumab has no ulceration at week 14, 22 or 26 after initiating treatment. In an embodiment, a Crohn's disease patient who is responsive to vedolizumab has no fistulae at week 14, 22, 26 or 30 after initiating treatment. A patient who is responsive to vedolizumab may continue to be treated, e.g., may continue a maintenance regimen, with vedolizumab. In one embodiment, a maintenance regimen comprises a dose of vedolizumab once every 2 weeks. In one embodiment, a maintenance regimen comprises a dose of vedolizumab once every 4 weeks. In one embodiment, a maintenance regimen comprises a dose of vedolizumab once every 6 weeks. In one embodiment, a maintenance regimen comprises a dose of vedolizumab once every 8 weeks.

Methods to determine whether a patient will respond to treatment with an anti-$\alpha4\beta7$ antibody or whether to continue treating a patient with an anti-$\alpha4\beta7$ antibody may further comprise measuring albumin concentration. In therapeutic antibody therapy, this can be a reflection of clearance activity, such as ability to bind the neonate FcR. In cases of low serum albumin levels, the anti-$\alpha4\beta7$ antibody can have a high clearance. Consequently, a patient with high serum albumin levels may not respond or may take longer to respond to treatment with anti-$\alpha4\beta7$ antibody. An albumin concentration greater than about 3.0 g/dL, about 3.2 g/dL, about 4.0 g/dL, about 4.7 g/dL, or about 5.0 g/dL, or in the range of 3.3 to 5.0 g/dL, in the range of 3.5 to 5.0 g/dL, in the range of 3.8 to 5.0 g/dL or in the range of 4.0 to 5.0 g/dL may further identify the patient for continued treatment with the anti-$\alpha4\beta7$ antibody, e.g., vedolizumab. The albumin concentration measurement may be accompanied by measurement of patient weight. A high weight patient, e.g., greater than 90 kg, greater than 100 kg, greater than 110 kg, or greater than 120 kg, with low albumin levels, e.g., less than 4.2 g/dL, less than 4.0 g/dL, less than 3.5 g/dL or less than 3.2 g/dL, may have high anti-$\alpha4\beta7$ antibody clearance and thus may not respond to therapy with the anti-$\alpha4\beta7$ antibody or may need a higher or more frequent dose of the anti-$\alpha4\beta7$ antibody for continued treatment.

The method may further comprise measuring an endoscopic subscore. Anti-$\alpha4\beta7$ antibody, e.g., vedolizumab treatment may be continued with an endoscopic subscore of less than about 3, less than about 2.5, less than about 2, between about 0-2, or less than or equal to 1.

In some embodiments, the method may further comprise assessing the levels of fecal calprotectin in the biological sample. The $\alpha4\beta7$/MAdCAM-1 axis is the main immune trafficking pathway to the gut. MAdCAM-1 is expressed during steady state to facilitate gut-selective trafficking of immune cells. Inflammation enhances expression of MAdCAM-1 but also leads to induction and enhanced expression of other integrin ligands such VCAM-1 and ICAM-1 in the gut. IBD tissues include broader and higher integrin ligand expression in inflamed vs uninflamed tissue from CD patients as well as in tissues from biologic non-responder patients vs responder patients. In line with this, high level of fecal calprotectin following induction treatment with vedolizumab is associated with non-response. Fecal calprotectin is a marker of intestinal inflammation and signifies the infiltration of neutrophils to the mucosa. This infiltration is dependent on ICAM-1 and VCAM-1. Thus, the presence of fecal calprotectin highlights the presence of redundant trafficking pathways in inflammation and its association with non-response. Combining fecal calprotectin with the anti-vedolizumab assessment, described herein, may further allow enhanced characterization of redundant trafficking in IBD patients, e.g., to facilitate early identification of patients with high risk of non-response to vedolizumab.

Fecal levels of calprotectin, a neutrophil cytosolic protein, correlate with endoscopic activity in ulcerative colitis. Typically, a non-diseased subject will have a fecal calprotectin level of less than 50 μg/g. A fecal calprotectin level greater than 50 but less than 150 μg/g may be a sign of possible mucosal inflammation, whereas fecal calprotectin levels greater than 150 μg/g is usually a sign of active inflammation. The methods described herein may further comprise measuring the fecal calprotectin concentration. Higher levels of fecal calprotectin are associated with a greater risk of relapse. Vedolizumab treatment may be continued with a fecal calprotectin concentration of less than 1500 μg/g, less 1250 μg/g, less than 1000 μg/g, less than 750 μg/g, less than 500 μg/g, less than 400 μg/g, less than 300 μg/g, less than 250 μg/g, between 200-1200 μg/g, between 350 to 800 μg/g, between 300-1000 μg/g, <50 μg/g, <100 μg/g, <150 μg/g, <200 μg/g, ≤250-499 μg/g, between 150-300 μg/g, or between 500 to 900 μg/g. Alternatively, fecal calprotectin may be reduced to less than about 50%, 45%, 40%, 35%, 30%, 25%, 20%, between 10-55%, between 10-30%, between 15-35%, between 15-45% or between 20-40% of the concentration before treatment. Fecal calprotectin in a stool sample can be measured using the PHICAL test kit (Calpro, Lysaker Norway).

Optionally, the method may further comprise measuring anti-$\alpha4\beta7$ antibody antibodies, i.e., antibodies produced by the subject as an immune response to the administered anti-$\alpha4\beta7$ antibody. A low or absent immune response to the anti-$\alpha4\beta7$ antibody, e.g., anti-vedolizumab antibody, e.g., a titer of ≤50, ≤125 or ≤575 may further identify the patient for continued treatment with vedolizumab.

Pharmacodynamic Assays

The anti-$\alpha4\beta7$ antibody, e.g., vedolizumab, bound to cells in a biological sample may be measured by any appropriate means known by those skilled in the art. In one aspect, the vedolizumab bound to cells is measured by a flow cytometry (e.g., Fluorescence-Activated Cell Sorting (FACS)), mass cytometry (CyTOF), immunohistochemistry, CITE-Seq, or oligonucleotide sequencing.

In some embodiments, the assay is a pharmacodynamic assay for measuring antigen-bound anti-$\alpha4\beta7$ antibody, or an antigen binding fragment thereof. In an embodiment, the assay measures the levels of anti-$\alpha4\beta7$ antibodies bound to cells in a biological sample. In some embodiments, the anti-$\alpha4\beta7$ antibody is detected using an anti-idiotypic antibody as described herein, which specifically binds to the anti-$\alpha4\beta7$ antibody. For example, the anti-idiotypic anti-$\alpha4\beta7$ antibody for use in the assay can be specific for, and thus bind, a variable region of the heavy and/or light chain, or antigen-binding fragment thereof, of anti-$\alpha4\beta7$ antibody (e.g., vedolizumab). In some embodiments, the anti-idiotypic antibody specifically binds to vedolizumab.

Accordingly, in one aspect, provided herein is a method of detecting vedolizumab in a biological sample comprising $\alpha4\beta7$ integrin by contacting the biological sample with an anti-idiotypic antibody or antigen-binding fragment thereof and detecting the anti-idiotypic antibody or fragment thereof bound to the vedolizumab. In some embodiments, the anti-idiotypic antibody further includes a detectable label. In some embodiments, the detectable label is selected from the group consisting of a fluorescent label, a metal label (e.g., a heavy metal isotope), a radionuclide, an oligonucleotide, horseradish peroxidase (HRP), alkaline phosphatase, galactosidase, glucoamylase, lysozyme, a saccharide oxidase, a heterocyclic oxidase coupled with an enzyme that employs hydrogen peroxide to oxidize a dye, biotin/avidin, a spin label, a bacteriophage label, and a stable free radical. A variety of methods known in the art may be used to detect the anti-idiotypic antibody (e.g., including a detectable label), such as flow cytometry (e.g., Fluorescence-Activated Cell Sorting (FACS)), mass cytometry (CyTOF), immuno-histochemistry, or oligonucleotide sequencing (e.g., Cellular Indexing of Transcriptomes and Epitopes by Sequencing (CITE-Seq, Stoeckius et al. *Nat Methods* 14:865-868 (2017))).

In another aspect, use of a pharmacodynamic assay, inhibition of MAdCAM-1-Fc binding to $\alpha_4\beta_7$-expressing peripheral blood cells by the anti-$\alpha4\beta7$ antibody, e.g., vedolizumab in the blood is used as a measure of the extent of $\alpha_4\beta_7$ saturation by the anti-$\alpha4\beta7$ antibody, e.g., vedolizumab.

In an embodiment, the anti-$\alpha4\beta7$ antibody amount in serum can be measured in a pharmacokinetic assay. An immobilized phase, such as a microtiter plate, vessel or bead is coated with a reagent which specifically binds to the anti-$\alpha4\beta7$ antibody. The immobilized reagent is contacted with a patient biological sample, e.g., serum, which may or may not comprise the anti-$\alpha4\beta7$ antibody. After incubation and washing, the anti-$\alpha4\beta7$ antibody complexed to the coating reagent is contacted with a reagent which binds to the captured antibody and may be detected, e.g., using a label such as horseradish peroxidase (HRP). The binding reagent may be an anti-human antibody, e.g., polyclonal or monoclonal, which binds to the Fc portion of the anti-$\alpha4\beta7$ antibody. Addition of an HRP substrate, such as 3,3',5,5'-tetramethylbenzidine (TMB), can allow signal accumulation, such as color development, that can be measured, e.g., spectrophotographically.

In certain embodiments, anti-idiotypic antibodies 6D8, 4D5, and/or 3110 are used in a pharmacokinetic assay described herein. Each of these anti-id antibodies showed strong signals in an ELISA assay as described in Example 2 below.

In some embodiments, the coating reagent is an anti-idiotypic antibody as described herein which specifically binds to the anti-$\alpha4\beta7$ antibody, e.g., vedolizumab, or an antigen binding fragment thereof. The anti-idiotypic anti-$\alpha4\beta7$ antibody for use in the assay can be specific for, and thus bind, a variable region of the heavy and/or light chain of anti-$\alpha4\beta7$ antibody, e.g., heavy chain variable region (SEQ ID NO: 78) and/or light chain variable region (SEQ ID NO: 82) of vedolizumab. The anti-idiotypic anti-$\alpha4\beta7$ antibody for use in the assay can be specific for, and thus bind, an antigen-binding fragment of the anti-$\alpha4\beta7$ antibody. Examples of MAdCAM reagents and fusion proteins are described in PCT publication WO 96/24673 and U.S. Pat. No. 7,803,904, the entire teachings of which are incorporated herein by reference.

In an embodiment wherein the patient generated anti-vedolizumab antibodies during treatment, anti-vedolizumab antibodies in the biological sample can interfere with the vedolizumab binding to standard capture reagents and/or contribute to the quantities detected by an anti-human IgG detection reagent, which may lead to inaccurate measurements. In this embodiment, both the coating reagent and the labeled detection reagent can be an anti-idiotypic antibody as described herein.

Methods for Assaying HAHA

Human anti-human antibody activity (HAHA), e.g., the mounting of an immune response to an anti-$\alpha4\beta7$ antibody such as vedolizumab, can be determined by detecting and/or measuring anti-drug antibodies (ADAs), e.g., antibodies specific to the anti-$\alpha4\beta7$ antibody vedolizumab (i.e., anti-vedolizumab antibodies). Formation of ADAs may be associated with increased clearance and reduced efficacy of treatment. In some embodiments, ADAs can affect, e.g., reduce, the therapeutic response to the biotherapeutic agent.

ADAs can be distinguished from anti-idiotypic antibodies provided herein because ADAs are human antibodies and can be detected by anti-human antibody reagents, whereas anti-idiotypic antibodies can be from another species, such as mouse, rabbit, goat, chicken, rat, sheep, etc., and can be detected by reagents targeting such other species.

To detect and/or measure ADAs, immunoassays such as an enzyme-linked immunosorbent assay (ELISA) or an electrochemiluminescence assay (i.e., an ECL assay or ECLIA) may be performed. Drug-tolerant electrochemiluminescence assays (e.g., based on the Meso Scale Discovery (MSD) platform (Rockville, MD)) may also be used to detect ADA titers in the presence of vedolizumab concentrations in serum samples.

Anti-idiotypic antibodies like those described herein or made using techniques described herein, can be used in assays, e.g., immunoassays, to detect and/or measure ADAs, including neutralizing antibodies, against vedolizumab (i.e., assess a human anti-human antibody (HAHA) response in a patient). Anti-idiotypic antibodies provided herein can be attached or fused to a tag such as biotin or histidine for analytic detection. Other ways of detecting or labeling an anti-idiotypic antibody for detection are described herein.

There are a number of options, for example, using a screening and titration assay, a confirmation assay, and/or a neutralizing assay, to assess a HAHA response (or lack thereof) resulting from ADAs in a sample, e.g., a serum sample, from a patient who was administered vedolizumab. For example, serum samples can be measured first in the screening sample at dilutions, for example, 1:5 and 1:50. Positive samples can be confirmed for specificity, titered, and examined for the ability to neutralize anti-$\alpha4\beta7$ antibody, e.g., inhibit vedolizumab activity.

A screening assay can use, for example, a bridging ELISA in which the plate is coated with the anti-$\alpha4\beta7$ antibody, i.e., vedolizumab. The immobilized anti-$\alpha4\beta7$ antibody captures ADAs in the test sample, where the ADAs are bound by an anti-$\alpha4\beta7$ antibody conjugated to biotin, which is tagged by horseradish peroxidase (HRP)-labeled streptavidin, then detected with an enzymatic substrate, such as TMB. A positive color development, e.g., as measured in a micro-plate reader, such as Spectramax, with analytical software, such as SOFTMAX Pro3.1.2, indicates the presence of ADAs in the sample. The assay cut point, e.g., in biotin-avidin-HRP based bridging assay, can be determined by using normal human serum samples as negative controls. The mean absorbance values of the 10 negative control serums can be added to 1.65 times the standard deviation of the negative controls to determine the cut point. Thus, the cut point can allow for approximately a 5% false positive rate. In the presence of 1 µg/mL vedolizumab, low titer responses are interfered with such that they may become undetectable, although high levels of immunogenicity are detectable at vedolizumab concentrations greater than 1

µg/mL. For example, while the standard assay sensitivity can be 0.44 ng/ml, in the presence of 0.5 µg/ml vedolizumab, the sensitivity of the assay can be 180 ng/ml. For these reasons, serum samples can be taken greater than 4 weeks, greater than 8 weeks, greater than 12 weeks or greater than 16 weeks after the final dose of anti-α4β7 antibody. With a longer time period between the prior dose and the sampling, serum drug levels typically can be below the interference level.

In certain embodiments, detection of the ADAs can be performed by contacting a plate that contains immobilized vedolizumab with an anti-idiotypic antibody, such as an anti-idiotypic antibody described herein, and measuring competition of the anti-idiotypic antibody to binding of immobilized vedolizumab with ADAs in the sample. The anti-idiotypic antibody can be labeled to measure the presence and/or level of the ADAs.

Another assay method uses streptavidin coated plates, biotin-labeled anti-α4β7 antibody anchored to streptavidin coated vessels, beads or microtiter plates for the immobilized side of the bridge and heavy metal, such as ruthenium, osmium or rhenium-labeled (e.g., via a sulfo tag) anti-α4β7 antibody for the other side of the bridge. The bridged complex can be built on the plate by stepwise additions and washes between or in solution, with both sides of the bridge contacting diluted serum sample, then transferred to the plate. An example of an assay using this method has a sensitivity of 3.90 ng/ml anti-anti-α4β7 antibody. Detection of the heavy metal labeled bridge complex, e.g., a ruthenium-labeled complex, by electrochemiluminescence (ECL), e.g., in an Meso Scale Discovery Sector Imager 6000 (Rockville, MD), may be more sensitive than an HRP method and/or have higher tolerance to the amount of anti-α4β7 antibody in the serum. Thus there would not be a need to wait for a delayed sample after the serum drug level lowers. In some embodiments, pretreatment of the serum sample with acid, e.g., acetic acid or low pH glycine, to release the anti-α4β7 antibody from the patient-derived anti-anti-α4β7 antibodies prior to contacting with the bridging anti-α4β7 antibodies can reduce the interference from the drug in the serum. For example, while the standard assay sensitivity can be 3.90 ng/ml, in the presence of 5 µg/ml vedolizumab in serum, the sensitivity of the assay can be 10 ng/ml.

In one embodiment, an assay to detect anti-vedolizumab antibodies (ADAs) in a sample of serum from a patient comprises diluting serum by a standard dilution factor, such as 1:5, 1:25, 1:50, and/or 1:125; treating with acetic acid; combining the acid treated diluted sample with an assay composition comprising a high pH reagent, such as high concentration TRIS buffer for neutralizing the acid, a biotin-labeled vedolizumab and a ruthenium-labeled vedolizumab for a time sufficient to form a bridge with serum-derived anti-vedolizumab antibodies between the two tagged versions of vedolizumab; transferring the complexes to a streptavidin-coated plate; washing the plate so only ruthenium complexed by the antibody bridge is present. Detection of the bound ruthenium-labeled complex and measuring the sample by electrochemiluminescence in the microplate reader can be achieved by adding a read solution such as tripropylamine and applying voltage to stimulate the ruthenium label complexed to the plate via the antibody bridge.

Some antibodies produced by HAHA responses may be anti-idiotypic antibodies. These antibodies may neutralize the therapeutic anti-α4β7 antibody by binding to its epitope binding region in the patient, e.g., in circulation or lymphatic system. In one embodiment, the assay method measures the presence of neutralizing antibodies in the patient serum samples. In this method, the assay comprises capturing ADAs on a streptavidin-plate coated with biotinylated anti-α4β7 antibody, e.g., vedolizumab. Through excess washing and acid treatment, the bound ADA is released from the streptavidin plate. The released ADA is preincubated with the heavy metal-bound, e.g., sulfo-rhodamine tagged anti-α4β7 antibody and then transferred to another plate, e.g., coated with α4β7 integrin, for detection. If ADAs are present in the serum, they will compete the heavy metal-bound anti-α4β7 antibody from binding to the second integrin-coated plate and lower the plate signals compared to the negative control, with no ADA present. An example of this assay can detect 80 ng/ml of neutralizing ADAs in the presence of 5 µg/ml anti-α4β7 antibody.

Anti-idiotypic antibodies described herein can be used to quantify ADAs bound to vedolizumab in a sample from a patient treated with vedolizumab. A biological sample comprising vedolizumab bound to ADAs can be contacted with anti-idiotypic antibody described herein. The biological sample can be a serum sample, and may comprise vedolizumab bound to ADAs if the patient had a HAHA response. In certain instances, an anti-idiotypic antibody can be incubated with a sample from a patient and subsequently will bind vedolizumab which is bound to ADAs. In such an instance, the anti-idiotypic antibody is a non-blocking, e.g., non-neutralizing antibody. The resulting complex can be detected by size exclusion chromatography or electrophoretic methods; such complexes will be multimeric in size, compared to smaller complexes of, e.g., anti-idiotypic antibodies bound to free vedolizumab. The multimeric complex and the determined levels thereof can be compared to a reference standard e.g., vedolizumab in samples from patients who do not generate ADAs following administration of vedolizumab or a sample from a person who did not receive vedolizumab. The presence or quantity of the complexed ADA/anti-idiotypic antibody (e.g., non-blocking)/vedolizumab complex can be determined according to standard means.

A HAHA assay for measuring neutralizing ADAs can include measuring α4β7 expressing cells from vedolizumab treated patients. An anti-idiotypic antibody, like those described herein, is immobilized on a plate and used to capture cells in a sample from a patient who was administered vedolizumab. A baseline or pre-determined value can be established for a patient who does not have ADAs. Immobilized anti-idiotypic antibody can be used to then capture vedolizumab bound to cells from a patient sample, where the anti-idiotypic antibodies will not capture vedolizumab if vedolizumab is bound by neutralizing ADA(s) (neutralizing ADAs prevent binding of vedolizumab to cells). The presence of neutralizing ADAs could be quantified by determining the number (or signal) of cells (from a patient sample) bound to the plate containing immobilized anti-idiotypic antibody and determining the difference or similarity between a baseline or a predetermined value representing a patient without a HAHA response. In one embodiment, if the number of bound cells is less than the baseline or predetermined value neutralizing ADAs would be present in the sample.

Another assay format for detecting ADAs to vedolizumab (and thereby assessing HAHA responses) is a competition assay (i.e., a binding hindrance assay). The competition assay measures the ability of ADAs in a biological sample to compete with an anti-idiotypic antibody for binding to an anti-α4β7 antibody, such as vedolizumab. The biological sample may be serially diluted to assess competition at different concentrations of ADAs with the anti-idiotypic antibody. In one embodiment, a biological sample taken from a patient treated with an anti-$\alpha4\beta7$ antibody is incubated with quantities of vedolizumab and a labeled anti-idiotypic antibody, or an antigen-binding fragment thereof, with binding specificity to vedolizumab. If ADAs are present in the sample, then they will compete for binding to vedolizumab with a labeled anti-idiotypic antibody like those described herein, and their presence will result in lower detectable signal compared to the negative control with only the labeled anti-idiotypic antibody.

In one embodiment, anti-idiotypic antibodies, like those described herein, can be used to detect vedolizumab in a competition assay between ADAs and vedolizumab for $\alpha4\beta7$ in an assay to determine the presence or level of ADAs in a sample from a patient who was administered vedolizumab. In a competition assay for binding to $\alpha4\beta7$, neutralizing ADA would compete for binding to $\alpha4\beta7$ with vedolizumab. Vedolizumab could then be detected and measured using an anti-idiotypic antibody, like those described herein. Alternatively, $\alpha4\beta7$ expressing cells could be used, such as RPMI8866 cells. The level of vedolizumab bound to $\alpha4\beta7$ could be measured to a positive control, such as a person who has not been administered vedolizumab (so would not have ADAs). A decrease in bound vedolizumab as measured by a labeled anti-idiotypic antibody, like those described herein, would indicate presence of ADAs. Quantification of ADAs could also be determined using this $\alpha4\beta7$ binding competition assay.

Fluorescence-activated cell sorting (FACS) or flow cytometry may be used to detect different subsets of cells bound to the labeled anti-idiotypic antibody. Examples of detectable labels that may be used include, but are not limited to, an oligonucleotide, horseradish peroxidase (HRP), alkaline phosphatase, galactosidase, glucoamylase, lysozyme, a saccharide oxidase, a heterocyclic oxidase coupled with an enzyme that employs hydrogen peroxide to oxidize a dye, biotin/avidin, a spin label, a bacteriophage label, and a stable free radical.

In certain embodiments, a cocktail of anti-idiotypic antibodies, like those described herein, is used in a HAHA assay, or other assay, described herein. Anti-idiotypic antibodies can bind to different epitopes on vedolizumab, e.g., antibody N17 vs. antibodies B4, D5, D8, and J24.

The results from a HAHA assay can indicate categories of immunogenicity status: Negative: no positive HAHA sample; Positive: at least 1 positive HAHA sample; Transiently positive: at least 1 positive HAHA sample and no consecutive positive HAHA samples; and Persistently positive: at least 2 or more consecutive positive HAHA samples. Negative patients are likely to respond to anti-$\alpha4\beta7$ antibody and can continue being treated with the antibody. Persistently positive patients are likely to have high clearance of anti-$\alpha4\beta7$ antibody and may not respond to anti-$\alpha4\beta7$ antibody treatment. Positive patients may have high clearance of anti-$\alpha4\beta7$ antibody and may not respond to anti-$\alpha4\beta7$ antibody. Positive patients can have an additional serum sample 2, 3, 4, 5 or 6 weeks after another dose of anti-$\alpha4\beta7$ antibody to determine if they are persistently positive or transiently positive. Transiently positive patients are likely to respond to anti-$\alpha4\beta7$ antibody treatment and treatment of these patients can be continued.

Titers of immunogenicity levels also may be determined. Titer categories include $\geq5$ (low), $\geq50$, $\geq125$, $\geq625$ and $\geq3125$ (high). A patient with a high titer in a positive sample may have high clearance of anti-$\alpha4\beta7$ antibody and may not respond to anti-$\alpha4\beta7$ antibody treatment. A patient with a low titer in a positive sample may respond to anti-$\alpha4\beta7$ antibody treatment.

The anti-idiotypic antibodies described herein may also be used as calibrators to generate standard curves for ELISA or ECL assays designed to detect and/or measure ADAs to vedolizumab in a biological sample. For example, after coating a microtiter plate with anti-$\alpha4\beta7$ capture antibodies and performing a blocking step, dilutions from a dilution series covering a range of concentrations of the anti-idiotypic antibody (e.g., 0.1 ng/ml to 10,000 ng/ml) can be added to the wells, and imaged using a fluorescently-labeled anti-$\alpha4\beta7$ detection antibody to generate standard curves of fluorescence as a function of anti-idiotypic antibody concentration. Following the generation of the standard curves, the ELISA or ECL assays can be used to detect and/or measure ADAs to vedolizumab in patient samples compared to a known level.

The non-blocking anti-idiotypic antibodies described herein may also be used in pharmacokinetic (PK) assays to measure total vedolizumab serum concentration in a sample taken from a patient treated with vedolizumab. As used herein, total vedolizumab serum concentration refers to free, partially bound, and fully bound vedolizumab. Specifically, in standard PK assays, the presence of neutralizing antibodies in the sample or the presence of vedolizumab bound to an antigen may interfere with the detection of total vedolizumab in a PK assay. By using a non-blocking anti-idiotypic antibody to vedolizumab as a capture antibody in an immunoassay such as an ELISA, vedolizumab bound to a neutralizing antibody or antigen can still be captured, including without requiring an acid dissociation step.

In one aspect, an anti-idiotypic antibody may be included in a kit with instructions for detecting and/or measuring ADAs in a biological sample. The assays to detect and/or measure ADAs may be performed at baseline prior to vedolizumab administration and/or at post-initial dose time points, including but not limited to weeks 2, 4, 6, 12, 24, 26, 36, 48, and 52.

An enzyme immunoassay (EIA) method may be used to measure ADAs in patient who was administered vedolizumab.

A separate, drug-tolerant electrochemiluminescence immunoassay (ECLIA) method for detecting ADAs to vedolizumab may also be used to determine the HAHA response in a patient undergoing vedolizumab treatment. With the ECLIA method, samples can be classified as either positive or negative for ADAs to vedolizumab without the need for the inconclusive category.

In certain instances, a multi-tiered strategy consisting of screening assay, confirmation assay, titration assay and neutralizing assay may be performed for the evaluation of immunogenicity and HAHA in a patient. Serum samples may be evaluated for ADA presence and ADA titer using a screening cut point, a confirmatory cut point, and a titration cut point. Serum samples may further be evaluated for neutralizing ADA presence using a neutralizing cut point. For example, the presence of ADAs using a validated electrochemiluminescence assay with a tiered approach of screening, confirmation, and titer/quantitation may be used. ADA-positive samples can be those that tested positive at both screening and confirmation, and have an ADA titer of a determined value. Confirmed ADA-positive samples can then be tested for neutralizing ADAs using a validated cell-based bioassay with a tiered approach of screening and titer/quantitation. Neutralizing antibody-positive samples can be those that tested positive at screening and had an neutralizing antibody titer of a determined value. The criteria for defining positive and negative results can be established as cut points during method validation against ADA and neutralizing ADA assays.

Transient ADA response can be defined as having treatment-induced ADA detected at at least two sampling time points during treatment (including the follow-up period), where the first and last ADA-positive samples (regardless of any negative samples in between) are separated by a given time, e.g., 2 weeks, 4 weeks, 8 weeks, and the patient's last sampling time point was ADA-negative.

In one embodiment, ADAs may be detected using a validated electrochemiluminescent bridging assay with acid dissociation. ADA-positive samples can undergo further analysis to confirm the specificity of binding and to quantify ADA titer. If a sample is confirmed positive for specific ADAs, the presence of neutralizing antibodies can be determined. A validated electrochemiluminescent assay with affinity capture elution can be used to measure neutralizing ADA activity in human serum.

Immunogenicity assessments using anti-idiotypic antibodies and non-blocking anti-idiotypic antibodies as reagents can also include monitoring for the development of ADAs, including neutralizing ADAs, in a human patient. Immunogenicity can be analyzed as either an "emergent" response, e.g., ≥1 positive ADA result up to week 24 among patients negative for ADAs at baseline) or a "boosted" response (ADAs with increased titers at any time compared with baseline). ADAs can be detected using Meso Scale Discovery electrochemiluminescence bridging, in which, e.g., an SB5 single-tagged immunoassay is utilized. Anti-drug antibody levels can be measured at a determined time point, e.g., 0 (baseline), 2, 6, 8, 10, 14, 16, 18, and so forth.

IV. Kits

In one aspect, an anti-idiotypic antibody may be provided in a kit with instructions for measuring anti-α4β7 antibody amounts in a biological sample. The sample may have been obtained from a patient undergoing treatment for IBD. The kit can also contain a control or reference sample or a series of control or reference samples which can be assayed and compared to the test sample. For example, the kit may have a positive control sample, e.g., including standard anti-α4β7 antibody described herein, to standardize the assay among samples or timepoints. By way of example, the kit may comprise fluids (e.g., buffer) suitable for binding the anti-idiotypic antibody with the anti-α4β7 antibody and one or more sample compartments. The kit can contain reagents to reduce the amount of non-specific binding of non-anti-α4β7 antibody material from the sample to the anti-idiotypic antibody. Examples of reagents include nonionic detergents, non-specific protein containing solutions, such as those containing albumin or casein, or other substances known to those skilled in the art. The kit of the invention may optionally comprise additional components useful for performing the methods of the invention, e.g., a sample collection vessel, e.g., a tube, and optionally, means for optimizing the amount of anti-α4β7 antibody detected, for example if there may be time or adverse storage and handling conditions between the time of sampling and the time of analysis. For example, the kit can contain means for increasing the relative amount of antibody in the sample, such as a protein A reagent, a buffering agent, a preservative, a stabilizing agent or additional reagents for preparation of cellular material or probes for use in the methods provided; and detectable label, alone or conjugated to or incorporated within the provided anti-idiotypic antibody. If the assay is a sandwich assay, the kit may comprise a second antibody, such as an anti-human IgG antibody, optionally conjugated to a label, for binding the anti-α4β7 antibody after it binds to the anti-idiotypic antibody for subsequent detection and/or measurement. In one exemplary embodiment, a kit comprising a sample collection vessel can comprise e.g., a tube comprising anti-coagulant and/or stabilizer, as described above, or known to those skilled in the art. The kit can further comprise components necessary for detecting the detectable label (e.g., an enzyme or a substrate). Kits also can include instructions for interpreting the results obtained using the kit.

EXAMPLES

The following examples are offered for illustrative purposes only, and are not intended to limit the scope of the present invention in any way. Commercially available reagents referred to in the example were used according to manufacturer's instructions unless otherwise indicated.

Example 1. Generation and Characterization of Anti-Idiotypic Antibodies Against Anti-α4β7 Antibody Vedolizumab The immunogen for immunizing mice to obtain an anti-vedolizumab was prepared using pepsin digestion. Briefly, 100 µg of vedolizumab and human IgG was buffer exchanged to sodium acetate buffer pH 4.2. A 1:20 weight ratio (pepsin/IgG) of pepsin was added to both samples and aliquoted as 20 µL aliquots. The aliquots were incubated at 37 degrees Celsius for various times. The aliquots were quenched by adding 1/10 volume of 1M Tris-HCl pH 9.0. About 3 µg were loaded on SDS-PAGE (non-reducing (NR)). Human IgG was completely digested by 1:20 w:w ratio of pepsin after 2 hrs of incubation. Vedolizumab was completely digested by 1:20 w:w ratio of pepsin after more than 3 hrs incubation. Under non-reduced SDS-PAGE there is a large molecular aggregate when vedolizumab was digested by pepsin likely due to the oligomerization of the (Fab)2. F(ab)2 of vedolizumab appeared as a smear on NR SDS-PAGE. This process was repeated with 100 µg of vedolizumab. Again, complete digestion was observed after 3 hours.

Endotoxin measurements confirmed all samples obtained from pepsin digestion were <5 EU/mg. The final yield was 2.62 mg of vedolizumab F(ab')2. The F(ab')2 was confirmed to bind α4β7-His by ELISA.

Ten Penta mice were hyperimmunized with the F(ab')2 vedolizumab fragments. Specifically, mice were hyperimmunized in each hind footpad and intraperitoneally with anti-α4β7-F(ab')2 in an adjuvant according to the methods known in the art (for example, E Harlow, D. Lane, Antibody: A Laboratory Manual, (Cold Spring Harbor Laboratory Press, Cold Spring Harbor, N.Y., 1998). After boosts, serum titers were evaluated by standard enzyme-linked immunosorbent assay (ELISA) to identify mice with positive serum titers to the anti-PDL1 antibody. B cells from spleens and popliteal lymph nodes were fused with mouse myeloma cells (X63.Ag8.653 or P3X63Ag.U1; American Type Culture Collection, Manassas, VA, USA) by electrofusion (Hybrimune-Hybridoma Production System; Harvard Apparatus, Inc., Holliston, MA, USA). After the final boost and fusion were performed for selected mice. After 10-14 days, hybridoma supernatants were harvested and screened for CDR specific antibody production by ELISA. Fused hybridomas were plated on 10×384 well plates, and the fusion efficiency was 4.4 hybridomas per well. The primary screen was performed by ELISA against vedolizumab (1 μg/mL). 96 hybridomas were selected from the primary screen using a cutoff value of 900,000 RLU. The confirmation ELISA screen was performed for 96 hybridomas against

76 firmed and isotyped by ELISA prior to purification. mRNA sequencing samples were generated for confirmed 'A' clones.

Isotyping was performed by ELISA for each 100 mL scale-up and a single heavy chain and light chain isotype was determined as shown below in Table 2.

TABLE 2

|  | IgG1 | IgG2a | IgG2b | IgG2c | IgG3 | kappa | lambda | IgG | Isotype |
|---|---|---|---|---|---|---|---|---|---|
| 15529-2-B4-A | 5194.5 | 998647.5 | 934.5 | 15134.5 | 1953.5 | 818693 | 261.5 | 579443.5 | IgG2a K |
| 15529-2-I3-A | 4429.5 | 6252.5 | 1000071 | 1876 | 4567.5 | 999986 | 411 | 727636.5 | IgG2b K |
| 15529-2-I8-A | 466641.5 | 5423.5 | 6559.5 | 179 | 4962.5 | 1000067 | 328.5 | 345613.5 | IgG1 K |
| 15529-3-I10-A | 2444.5 | 5317 | 1000071 | 2502 | 5867 | 1000071 | 313 | 765135 | IgG2b K |
| 15529-4-D5-A | 548151.5 | 4601 | 1088.5 | 249.5 | 5962 | 1000070 | 244 | 404447.5 | IgG1 K |
| 15529-4-J24-A | 567 | 5813 | 1000070 | 1779.5 | 5488 | 145355 | 349.5 | 667459 | IgG2b K |
| 15529-5-N17-A | 655.5 | 5608.5 | 1000071 | 1968 | 7663.5 | 1000071 | 451.5 | 739548 | IgG2b K |
| 15529-6-C13-A | 294.5 | 5142.5 | 1000071 | 1586 | 4271 | 1000064 | 363 | 751684.5 | IgG2b K |
| 15529-6-D8-A | 467713.5 | 3412 | 856.5 | 175.5 | 8427.5 | 852073 | 148.5 | 246304.5 | IgG1 K | vedolizumab (1 μg/mL). The top 95 hybridomas were selected for expansion and cryopreservation.

HT Hock immunization with anti α4β7 F(ab')2 Initiated on day 0 in the PentaMice Platform described above. Titer from the selected mice was confirmed, and fusion was performed on day 26 to produce hybridoma cells. Lymphocytes for fusion were pooled (35M needed) and the fusion material were plated in 8×384 well plates.

To clone out antibody sequences of hybridoma cells for recombinant antibody production, total RNA isolated from cultured hybridoma cells was used for generating cDNA, the PCR template for antibody variable region amplification. The oligos used for PCR are based on mouse V-gene and J-gene germline sequences. In order to subclone PCR products directly to the mammalian expression vectors, flanking vector sequences were appended in the 5'- and 3'-end of forward and reverse primers respectively. The variable regions of heavy and light chain were amplified separately with pooled germline oligos, PCR products were visualized on DNA gel to confirm a single band at expected size (400 bps for heavy chain and 350 bps for light chain).

10 hybridomas were selected for subcloning to identify monoclonal antibodies against vedolizumab. Briefly, cells were plated at a 1 cell per well density in 384 well plates, confirmed by microscopy, and expanded. After expansion, supernatants were screened by ELISA against vedolizumab. Plate coated with 1 μg/mL vedolizumab. Parental hybridoma supernatants (collected post thaw) were included for comparison. From the clone screen, 2 independent clones ('Clone A' and 'Clone B') were identified for 7 of 10 hybridomas. A single clone ('Clone A') was identified for 1 hybridoma: 15529 2 I8. A second round of subcloning was performed to identify stable subclones for 3 hybridomas. As shown in FIG. 1, in the second round, clones were identified for 2 hybridomas. 'A' and 'B' clones were identified for 2 J3, and a 'B' clone was identified for 2 I8. Stable subclones could not be identified for the hybridoma 3 F3. 'A' and 'B' clones were cryopreserved. The 'A' clones were expanded to generate saturated supernatants (100 mL) and were con- Purification of each antibody was performed using Protein A resin. 100 mL scale-ups from 9 clonal hybridomas were subjected to Protein A purification using a batch method.

Figure 2:
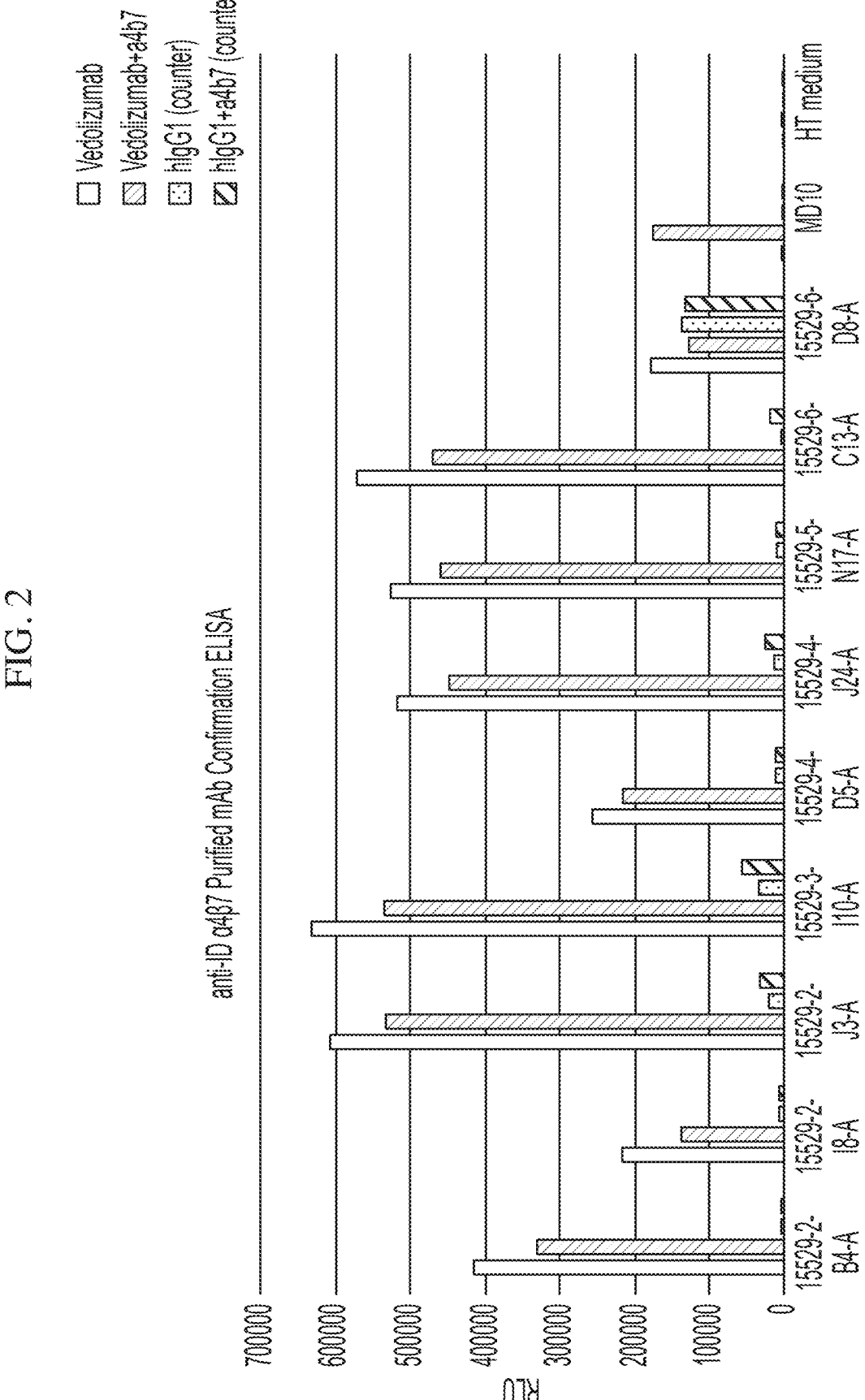
FIG. 2 shows ELISA binding data of the unlabeled anti-idiotypic monoclonal antibodies purified from hybridomas to vedolizumab and vedolizumab-α4β7 complex.

Monoclonal antibodies (mAbs) purified from hybridomas were assessed by ELISA for binding to vedolizumab and vedolizumab-α4β7 complex. Purified mAbs were counter screened against human IgG1 isotype control antibody in the presence and absence of α4β7 protein. Hybridoma medium and a control anti-His antibody (MD10) were included as controls. As shown in FIG. 2, one mAb (6-D8-A) showed non-specific binding to hIgG1 but all other mAbs had clean anti-idiotype profile in this screen.

mAbs (pre- and post-labeling with Fluoroscein) were assessed by ELISA for binding to vedolizumab and vedolizumab-α4β7 complex. Three mAbs were selected for labeling with fluorescein. mAbs were counter screened against natalizumab in the presence and absence of α4β7 protein. Hybridoma medium and a control anti-His antibody (MD10) were included as controls. ELISA binding was retained post-labeling with fluorophore.

Example 2: ELISA and FACS Screening of Anti-Idiotypic Antibodies

The following experiments determined the ability of the anti-idiotypic antibodies identified in Example 1 to bind α4β7 antibody vedolizumab, or fragment thereof, in an ELISA.

The primary screen was performed by ELISA against vedolizumab (1 μg/mL). 96 hybridomas were selected from the primary screen using a cutoff value of 900,000 RLU. The confirmation ELISA screen was performed for 96 hybridomas against vedolizumab (1 μg/mL). The top 95 hybridomas were selected for expansion and cryopreservation. The ELISA procedure is well known to a person of skill in the art. Briefly, plates were coated with either vedolizumab or with purified human IgG1 isotype control recombinant antibody (1 mg, Biolegend #403502) at 1 μg/mL at 37° C. 1 hr. Recombinant human integrin alpha 4 beta 7 protein, CF (0.5 mg, R&D Systems 5397 A3) was added to half of the vedolizumab coated plate and to half of the huIgG1 coated plate and the remaining wells not treated with α4β7. The supernatant was added to the wells and incubated for 1 hr (HT medium, irrelevant supernatant and PBS as negative control). The plates were washed and then blocked for 1 hr at room temperature. All washes were performed using PBS-Tween (0.05%). Anti HIS HRP was used for α4β7 binding control. Serial dilutions of α4β7-His were tested, starting from 30 µg/mL, 3-fold down and up to 11 dilutions. Plates were then washed before adding HRP-His and incubating for 1 hr at room temperature. The plates were again washed before adding the substrate. Mouse anti-mouse IgG 1-HRP (horseradish peroxidase) was used for detection and incubated for 1 hour at RT. The wells were then read by a luminescent plate reader.

The top 96 clones were selected in the primary screen using a cutoff value of >900,000. A confirmation ELISA screen was performed for 96 hybridomas against vedolizumab (1 µg/mL). 95 of 96 hybridomas were selected for cryopreservation and saturated supe generation. The F(ab')2 and full-length vedolizumab were confirmed to bind α4β7-His by ELISA.

FACs screening of the mAbs was also performed. These experiments were to determine the ability of the produced anti-idiotypic antibodies to bind α4β7 antibody or fragment thereof. FACS screening was used to determine the ability of the anti-idiotypic antibodies described herein to bind α4β7 antibody or fragment thereof on the surface of HuT78 cells (human T-cell lymphoma cell line) expressing α4β7.

(ATCC CRM TIB 161). The supernatant was added to the wells and incubated for 1 hr (HT medium, irrelevant supernatant and FACS buffer as negative control). Mouse anti-mouse IgG 1-HRP (horseradish peroxidase) was used for detection and incubated for 1 hour at RT. HRP. Anti human HRP was used as a cell binding control. The wells were then read by FACS.

Figure 3A:
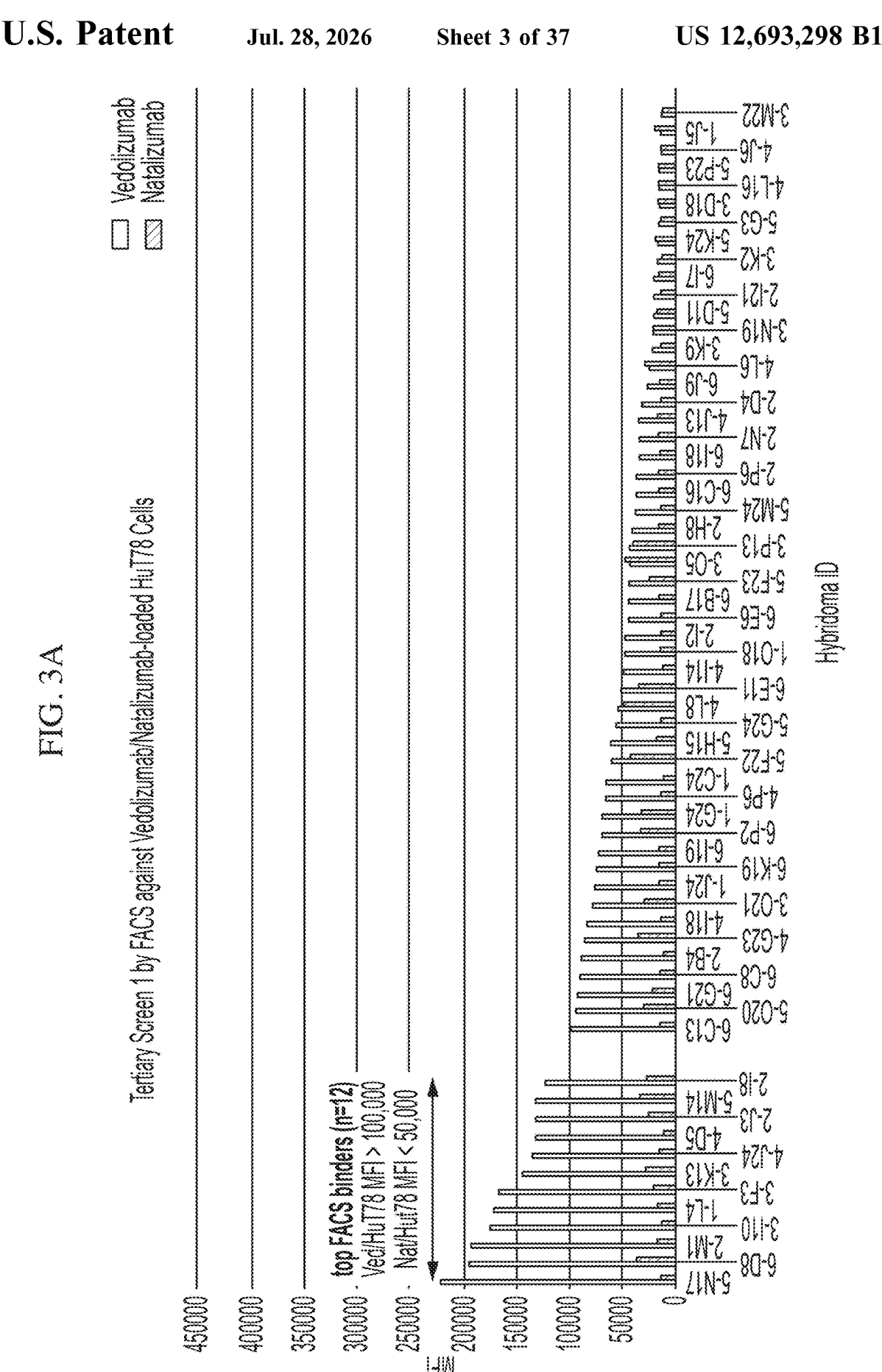
Figures 1, 3A:
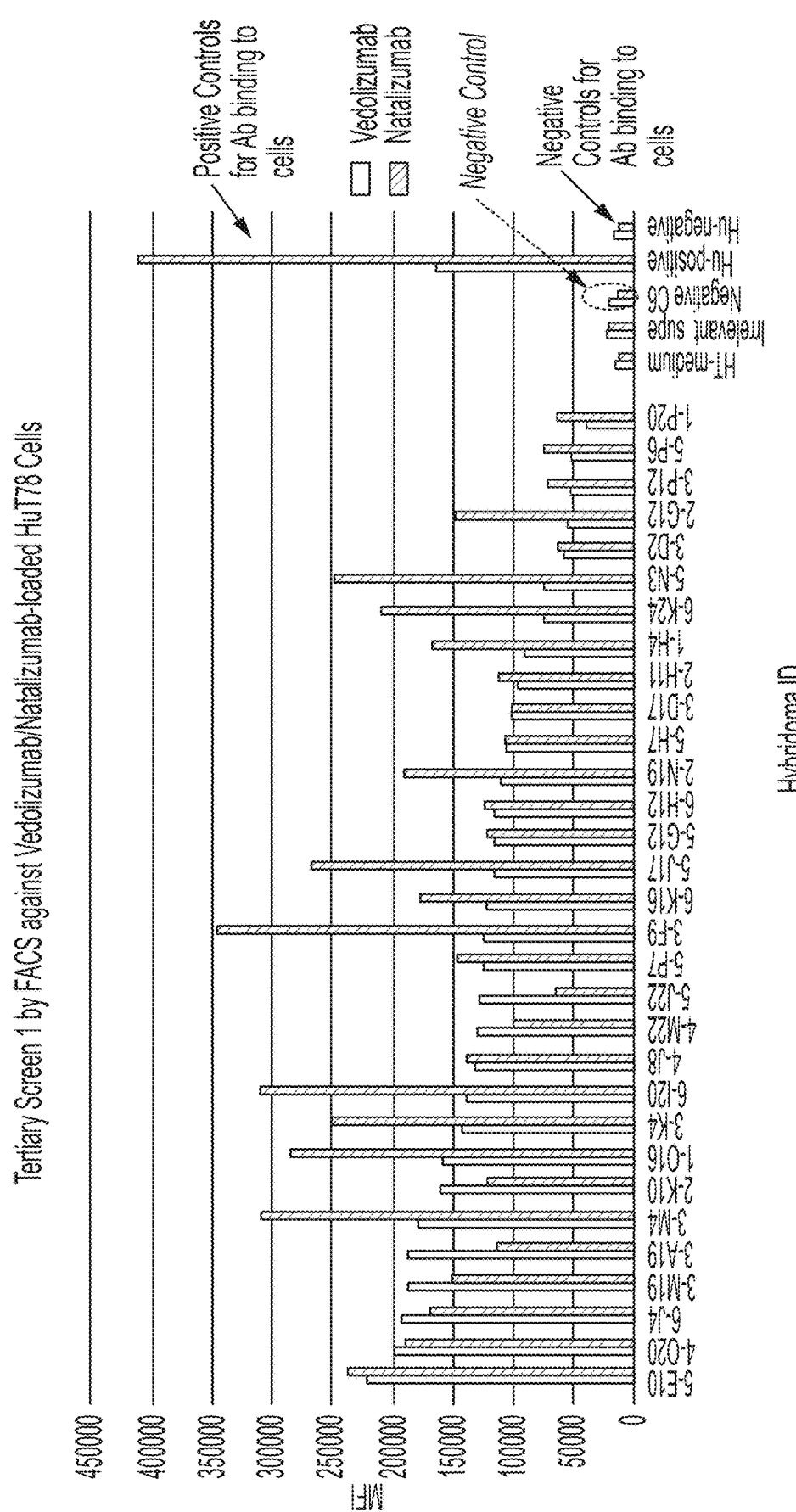
Figure 3B:
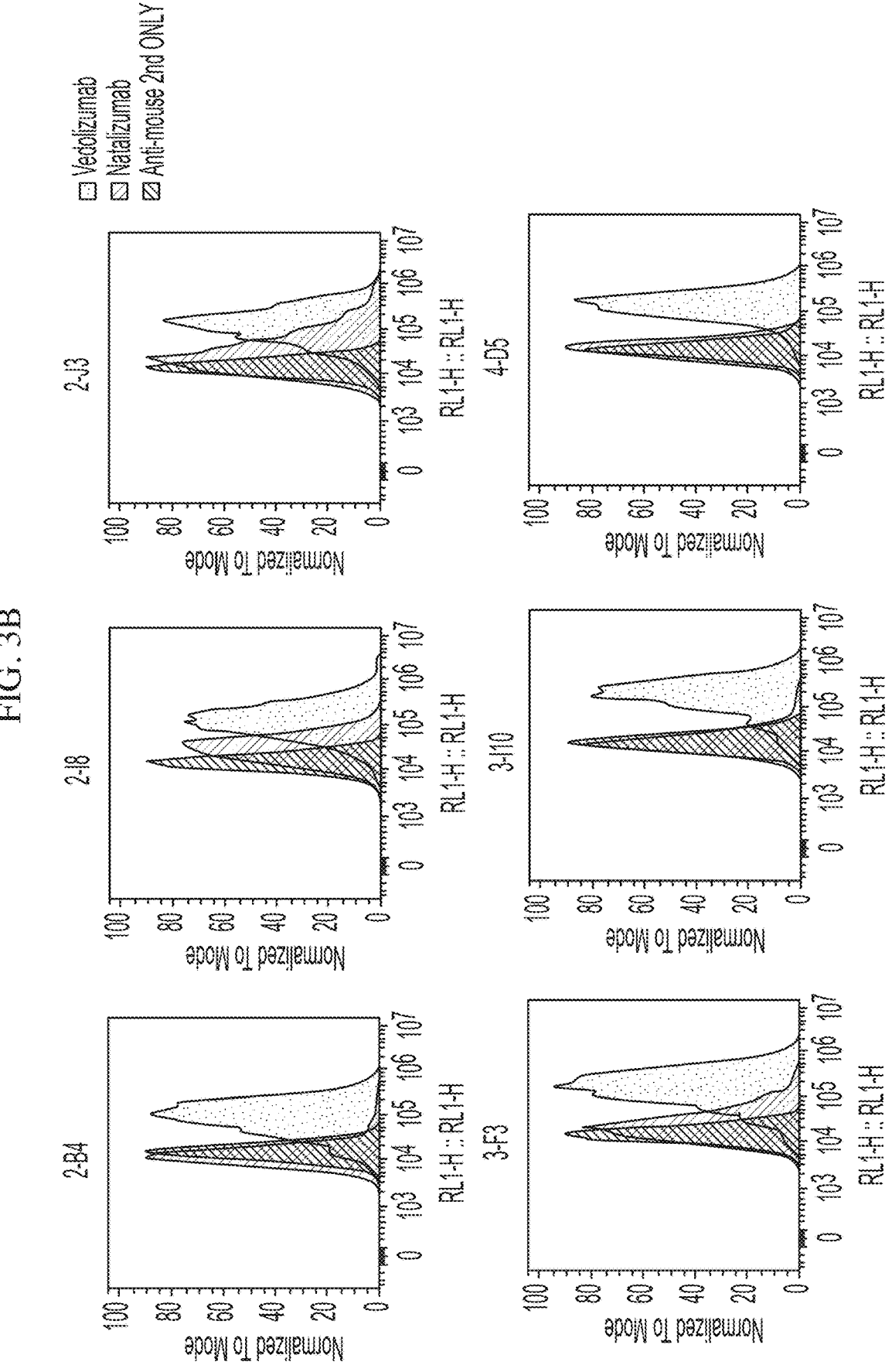
Figures 1, 3B:
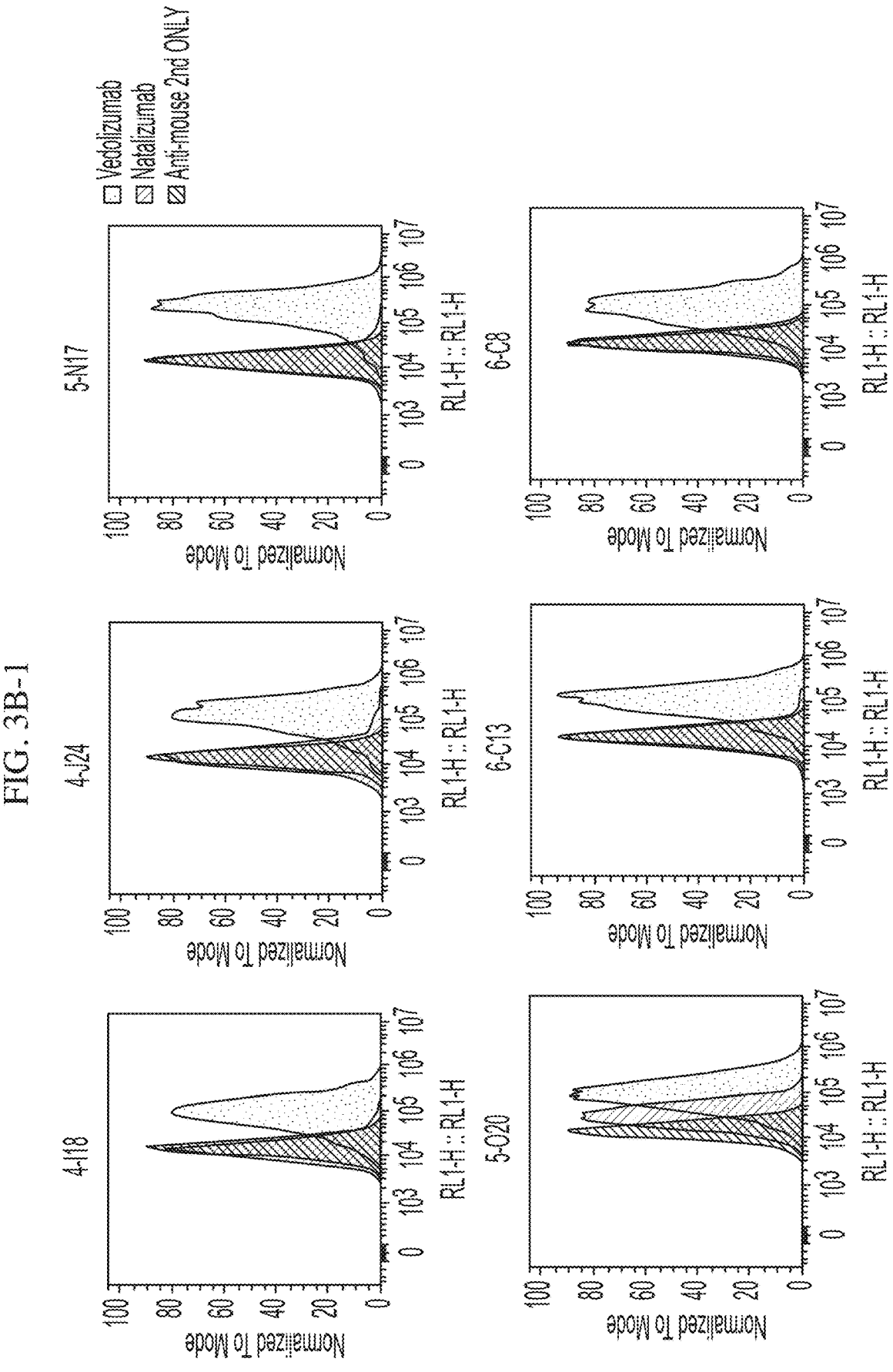
Figures 2, 3B:
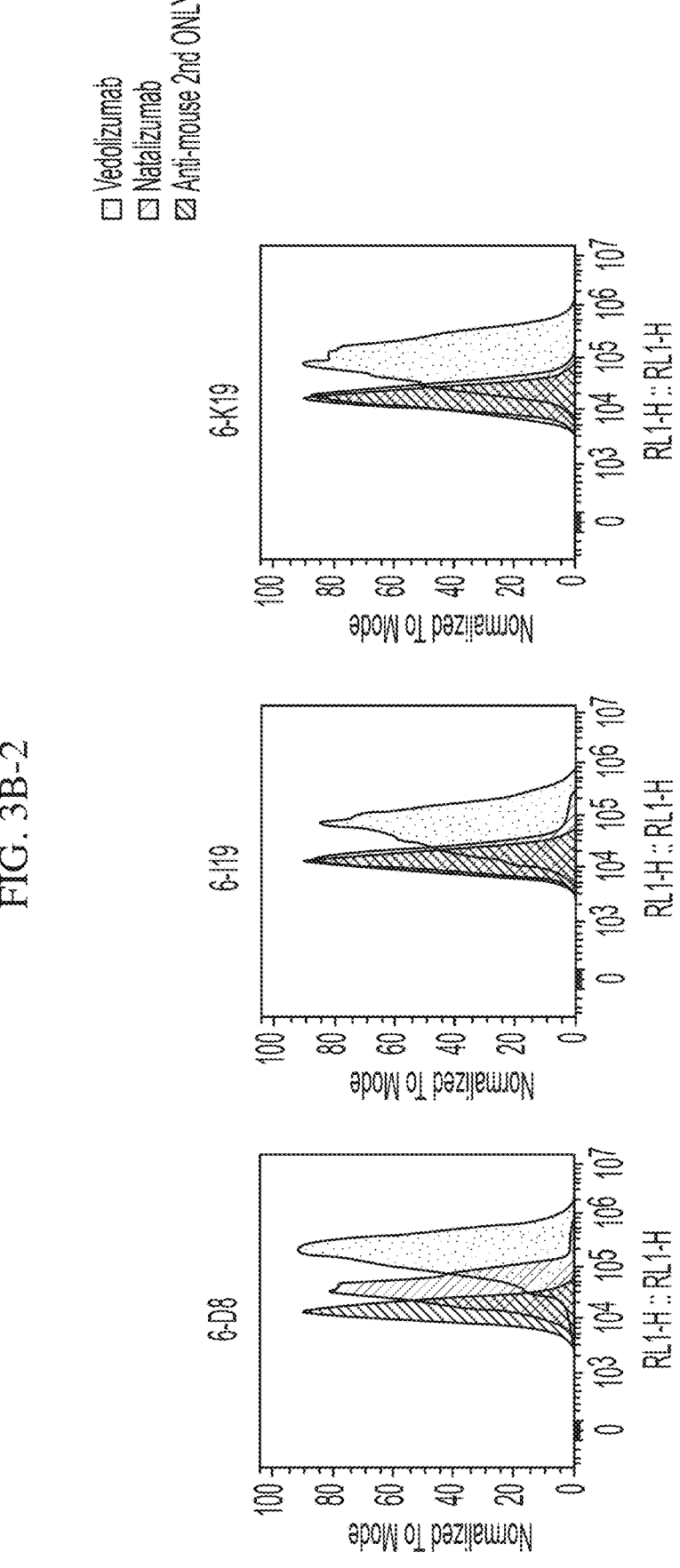
Figure 4A:
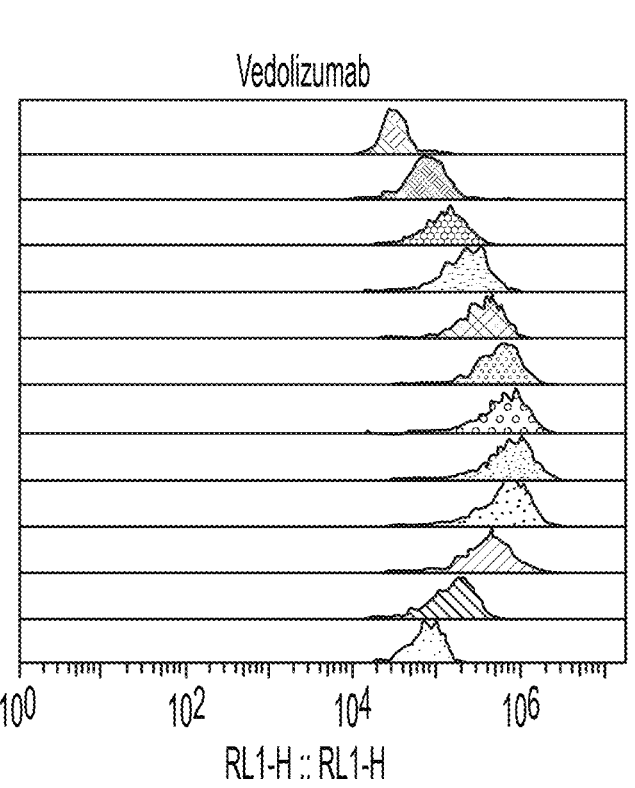
FIGS. 4A-4B show cell FACS quality control (QC) data.
Figure 4A:
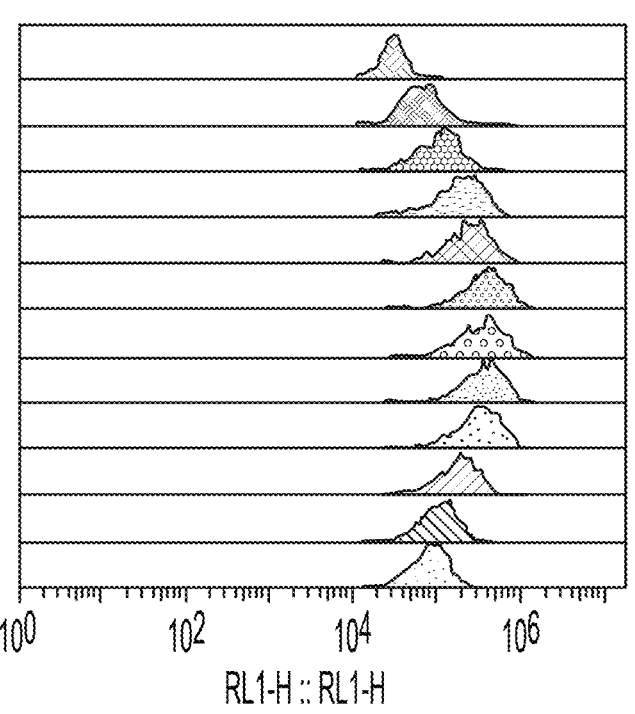
Figures 1, 4A:
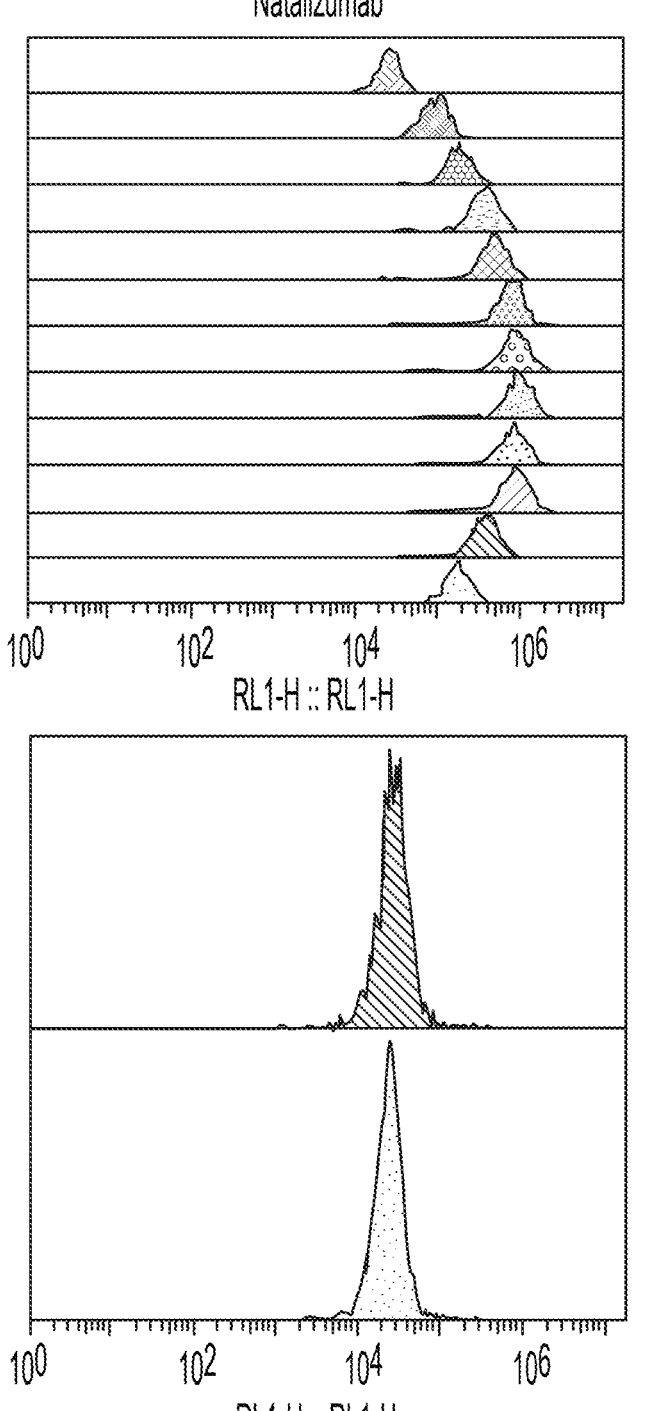
Figure 4B:
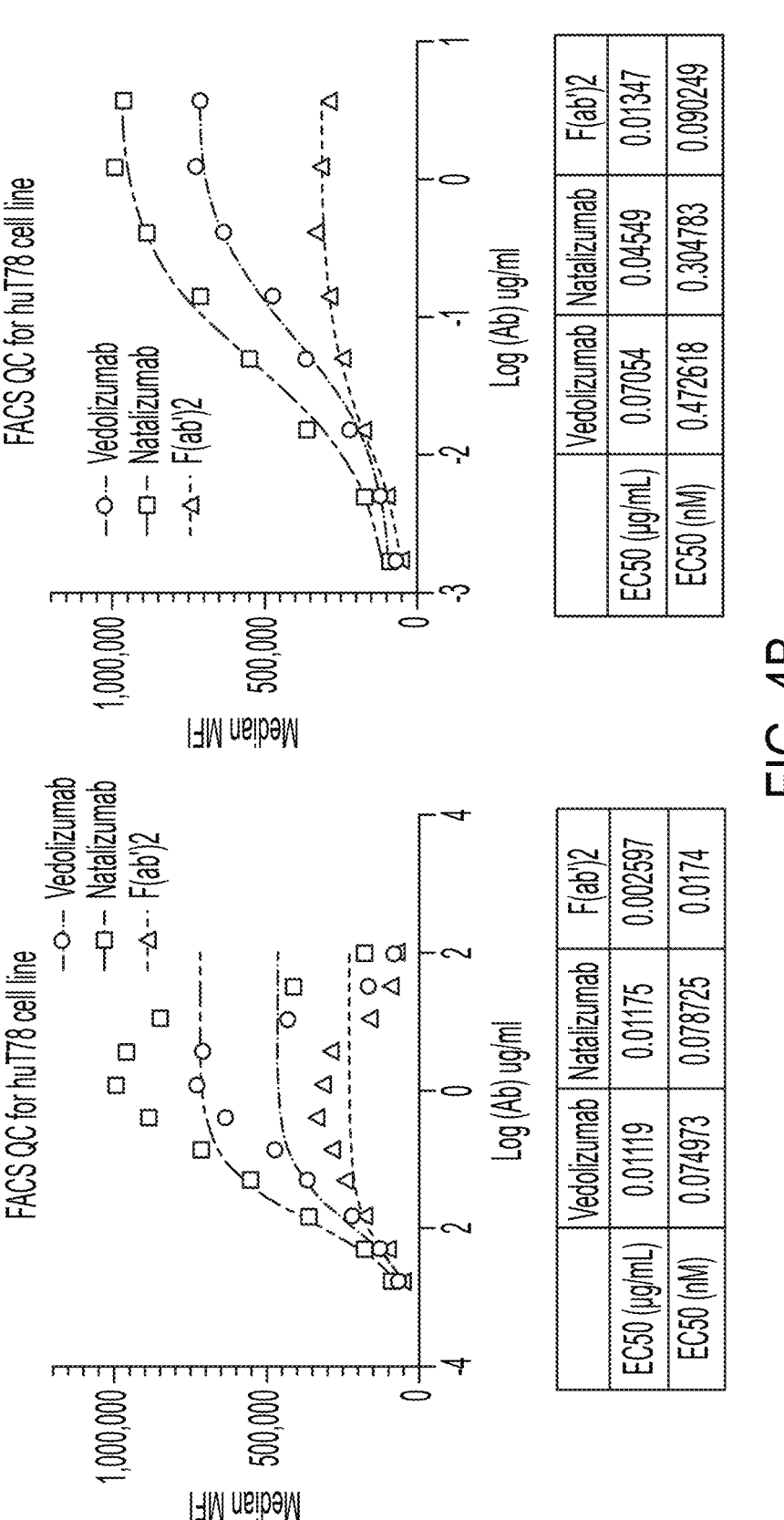

Tertiary FACS screen were performed using non clonal saturated supernatants of 95 hits for binding to vedolizumab/HuT78 cells. As shown in FIG. 3A, at least 10 hybridomas that bound specifically to vedolizumab/HUT78 cells were identified by FACS. FIG. 3A also shows the counter screen by FACS against natalizumab/HuT78 cells. FIG. 3B shows the tertiary FACS screen overlay of the top 15 hits from the experiment with the results shown in FIG. 3A. A duplicate experiment of the above referenced FACS screen was also performed to confirm reproducibility. A tertiary summary heat map was created. The top 15 hits highlighted were identified based on reproducible Ved/HuT78 FACS staining. They were sorted 'by eye' top-to-bottom, and were based on specificity in ELISA and in staining intensity by FACS. FIG. 3C shows the focused view of the top 15 hits that were identified. FIG. 4A-4B show cell FACS quality control (QC) data.

The sequences of the heavy and light chain variable domains for selected anti-vedolizumab monoclonal antibodies described above and the results are summarized with their respective CDR3 amino acid sequences in Table 3.

TABLE 3

| ID | VH | JH | CDR_H3 | ID | VL | JL | CDR_L3 |
|---|---|---|---|---|---|---|---|
| Heavy chains | | | | Light chains | | | |
| 15529-2-18-A HC | IGHV1-12*01 | IGHJ1*03 | ARGWFHWYFDV | 15529-2-I8-A LC | IGKV4-91*01 | IGKJ5*01 | QQGSTIPLT |
| 15529-6-D8-A HC | IGHV1-18*01 | IGHJ2*01 | ARDLVYYFDY | 15529-6-D8-A LC | IGKV5-48*01 | IGKJ4*01 | QQSNSWPFT |
| 15529-2-J3-A HC | IGHV2-2*01 | IGHJ4*01 | ARIGGYGTTYEDGMDY | 15529-2-J3-A LC | IGKV3-5*01 | IGKJ5*01 | QQSNKDPLT |
| 15529-3-I10-A HC | IGHV2-2*01 | IGHJ4*01 | ARIGGYGTSYEDGMDY | 15529-3-I10-A LC | IGKV3-5*01 | IGKJ5*01 | QQSNKDPLT |
| 15529-5-N17-A HC | IGHV2-2*01 | IGHJ4*01 | ARIGGYGTTYEDAMDY | 15529-5-N17-A LC | IGKV3-5*01 | IGKJ5*01 | QQSNKDPLT |
| 15529-6-C13-A HC | IGHV2-2*01 | IGHJ4*01 | ARIGGYGTTYEDAMDY | 15529-6-C13-A LC | IGKV3-5*01 | IGKJ5*01 | QQSNKDPLT |
| 15529-2-B4-A HC | IGHV2S3*01 | IGHJ3*01 | VGAPYDYGGFAY | 15529-2-B4-A LC | IGKV2-109*04 | IGKJ2*03 | AQMLEFPYT |
| 15529-4-J24-A HC | IGHV5-15*01 | IGHJ4*01 | AREDGTTGESAMDY | 15529-4-J24-A LC | IGKV16-104*01 | IGKJ2*02 | QQHYEYPYT |
| 15529-4-D5-A HC | IGHV5-6-1*01 | IGHJ2*01 | ARHGTGVGFDY | 15529-4-D5-ALC | IGKV1-135*01 | IGKJ1*01 | WQGTHFPQT |

Hybridoma clones producing antibodies that showed high specific binding activity were subcloned and purified and their affinity to bind α4β7 antibody or fragment thereof, were characterized as follows. Vedolizumab (0.5 mg, R&D Systems 5397 A3) or anti integrin alpha 4 (natalizumab), human IgG4 Antibody (200 ug, BioVision #A1444) were added at a saturated concentration to HuT78 cells 78 cells One Sibling group (Sib1, bolded and underlined on Table 3) and five unique antibodies were discovered. In terms of overall diversity, 6 types of vedolizumab-binding antibodies were identified based on sequence analysis. Good sequence diversity was obtained. Sib1 comprises 4 mAbs, all of which use the same heavy and light chain V and J gene alleles and have the same light chain CDR3. 5-N17-A and 6-C13-A have identical heavy chain CDR3 domains (Sib1/Id1). The variable region sequences of the mAbs described above are provided in Table 1.

Figure 5A:
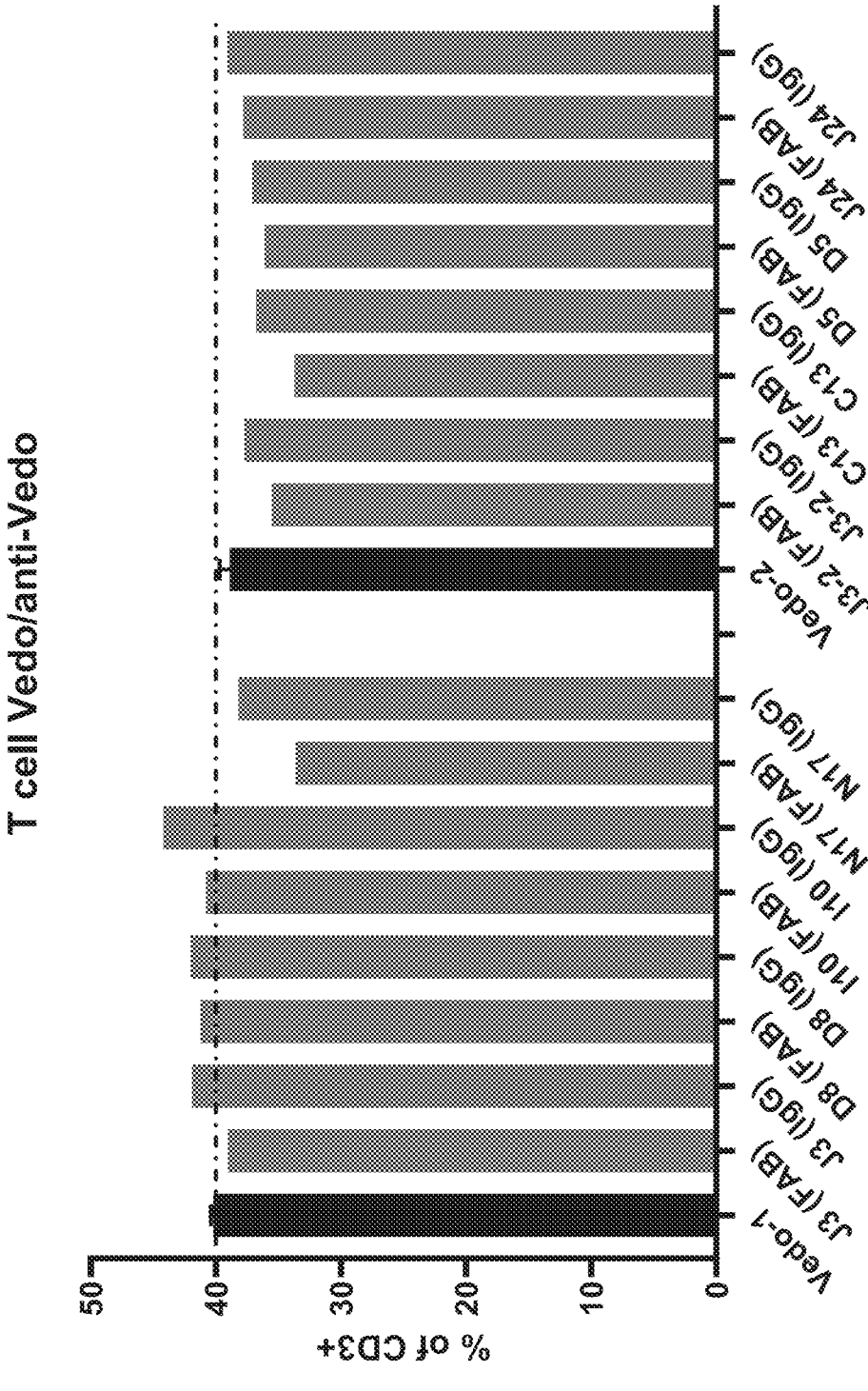
Figure 5B:
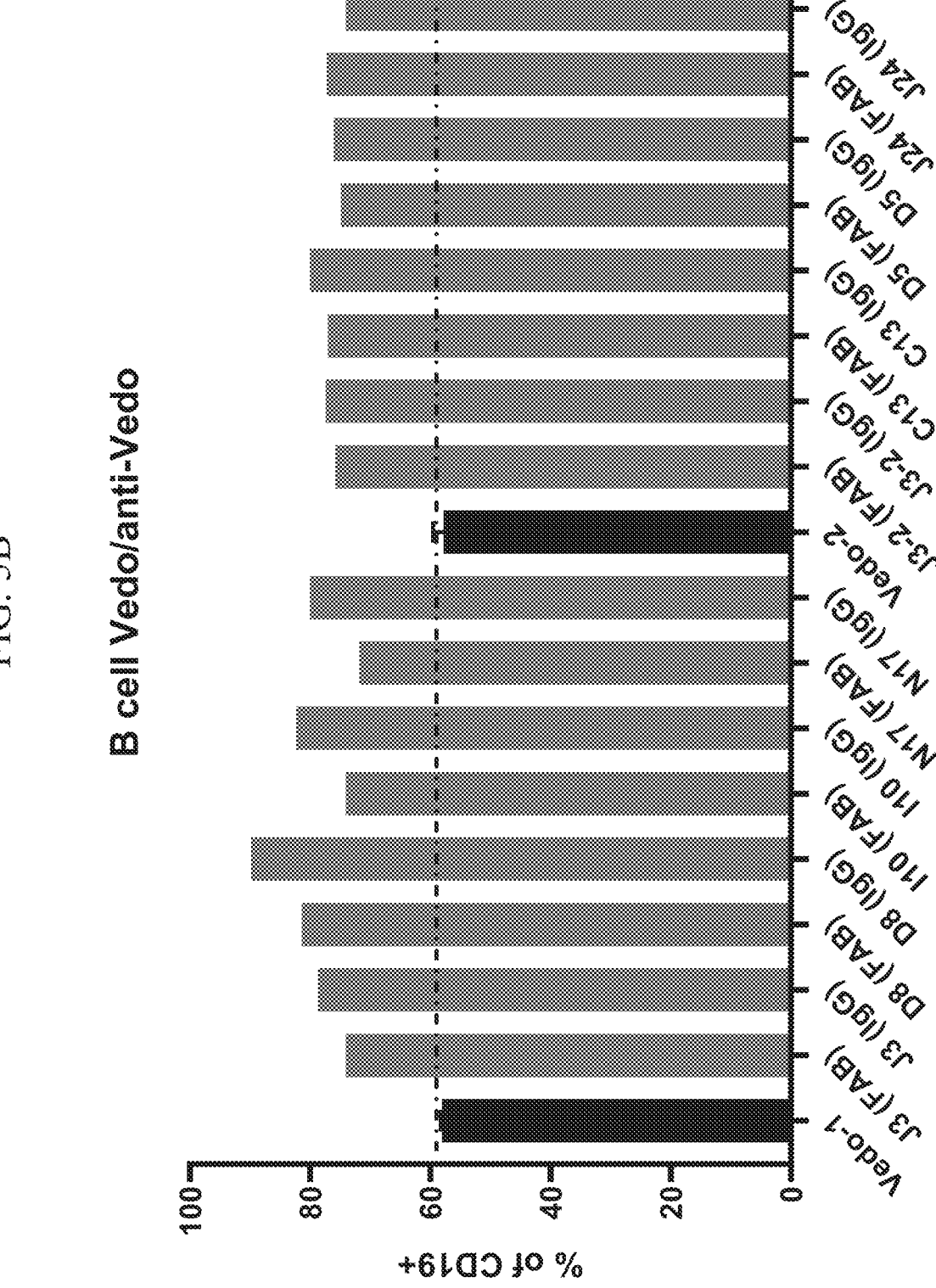
Figure 5C:
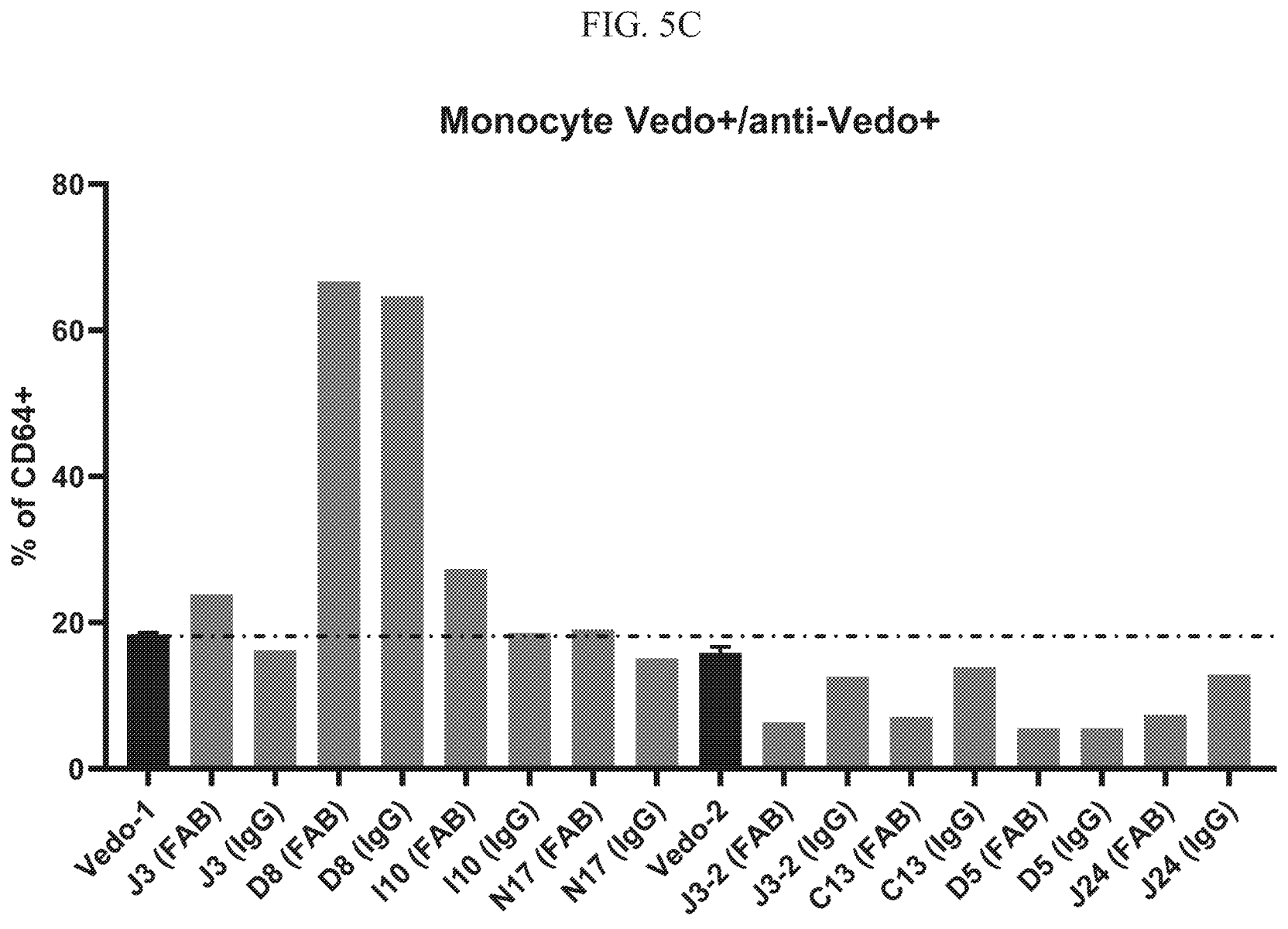
Figure 5D:
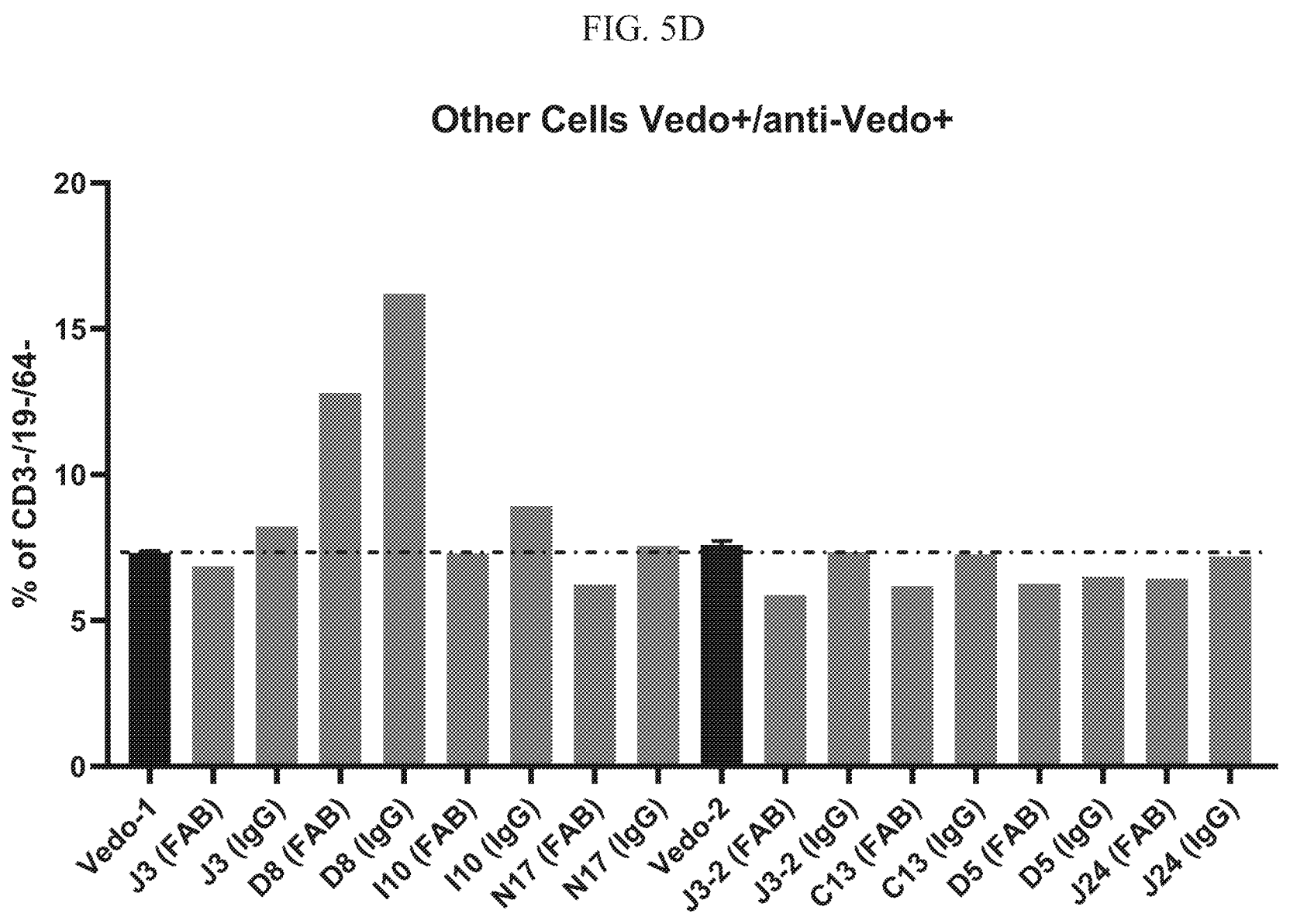

Example 3. Anti-Vedolizumab Antibody Clones—FACS Panel for Detection of Vedolizumab Bound to Human PBMC Seven anti-vedolizumab idiotypic antibody clones, or antigen binding fragments thereof, identified in Examples 1 and 2 were evaluated via a flow cytometry panel to assess the capability of each clone to detect vedolizumab-bound PBMCs from healthy donors treated with vedolizumab in vitro. Fluorescence-activated cell sorting (FACS) was used to detect vedolizumab bound to different subsets of cells, including T cells (CD3+ cells), B cells (CD19+ cells), monocytes (CD64+ cells), or other cells (CD3−, CD19− CD64−). Detection of vedolizumab by vedolizumab-AF647 primary staining of cells was assessed as a comparator.
Flow Cytometry—Experimental Methods
1 million PBMC per sample were stained. All incubations and washes were at 4° C. in the dark in FACS Buffer unless otherwise noted. PBMC were incubated with 5 μg/mL vedolizumab and Human BD FC block for 10 minutes. The samples were washed two times and incubated in 0.5 μg/mL of an anti-vedolizumab idiotype antibody at room temperature for 20 minutes. The cells were washed twice and resuspended in anti-mouse-AF647 antibody Streptavidin-AF647 for 15 minutes. PBMC were washed in FACS Buffer followed by dPBS-Ca/-Mg and resuspended in Zombie Aqua fixable viability dye according to manufacturer's instructions for 10 minutes. The samples were washed twice and resuspended in Human TruStain FcX block and the following antibodies: CD56-Percpcy5.5, CD3e-BV786, CD19-BUV496, CD8-BUV737, CD4-BUV805, CD16-AF700, CD14-Apccy7, and CD11c-PeCF594. After two washes, the samples were resuspended in IC Fixation buffer. 500,000 events were collected on the BD Fortessa X-20 flow cytometer and compensated appropriately in FACS DiVa. Data analyses were conducted using FlowJo software.
Results
Each of the assessed anti-idiotypic antibody clones detected vedolizumab bound to T cells to a similar degree as vedolizumab-AF647 primary staining (FIG. 5A). Further, all assessed clones detected vedolizumab on B cells, but over stained by about 15% relative to vedolizumab-AF647 primary staining (FIG. 5B). In contrast, in monocytes, only clones J3, N17, 110, and J24 detected similar levels of vedolizumab-bound cells as observed with vedolizumab-AF647 primary staining (FIG. 5C). In other cell types, all assessed clones, except for D8, displayed similar levels of vedolizumab-bound cells as observed with vedolizumab-AF647 primary staining (FIG. 5D).

Figure 6A:
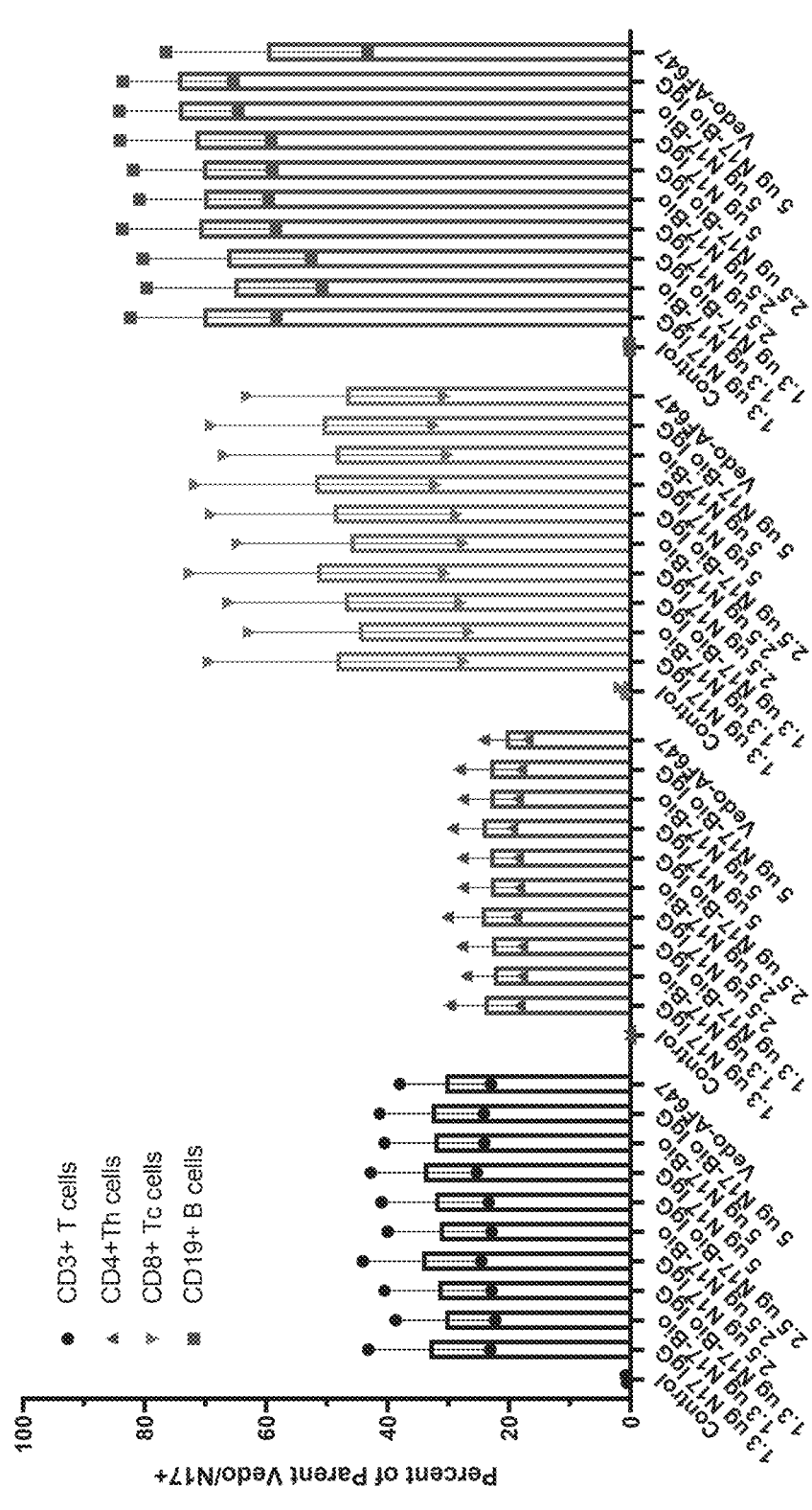
FIGS. 6A-6B graphically depict the results of a study analyzing detection of vedolizumab on lymphocytes (FIG. 6A) and monocytes (FIG. 6B) by anti-vedolizumab idiotypic antibody N17 identified in Examples 1 and 2. Detection of vedolizumab by vedolizumab-AF647 primary staining of cells was assessed as a comparator (Vedo-AF647). The results are presented as the detected percentage of cells bound to vedolizumab (y-axis) for each of the indicated conditions (x-axis).
Figure 6B:
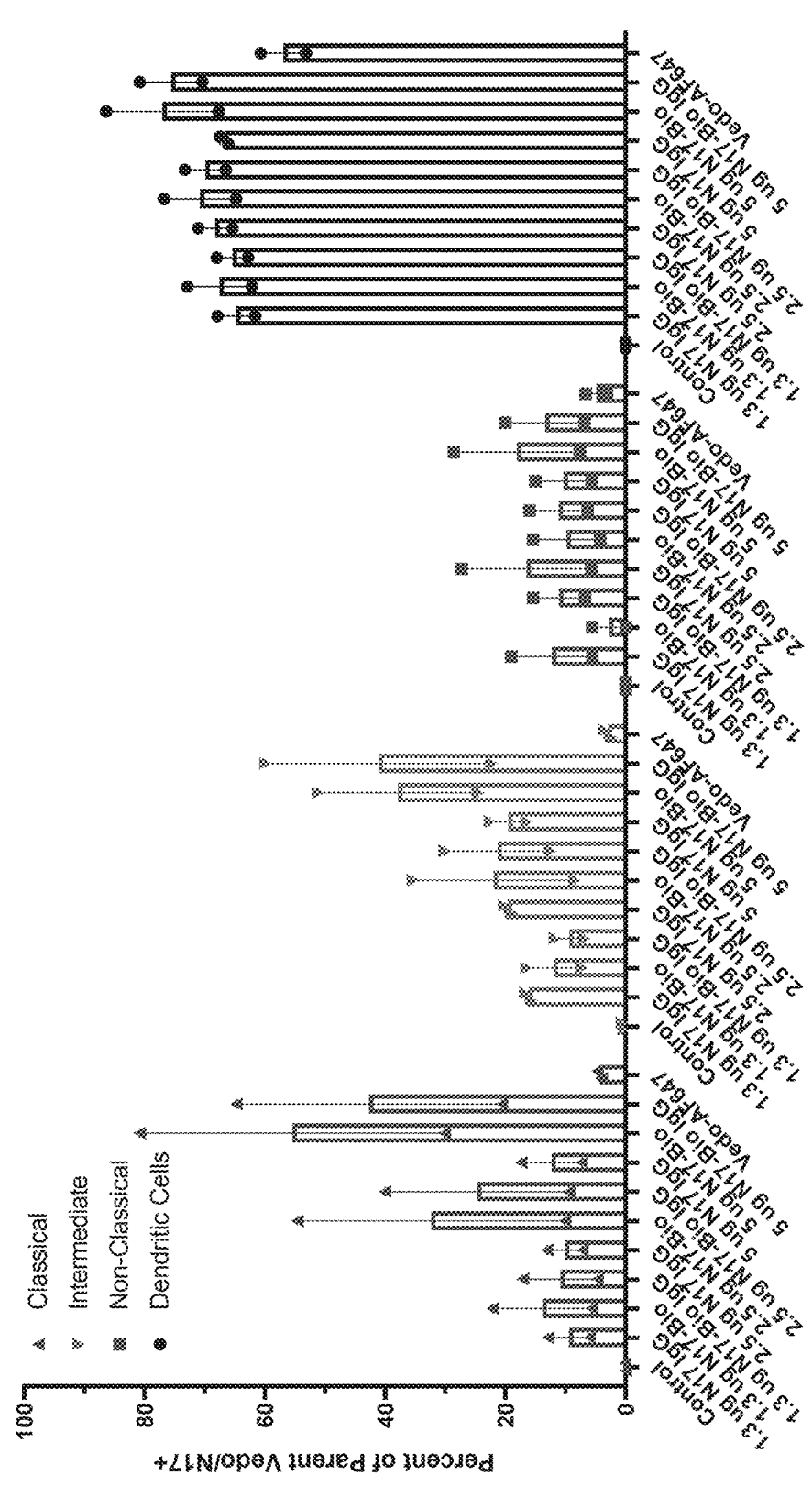

Example 4. Anti-Vedolizumab Antibody N17—FACS Panel for Detection of Vedolizumab Bound to Human PBMC The anti-vedolizumab antibody N17 identified in Examples 1 and 2 was tested on PBMCs from healthy donors treated with vedolizumab in vitro to detect cells bound by vedolizumab. Fluorescence-activated cell sorting (FACS) was used to detect vedolizumab bound to different subsets of cells, including CD3+ T cells, CD4+ T cells (Th cells), CD8+ T cells (Tc cells), CD19+ B cells, classical monocytes, intermediate monocytes, non-classical monocytes, and dendritic cells. Detection of vedolizumab by vedolizumab-AF647 primary staining of cells was assessed as a comparator.
Flow Cytometry—Experimental Methods
1 million PBMC per sample were stained. All incubations and washes were at 4° C. in the dark in FACS Buffer unless otherwise noted. PBMC were incubated with 5 μg/mL vedolizumab and Human BD FC block for 10 minutes. The samples were washed two times and incubated in 0.5 μg/mL of N17 anti-vedolizumab idiotype antibody conjugated to biotin at room temperature for 20 minutes. The cells were washed twice and resuspended in Streptavidin-AF647 for 15 minutes. PBMC were washed in FACS Buffer followed by dPBS Ca/-Mg and resuspended in Zombie Aqua fixable viability dye according to manufacturer's instructions for 10 minutes. The samples were washed twice and resuspended in Human TruStain FcX block and the following antibodies: CD56-Percpcy5.5, CD3e-BV786, CD19-BUV496, CD8-BUV737, CD4-BUV805, CD16-AF700, CD14-Apccy7, and CD11c-PeCF594. After two washes, the samples were resuspended in IC Fixation buffer. 500,000 events were collected on the BD Fortessa X-20 flow cytometer and compensated appropriately in FACS DiVa. Data analyses were conducted using FlowJo software.
Results
As shown in FIGS. 6A and 6B, the N17 clone can detect vedolizumab bound on T cells, B cells, NK cells as well as dendritic cells and minimal binding to monocytes.

Figure 7A:
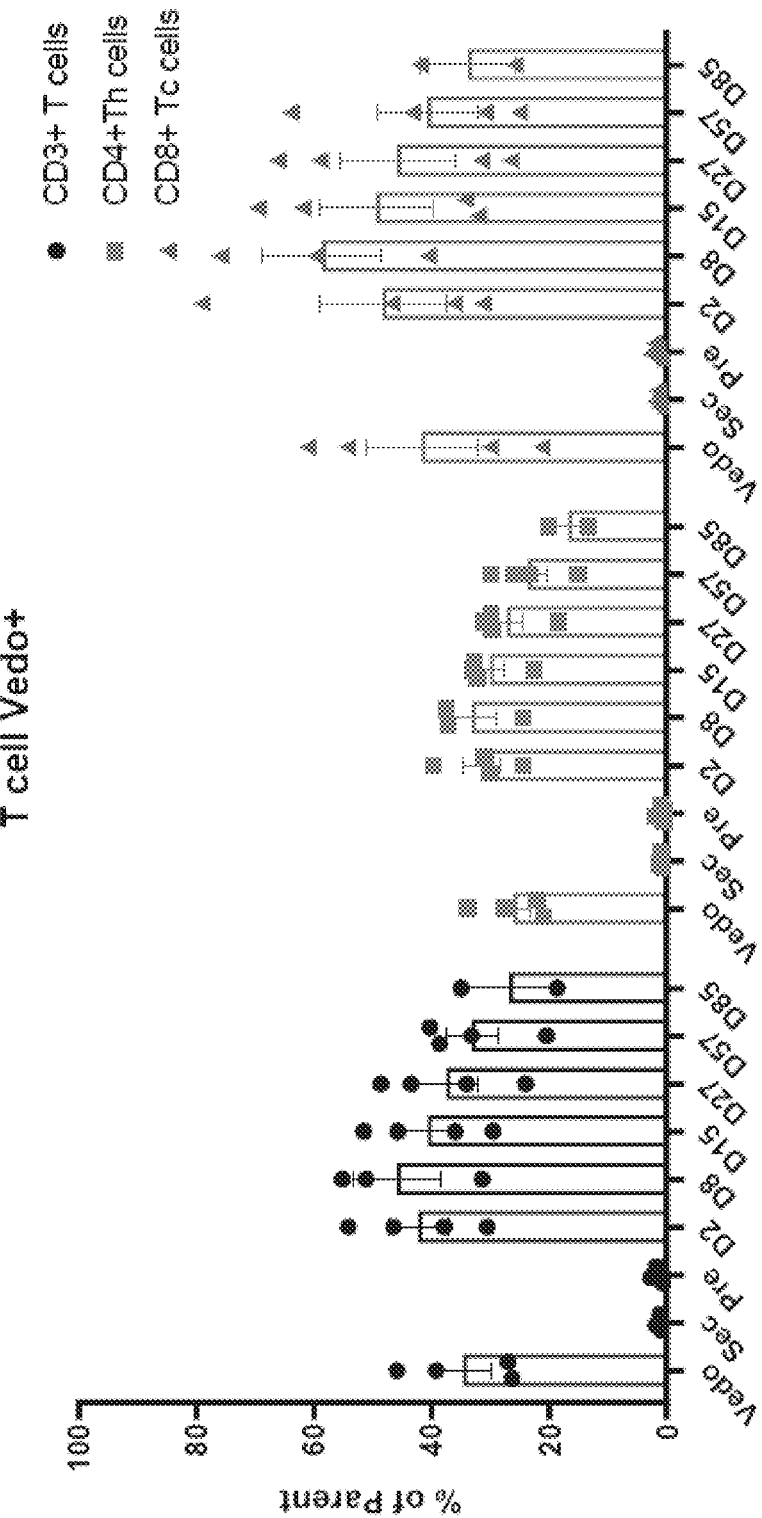
Figure 7B:
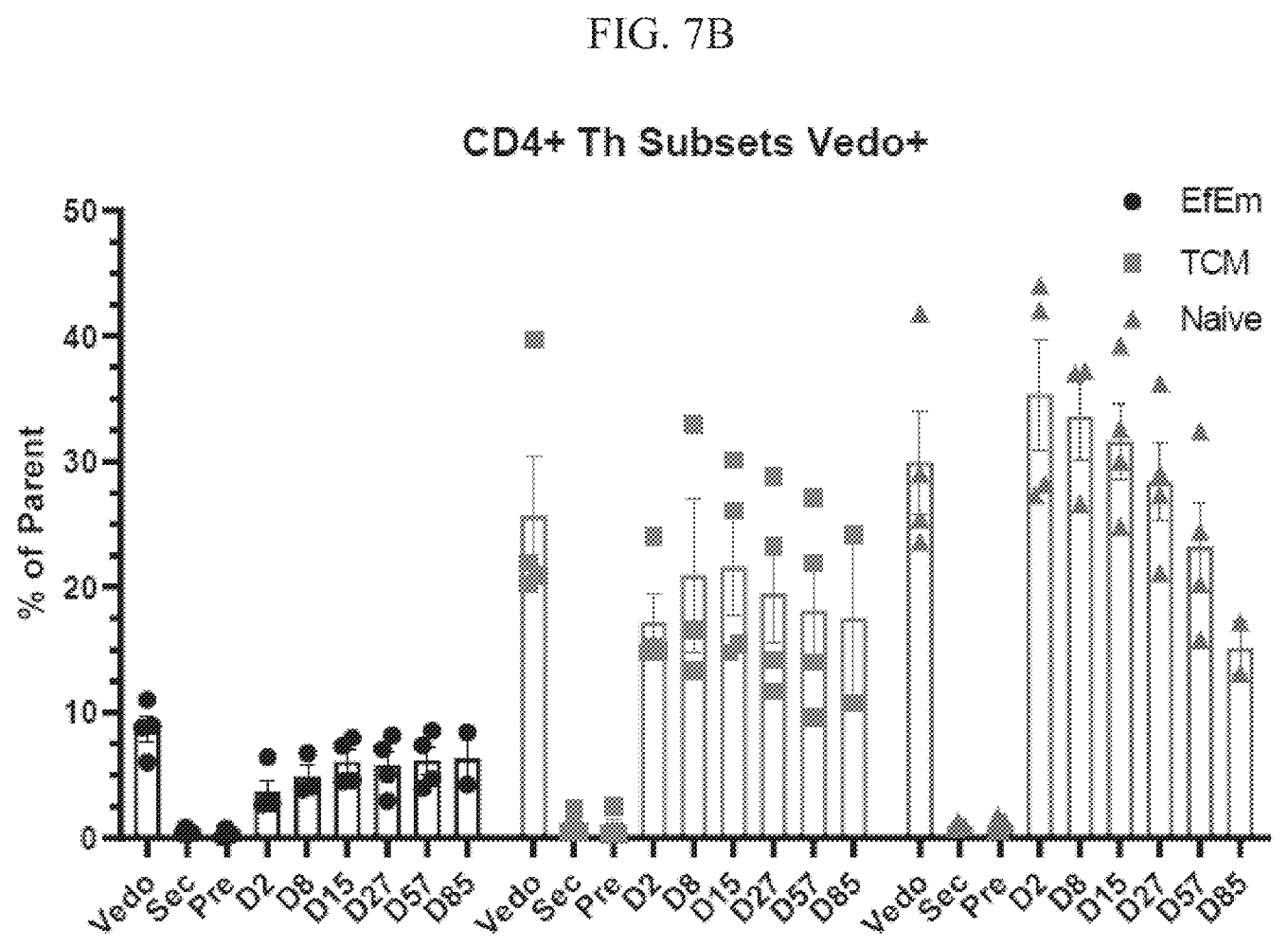
Figure 7C:
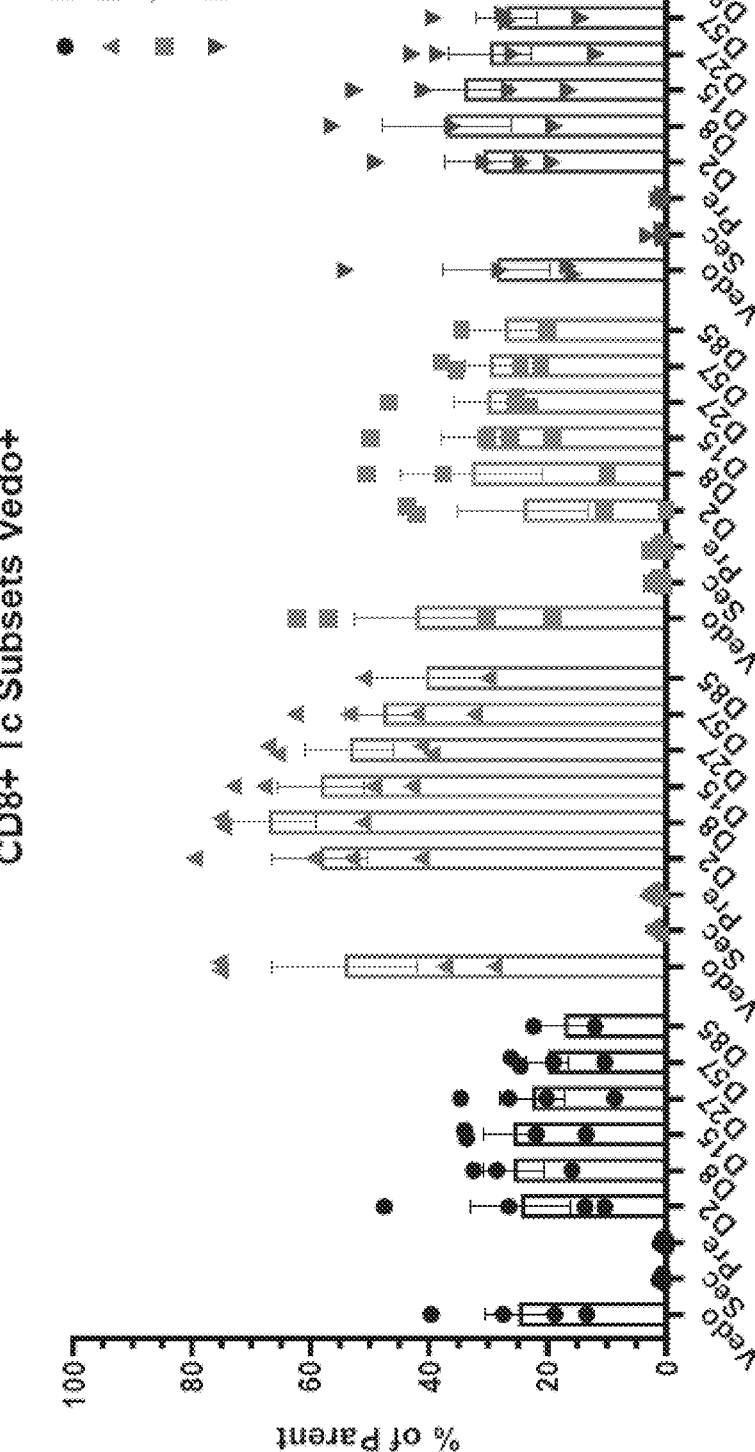
Figure 7D:
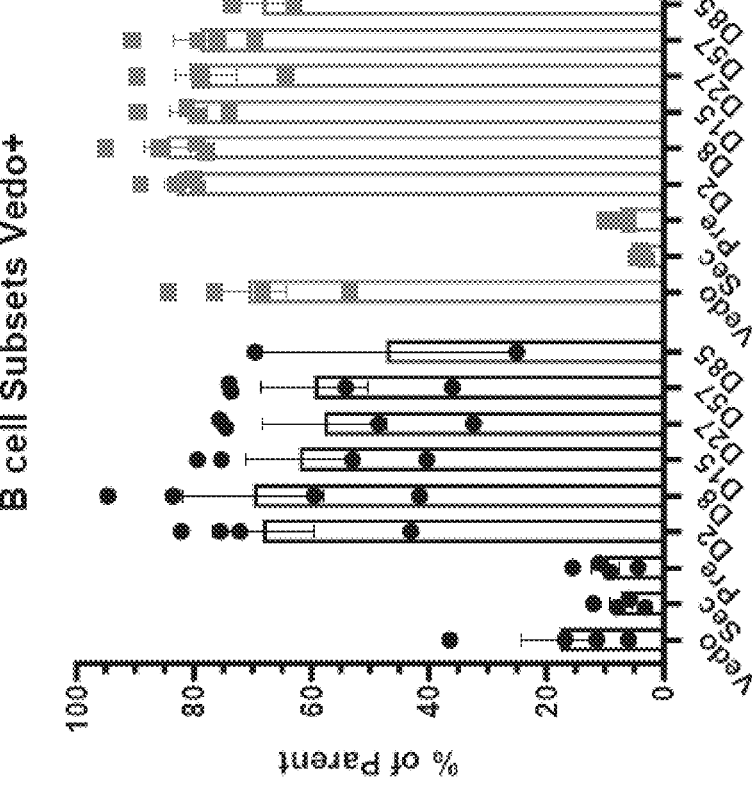
Figure 7E:
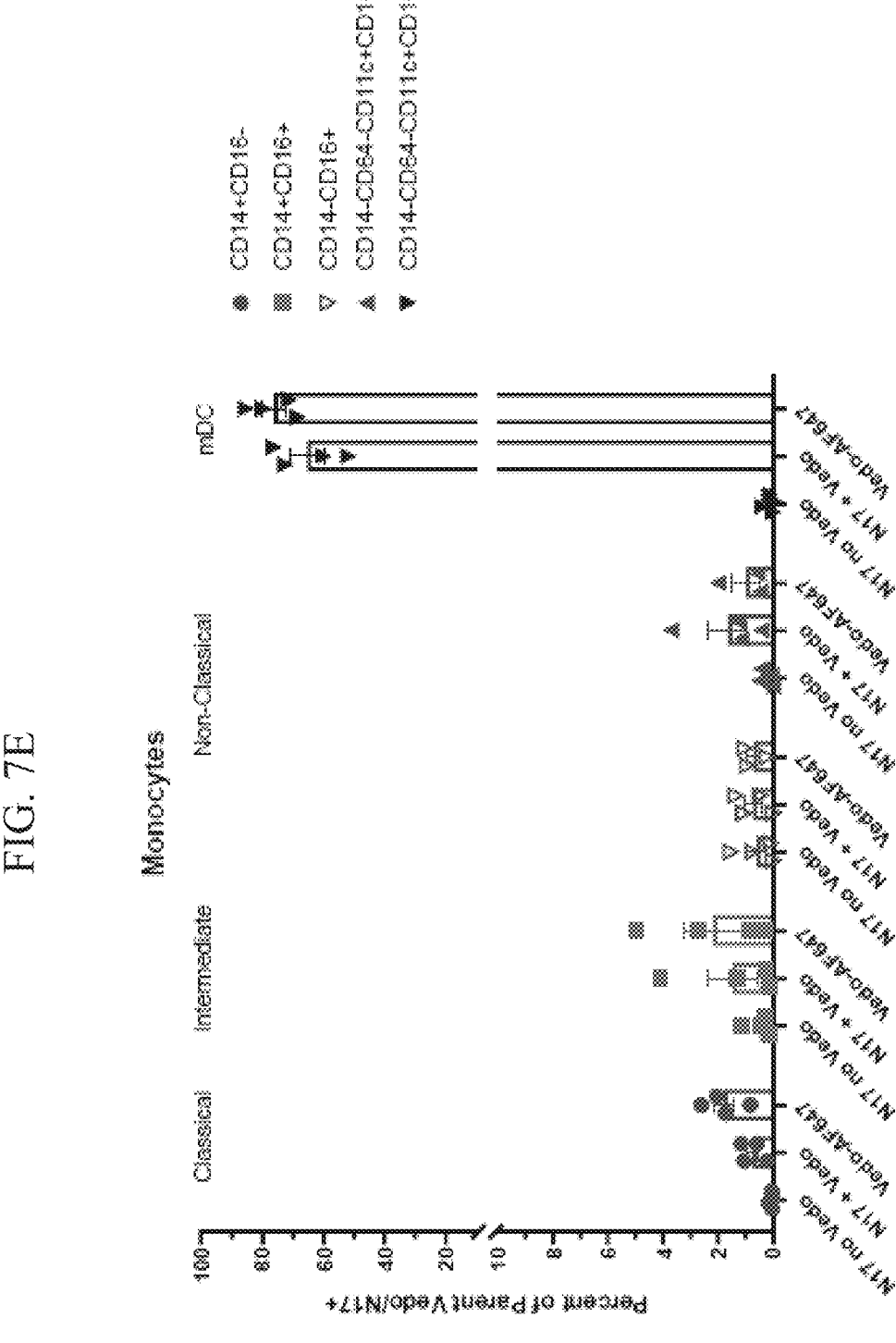

Example 5. Characterization of Longitudinal PBMC Samples with an Anti-Vedolizumab Antibody The anti-vedolizumab antibody N17 identified in Examples 1 and 2 was assessed in longitudinal PBMC samples from healthy donors at various time points (e.g., Day 2, Day 8, Day 15, Day 27, Day 57, and Day 85 post-treatment) following treatment with vedolizumab to detect cells bound by vedolizumab. Fluorescence-activated cell sorting (FACS) was used to detect vedolizumab bound to different subsets of cells, including CD3+ T cells, CD4+ T cells (Th cells), CD8+ T cells (Tc cells), CD19+ B cells, classical monocytes, intermediate monocytes, non-classical monocytes, and dendritic cells. Detection of vedolizumab by vedolizumab-AF647 primary staining of cells was assessed as a comparator. A similar methodology was followed to assess subsets of vedolizumab-bound cells using the flow cytometry procedure described in Examples 2 and 3.
Results
As shown in FIG. 7A, vedolizumab binding was detected on total T cells, CD4+ T cells, and CD8+ T cells, with peak binding at Day 8 post-treatment. In CD4+ T cells, vedolizumab-bound CD4+ effector memory T cells (EfEm) did not decrease with time, whereas vedolizumab-bound CD4+na-ïve T cells decreased over time (FIG. 7B). In CD8+ T cells, vedolizumab-bound CD8+ naïve, central memory, and effector memory subsets peaked at Day 15 post-treatment (FIG. 7C). In contrast, in B cells, vedolizumab-bound B cell subsets peaked at Day 8 (FIG. 7D). Further, vedolizumab binding was detected in dendritic cells in PBMCs from healthy donors (FIG. 7E).

Example 6. N17 Antibody Binding Site Competition Assay

The anti-vedolizumab antibody N17 was assessed in an antibody binding site competition assay (i.e., a binding hindrance assay) against anti-vedolizumab monoclonal anti-bodies 110, B4, J3, C13, D5, D8, and J24 identified in Examples 1 and 2. This assay aimed to detect whether the indicated anti-vedolizumab antibodies compete for the same epitope on vedolizumab as N17. PBMC were exposed to vedolizumab and an unlabeled, anti-vedolizumab antibody clone (I10, B4, J3, C13, D5, D8, and J24) at titrated doses (5 µg/mL, 0.5 µg/mL, 0.05 µg/mL, and 0.005 g/mL). Subsequently, the cells were exposed to N17-Biotin and strepta-vidin. Fluorescence-activated cell sorting (FACS) was used to detect N17-biotin/streptavidin bound to different subsets of cells, including CD3+ T cells, CD19+ B cells, and CD64+ monocytes. Detection of N17 binding without competition or detection of vedolizumab by vedolizumab-AF647 primary staining of cells was assessed as a positive control (Vedo-AF647).

Flow Cytometry—Experimental Method 1 million PBMC per sample were stained. All incubations and washes were at 4° C. in the dark in FACS Buffer unless otherwise noted. PBMC were incubated with 5 µg/mL vedolizumab and Human BD FC block for 10 minutes. The samples were washed two times and incubated in 0.5 µg/mL of N17 anti-vedolizumab idiotype antibody conjugated to biotin at room temperature for 20 minutes. The cells were washed twice and resuspended in Streptavidin-AF647 for 15 minutes. PBMC were washed in FACS Buffer followed by dPBS-Ca/-Mg and resuspended in Zombie Aqua fixable viability dye according to manufacture's instructions for 10 minutes. The samples were washed twice and resuspended in Human TruStain FcX block and the following antibodies: CD56-Percpcy5.5, CD3e-BV786, CD19-BUV496, CD8-BUV737, CD4-BUV805, CD16-AF700, CD14-Apccy7, and CD11c-PeCF594. After two washes, the samples were resuspended in IC Fixation buffer. 500,000 events were collected on the BD Fortessa X-20 flow cytometer and compensated appropriately in FACS DiVa. Data analyses were conducted using FlowJo software.

Results

Figure 8A:
FIGS. 8A-8G graphically depict the results of a binding site competition assay with the anti-vedolizumab idiotypic antibody N17 identified in Examples 1 and 2. N17 was assessed in an antibody binding site competition assay against anti-vedolizumab monoclonal antibodies 110 (FIG. 8A), B4 (FIG. 8B), J3 (FIG. 8C), C13 (FIG. 8D), D5 (FIG. 8E), D8 (FIG. 8F), and J24 (FIG. 8G) in CD3+ T cells, CD19+ B cells, and monocytes at titrated doses (5 µg/mL, 0.5 µg/mL, 0.05 µg/mL, and 0.005 µg/mL). After vedolizumab and then respective clone titrations, the cells were exposed to N17-Biotin and streptavidin. Flow cytometry was used to detect N17-biotin/streptavidin bound to different subsets of cells, including CD3+ T cells, CD19+ B cells, and CD64+ monocytes. Detection of N17 binding to vedolizumab-bound cells without competition ("N17 only") or detection of vedolizumab by vedolizumab-AF647 primary staining of cells was assessed as a positive control ("Vedo-AF647"). The results are presented as the detected percentage of the total or parental CD3+CD19+ or CD64+, respectively, which have N17 bound to cells (y-axis) with or without competition anti-vedolizumab clones for each of the indicated cell types and doses (x-axis).
Figure 8A:
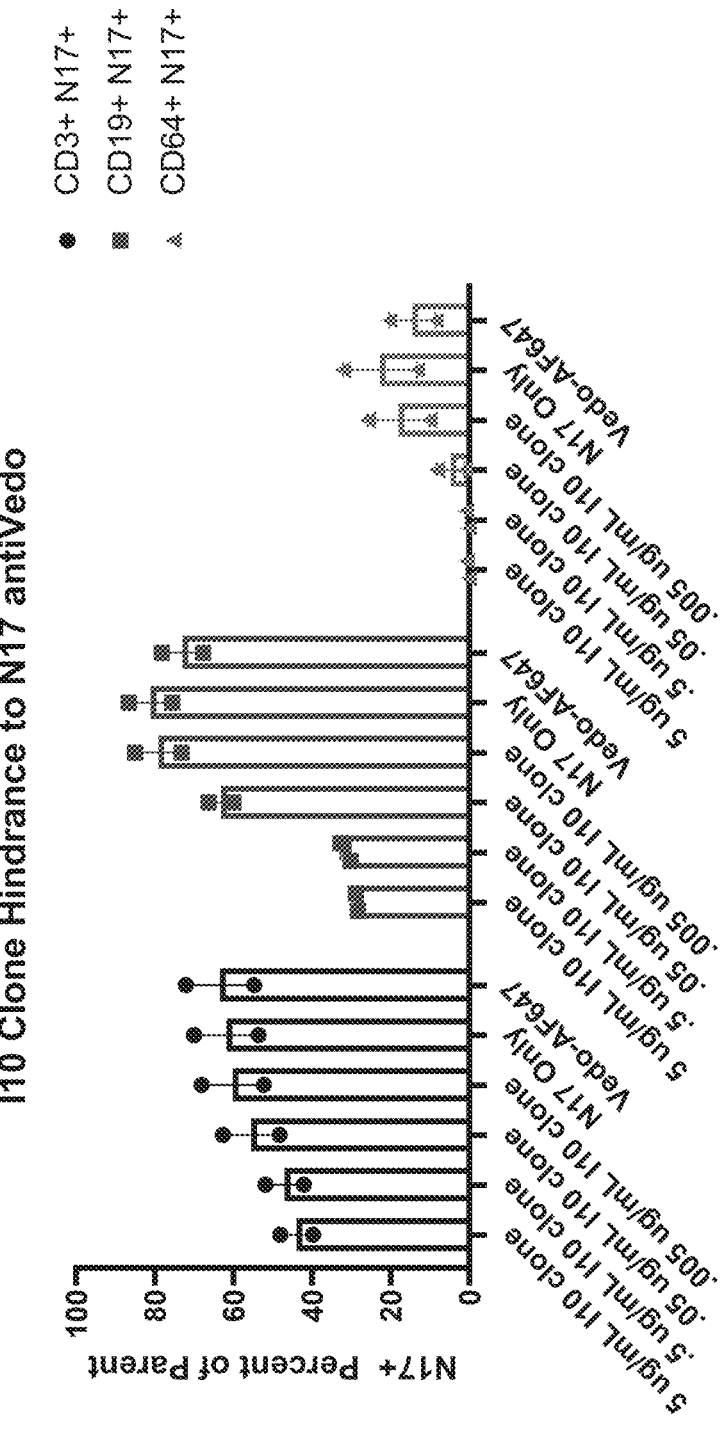
Figure 8B:
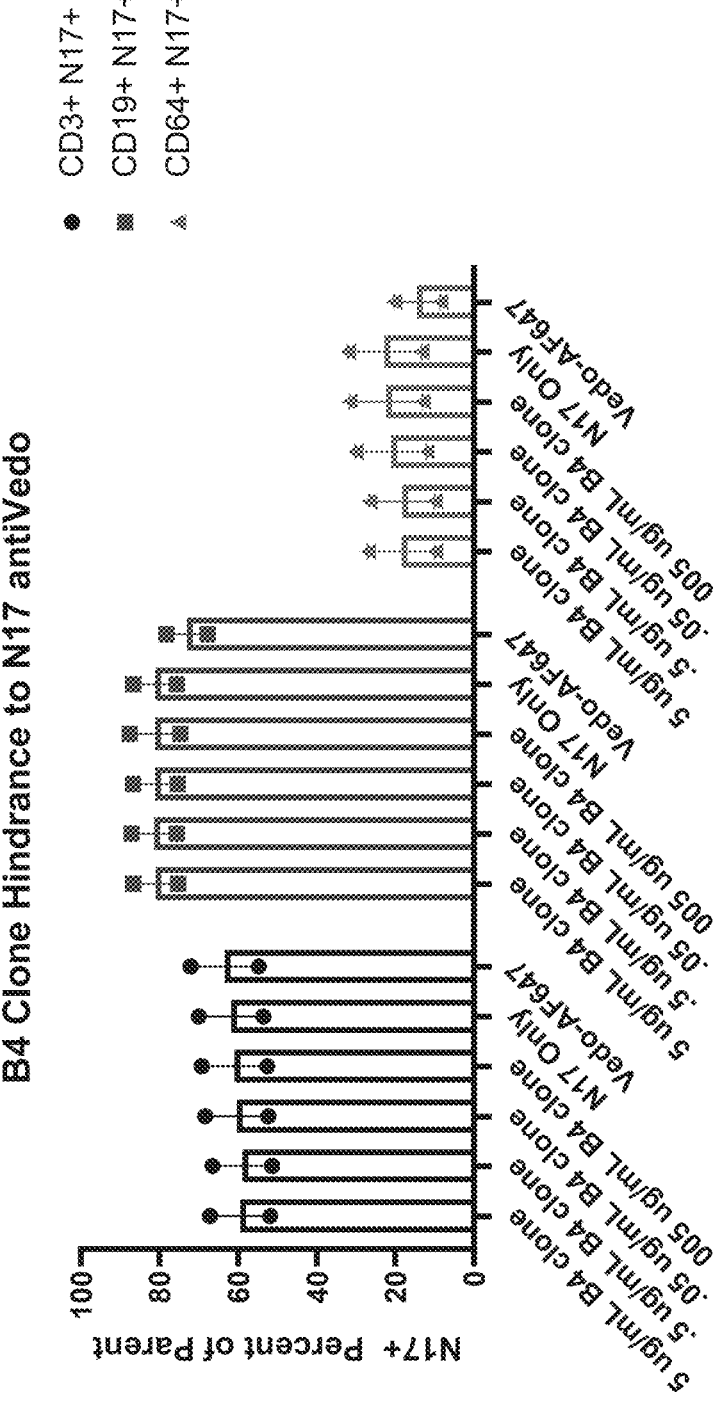
Figure 8C:
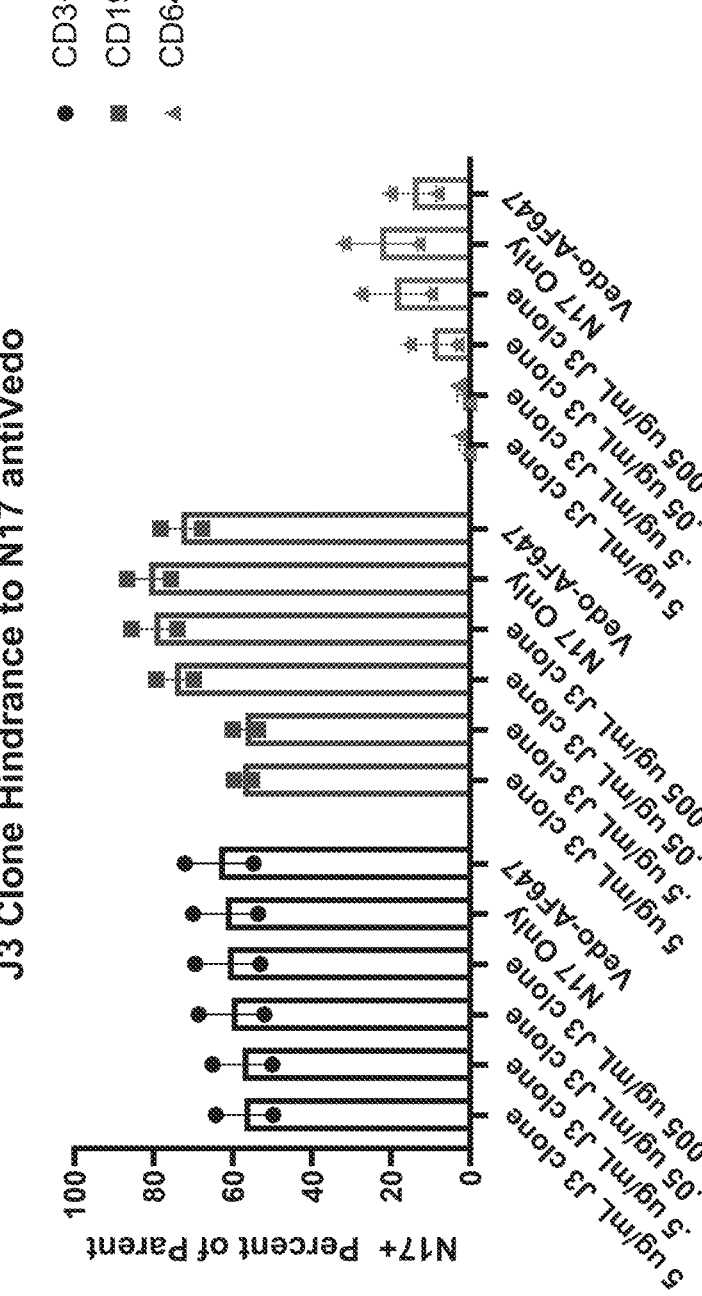
Figure 8D:
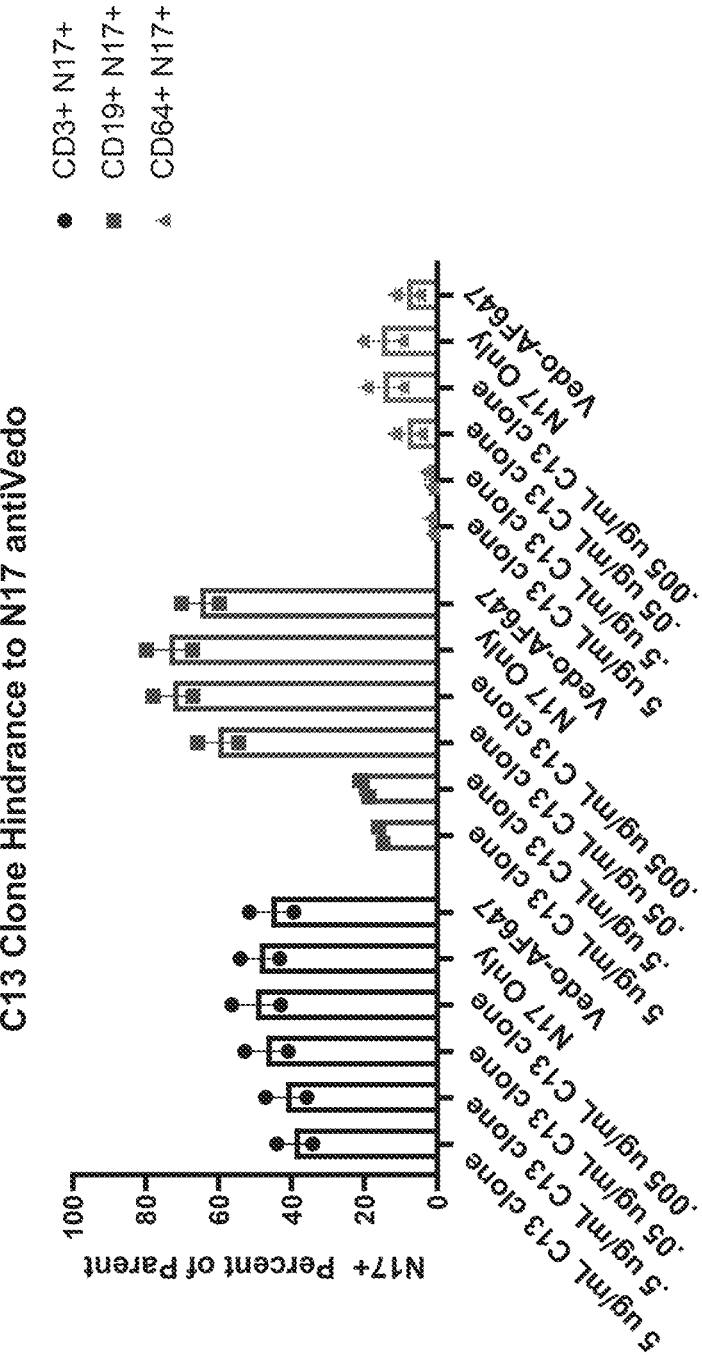
Figure 8E:
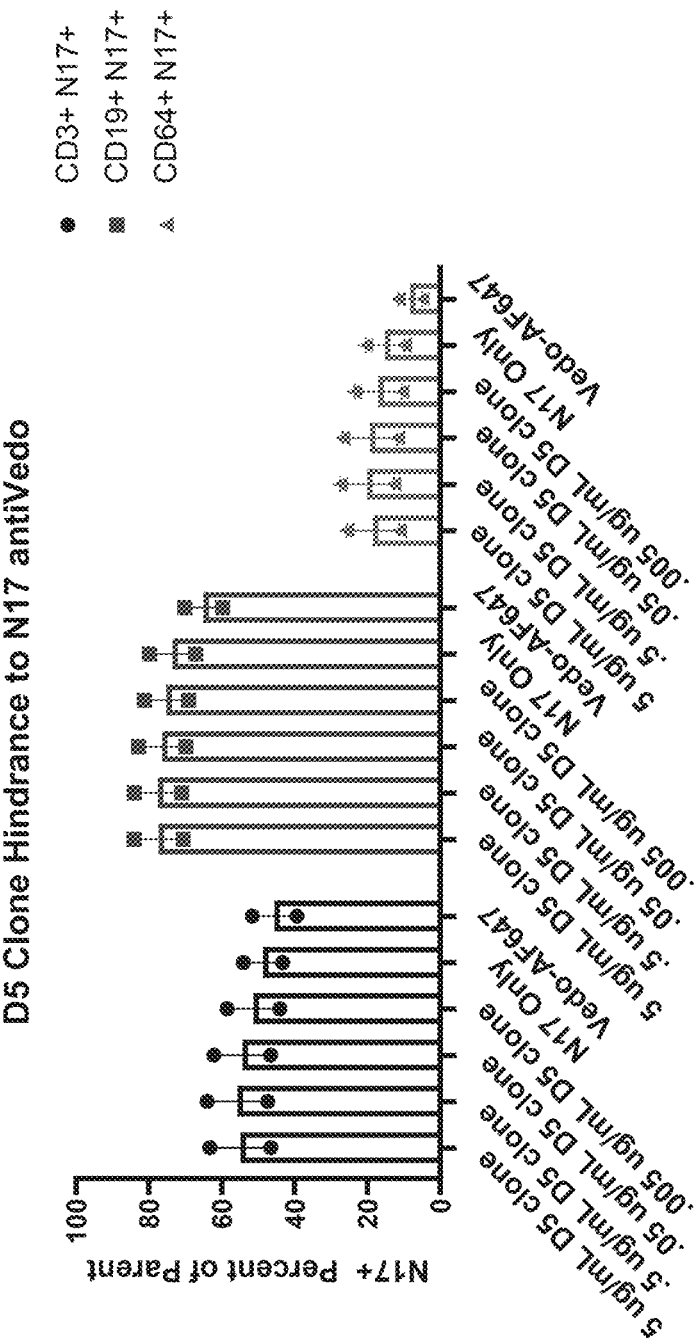
Figure 8F:
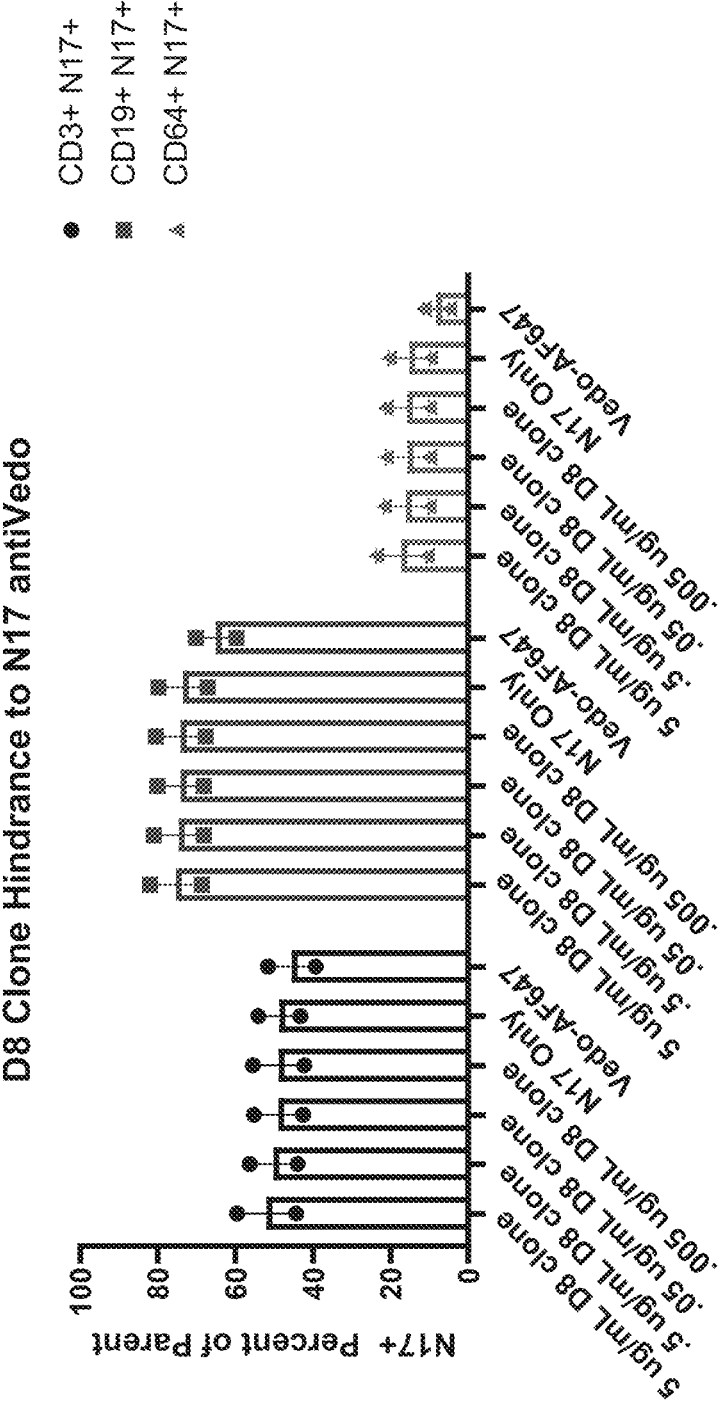
Figure 8G:
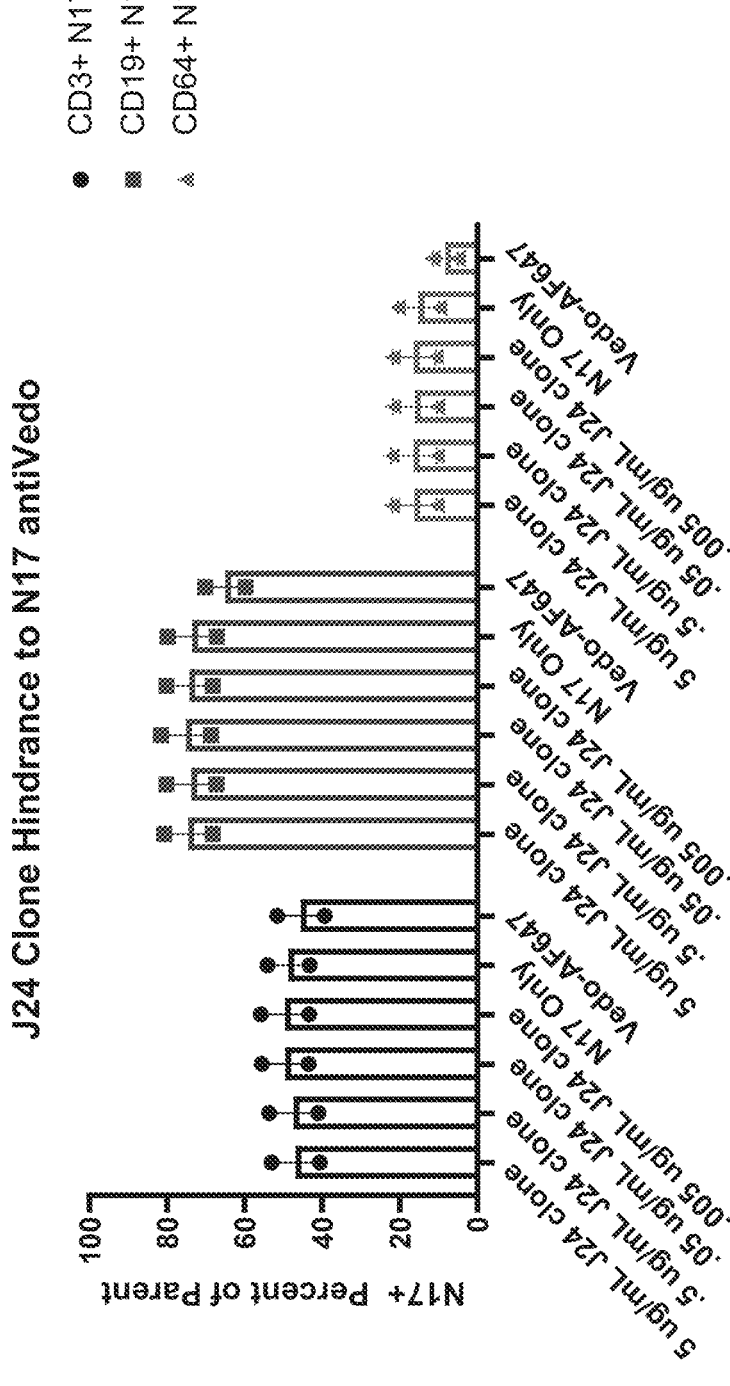
Figure 9A:
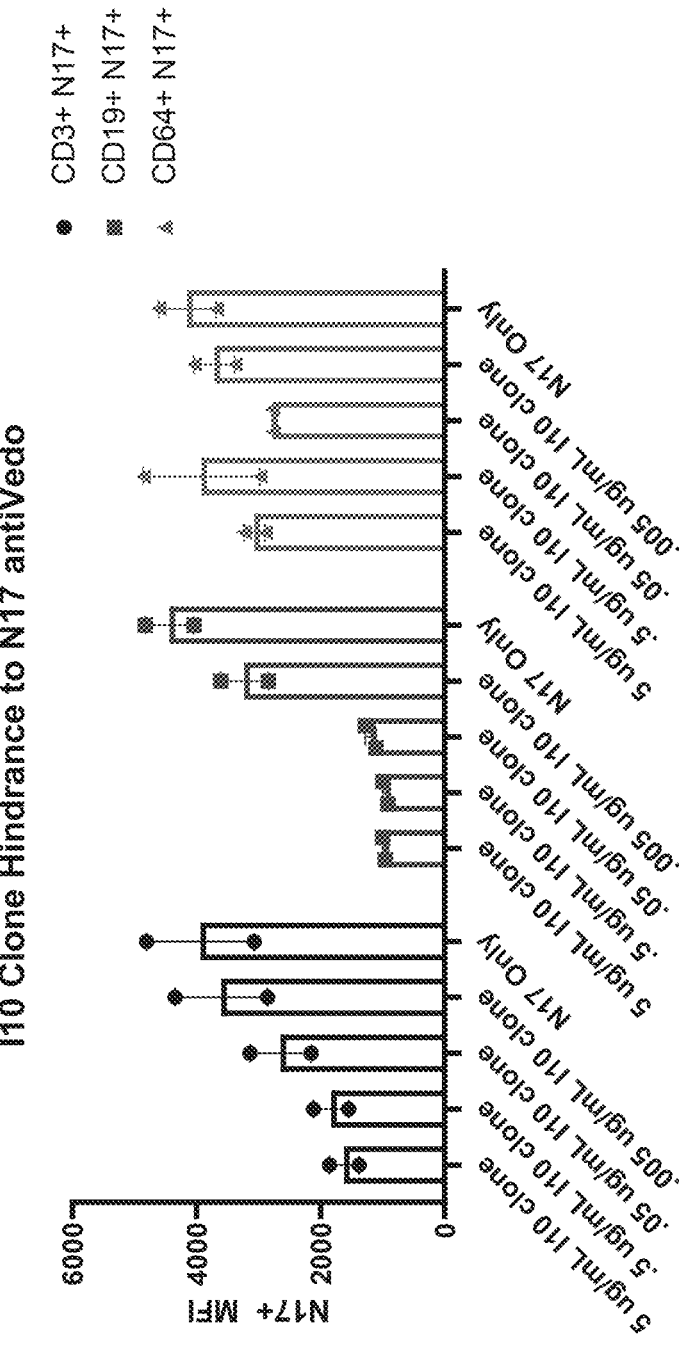
FIGS. 9A-9G graphically depict the mean fluorescence intensity (MFI) of anti-vedolizumab idiotypic antibody N17 bound to cells in the binding site competition assay described in Example 6 and FIGS. 8A-8G. The results are presented as the mean fluorescence intensity of N17 bound to vedolizumab-bound cells (y-axis) for each of the indicated cell types (CD3+ T cells, CD19+ B cells, and monocytes) and doses (x-axis) following a competition assay with 110 (FIG. 9A), B4 (FIG. 9B), J3 (FIG. 9C), C13 (FIG. 9D), D5 (FIG. 9E), D8 (FIG. 9F), and J24 (FIG. 9G).
Figure 9B:
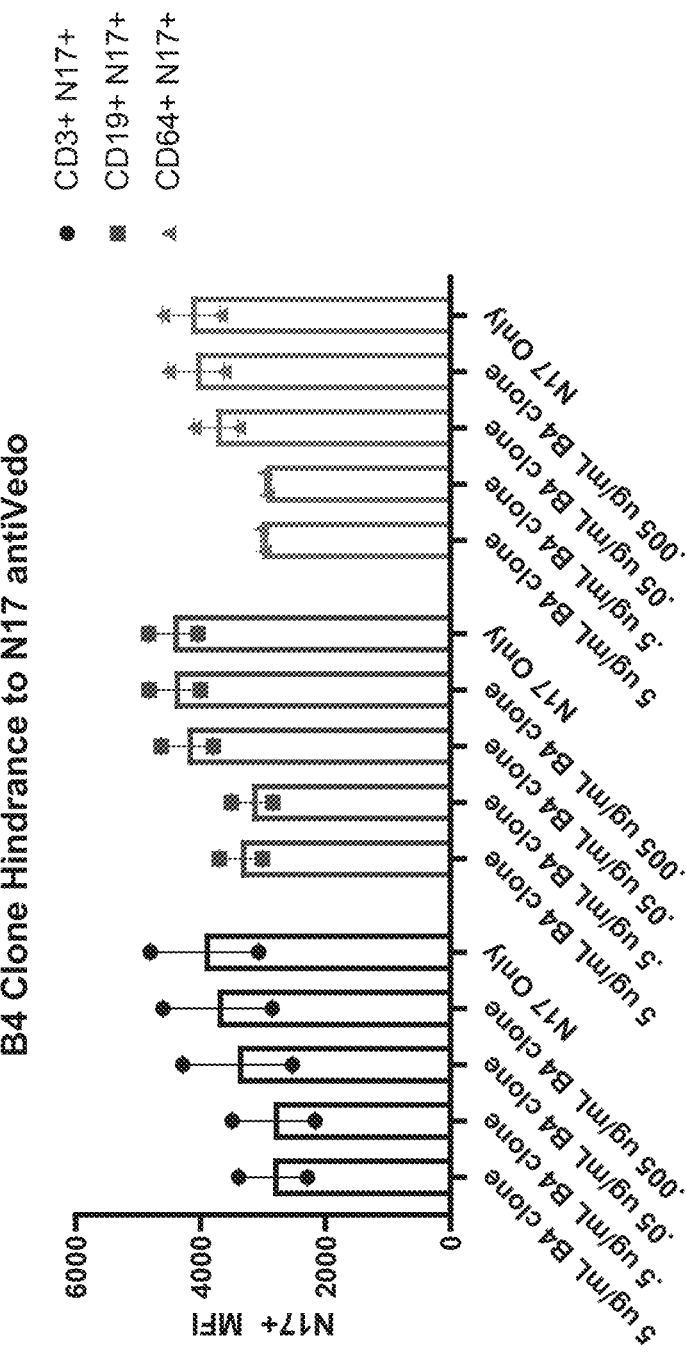
Figure 9C:
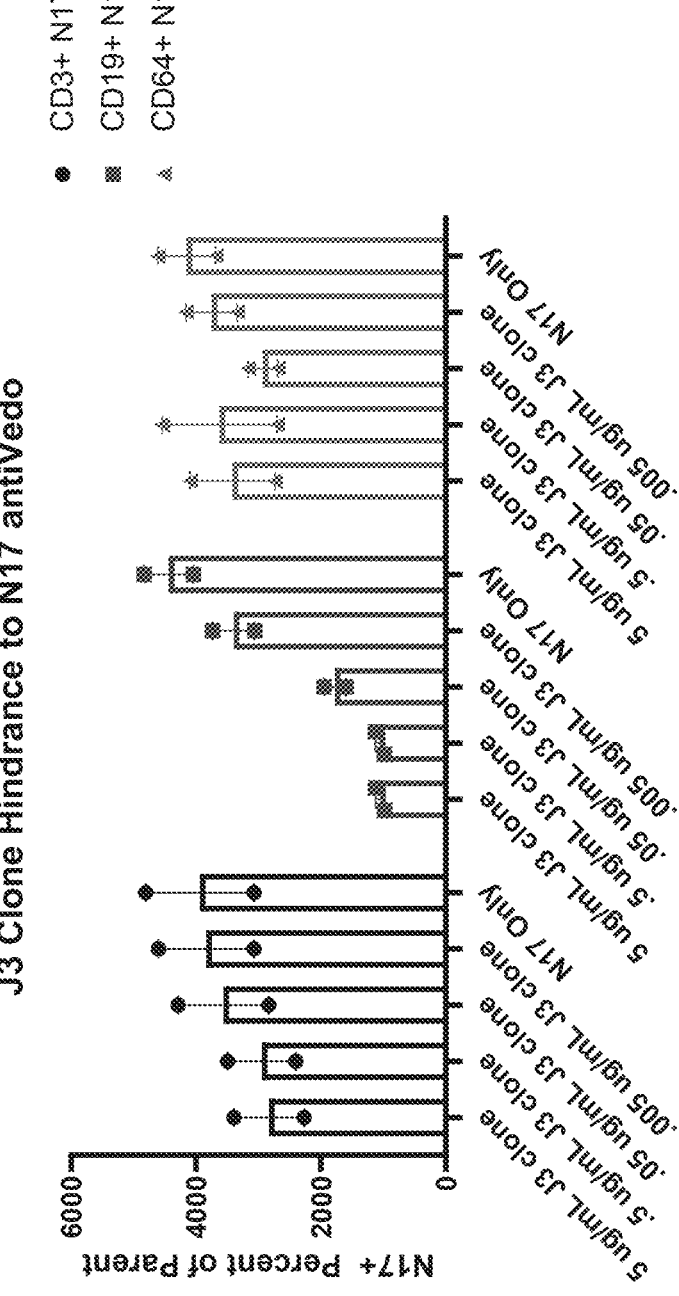
Figure 9D:
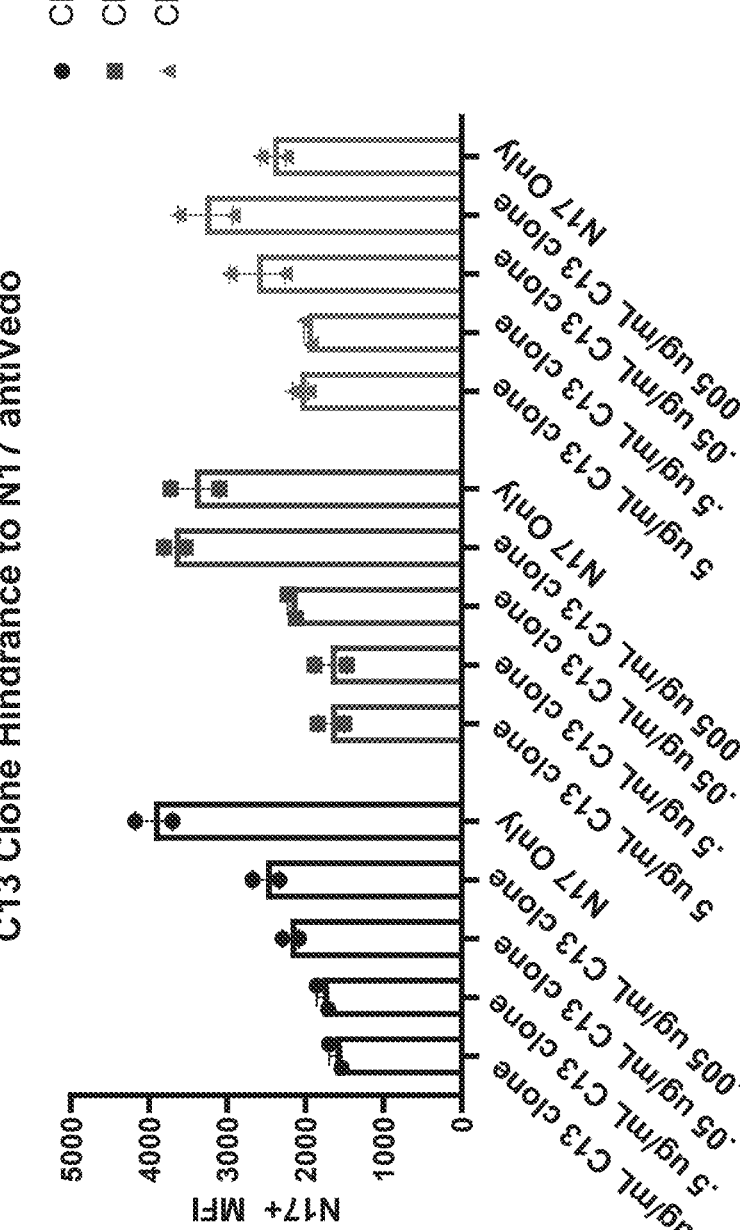
Figure 9E:
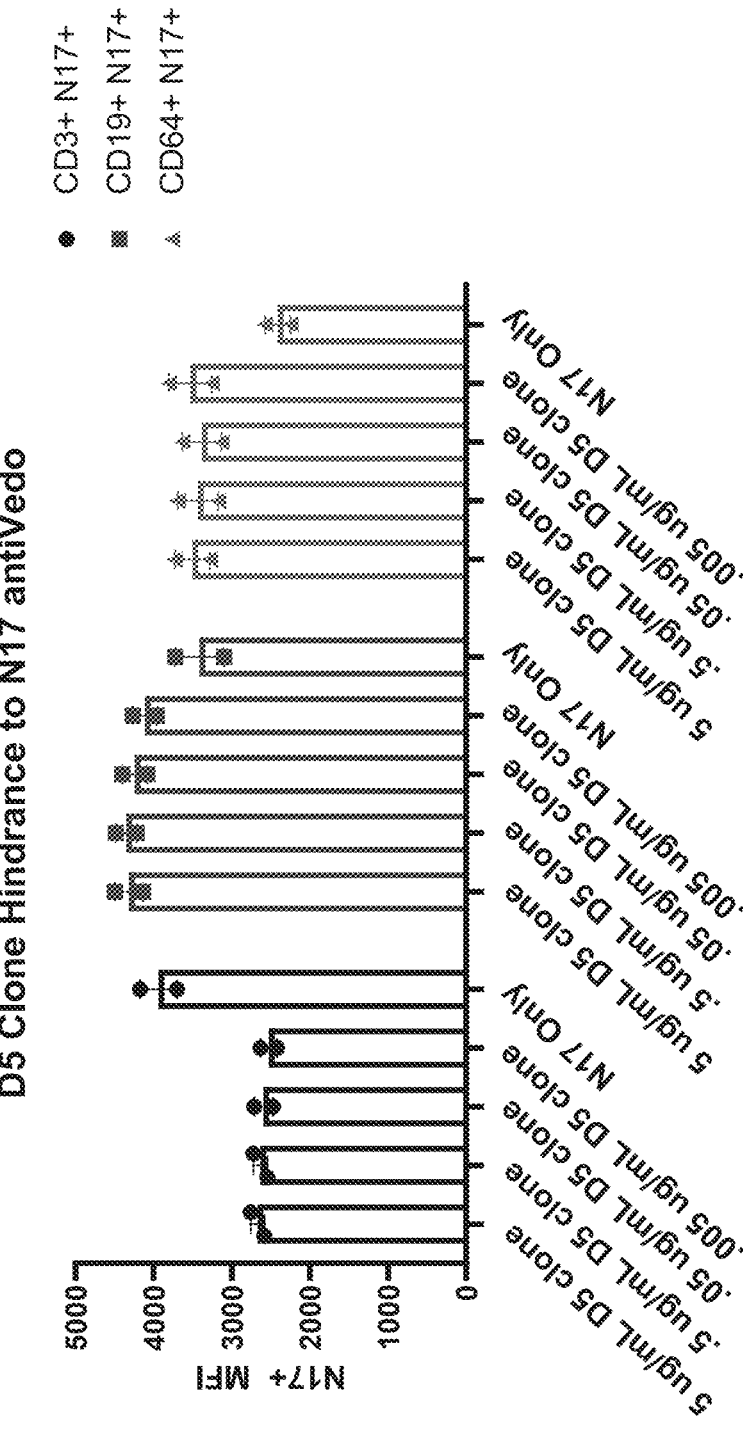
Figure 9F:
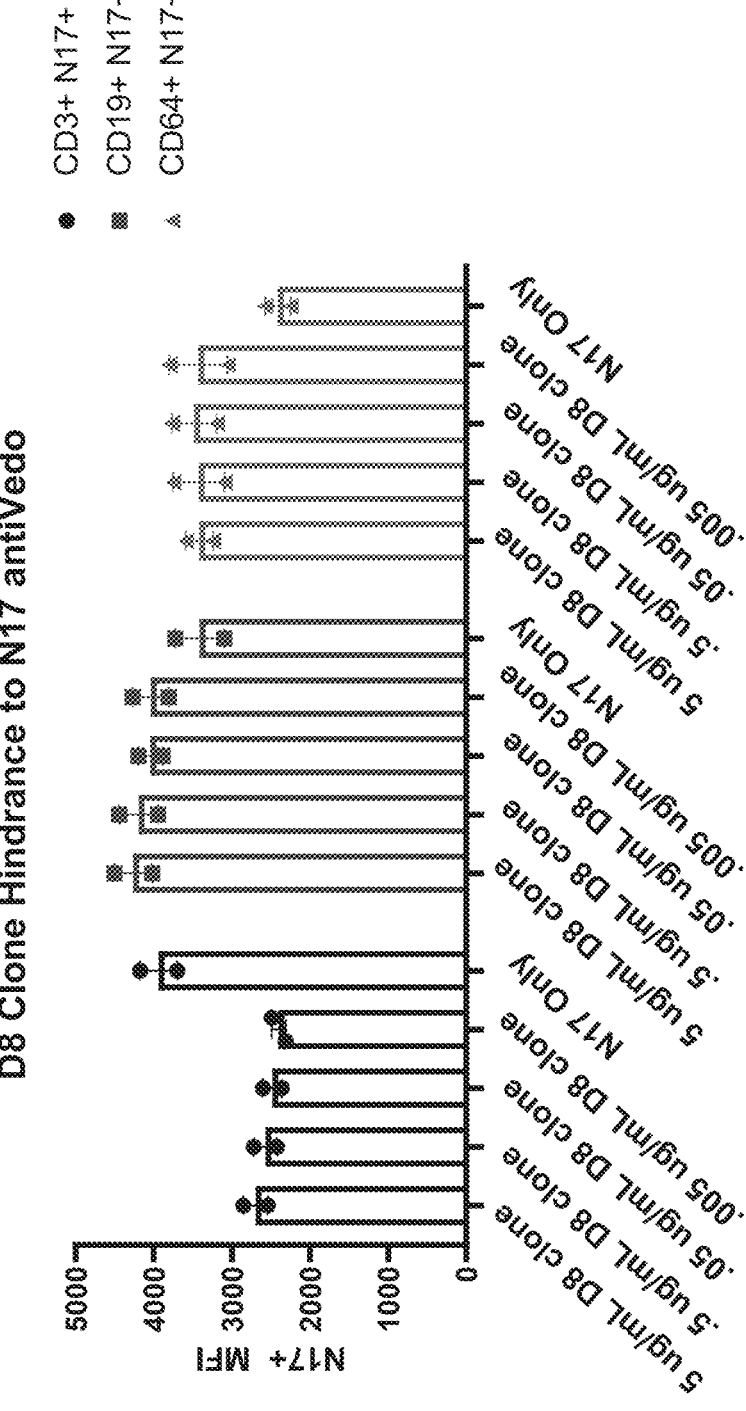
Figure 9G:
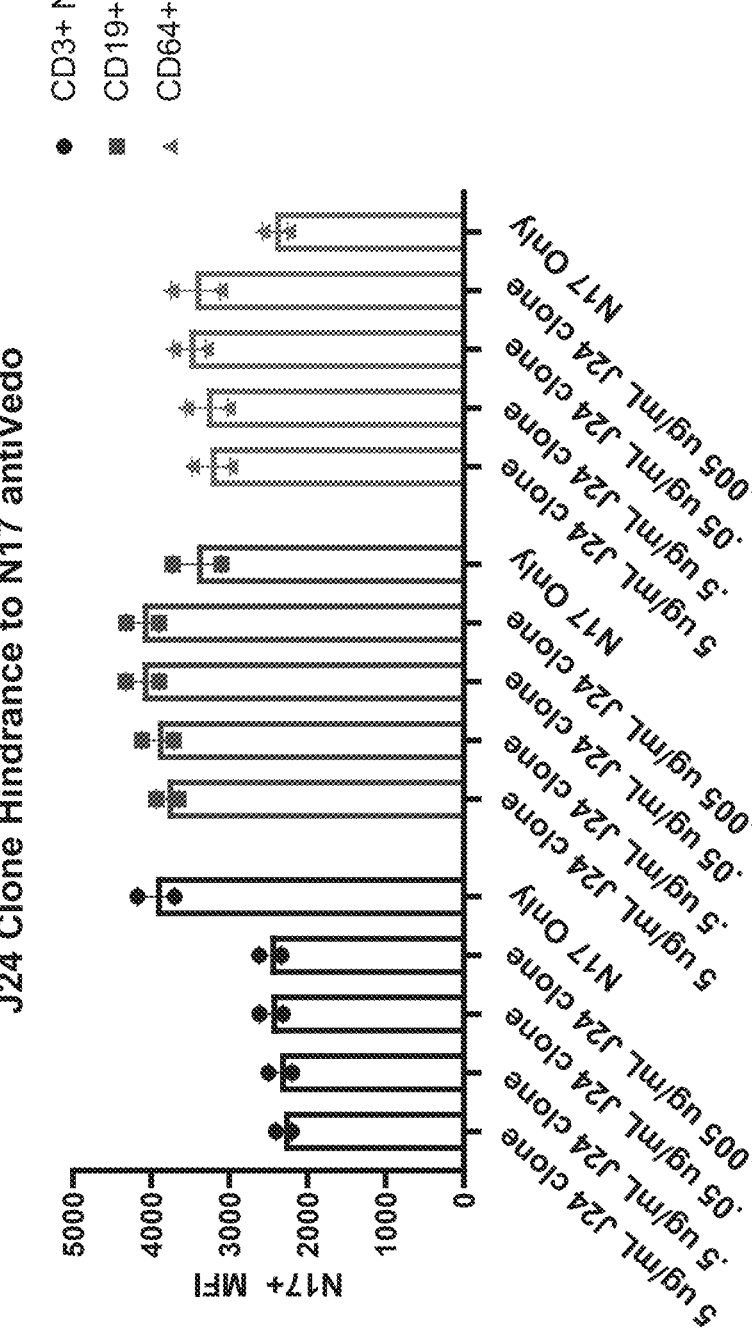

As shown in FIGS. 8A-8G, clones 110, J3, and C13 at least partially blocked N17 binding to vedolizumab, whereas clones B4, D5, D8, and J24 did not block N17 binding to vedolizumab. Increasing concentrations of the unlabeled clones 110 and C13 clones decreased N17 binding to ved-olizumab, indicating that clones 110 and C13 competed for vedolizumab binding with N17 on each of the assessed cell types (FIGS. 8A and 8D). In contrast, clone J3 clone showed partial competition for binding with N17, with less of a competition effect on T cells.

Increased concentrations of clones B4, D5, D8, and J24 did not interfere with N17 binding to vedolizumab, suggesting that B4, D5, D8, and J24 did not compete for binding with N17 (FIG. 8B).

The mean fluorescence intensity (MFI) of N17 for each of the indicated experimental conditions was additionally assessed. As shown in FIGS. 9A-9G, the decrease in fluorescence intensity confirms the N17 epitope occupation on vedolizumab by clones 110, J3, and C13.

| SEQUENCE TABLE | | |
|---|---|---|
| SEQ ID NO: | SEQUENCE DESCRIPTION and ANTIBODY NAME | SEQUENCE |
| 1 | HC CDR1 (amino acid) B4 | GFSLSSYE |
| 2 | HC CDR2 (amino acid) B4 | IWTGGST |
| 3 | HC CDR3 (amino acid) B4 | VGAPYDYGGFAY |
| 4 | LC CDR1 (amino acid) B4 | KSLLHNDGITY |
| 5 | LC CDR2 (amino acid) B4 | RMS |
| 6 | LC CDR3 (amino acid) B4 | AQMLEFPYT |
| 7 | Heavy chain variable region (HCVR) (amino acid) B4 | QVQLKESGPGLAAPSQNLFITCTVSGFSLSSYEI HWFRQPPGKGLEWLGVIWTGGSTDYNSALISR LNISKDNSKSLAFLNVNSLQTDDTAIYYCVGAP YDYGGFAYWGQGTLVTVSA |
| 8 | Light chain (LC) variable region (amino acid) B4 | DIVMTQAAFSNPVTLGTSASISCRSSKSLLHND GITYLYWYLQRPGQSPQLLLFRMSNLASGVPD RFSGSGSGTDFTLRISRVEAEDVGVYYCAQML EFPYTFGSGTKLEIK |
| 9 | Heavy chain variable region (nucleic acid) B4 | CAGGTGCAGCTGAAGGAGTCAGGACCTGGCC TGGCGGCGCCCTCACAGAACCTGTTCATCAC ATGTACCGTCTCAGGATTCTCATTAAGCAGCT ATGAAATACACTGGTTTCGCCAGCCTCCAGG AAAGGGTCTGGAGTGGCTGGGAGTGATATGG ACTGGTGGAAGTACAGATTATAATTCAGCTC TCATATCCAGACTGAACATAAGTAAAGACAA CTCCAAGAGCCTAGCTTTCTTAAATGTGAAT |

-continued

| SEQUENCE TABLE | | |
|---|---|---|
| SEQ ID NO: | SEQUENCE DESCRIPTION and ANTIBODY NAME | SEQUENCE |
| | | AGTCTGCAAACTGATGACACAGCCATATATT ACTGTGTAGGAGCCCCCTATGATTACGGGGG GTTTGCTTATTGGGGCCAAGGGACTCTGGTC ACTGTCTCTGCA |
| 10 | Light chain variable region (nucleic acid) B4 | GATATTGTGATGACGCAGGCTGCATTCTCCA ATCCAGTCACTCTTGGAACGTCAGCTTCCATC TQCTGCAGGTCTAGTAAGAGTCTQCTACATA ATGATGGCATCACTTATTTGTATTGGTATCTG CAGAGGCCAGGCCAGTCTCCTCAGCTCCTGC TTTTTCGGATGTCCAACCTTGCCTCAGGAGTC CCAGACAGGTTCAGTGGCAGTGGGTCAGGAA CTGATTTCACACTGAGAATCAGCAGAGTAGA GGCTGAGGATGTGGGTGTTTATTACTGTGCTC AAATGCTAGAATTCCCGTATACGTTCGGATC GGGGACCAAGCTGGAAATAAAA |
| 11 | HC CDR1 (amino acid) I8 | GYTFTSYN |
| 12 | HC CDR2 (amino acid) I8 | IYPGNGDT |
| 13 | HC CDR3 (amino acid) I8 | ARGWFHWYFDV |
| 14 | LC CDR1 (amino acid) I8 | SSISSNY |
| 15 | LC CDR2 (amino acid) I8 | RTS |
| 16 | LC CDR3 (amino acid) I8 | QQGSTIPLT |
| 17 | Heavy chain (HC) variable region (amino acid) I8 | QAYLQQSGAELVRPGASVKMSCKASGYTFTSY NMHWVKQTPRQGLEWIGAIYPGNGDTSYNQK FKGKATLTVDKSSSTAYMQLSSLTSEDSAVYFC ARGWFHWYFDVWGTGTTVTVSS |
| 18 | Light chain (LC) variable region (amino acid) I8 | EIVLTQSPTAMAASPGEKITITCSASSSISSNYLH WYLQKPGFSPKLLIYRTSNLASGVPARFSGSGS GTSYSLTIGTMEAEDVATYYCQQGSTIPLTFGA GTRLELK |
| 19 | Heavy chain variable region (nucleic acid) I8 | CAGGCTTATCTACAGCAGTCTGGGGCTGAGC TGGTGAGGCCTGGGGCCTCAGTGAAGATGTC CTGCAAGGCTTCTGGCTACACATTTACCAGTT ACAATATGCACTGGGTAAAGCAGACACCTAG ACAGGGCCTGGAATGGATTGGAGCTATTTAT CCAGGAAATGGTGATACTTCCTACAATCAGA AGTTCAAGGGCAAGGCCACACTGACTGTAGA CAAATCCTCCAGCACAGCCTACATGCAGCTC AGCAGCCTGACATCTGAAGACTCTGCGGTCT ATTTCTGTGCAAGAGGATGGTTTCACTGGTA CTTCGATGTCTGGGGCACAGGGACCACGGTC ACCGTCTCCTCA |
| 20 | Light chain variable region (nucleic acid) I8 | GAAATTGTGCTCACCCAGTCTCCAACCGCCA TGGCTGCATCTCCCGGGGAGAAGATCACTAT CACCTGCAGTGCCAGCTCAAGTATAAGTTCC AATTACTTGCATTGGTATCTGCAGAAGCCAG GATTCTCCCCTAAACTCTTGATTTATAGGACA TCCAATCTGGCTTCTGGAGTCCCAGCTCGCTT CAGTGGCAGTGGGTCTGGGACCTCTTACTCT CTCACAATTGGCACCATGGAGGCTGAAGATG TTGCCACTTACTACTGCCAGCAGGGTAGTAC TATACCGCTCACGTTCGGTGCTGGGACCAGG CTGGAGCTGAAA |
| 21 | HC CDR1 (amino acid) J3 | GFSLTNYG |

| SEQ ID NO: | SEQUENCE DESCRIPTION and ANTIBODY NAME | SEQUENCE |
|---|---|---|
| 22 | HC CDR2 (amino acid) J3 I10 N17 C13 | IWSGGST |
| 23 | HC CDR3 (amino acid) J3 | ARIGGYGTTYEDGMDY |
| 24 | LC CDR1 (amino acid) J3 N17 C13 | ESVDNFGISF |
| 25 | LC CDR2 (amino acid) J3 I10 N17 C13 | RAS |
| 26 | LC CDR3 (amino acid) J3 I10 N17 C16 | QQSNKDPLT |
| 27 | Heavy chain (HC) variable region (amino acid) J3 | QVQLKQSGPGLVQPSQSLSITCTVSGFSLTNYG VHWVRQSPGKGLEWLGVIWSGGSTDYNAAVI SRLTISKDNSKSQVFFKMNSLQADDTAIYYCAR IGGYGTTYEDGMDYWGQGTSVTVSS |
| 28 | Light chain (LC) variable region (amino acid) J3 | DIVLTQSPASLAVSLGQRATISCRASESVDNFGI SFMHWYQQKSGQPPKLLIYRASNLESGIPARFS GSGSRTDFTLTINPVETDDVATYYCQQSNKDPL TFGAGTKLELK |
| 29 | Heavy chain variable region (nucleic acid) J3 | CAGGTGCAGCTGAAGCAGTCAGGACCTGGCC TAGTGCAGCCCTCACAGAGCCTGTCCATCAC CTGCACAGTCTCTGGTTTCTCATTAACTAACT ATGGTGTACACTGGGTTCGCCAGTCTCCAGG AAAGGGTCTGGAGTGGCTGGGAGTGATATGG AGTGGTGGAAGCACAGACTATAATGCAGCTG TCATATCCAGACTGACCATCAGCAAGGACAA TTCCAAGAGCCAAGTTTTCTTTAAAATGAAC AGTCTGCAAGCTGATGACACAGCCATTTATT ACTGTGCCAGAATAGGGGGCTACGGTACTAC CTACGAGGATGGTATGGACTACTGGGGTCAA GGAACCTCAGTCACCGTCTCCTCA |
| 30 | Light chain variable region (nucleic acid) J3 | GACATTGTGCTGACCCAATCTCCAGCTTCTTT GGCTGTGTCTCTAGGGCAGAGGGCCACCATC TCCTGCAGAGCCAGCGAAAGTGTTGATAATT TTGGCATTAGTTTTATGCACTGGTACCAGCAG AAATCAGGACAGCCACCCAAACTCCTCATCT ATCGTGCATCCAACCTAGAATCTGGGATCCC TGCCAGGTTCAGTGGCAGTGGGTCTAGGACA GACTTCACCCTCACCATTAATCCTGTGGAGA CTGATGATGTTGCAACCTATTACTGTCAGCA AAGTAATAAGGATCCGCTCACGTTCGGTGCT GGGACCAAGCTGGAGCTGAAA |
| 31 | HC CDR1 (amino acid) I10 N17 | GFSLTSYG |
| 32 | HC CDR3 (amino acid) I10 | ARIGGYGTSYEDGMDY |
| 33 | LC CDR1 (amino acid) I10 | ESVDNFGVSF |

US 12,693,298 B1

87                                                                88

-continued

| SEQUENCE TABLE | | |
|---|---|---|
| SEQ ID NO: | SEQUENCE DESCRIPTION and ANTIBODY NAME | SEQUENCE |
| 34 | Heavy chain (HC) variable region (amino acid) I1C | QVQLKQSGPGLVQPSQSLSITCTVSGFSLTSYG VHWVRQSPGKGLEWLGVIWSGGSTDYNAAFR SRLTISKDNSKSQVFFKMNSLQADDTAIYYCAR IGGYGTSYEDGMDYWGQGTSVTVSS |
| 35 | Light chain (LC) variable region (amino acid) I10 | DIVLTQSPASLAVSLGQRATISCRASESVDNFG VSFMHWYQQKPGQPPKLLIYRASNLESGIPARF SGSGSRTDFTLTINPVETDDVATYYCQQSNKDP LTFGAGTKLELK |
| 36 | Heavy chain variable region (nucleic acid) I10 | CAGGTGCAGCTGAAGCAGTCAGGACCTGGCC TAGTGCAGCCCTCACAGAGCCTGTCCATCAC CTGCACAGTCTCTGGTTTCTCATTAACTAGCT ATGGTGTACACTGGGTTCGCCAGTCTCCAGG AAAGGGTCTGGAGTGGCTGGGAGTGATATGG AGTGGTGGAAGCACAGACTATAATGCAGCTT TCAGATCCAGACTGACCATCAGCAAGGACAA TTCCAAGAGCCAAGTTTTCTTTAAAATGAAC AGTCTGCAAGCTGATGACACAGCCATATATT ACTGTGCCAGAATAGGGGGCTACGGTACTAG CTACGAGGATGGTATGGACTACTGGGGTCAA GGAACCTCAGTCACCGTCTCCTCA |
| 37 | Light chain variable region (nucleic acid) I10 | GACATTGTGCTGACCCAATCTCCAGCTTCTTT GGCTGTGTCTCTAGGGCAGAGGGCCACCATC TCCTGCAGAGCCAGCGAAAGTGTTGATAATT TTGGCGTTAGTTTTATGCACTGGTATCAACAG AAACCAGGACAGCCACCCAAACTCCTCATCT ATCGTGCATCCAACCTAGAATCTGGGATCCC TGCCAGGTTCAGTGGCAGTGGGTCTAGGACA GACTTCACCCTCACCATTAATCCTGTGGAGA CTGATGATGTTGCAACCTATTACTGTCAGCA AAGTAATAAGGATCCGCTCACGTTCGGTGCT GGGACCAAGCTGGAACTGAAA |
| 38 | HC CDR1 (amino acid) D5 | GFTFSSYG |
| 39 | HC CDR2 (amino acid) D5 | ISSGGSYT |
| 40 | HC CDR3 (amino acid) D5 | ARHGTGVGFDY |
| 41 | LC CDR1 (amino acid) D5 | QSLLDSDGKTY |
| 42 | LC CDR2 (amino acid) D5 | LVS |
| 43 | LC CDR3 (amino acid) D5 | WQGTHFPQT |
| 44 | Heavy chain (HC) variable region (amino acid) D5 | EVQLVESGGDLVKPGGSLKLSCAASGFTFSSYG MSWVRQTPDKRLEWVASISSGGSYTHYPDSVK GRFTISRDNAKNTLYLQMSSLKSEDTAMYYCA RHGTGVGFDYWGQGTTLTVSS |
| 45 | Light chain (LC) variable region (amino acid) D5 | DVVMTQTPLTLSVTIGQPASISCKSSQSLLDSDG KTYLNWLLQRPGQSPKRLIYLVSKLDSGVPDRF TGSGSGTDFTLKISRVEAEDLGVYYCWQGTHF PQTFGGGTKLEIK |
| 46 | Heavy chain variable region (nucleic acid) D5 | GAGGTGCAGCTGGTGGAGTCTGGGGGAGACT TAGTGAAGCCTGGAGGGTCCCTGAAACTCTC CTGTGCTGCCTCTGGATTCACTTTCAGTAGCT ATGGCATGTCTTGGGTTCGCCAGACTCCAGA CAAGAGGCTGGAGTGGGTCGCATCCATTAGT AGTGGTGGTAGTTACACCCACTATCCAGACA GTGTGAAGGGGCGATTCACCATCTCCAGAGA CAATGCCAAGAACACCCTGTACCTGCAAATG AGCAGTCTGAAGTCTGAGGACACAGCCATGT ATTACTGTGCAAGACATGGGACTGGGGTCGG |

-continued

| SEQ ID NO: | SEQUENCE DESCRIPTION and ANTIBODY NAME | SEQUENCE |
|---|---|---|
| | | TTTTGACTACTGGGGCCAAGGCACCACTCTC ACAGTCTCCTCA |
| 47 | Light chain variable region (nucleic acid) D5 | GATGTTGTGATGACCCAGACTCCACTCACTTT GTCGGTTACCATTGGACAACCAGCCTCCATC TCTTGCAAGTCAAGTCAGAGCCTCTTAGATA GTGATGGAAAGACATATTTGAATTGGTTGTT ACAGAGGCCAGGCCAGTCTCCAAAGCGCCTA ATCTATCTGGTGTCTAAACTGGACTCTGGAGT CCCTGACAGGTTCACTGGCAGTGGATCAGGG ACAGATTTCACACTGAAAATCAGCAGAGTGG AGGCTGAGGATTTGGGAGTTTATTATTGCTG GCAAGGTACACATTTTCCTCAGACGTTCGGT GGAGGCACCAAGCTGGAAATCAAA |
| 48 | HC CDR1 (amino acid) J24 | GFTFSDYG |
| 49 | HC CDR2 (amino acid) J24 | ISNLAYSI |
| 50 | HC CDR3 (amino acid) J24 | AREDGTTGESAMDY |
| 51 | LC CDR1 (amino acid) J24 | KSISKY |
| 52 | LC CDR2 (amino acid) J24 | SGS |
| 53 | LC CDR3 (amino acid) J24 | QQHYEYPYT |
| 54 | Heavy chain (HC) variable region (amino acid) J24 | EVKLVESGGGLVQPGGSLKLSCAASGFTFSDY GMAWVRQAPRKGPEWVGFISNLAYSIYYADT VTGRFTISRENAKNTLYLEMSSLRSEDTAMYY CAREDGTTGESAMDYWGQGTSVTVSS |
| 55 | Light chain (LC) variable region (amino acid) J24 | DVQITQSPSYLAASPGETITINCRASKSISKYLA WYQEKPGKTNKLLIYSGSTLQSGIPSRFSGSGS GTDFTLTISSLEPEDFAMYYCQQHYEYPYTFGS GTKLEMK |
| 56 | Heavy chain variable region (nucleic acid) J24 | GAGGTGAAGCTGGTGGAGTCTGGGGGAGGCT TAGTGCAGCCTGGAGGGTCCCTGAAACTCTC CTGTGCAGCCTCTGGATTCACTTTCAGTGACT ACGGAATGGCGTGGGTTCGACAGGCTCCAAG GAAGGGGCCTGAGTGGGTAGGATTCATTAGT AATTTGGCGTATAGTATCTACTATGCAGACA CTGTGACGGGCCGATTCACCATCTCTAGAGA GAATGCCAAGAACACCCTGTACCTGGAAATG AGCAGTCTGAGGTCTGAGGACACGGCCATGT ATTACTGTGCAAGAGAGGATGGCACTACGGG AGAAAGTGCTATGGACTACTGGGGTCAAGGA ACCTCAGTCACCGTCTCCTCA |
| 57 | Light chain variable region (nucleic acid) J24 | GATGTCCAGATAACCCAGTCTCCATCTTATCT TGCTGCATCTCCTGGAGAAACCATTACTATTA ATTGCAGGGCAAGTAAGAGCATTAGCAAATA TTTAGCCTGGTATCAAGAGAAACCTGGGAAA ACTAATAAGCTTCTTATCTACTCTGGATCCAC TTTGCAATCTGGAATTCCATCAAGGTTCAGTG GCAGTGGATCTGGTACAGATTTCACTCTCAC CATCAGTAGCCTGGAGCCTGAAGATTTTGCA ATGTATTACTGTCAACAGCACTATGAATACC CGTACACGTTCGGCTCGGGGACAAAGTTGGA AATGAAG |
| 58 | HC CDR3 (amino acid) N17 C13 | ARIGGYGTTYEDAMDY |

-continued

| SEQUENCE TABLE | | |
|---|---|---|
| SEQ ID NO: | SEQUENCE DESCRIPTION and ANTIBODY NAME | SEQUENCE |
| 59 | Heavy chain (HC) variable region (amino acid) N17 | QVQLKQSGPGLVQPSQSLSITCTVSGFSLTSYG VHWVRQSPGKGLEWLGVIWSGGSTDYNAAFIS RLTISKDNSKTQVFFKMNSLQADDTAIYYCARI GGYGTTYEDAMDYWGQGTSVTVSS |
| 60 | Light chain (LC) variable region (amino acid) N17 | DIALTQSPASLAVSLGQRATISCRASESVDNFGI SFMHWYQQKPGQPPKVLIYRASKLESGIPARFS GSGSRTDFTLTINPVETEDVATYYCQQSNKDPL TFGAGTKLELK |
| 61 | Heavy chain variable region (nucleic acid) N17 | CAGGTGCAGCTGAAGCAGTCAGGACCTGGCC TAGTGCAGCCCTCACAGAGCCTGTCCATCAC CTGCACAGTCTCTGGTTTCTCATTAACTAGCT ATGGTGTACACTGGGTTCGCCAGTCTCCAGG AAAGGGTCTGGAGTGGCTGGGAGTGATATGG AGTGGTGGAAGCACAGACTATAATGCAGCTT TCATATCCAGACTGACCATCAGCAAGGACAA TTCCAAGACCCAAGTTTTCTTTAAAATGAAC AGTCTGCAAGCTGATGACACAGCCATATATT ACTGTGCCAGAATAGGGGGCTACGGTACTAC CTACGAGGATGCTATGGACTACTGGGGTCAA GGAACCTCAGTCACCGTCTCCTCA |
| 62 | Light chain variable region (nucleic acid) N17 | GACATTGCGCTGACCCAATCTCCAGCTTCTTT GGCTGTGTCTCTAGGGCAGAGGGCCACCATC TCCTGCAGAGCCAGCGAAAGTGTTGATAATT TTGGCATTAGTTTTATGCACTGGTACCAGCAG AAACCAGGACAGCCACCCAAAGTCCTCATCT ATCGTGCATCCAAGCTAGAATCTGGGATCCC TGCCAGGTTCAGTGGCAGTGGGTCTAGGACA GACTTCACCCTCACCATTAATCCTGTGGAGA CTGAAGATGTTGCAACCTATTACTGTCAGCA AAGTAATAAGGATCCTCTCACGTTCGGTGCT GGGACCAAGCTGGAGCTGAAA |
| 63 | HC CDR1 (amino acid) C13 | GFSLTSYG |
| 64 | Heavy chain (HC) variable region (amino acid) C13 | QVQLKQSGPGLVQPSQSLSVTCTVSGFSLTSYG VHWVRQSPGKGLEWLGVIWSGGSTDYNAAFIS RLTISKDNSKSQVFFKMNSLQADDTAIYYCARI GGYGTTYEDAMDYWGQGTSVTVSS |
| 65 | Light chain (LC) variable region (amino acid) C13 | DIVLTQSPASLSVSLGQRATISCRASESVDNFGI SFMFWYQQKPGQPPRLLIYRASNLESGIPARFS GSGSRTDFTLTINPVETDDVATYYCQQSNKDPL TFGAGTKLELK |
| 66 | Heavy chain variable region (nucleic acid) C13 | CAGGTGCAGCTGAAGCAATCAGGACCTGGCC TAGTGCAGCCCTCACAGAGCCTGTCCGTCAC CTGCACAGTCTCTGGTTTCTCATTAACTAGCT ATGGTGTACACTGGGTTCGCCAGTCTCCAGG AAAGGGTCTGGAGTGGCTGGGAGTGATATGG AGTGGTGGAAGCACAGACTATAATGCAGCTT TCATATCCAGACTGACCATCAGCAAGGACAA TTCCAAGAGCCAAGTTTTCTTTAAAATGAAC AGTCTGCAAGCTGATGACACAGCCATATATT ACTGTGCCAGAATAGGGGGCTACGGTACTAC CTACGAGGATGCTATGGACTACTGGGGTCAA GGAACCTCAGTCACCGTCTCCTCA |
| 67 | Light chain variable region (nucleic acid) C13 | GACATTGTGCTGACCCAATCTCCAGCTTCTTT GTCTGTGTCTCTAGGGCAGAGGGCCACCATC TCCTGCAGAGCCAGCGAAAGTGTTGATAATT TTGGCATTAGTTTTATGTTTTGGTACCAGCAG AAACCAGGACAGCCACCCAGACTCCTCATCT ATCGTGCATCCAACCTAGAATCTGGGATCCC TGCCAGGTTCAGTGGCAGTGGGTCTAGGACA GACTTCACCCTCACCATTAATCCTGTGGAGA CTGATGATGTTGCAACCTATTACTGTCAGCA AAGTAATAAGGATCCGCTCACGTTCGGTGCT GGGACCAAGCTGGAGCTGAAA |

-continued

| SEQ ID NO: | SEQUENCE DESCRIPTION and ANTIBODY NAME | SEQUENCE |
|---|---|---|
| 68 | HC CDR1 (amino acid) D8 | GYTFTDYN |
| 69 | HC CDR2 (amino acid) D8 | INPNNGGT |
| 70 | HC CDR32 (amino acid) D8 | ARDLVYYFDY |
| 71 | LC CDR1 (amino acid) D8 | QSIGRS |
| 72 | LC CDR2 (amino acid) D8 | YAS |
| 73 | LC CDR3 (amino acid) D8 | QQSNSWPFT |
| 74 | Heavy chain (HC) variable region (amino acid) D8 | EVQLQQSGPELVKPGASVKIPCKASGYTFTDYN MDWVKQSHGKSLEWIGDINPNNGGTIYNQKFK GKATLTVDKSSSTAYMELRSLTSEDTAVYYCA RDLVYYFDYWGQGTTLTVSS |
| 75 | Light chain (LC) variable region (amino acid) D8 | DILLTQSPAILSVSPGERVSFSCRASQSIGRSIHW YQQRTNGSPRLLIKYASESISGIPSRFSGSGSGTD FTLSINSVESEDIADYYCQQSNSWPFTFGSGTKL EIK |
| 76 | Heavy chain variable region (nucleic acid) D8 | GAGGTCCAGCTGCAACAGTCTGGACCTGAGC TGGTGAAGCCTGGGGCTTCAGTGAAGATACC CTGCAAGGCTTCTGGATACACATTCACTGAC TACAACATGGACTGGGTGAAGCAGAGCCATG GAAAGAGCCTTGAGTGGATTGGAGATATTAA TCCTAACAATGGTGGTACTATCTACAACCAG AAGTTCAAGGGCAAGGCCACATTGACTGTAG ACAAGTCCTCCAGCACAGCCTACATGGAGCT CCGCAGCCTGACATCTGAGGACACTGCAGTC TATTACTGTGCAAGAGACCTCGTTTACTACTT TGACTACTGGGGCCAAGGCACCACTCTCACA GTCTCCTCA |
| 77 | Light chain variable region (nucleic acid) D8 | GACATCTTGCTGACTCAGTCTCCAGCCATCCT GTCTGTGAGTCCAGGAGAAAGAGTCAGTTTC TCCTGCAGGGCCAGTCAGAGCATTGGCAGAA GCATACACTGGTATCAGCAAAGAACAAATGG TTCTCCAAGGCTTCTCATAAAGTATGCTTCTG AGTCTATCTCTGGGATCCCTTCCAGGTTTAGT GGCAGTGGATCAGGGACAGATTTTACTCTTA GCATCAACAGTGTGGAGTCTGAAGATATTGC AGATTATTACTGTCAACAAAGTAATAGCTGG CCATTCACGTTCGGCTCGGGGACAAAGTTGG AAATAAAA |
| 78 | Vedolizumab heavy chain (HC) variable region (amino acid) | QVQLVQSGAEVKKPGASVKVSCKGSGYTFTSY WMHWVRQAPGQRLEWIGEIDPSESNTNYNQK FKGRVTLTVDISASTAYMELSSLRSEDTAVYYC ARGGYDGWDYAIDYWGQGTLVTVSS |
| 79 | Vedolizumab HC CDR1 (amino acid) | SYWMH |
| 80 | Vedolizumab HC CDR2 (amino acid) | EIDPSESNTNYNQKFKG |
| 81 | Vedolizumab HC CDR3 (amino acid) | GGYDGWDYAIDY |
| 82 | Vedolizumab light chain (LC) variable region (amino acid) | DVVMTQSPLSLPVTPGEPASISCRSSQSLAKSYG NTYLSWYLQKPGQSPQLLIYGISNRFSGVPDRF SGSGSGTDFTLKISRVEAEDVGVYYCLQGTHQP YTFGQGTKVEIK |

-continued

SEQUENCE TABLE

| SEQ ID NO: | SEQUENCE DESCRIPTION and ANTIBODY NAME | SEQUENCE |
|---|---|---|
| 83 | Vedolizumab LC CDR1 (amino acid) | RSSQSLAKSYGNTYLS |
| 84 | Vedolizumab LC CDR2 (amino acid) | GISNRFS |
| 85 | Vedolizumab LC CDR3 (amino acid) | LQGTHQPYT |
| 86 | Vedolizumab heavy chain amino acid sequence | QVQLVQSGAEVKKPGASVKVSCKGSGYTFTSY WMHWVRQAPGQRLEWIGEIDPSESNTNYNQK FKGRVTLTVDISASTAYMELSSLRSEDTAVYYC ARGGYDGWDYAIDYWGQGTLVTVSSASTKGP SVFPLAPSSKSTSGGTAALGCLVKDYFPEPVTV SWNSGALTSGVHTFPAVLQSSGLYSLSSVVTVP SSSLGTQTYICNVNHKPSNTKVDKKVEPKSCD KTHTCPPCPAPELAGAPSVFLFPPKPKDTLMISR TPEVTCVVVDVSHEDPEVKFNWYVDGVEVHN AKTKPREEQYNSTYRVVSVLTVLHQDWLNGK EYKCKVSNKALPAPIEKTISKAKGQPREPQVYT LPPSRDELTKNQVSLTCLVKGFYPSDIAVEWES NGQPENNYKTTPPVLDSDGSFFLYSKLTVDKSR WQQGNVFSCSVMHEALHNHYTQKSLSLSPGK |
| 87 | Vedolizumab light chain amino acid sequence | DVVMTQSPLSLPVTPGEPASISCRSSQSLAKSYG NTYLSWYLQKPGQSPQLLIYGISNRFSGVPDRF SGSGSGTDFTLKISRVEAEDVGVYYCLQGTHQP YTFGQGTKVEIKRTVAAPSVFIFPPSDEQLKSGT ASVVCLLNNFYPREAKVQWKVDNALQSGNSQ ESVTEQDSKDSTYSLSSTLTLSKADYEKHKVYA CEVTHQGLSSPVTKSFNRGEC |

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

What is claimed:

1. A method of treating a human patient having an inflammatory bowel disease (IBD), the method comprising (i) administering a dose of vedolizumab to the human patient having IBD, (ii) contacting a biological sample comprising a population of cells from the human patient 1 to 2 weeks after administration of vedolizumab with an anti-idiotypic antibody, or an antigen-binding fragment thereof, with binding specificity to vedolizumab, under conditions in which the anti-idiotypic antibody, or antigen-binding fragment thereof, binds to vedolizumab, (iii) measuring a level of vedolizumab bound to immune cells in the biological sample with the anti-idiotypic antibody, or antigen-binding fragment thereof, and (iv) administering one or more doses of vedolizumab to the human patient, wherein the level of vedolizumab bound to immune cells in the biological sample is increased relative to a reference level, wherein the reference level is a baseline sample obtained from the human patient prior to treatment with vedolizumab, thereby treating the human patient having IBD,
wherein the anti-idiotypic antibody or antigen-binding
fragment thereof, comprises:

(i) a heavy chain variable region comprising a CDR1
domain comprising the amino acid sequence of SEQ ID
NO: 1, a CDR2 domain comprising the amino acid
sequence of SEQ ID NO: 2, and a CDR3 domain
comprising the amino acid sequence of SEQ ID NO: 3;
and a light chain variable region comprising a CDR1
domain comprising the amino acid sequence of SEQ ID
NO: 4, a CDR2 domain comprising the amino acid
sequence of RMS, and a CDR3 domain comprising the
amino acid sequence of SEQ ID NO: 6;

(ii) a heavy chain variable region comprising a CDR1
domain comprising the amino acid sequence of SEQ ID
NO: 11, a CDR2 domain comprising the amino acid
sequence of SEQ ID NO: 12, and a CDR3 domain
comprising the amino acid sequence of SEQ ID NO:
13; and a light chain variable region comprising a
CDR1 domain comprising the amino acid sequence of
SEQ ID NO: 14, a CDR2 domain comprising the amino
acid sequence of RTS, and a CDR3 domain comprising
the amino acid sequence of SEQ ID NO: 16;

(iii) a heavy chain variable region comprising a CDR1
domain comprising the amino acid sequence of SEQ ID
NO: 21, a CDR2 domain comprising the amino acid
sequence of SEQ ID NO: 22, and a CDR3 domain
comprising the amino acid sequence of SEQ ID NO:
23; and a light chain variable region comprising a
CDR1 domain comprising the amino acid sequence of
SEQ ID NO: 24, a CDR2 domain comprising the amino
acid sequence of RAS, and a CDR3 domain comprising
the amino acid sequence of SEQ ID NO: 26;

(iv) a heavy chain variable region comprising a CDR1
domain comprising the amino acid sequence of SEQ ID
NO: 31, a CDR2 domain comprising the amino acid
sequence of SEQ ID NO: 22, and a CDR3 domain
comprising the amino acid sequence of SEQ ID NO:
32; and a light chain variable region comprising a
CDR1 domain comprising the amino acid sequence of
SEQ ID NO: 33, a CDR2 domain comprising the amino
acid sequence of RAS, and a CDR3 domain comprising
the amino acid sequence of SEQ ID NO: 26;

(v) a heavy chain variable region comprising a CDR1
domain comprising the amino acid sequence of SEQ ID
NO: 38, a CDR2 domain comprising the amino acid
sequence of SEQ ID NO: 39, and a CDR3 domain
comprising the amino acid sequence of SEQ ID NO:
40; and a light chain variable region comprising a
CDR1 domain comprising the amino acid sequence of
SEQ ID NO: 41, a CDR2 domain comprising the amino
acid sequence of LVS, and a CDR3 domain comprising
the amino acid sequence of SEQ ID NO: 43;

(vi) a heavy chain variable region comprising a CDR1
domain comprising the amino acid sequence of SEQ ID
NO: 48, a CDR2 domain comprising the amino acid
sequence of SEQ ID NO: 49, and a CDR3 domain
comprising the amino acid sequence of SEQ ID NO:
50; and a light chain variable region comprising a
CDR1 domain comprising the amino acid sequence of
SEQ ID NO: 51, a CDR2 domain comprising the amino
acid sequence of SGS, and a CDR3 domain comprising
the amino acid sequence of SEQ ID NO: 53;

(vii) a heavy chain variable region comprising a CDR1
domain comprising the amino acid sequence of SEQ ID
NO: 31 a CDR2 domain comprising the amino acid
sequence of SEQ ID NO: 22, and a CDR3 domain comprising the amino acid sequence of SEQ ID NO:
58; and a light chain variable region comprising a
CDR1 domain comprising the amino acid sequence of
SEQ ID NO: 24, a CDR2 domain comprising the amino
acid sequence of RAS, and a CDR3 domain comprising
the amino acid sequence of SEQ ID NO: 26;

(viii) a heavy chain variable region comprising a CDR1
domain comprising the amino acid sequence of SEQ ID
NO: 63 a CDR2 domain comprising the amino acid
sequence of SEQ ID NO: 22, and a CDR3 domain
comprising the amino acid sequence of SEQ ID NO:
58; and a light chain variable region comprising a
CDR1 domain comprising the amino acid sequence of
SEQ ID NO: 24, a CDR2 domain comprising the amino
acid sequence of RAS, and a CDR3 domain comprising
the amino acid sequence of SEQ ID NO: 26; or (ix) a heavy chain variable region comprising a CDR1
domain comprising the amino acid sequence of SEQ ID
NO: 68 a CDR2 domain comprising the amino acid
sequence of SEQ ID NO: 69, and a CDR3 domain
comprising the amino acid sequence of SEQ ID NO:
70; and a light chain variable region comprising a
CDR1 domain comprising the amino acid sequence of
SEQ ID NO: 71, a CDR2 domain comprising the amino
acid sequence of YAS, and a CDR3 domain comprising
the amino acid sequence of SEQ ID NO: 73.

2. The method of claim 1, wherein the method comprises
administering to the human patient a dose of vedolizumab
and a dose of an additional therapeutic agent, wherein the
level of vedolizumab bound to immune cells in the biologi-
cal sample is increased relative to a reference level.

3. A method of treating a human patient having an
inflammatory bowel disease (IBD), the method comprising
   administering a dose of vedolizumab to the patient at an
      initial time point,
   measuring the amount of vedolizumab-bound immune
      cells in a biological sample obtained from the human
      patient about two weeks after the initial time point with
      an anti-idiotypic antibody, or an antigen-binding frag-
      ment thereof, with binding specificity to vedolizumab;
      and
   administering one or more doses of vedolizumab to the
      human patient, wherein if the level of vedolizumab-
      bound immune cells in the biological sample is
      increased relative to a reference level, wherein the
      reference level is a baseline sample obtained from the
      human patient prior to treatment with vedolizumab,
   thereby treating the human patient having IBD
   wherein the anti-idiotypic antibody or antigen-binding
      fragment thereof, comprises:

(i) a heavy chain variable region comprising a CDR1
domain comprising the amino acid sequence of SEQ ID
NO: 1, a CDR2 domain comprising the amino acid
sequence of SEQ ID NO: 2, and a CDR3 domain
comprising the amino acid sequence of SEQ ID NO: 3;
and a light chain variable region comprising a CDR1
domain comprising the amino acid sequence of SEQ ID
NO: 4, a CDR2 domain comprising the amino acid
sequence of RMS, and a CDR3 domain comprising the
amino acid sequence of SEQ ID NO: 6;

(ii) a heavy chain variable region comprising a CDR1
domain comprising the amino acid sequence of SEQ ID
NO: 11, a CDR2 domain comprising the amino acid
sequence of SEQ ID NO: 12, and a CDR3 domain
comprising the amino acid sequence of SEQ ID NO:
13; and a light chain variable region comprising a
CDR1 domain comprising the amino acid sequence of SEQ ID NO: 14, a CDR2 domain comprising the amino acid sequence of RTS, and a CDR3 domain comprising the amino acid sequence of SEQ ID NO: 16;

(iii) a heavy chain variable region comprising a CDR1 domain comprising the amino acid sequence of SEQ ID NO: 21, a CDR2 domain comprising the amino acid sequence of SEQ ID NO: 22, and a CDR3 domain comprising the amino acid sequence of SEQ ID NO: 23; and a light chain variable region comprising a CDR1 domain comprising the amino acid sequence of SEQ ID NO: 24, a CDR2 domain comprising the amino acid sequence of RAS, and a CDR3 domain comprising the amino acid sequence of SEQ ID NO: 26;

(iv) a heavy chain variable region comprising a CDR1 domain comprising the amino acid sequence of SEQ ID NO: 31, a CDR2 domain comprising the amino acid sequence of SEQ ID NO: 22, and a CDR3 domain comprising the amino acid sequence of SEQ ID NO: 32; and a light chain variable region comprising a CDR1 domain comprising the amino acid sequence of SEQ ID NO: 33, a CDR2 domain comprising the amino acid sequence of RAS, and a CDR3 domain comprising the amino acid sequence of SEQ ID NO: 26;

(v) a heavy chain variable region comprising a CDR1 domain comprising the amino acid sequence of SEQ ID NO:38, a CDR2 domain comprising the amino acid sequence of SEQ ID NO: 39, and a CDR3 domain comprising the amino acid sequence of SEQ ID NO: 40; and a light chain variable region comprising a CDR1 domain comprising the amino acid sequence of SEQ ID NO: 41, a CDR2 domain comprising the amino acid sequence of LVS, and a CDR3 domain comprising the amino acid sequence of SEQ ID NO: 43;

(vi) a heavy chain variable region comprising a CDR1 domain comprising the amino acid sequence of SEQ ID NO: 48, a CDR2 domain comprising the amino acid sequence of SEQ ID NO: 49, and a CDR3 domain comprising the amino acid sequence of SEQ ID NO: 50; and a light chain variable region comprising a CDR1 domain comprising the amino acid sequence of SEQ ID NO: 51, a CDR2 domain comprising the amino acid sequence of SGS, and a CDR3 domain comprising the amino acid sequence of SEQ ID NO: 53;

(vii) a heavy chain variable region comprising a CDR1 domain comprising the amino acid sequence of SEQ ID NO: 31 a CDR2 domain comprising the amino acid sequence of SEQ ID NO: 22, and a CDR3 domain comprising the amino acid sequence of SEQ ID NO: 58; and a light chain variable region comprising a CDR1 domain comprising the amino acid sequence of SEQ ID NO: 24, a CDR2 domain comprising the amino acid sequence of RAS, and a CDR3 domain comprising the amino acid sequence of SEQ ID NO: 26;

(viii) a heavy chain variable region comprising a CDR1 domain comprising the amino acid sequence of SEQ ID NO: 63 a CDR2 domain comprising the amino acid sequence of SEQ ID NO: 22, and a CDR3 domain comprising the amino acid sequence of SEQ ID NO: 58; and a light chain variable region comprising a CDR1 domain comprising the amino acid sequence of SEQ ID NO: 24, a CDR2 domain comprising the amino acid sequence of RAS, and a CDR3 domain comprising the amino acid sequence of SEQ ID NO: 26; or (ix) a heavy chain variable region comprising a CDR1 domain comprising the amino acid sequence of SEQ ID NO: 68 a CDR2 domain comprising the amino acid sequence of SEQ ID NO: 69, and a CDR3 domain comprising the amino acid sequence of SEQ ID NO: 70; and a light chain variable region comprising a CDR1 domain comprising the amino acid sequence of SEQ ID NO: 71, a CDR2 domain comprising the amino acid sequence of YAS, and a CDR3 domain comprising the amino acid sequence of SEQ ID NO: 73.

4. The method of claim 1, wherein the immune cells are T cells, B cells, NK cells, monocytes, dendritic cells, plasma cells, and/or eosinophils.

5. The method of claim 3, wherein the immune cells are T cells, B cells, NK cells, monocytes, dendritic cells, plasma cells, and/or eosinophils.

6. The method of claim 1, wherein the anti-idiotypic antibody, or antigen-binding fragment thereof, comprises a detectable label.

7. The method of claim 3, wherein the anti-idiotypic antibody, or antigen-binding fragment thereof, comprises a detectable label.

8. The method of claim 6, wherein the anti-idiotypic antibody, or antigen-binding fragment thereof, is detected by flow cytometry, mass spectrometry, immunohistochemistry, Cellular Indexing of Transcriptomes and Epitopes by Sequencing (CITE-Seq), or oligonucleotide sequencing.

9. The method of claim 7, wherein the anti-idiotypic antibody, or antigen-binding fragment thereof, is detected by flow cytometry, mass spectrometry, immunohistochemistry, Cellular Indexing of Transcriptomes and Epitopes by Sequencing (CITE-Seq), or oligonucleotide sequencing.

10. The method of claim 1, wherein the inflammatory bowel disease is Crohn's disease, pouchitis, or ulcerative colitis.

11. The method of claim 3, herein the inflammatory bowel disease is Crohn's disease, pouchitis, or ulcerative colitis.

12. The method of claim 1, wherein the method further comprises measuring the level of $\alpha4\beta1$, $\alpha L\beta2$, $\alpha E\beta7$, $\alpha6\beta1$, or $\alpha6\beta4$ in the biological sample.

13. The method of claim 6, wherein the method further comprises measuring the level of $\alpha4\beta1$, $\alpha L\beta2$, $\alpha E\beta7$, $\alpha6\beta1$, or $\alpha6\beta4$ in the biological sample.

14. The method of claim 1, wherein the method further comprises measuring the fecal calprotectin, C-reactive protein (CRP), and/or albumin concentration in the biological sample.

15. The method of claim 3, wherein the method further comprises measuring the fecal calprotectin, C-reactive protein (CRP), and/or albumin concentration in the biological sample.

16. The method of claim 1, wherein the anti-idiotypic antibody, or antigen-binding fragment thereof, comprises:

(i) a heavy chain variable region comprising the amino acid sequence of SEQ ID NO: 7, and a light chain variable region comprising the amino acid sequence of SEQ ID NO: 8;

(ii) a heavy chain variable region comprising the amino acid sequence of SEQ ID NO: 17, and a light chain variable region comprising the amino acid sequence of SEQ ID NO: 18;

(iii) a heavy chain variable region comprising the amino acid sequence of SEQ ID NO: 27, and a light chain variable region comprising the amino acid sequence of SEQ ID NO: 28;

(iv) a heavy chain variable region comprising the amino acid sequence of SEQ ID NO: 34, and a light chain variable region comprising the amino acid sequence of SEQ ID NO: 35;

(v) a heavy chain variable region comprising the amino acid sequence of SEQ ID NO: 44, and a light chain variable region comprising the amino acid sequence of SEQ ID NO: 45;

(vi) a heavy chain variable region comprising the amino acid sequence of SEQ ID NO: 54, and a light chain variable region comprising the amino acid sequence of SEQ ID NO: 55;

(vii) a heavy chain variable region comprising the amino acid sequence of SEQ ID NO: 59, and a light chain variable region comprising the amino acid sequence of SEQ ID NO: 60;

(viii) a heavy chain variable region comprising the amino acid sequence of SEQ ID NO: 64, and a light chain variable region comprising the amino acid sequence of SEQ ID NO: 65; or (ix) a heavy chain variable region comprising the amino acid sequence of SEQ ID NO: 74, and a light chain variable region comprising the amino acid sequence of SEQ ID NO: 75.

17. The method of claim 3, wherein the anti-idiotypic antibody, or antigen-binding fragment thereof, comprises:

(i) a heavy chain variable region comprising the amino acid sequence of SEQ ID NO: 7, and a light chain variable region comprising the amino acid sequence of SEQ ID NO: 8;

(ii) a heavy chain variable region comprising the amino acid sequence of SEQ ID NO: 17, and a light chain variable region comprising the amino acid sequence of SEQ ID NO: 18;

(iii) a heavy chain variable region comprising the amino acid sequence of SEQ ID NO: 27, and a light chain variable region comprising the amino acid sequence of SEQ ID NO: 28;

(iv) a heavy chain variable region comprising the amino acid sequence of SEQ ID NO: 34, and a light chain variable region comprising the amino acid sequence of SEQ ID NO: 35;

(v) a heavy chain variable region comprising the amino acid sequence of SEQ ID NO: 44, and a light chain variable region comprising the amino acid sequence of SEQ ID NO: 45;

(vi) a heavy chain variable region comprising the amino acid sequence of SEQ ID NO: 54, and a light chain variable region comprising the amino acid sequence of SEQ ID NO: 55;

(vii) a heavy chain variable region comprising the amino acid sequence of SEQ ID NO: 59, and a light chain variable region comprising the amino acid sequence of SEQ ID NO: 60;

(viii) a heavy chain variable region comprising the amino acid sequence of SEQ ID NO: 64, and a light chain variable region comprising the amino acid sequence of SEQ ID NO: 65; or (ix) a heavy chain variable region comprising the amino acid sequence of SEQ ID NO: 74, and a light chain variable region comprising the amino acid sequence of SEQ ID NO: 75.

18. The method of claim 4, wherein the immune cell expresses one or more phenotypic markers selected from CD3, CD4, CD6, CD11c, CD14, CD16, CD19, CD25, CD28, CD38, CD45RA, CD64, CD127, CCR7, CCR9, FoxP3, GPR15, Th17, or miR-301a.

19. The method of claim 5, wherein the immune cell expresses one or more phenotypic markers selected from CD3, CD4, CD6, CD11c, CD14, CD16, CD19, CD25, CD28, CD38, CD45RA, CD64, CD127, CCR7, CCR9, FoxP3, GPR15, Th17, or miR-301a.

20. The method of claim 4, wherein the T cells are memory T cells, naïve T cells, or regulatory T cells.

21. The method of claim 5, wherein the T cells are memory T cells, naïve T cells, or regulatory T cells.

* * * * *

SEQUENCE LISTING

```
Sequence total quantity: 87
SEQ ID NO: 1              moltype = AA  length = 8
FEATURE                  Location/Qualifiers
source                   1..8
                         mol_type = protein
                         organism = synthetic construct
SEQUENCE: 1
GFSLSSYE                                                          8

SEQ ID NO: 2              moltype = AA  length = 7
FEATURE                  Location/Qualifiers
source                   1..7
                         mol_type = protein
                         organism = synthetic construct
SEQUENCE: 2
IWTGGST                                                           7

SEQ ID NO: 3              moltype = AA  length = 12
FEATURE                  Location/Qualifiers
source                   1..12
                         mol_type = protein
                         organism = synthetic construct
SEQUENCE: 3
VGAPYDYGGF AY                                                     12

SEQ ID NO: 4              moltype = AA  length = 11
FEATURE                  Location/Qualifiers
source                   1..11
```

```
                             mol_type = protein
                             organism = synthetic construct
SEQUENCE: 4
KSLLHNDGIT Y                                                            11

SEQ ID NO: 5              moltype =   length =
SEQUENCE: 5
000

SEQ ID NO: 6             moltype = AA   length = 9
FEATURE                  Location/Qualifiers
source                   1..9
                         mol_type = protein
                         organism = synthetic construct
SEQUENCE: 6
AQMLEFPYT                                                               9

SEQ ID NO: 7             moltype = AA   length = 118
FEATURE                  Location/Qualifiers
source                   1..118
                         mol_type = protein
                         organism = synthetic construct
SEQUENCE: 7
QVQLKESGPG LAAPSQNLFI TCTVSGFSLS SYEIHWFRQP PGKGLEWLGV IWTGGSTDYN       60
SALISRLNIS KDNSKSLAFL NVNSLQTDDT AIYYCVGAPY DYGGFAYWGQ GTLVTVSA        118

SEQ ID NO: 8             moltype = AA   length = 112
FEATURE                  Location/Qualifiers
source                   1..112
                         mol_type = protein
                         organism = synthetic construct
SEQUENCE: 8
DIVMTQAAFS NPVTLGTSAS ISCRSSKSLL HNDGITYLYW YLQRPGQSPQ LLLFRMSNLA       60
SGVPDRFSGS GSGTDFTLRI SRVEAEDVGV YYCAQMLEFP YTFGSGTKLE IK              112

SEQ ID NO: 9             moltype = DNA   length = 354
FEATURE                  Location/Qualifiers
source                   1..354
                         mol_type = other DNA
                         organism = synthetic construct
SEQUENCE: 9
caggtgcagc tgaaggagtc aggacctggc ctggcggcgc cctcacagaa cctgttcatc       60
acatgtaccg tctcaggatt ctcattaagc agctatgaaa tacactggtt cgccagcct      120
ccaggaaagg gtctggagtg gctgggagtg atatggactg gtggaagtac agattataat      180
tcagctctca tatccagact gaacataagt aaagacaact ccaagagcct agctttctta      240
aatgtgaata gtctgcaaac tgatgacaca gccatatatt actgtgtagg agccccctat      300
gattacgggg ggtttgctta ttggggccaa gggactctgg tcactgtctc tgca            354

SEQ ID NO: 10            moltype = DNA   length = 336
FEATURE                  Location/Qualifiers
source                   1..336
                         mol_type = other DNA
                         organism = synthetic construct
SEQUENCE: 10
gatattgtga tgacgcaggc tgcattctcc aatccagtca ctcttggaac gtcagcttcc       60
atctcctgca ggtctagtaa gagtctccta cataatgatg gcatcactta tttgtattgg      120
tatctgcaga ggccaggcca gtctcctcag ctcctgcttt ttcggatgtc caaccttgcc      180
tcaggagtcc cagacaggtt cagtggcagt gggtcaggaa ctgatttcac actgagaatc      240
agcagagtag aggctgagga tgtgggtgtt tattactgtg ctcaaatgct agaattcccg      300
tatacgttcg gatcggggac caagctggaa ataaaa                                336

SEQ ID NO: 11            moltype = AA   length = 8
FEATURE                  Location/Qualifiers
source                   1..8
                         mol_type = protein
                         organism = synthetic construct
SEQUENCE: 11
GYTFTSYN                                                                8

SEQ ID NO: 12            moltype = AA   length = 8
FEATURE                  Location/Qualifiers
source                   1..8
                         mol_type = protein
                         organism = synthetic construct
SEQUENCE: 12
IYPGNGDT                                                                8

SEQ ID NO: 13            moltype = AA   length = 11
FEATURE                  Location/Qualifiers
```

-continued

```
source                    1..11
                          mol_type = protein
                          organism = synthetic construct
SEQUENCE: 13
ARGWFHWYFD V                                                              11

SEQ ID NO: 14             moltype = AA  length = 7
FEATURE                   Location/Qualifiers
source                    1..7
                          mol_type = protein
                          organism = synthetic construct
SEQUENCE: 14
SSISSNY                                                                   7

SEQ ID NO: 15             moltype =    length =
SEQUENCE: 15
000

SEQ ID NO: 16             moltype = AA  length = 9
FEATURE                   Location/Qualifiers
source                    1..9
                          mol_type = protein
                          organism = synthetic construct
SEQUENCE: 16
QQGSTIPLT                                                                 9

SEQ ID NO: 17             moltype = AA  length = 118
FEATURE                   Location/Qualifiers
source                    1..118
                          mol_type = protein
                          organism = synthetic construct
SEQUENCE: 17
QAYLQQSGAE LVRPGASVKM SCKASGYTFT SYNMHWVKQT PRQGLEWIGA IYPGNGDTSY  60
NQKFKGKATL TVDKSSSTAY MQLSSLTSED SAVYFCARGW FHWYFDVWGT GTTVTVSS    118

SEQ ID NO: 18             moltype = AA  length = 108
FEATURE                   Location/Qualifiers
source                    1..108
                          mol_type = protein
                          organism = synthetic construct
SEQUENCE: 18
EIVLTQSPTA MAASPGEKIT ITCSASSSIS SNYLHWYLQK PGFSPKLLIY RTSNLASGVP  60
ARFSGSGSGT SYSLTIGTME AEDVATYYCQ QGSTIPLTFG AGTRLELK             108

SEQ ID NO: 19             moltype = DNA  length = 354
FEATURE                   Location/Qualifiers
source                    1..354
                          mol_type = other DNA
                          organism = synthetic construct
SEQUENCE: 19
caggcttatc tacagcagtc tgggggctgag ctggtgaggc ctggggcctc agtgaagatg   60
tcctgcaagg cttctggcta cacatttacc agttacaata tgcactgggt aaagcagaca  120
cctagacagg gcctggaatg gattggagct atttatccag gaaatggtga tacttcctac  180
aatcagaagt tcaagggcaa ggccacactg actgtagaca atcctccag cacagcctac  240
atgcagctca gcagcctgac atctgaagac tctgcggtct atttctgtgc aagaggatgg  300
tttcactggt acttcgatgt ctgggggcaca gggaccacgg tcaccgtctc ctca        354

SEQ ID NO: 20             moltype = DNA  length = 324
FEATURE                   Location/Qualifiers
source                    1..324
                          mol_type = other DNA
                          organism = synthetic construct
SEQUENCE: 20
gaaattgtgc tcacccagtc tccaaccgcc atggctgcat ctcccgggga gaagatcact   60
atcacctgca gtgccagctc aagtataagt tccaattact tgcattggta tctgcagaag  120
ccaggattct ccctaaact cttgatttat aggacatcca atctggcttc tggagtccca  180
gctcgcttca gtggcagtgg gtctgggacc tcttactctc tcacaattgg caccatggag  240
gctgaagatg ttgccactta ctactgccag caggtagta ctataccgct cacgttcggt  300
gctgggacca ggctggagct gaaa                                          324

SEQ ID NO: 21             moltype = AA  length = 8
FEATURE                   Location/Qualifiers
source                    1..8
                          mol_type = protein
                          organism = synthetic construct
SEQUENCE: 21
GFSLTNYG                                                                  8

SEQ ID NO: 22             moltype = AA  length = 7
```

```
FEATURE               Location/Qualifiers
source                1..7
                      mol_type = protein
                      organism = synthetic construct
SEQUENCE: 22
IWSGGST                                                              7

SEQ ID NO: 23         moltype = AA  length = 16
FEATURE               Location/Qualifiers
source                1..16
                      mol_type = protein
                      organism = synthetic construct
SEQUENCE: 23
ARIGGYGTTY EDGMDY                                                    16

SEQ ID NO: 24         moltype = AA  length = 10
FEATURE               Location/Qualifiers
source                1..10
                      mol_type = protein
                      organism = synthetic construct
SEQUENCE: 24
ESVDNFGISF                                                           10

SEQ ID NO: 25         moltype =    length =
SEQUENCE: 25
000

SEQ ID NO: 26         moltype = AA  length = 9
FEATURE               Location/Qualifiers
source                1..9
                      mol_type = protein
                      organism = synthetic construct
SEQUENCE: 26
QQSNKDPLT                                                            9

SEQ ID NO: 27         moltype = AA  length = 122
FEATURE               Location/Qualifiers
source                1..122
                      mol_type = protein
                      organism = synthetic construct
SEQUENCE: 27
QVQLKQSGPG LVQPSQSLSI TCTVSGFSLT NYGVHWVRQS PGKGLEWLGV IWSGGSTDYN   60
AAVISRLTIS KDNSKSQVFF KMNSLQADDT AIYYCARIGG YGTTYEDGMD YWGQGTSVTV   120
SS                                                                  122

SEQ ID NO: 28         moltype = AA  length = 111
FEATURE               Location/Qualifiers
source                1..111
                      mol_type = protein
                      organism = synthetic construct
SEQUENCE: 28
DIVLTQSPAS LAVSLGQRAT ISCRASESVD NFGISFMHWY QQKSGQPPKL LIYRASNLES   60
GIPARFSGSG SRTDFTLTIN PVETDDVATY YCQQSNKDPL TFGAGTKLEL K            111

SEQ ID NO: 29         moltype = DNA  length = 366
FEATURE               Location/Qualifiers
source                1..366
                      mol_type = other DNA
                      organism = synthetic construct
SEQUENCE: 29
caggtgcagc tgaagcagtc aggacctggc ctagtgcagc cctcacagag cctgtccatc   60
acctgcacag tctctggttt ctcattaact aactatggtg tacactgggt tcgccagtct   120
ccaggaaagg gtctggagtg gctgggagtg atatggagtg gtggaagcac agactataat   180
gcagctgtca tatccagact gaccatcagc aaggacaatt ccaagagcca agtttttctt   240
aaaatgaaca gtctgcaagc tgatgacaca gccatttatt actgtgccag aataggggc   300
tacggtacta cctacgagga tggtatggac tactggggtc aaggaacctc agtcaccgtc   360
tcctca                                                              366

SEQ ID NO: 30         moltype = DNA  length = 333
FEATURE               Location/Qualifiers
source                1..333
                      mol_type = other DNA
                      organism = synthetic construct
SEQUENCE: 30
gacattgtgc tgacccaatc tccagcttct ttggctgtgt ctctagggca gagggccacc   60
atctcctgca gagccagcga aagtgttgat aattttggca ttagttttat gcactggtac   120
cagcagaaat caggacagcc acccaaactc ctcatctatc gtgcatccaa cctagaatct   180
gggatccctg ccaggttcag tggcagtggg tctaggacag acttcaccct caccattaat   240
cctgtggaga ctgatgatgt tgcaacctat tactgtcagc aaagtaataa ggatccgctc   300
```

-continued

```
acgttcggtg ctgggaccaa gctggagctg aaa                                    333

SEQ ID NO: 31            moltype = AA   length = 8
FEATURE                  Location/Qualifiers
source                   1..8
                         mol_type = protein
                         organism = synthetic construct
SEQUENCE: 31
GFSLTSYG                                                                 8

SEQ ID NO: 32            moltype = AA   length = 16
FEATURE                  Location/Qualifiers
source                   1..16
                         mol_type = protein
                         organism = synthetic construct
SEQUENCE: 32
ARIGGYGTSY EDGMDY                                                        16

SEQ ID NO: 33            moltype = AA   length = 10
FEATURE                  Location/Qualifiers
source                   1..10
                         mol_type = protein
                         organism = synthetic construct
SEQUENCE: 33
ESVDNFGVSF                                                               10

SEQ ID NO: 34            moltype = AA   length = 122
FEATURE                  Location/Qualifiers
source                   1..122
                         mol_type = protein
                         organism = synthetic construct
SEQUENCE: 34
QVQLKQSGPG LVQPSQSLSI TCTVSGFSLT SYGVHWVRQS PGKGLEWLGV IWSGGSTDYN        60
AAFRSRLTIS KDNSKSQVFF KMNSLQADDT AIYYCARIGG YGTSYEDGMD YWGQGTSVTV        120
SS                                                                       122

SEQ ID NO: 35            moltype = AA   length = 111
FEATURE                  Location/Qualifiers
source                   1..111
                         mol_type = protein
                         organism = synthetic construct
SEQUENCE: 35
DIVLTQSPAS LAVSLGQRAT ISCRASESVD NFGVSFMHWY QQKPGQPPKL LIYRASNLES        60
GIPARFSGSG SRTDFTLTIN PVETDDVATY YCQQSNKDPL TFGAGTKLEL K                 111

SEQ ID NO: 36            moltype = DNA   length = 366
FEATURE                  Location/Qualifiers
source                   1..366
                         mol_type = other DNA
                         organism = synthetic construct
SEQUENCE: 36
caggtgcagc tgaagcagtc aggacctggc ctagtgcagc cctcacagag cctgtccatc        60
acctgcacag tctctggttt ctcattaact agctatggtg tacactgggt tcgccagtct       120
ccaggaaagg gtctggagtg gctgggagtg atatggagtg gtggaagcac agactataat       180
gcagctttca gatccagact gaccatcagc aaggacaatt ccaagagcca agtttttctt       240
aaaatgaaca gtctgcaagc tgatgacaca gccatatatt actgtgccag aataggggggc      300
tacggtacta gctacgagga tggtatggac tactggggtc aaggaacctc agtcaccgtc       360
tcctca                                                                   366

SEQ ID NO: 37            moltype = DNA   length = 333
FEATURE                  Location/Qualifiers
source                   1..333
                         mol_type = other DNA
                         organism = synthetic construct
SEQUENCE: 37
gacattgtgc tgacccaatc tccagcttct ttggctgtgt ctctagggca gagggccacc        60
atctcctgca gagccagcga aagtgttgat aattttggcg ttagttttat gcactggtat       120
caacagaaac caggacagcc acccaaactc ctcatctatc gtgcatccaa cctagaatct       180
gggatccctg ccaggttcag tggcagtggg tctaggacag acttcaccct caccattaat       240
cctgtggaga ctgatgatgt tgcaacctat tactgtcagc aaagtaataa ggatccgctc       300
acgttcggtg ctgggaccaa gctggaactg aaa                                    333

SEQ ID NO: 38            moltype = AA   length = 8
FEATURE                  Location/Qualifiers
source                   1..8
                         mol_type = protein
                         organism = synthetic construct
SEQUENCE: 38
GFTFSSYG                                                                 8
```

-continued

```
SEQ ID NO: 39         moltype = AA   length = 8
FEATURE               Location/Qualifiers
source                1..8
                      mol_type = protein
                      organism = synthetic construct
SEQUENCE: 39
ISSGGSYT                                                                    8

SEQ ID NO: 40         moltype = AA   length = 11
FEATURE               Location/Qualifiers
source                1..11
                      mol_type = protein
                      organism = synthetic construct
SEQUENCE: 40
ARHGTGVGFD Y                                                                11

SEQ ID NO: 41         moltype = AA   length = 11
FEATURE               Location/Qualifiers
source                1..11
                      mol_type = protein
                      organism = synthetic construct
SEQUENCE: 41
QSLLDSDGKT Y                                                                11

SEQ ID NO: 42         moltype =    length =
SEQUENCE: 42
000

SEQ ID NO: 43         moltype = AA   length = 9
FEATURE               Location/Qualifiers
source                1..9
                      mol_type = protein
                      organism = synthetic construct
SEQUENCE: 43
WQGTHFPQT                                                                   9

SEQ ID NO: 44         moltype = AA   length = 118
FEATURE               Location/Qualifiers
source                1..118
                      mol_type = protein
                      organism = synthetic construct
SEQUENCE: 44
EVQLVESGGD LVKPGGSLKL SCAASGFTFS SYGMSWVRQT PDKRLEWVAS ISSGGSYTHY   60
PDSVKGRFTI SRDNAKNTLY LQMSSLKSED TAMYYCARHG TGVGFDYWGQ GTTLTVSS     118

SEQ ID NO: 45         moltype = AA   length = 112
FEATURE               Location/Qualifiers
source                1..112
                      mol_type = protein
                      organism = synthetic construct
SEQUENCE: 45
DVVMTQTPLT LSVTIGQPAS ISCKSSQSLL DSDGKTYLNW LLQRPGQSPK RLIYLVSKLD   60
SGVPDRFTGS GSGTDFTLKI SRVEAEDLGV YYCWQGTHFP QTFGGGTKLE IK           112

SEQ ID NO: 46         moltype = DNA   length = 354
FEATURE               Location/Qualifiers
source                1..354
                      mol_type = other DNA
                      organism = synthetic construct
SEQUENCE: 46
gaggtgcagc tggtggagtc tgggggagac ttagtgaagc ctggagggtc cctgaaactc   60
tcctgtgctg cctctggatt cactttcagt agctatggca tgtcttgggt tcgccagact   120
ccagacaaga ggctggagtg ggtcgcatcc attagtggtg gtggtagtta cacccactat   180
ccagacagtg tgaaggggcg attcaccatc tccagagaca tgccaagaa cacccctgtac  240
ctgcaaatga gcagtctgaa gtctgaggac acagccatgt attactgtgc aagacatggg   300
actggggtcg gttttgacta ctggggccaa ggcaccactc tcacagtctc ctca         354

SEQ ID NO: 47         moltype = DNA   length = 336
FEATURE               Location/Qualifiers
source                1..336
                      mol_type = other DNA
                      organism = synthetic construct
SEQUENCE: 47
gatgttgtga tgacccagac tccactcact ttgtcggtta ccattggaca accagcctcc   60
atctcttgca gtcaagtca gagcctctta gatagtgatg gaaagacata tttgaattgg    120
ttgttacaga ggccaggcca gtctccaaag cgcctaatct atctggtgtc taaactggac   180
tctgagtcc ctgacaggtt cactggcagt ggatcaggga cagatttcac actgaaaatc    240
agcagagtgg aggctgagga tttgggagtt tattattgct ggcaaggtac acattttcct   300
```

```
cagacgttcg gtggaggcac caagctggaa atcaaa                                    336

SEQ ID NO: 48              moltype = AA   length = 8
FEATURE                    Location/Qualifiers
source                     1..8
                           mol_type = protein
                           organism = synthetic construct
SEQUENCE: 48
GFTFSDYG                                                                   8

SEQ ID NO: 49              moltype = AA   length = 8
FEATURE                    Location/Qualifiers
source                     1..8
                           mol_type = protein
                           organism = synthetic construct
SEQUENCE: 49
ISNLAYSI                                                                   8

SEQ ID NO: 50              moltype = AA   length = 14
FEATURE                    Location/Qualifiers
source                     1..14
                           mol_type = protein
                           organism = synthetic construct
SEQUENCE: 50
AREDGTTGES AMDY                                                            14

SEQ ID NO: 51              moltype = AA   length = 6
FEATURE                    Location/Qualifiers
source                     1..6
                           mol_type = protein
                           organism = synthetic construct
SEQUENCE: 51
KSISKY                                                                     6

SEQ ID NO: 52              moltype =    length =
SEQUENCE: 52
000

SEQ ID NO: 53              moltype = AA   length = 9
FEATURE                    Location/Qualifiers
source                     1..9
                           mol_type = protein
                           organism = synthetic construct
SEQUENCE: 53
QQHYEYPYT                                                                  9

SEQ ID NO: 54              moltype = AA   length = 121
FEATURE                    Location/Qualifiers
source                     1..121
                           mol_type = protein
                           organism = synthetic construct
SEQUENCE: 54
EVKLVESGGG LVQPGGSLKL SCAASGFTFS DYGMAWVRQA PRKGPEWVGF ISNLAYSIYY         60
ADTVTGRFTI SRENAKNTLY LEMSSLRSED TAMYYCARED GTTGESAMDY WGQGTSVTVS         120
S                                                                         121

SEQ ID NO: 55              moltype = AA   length = 107
FEATURE                    Location/Qualifiers
source                     1..107
                           mol_type = protein
                           organism = synthetic construct
SEQUENCE: 55
DVQITQSPSY LAASPGETIT INCRASKSIS KYLAWYQEKP GKTNKLLIYS GSTLQSGIPS         60
RFSGSGSGTD FTLTISSLEP EDFAMYYCQQ HYEYPYTFGS GTKLEMK                       107

SEQ ID NO: 56              moltype = DNA   length = 363
FEATURE                    Location/Qualifiers
source                     1..363
                           mol_type = other DNA
                           organism = synthetic construct
SEQUENCE: 56
gaggtgaagc tggtggagtc tgggggaggc ttagtgcagc ctggagggtc cctgaaactc         60
tcctgtgcag cctctggatt cactttcagt gactacggaa tggcgtgggt tcgacaggct         120
ccaaggaagg ggcctgagtg ggtaggattc attagtaatt tggcgtatag tatctactat         180
gcagacactg tgacgggccg attcaccatc tctagagaga atgccaagaa caccctgtac         240
ctggaaatga gcagtctgag gtctgaggac acggccatgt attactgtgc aagagaggat         300
ggcactacgg gagaaagtgc tatggactac tggggtcaag aacctcagt caccgtctcc         360
tca                                                                       363
```

-continued

```
SEQ ID NO: 57              moltype = DNA   length = 321
FEATURE                    Location/Qualifiers
source                     1..321
                           mol_type = other DNA
                           organism = synthetic construct
SEQUENCE: 57
gatgtccaga taacccagtc tccatcttat cttgctgcat ctcctggaga aaccattact   60
attaattgca gggcaagtaa gagcattagc aaatatttag cctggtatca agagaaacct  120
gggaaaacta ataagcttct tatctactct ggatccactt tgcaatctgg aattccatca  180
aggttcagtg gcagtggatc tggtacagat ttcactctca ccatcagtag cctggagcct  240
gaagattttg caatgtatta ctgtcaacag cactatgaat acccgtacac gttcggctcg  300
gggacaaagt tggaaatgaa g                                            321

SEQ ID NO: 58              moltype = AA   length = 16
FEATURE                    Location/Qualifiers
source                     1..16
                           mol_type = protein
                           organism = synthetic construct
SEQUENCE: 58
ARIGGYGTTY EDAMDY                                                    16

SEQ ID NO: 59              moltype = AA   length = 122
FEATURE                    Location/Qualifiers
source                     1..122
                           mol_type = protein
                           organism = synthetic construct
SEQUENCE: 59
QVQLKQSGPG LVQPSQSLSI TCTVSGFSLT SYGVHWVRQS PGKGLEWLGV IWSGGSTDYN   60
AAFISRLTIS KDNSKTQVFF KMNSLQADDT AIYYCARIGG YGTTYEDAMD YWGQGTSVTV  120
SS                                                                 122

SEQ ID NO: 60              moltype = AA   length = 111
FEATURE                    Location/Qualifiers
source                     1..111
                           mol_type = protein
                           organism = synthetic construct
SEQUENCE: 60
DIALTQSPAS LAVSLGQRAT ISCRASESVD NFGISFMHWY QQKPGQPPKV LIYRASKLES   60
GIPARFSGSG SRTDFTLTIN PVETEDVATY YCQQSNKDPL TFGAGTKLEL K           111

SEQ ID NO: 61              moltype = DNA   length = 366
FEATURE                    Location/Qualifiers
source                     1..366
                           mol_type = other DNA
                           organism = synthetic construct
SEQUENCE: 61
caggtgcagc tgaagcagtc aggacctggc ctagtgcagc cctcacagag cctgtccatc   60
acctgcacag tctctggttt ctcattaact agctatggtg tacactgggt tcgccagtct  120
ccaggaaagg gtctggagtg gctgggagtg atatggagtg gtggaagcac agactataat  180
gcagctttca tatccagact gaccatcagc aaggacaatt ccaagaccca gttttcttt   240
aaaatgaaca gtctgcaagc tgatgacaca gccatatatt actgtgccag aatagggggc  300
tacggtacta cctacgagga tgctatggac tactgggtc aaggaacctc agtcaccgtc  360
tcctca                                                             366

SEQ ID NO: 62              moltype = DNA   length = 333
FEATURE                    Location/Qualifiers
source                     1..333
                           mol_type = other DNA
                           organism = synthetic construct
SEQUENCE: 62
gacattgcgc tgacccaatc tccagcttct ttggctgtgt ctctagggca gagggccacc   60
atctcctgca gagccagcga aagtgttgat aattttggca ttagtttat gcactggtac  120
cagcagaaac aggacagcc acccaaagtc ctcatctatc gtgcatccaa gctagaatct  180
gggatccctg ccaggttcag tggcagtggg tctaggacag acttcaccct caccattaat  240
cctgtggaga ctgaagatgt tgcaacctat tactgtcagc aaagtaataa ggatcctctc  300
acgttcggtg ctgggaccaa gctggagctg aaa                              333

SEQ ID NO: 63              moltype = AA   length = 8
FEATURE                    Location/Qualifiers
source                     1..8
                           mol_type = protein
                           organism = synthetic construct
SEQUENCE: 63
GFSLTSYG                                                             8

SEQ ID NO: 64              moltype = AA   length = 122
FEATURE                    Location/Qualifiers
source                     1..122
                           mol_type = protein
```

```
                          organism = synthetic construct
SEQUENCE: 64
QVQLKQSGPG LVQPSQSLSV TCTVSGFSLT SYGVHWVRQS PGKGLEWLGV IWSGGSTDYN    60
AAFISRLTIS KDNSKSQVFF KMNSLQADDT AIYYCARIGG YGTTYEDAMD YWGQGTSVTV    120
SS                                                                     122

SEQ ID NO: 65        moltype = AA   length = 111
FEATURE              Location/Qualifiers
source               1..111
                     mol_type = protein
                     organism = synthetic construct
SEQUENCE: 65
DIVLTQSPAS LSVSLGQRAT ISCRASESVD NFGISFMFWY QQKPGQPPRL LIYRASNLES    60
GIPARFSGSG SRTDFTLTIN PVETDDVATY YCQQSNKDPL TFGAGTKLEL K             111

SEQ ID NO: 66        moltype = DNA   length = 366
FEATURE              Location/Qualifiers
source               1..366
                     mol_type = other DNA
                     organism = synthetic construct
SEQUENCE: 66
caggtgcagc tgaagcaatc aggacctggc ctagtgcagc cctcacagag cctgtccgtc    60
acctgcacag tctctggttt ctcattaact agctatggtg tacactgggt tcgccagtct    120
ccaggaaagg gtctggagtg gctgggagtg atatggagtg gtggaagcac agactataat    180
gcagctttca tatccagact gaccatcagc aaggacaatt ccaagagcca gttttctttt    240
aaaatgaaca gtctgcaagc tgatgacaca gccatatatt actgtgccag aatagggggc    300
tacggtacta cctacgagga tgctatggac tactggggtc aaggaacctc agtcaccgtc    360
tcctca                                                                366

SEQ ID NO: 67        moltype = DNA   length = 333
FEATURE              Location/Qualifiers
source               1..333
                     mol_type = other DNA
                     organism = synthetic construct
SEQUENCE: 67
gacattgtgc tgacccaatc tccagcttct ttgtctgtgt ctctagggca gagggccacc    60
atctcctgca gagccagcga aagtgttgat aattttggca ttagtttttat gttttggtac    120
cagcagaaac caggacagcc acccagactc ctcatctatc gtgcatccaa cctagaatct    180
gggatccctg ccaggttcag tggcagtggg tctaggacag acttcaccct caccattaat    240
cctgtggaga ctgatgatgt tgcaacctat tactgtcagc aaagtaataa ggatccgctc    300
acgttcggtg ctgggaccaa gctggagctg aaa                                  333

SEQ ID NO: 68        moltype = AA   length = 8
FEATURE              Location/Qualifiers
source               1..8
                     mol_type = protein
                     organism = synthetic construct
SEQUENCE: 68
GYTFTDYN                                                               8

SEQ ID NO: 69        moltype = AA   length = 8
FEATURE              Location/Qualifiers
source               1..8
                     mol_type = protein
                     organism = synthetic construct
SEQUENCE: 69
INPNNGGT                                                               8

SEQ ID NO: 70        moltype = AA   length = 10
FEATURE              Location/Qualifiers
source               1..10
                     mol_type = protein
                     organism = synthetic construct
SEQUENCE: 70
ARDLVYYFDY                                                             10

SEQ ID NO: 71        moltype = AA   length = 6
FEATURE              Location/Qualifiers
source               1..6
                     mol_type = protein
                     organism = synthetic construct
SEQUENCE: 71
QSIGRS                                                                 6

SEQ ID NO: 72        moltype =    length =
SEQUENCE: 72
000

SEQ ID NO: 73        moltype = AA   length = 9
```

-continued

```
FEATURE                Location/Qualifiers
source                 1..9
                       mol_type = protein
                       organism = synthetic construct
SEQUENCE: 73
QQSNSWPFT                                                                    9

SEQ ID NO: 74          moltype = AA   length = 117
FEATURE                Location/Qualifiers
source                 1..117
                       mol_type = protein
                       organism = synthetic construct
SEQUENCE: 74
EVQLQQSGPE LVKPGASVKI PCKASGYTFT DYNMDWVKQS HGKSLEWIGD INPNNGGTIY   60
NQKFKGKATL TVDKSSSTAY MELRSLTSED TAVYYCARDL VYYFDYWGQG TTLTVSS     117

SEQ ID NO: 75          moltype = AA   length = 107
FEATURE                Location/Qualifiers
source                 1..107
                       mol_type = protein
                       organism = synthetic construct
SEQUENCE: 75
DILLTQSPAI LSVSPGERVS FSCRASQSIG RSIHWYQQRT NGSPRLLIKY ASESISGIPS   60
RFSGSGSGTD FTLSINSVES EDIADYYCQQ SNSWPFTFGS GTKLEIK              107

SEQ ID NO: 76          moltype = DNA   length = 351
FEATURE                Location/Qualifiers
source                 1..351
                       mol_type = other DNA
                       organism = synthetic construct
SEQUENCE: 76
gaggtccagc tgcaacagtc tggacctgag ctggtgaagc ctggggcttc agtgaagata   60
ccctgcaagg cttctggata cacattcact gactacaaca tggactgggt gaagcagagc  120
catggaaaga gccttgagtg gattggagat attaatccta caaatggtgg tactatctac  180
aaccagaagt tcaagggcaa ggccacattg actgtagaca agtcctccaa cacagcctac  240
atggagctcc gcagcctgac atctgaggac actgcagtct attactgtgc aagagacctc  300
gtttactact ttgactactg gggccaaggc accactctca cagtctcctc a           351

SEQ ID NO: 77          moltype = DNA   length = 321
FEATURE                Location/Qualifiers
source                 1..321
                       mol_type = other DNA
                       organism = synthetic construct
SEQUENCE: 77
gacatcttgc tgactcagtc tccagccatc ctgtctgtga gtccaggaga aagagtcagt   60
ttctcctgca gggccagtca gagcattggc agaagcatac actggtatca gcaaagaaca  120
aatggttctc caaggcttct cataaagtat gcttctgagt ctatctctgg gatcccttcc  180
aggtttagtg gcagtggatc agggacagat tttactctta gcatcaacag tgtggagtct  240
gaagatattg cagattatta ctgtcaacaa agtaatagct ggccattcac gttcggctcg  300
gggacaaagt tggaaataaa a                                            321

SEQ ID NO: 78          moltype = AA   length = 121
FEATURE                Location/Qualifiers
source                 1..121
                       mol_type = protein
                       organism = synthetic construct
SEQUENCE: 78
QVQLVQSGAE VKKPGASVKV SCKGSGYTFT SYWMHWVRQA PGQRLEWIGE IDPSESNTNY   60
NQKFKGRVTL TVDISASTAY MELSSLRSED TAVYYCARGG YDGWDYAIDY WGQGTLVTVS  120
S                                                                  121

SEQ ID NO: 79          moltype = AA   length = 5
FEATURE                Location/Qualifiers
source                 1..5
                       mol_type = protein
                       organism = synthetic construct
SEQUENCE: 79
SYWMH                                                                        5

SEQ ID NO: 80          moltype = AA   length = 17
FEATURE                Location/Qualifiers
source                 1..17
                       mol_type = protein
                       organism = synthetic construct
SEQUENCE: 80
EIDPSESNTN YNQKFKG                                                          17

SEQ ID NO: 81          moltype = AA   length = 12
FEATURE                Location/Qualifiers
```

-continued

```
source                    1..12
                          mol_type = protein
                          organism = synthetic construct
SEQUENCE: 81
GGYDGWDYAI DY                                                    12

SEQ ID NO: 82             moltype = AA  length = 112
FEATURE                   Location/Qualifiers
source                    1..112
                          mol_type = protein
                          organism = synthetic construct
SEQUENCE: 82
DVVMTQSPLS LPVTPGEPAS ISCRSSQSLA KSYGNTYLSW YLQKPGQSPQ LLIYGISNRF  60
SGVPDRFSGS GSGTDFTLKI SRVEAEDVGV YYCLQGTHQP YTFGQGTKVE IK          112

SEQ ID NO: 83             moltype = AA  length = 16
FEATURE                   Location/Qualifiers
source                    1..16
                          mol_type = protein
                          organism = synthetic construct
SEQUENCE: 83
RSSQSLAKSY GNTYLS                                                16

SEQ ID NO: 84             moltype = AA  length = 7
FEATURE                   Location/Qualifiers
source                    1..7
                          mol_type = protein
                          organism = synthetic construct
SEQUENCE: 84
GISNRFS                                                          7

SEQ ID NO: 85             moltype = AA  length = 9
FEATURE                   Location/Qualifiers
source                    1..9
                          mol_type = protein
                          organism = synthetic construct
SEQUENCE: 85
LQGTHQPYT                                                        9

SEQ ID NO: 86             moltype = AA  length = 451
FEATURE                   Location/Qualifiers
source                    1..451
                          mol_type = protein
                          organism = synthetic construct
SEQUENCE: 86
QVQLVQSGAE VKKPGASVKV SCKGSGYTFT SYWMHWVRQA PGQRLEWIGE IDPSESNTNY  60
NQKFKGRVTL TVDISASTAY MELSSLRSED TAVYYCARGG YDGWDYAIDY WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELAG  240
APSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG K                               451

SEQ ID NO: 87             moltype = AA  length = 219
FEATURE                   Location/Qualifiers
source                    1..219
                          mol_type = protein
                          organism = synthetic construct
SEQUENCE: 87
DVVMTQSPLS LPVTPGEPAS ISCRSSQSLA KSYGNTYLSW YLQKPGQSPQ LLIYGISNRF  60
SGVPDRFSGS GSGTDFTLKI SRVEAEDVGV YYCLQGTHQP YTFGQGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219
```